US007053076B2

(12) United States Patent
Bhat et al.

(10) Patent No.: US 7,053,076 B2
(45) Date of Patent: May 30, 2006

(54) BILE-ACID DERIVED COMPOUNDS FOR ENHANCING ORAL ABSORPTION AND SYSTEMIC BIOAVAILABILITY OF DRUGS

(75) Inventors: Laxminarayan Bhat, Santa Clara, CA (US); Mark A. Gallop, Los Altos, CA (US); Bernd Jandeleit, Menlo Park, CA (US)

(73) Assignee: XenoPort, Inc., Santa Clara, CA (US)

( * ) Notice: Subject to any disclaimer, the term of this patent is extended or adjusted under 35 U.S.C. 154(b) by 535 days.

(21) Appl. No.: 10/229,565

(22) Filed: Aug. 28, 2002

(65) Prior Publication Data
US 2003/0130246 A1    Jul. 10, 2003

Related U.S. Application Data

(60) Provisional application No. 60/316,182, filed on Aug. 29, 2001.

(51) Int. Cl.
A61K 31/58     (2006.01)
C07J 7/00      (2006.01)

(52) U.S. Cl. .................... 514/176; 514/172; 540/48; 540/49; 540/52

(58) Field of Classification Search .............. 540/48, 540/49, 52; 514/172, 176
See application file for complete search history.

(56) References Cited

U.S. PATENT DOCUMENTS

| | | | |
|---|---|---|---|
| 4,848,349 A | 7/1989 | Sherman et al. | |
| 4,866,044 A | 9/1989 | Sato et al. | |
| 5,462,933 A | 10/1995 | Kramer et al. | |
| 5,646,272 A | 7/1997 | Kramer et al. | |
| 5,668,126 A | 9/1997 | Kramer et al. | |

FOREIGN PATENT DOCUMENTS

| | | |
|---|---|---|
| EP | 0 285 285 | 10/1988 |
| EP | 0 624 593 | 11/1994 |
| EP | 0 676 410 | 10/1995 |
| EP | 0 702 026 | 6/1997 |
| JP | 10-286453 | 10/1998 |
| JP | 11-60594 | 3/1999 |
| WO | WO 90/13298 | 11/1990 |
| WO | WO 94/00126 | 1/1994 |
| WO | WO 95/03056 | 2/1995 |
| WO | WO 97/18816 | 5/1997 |
| WO | WO 97/44043 | 11/1997 |
| WO | WO 98/01159 | 1/1998 |
| WO | WO 99/15179 | 4/1999 |
| WO | WO 99/52932 | 10/1999 |
| WO | WO 00/20437 | 4/2000 |
| WO | WO 00/34461 | 6/2000 |
| WO | WO 00/38738 | 7/2000 |
| WO | WO 00/40965 | 7/2000 |
| WO | WO 00/57915 | 10/2000 |
| WO | WO 00/66611 | 11/2000 |

OTHER PUBLICATIONS

Baringhaus, et al., "Substrate Specificity of the Ileal and the Hepatic Na+/bile acid Cotransporters of the Rabbit. II.A Relaible 3D QSAR Pharmacophore Model for the Ileal Na+/bile acid Cotransporter", *J. of Lipid Res.*, vol. 40, pp. 2158-2168 (1999).

Begum, et al., "Synthesis of 2β-Hydroxyursolic Acid and Other Ursane Analogues from Ursonic Acid", *Aust. J. Chem*, vol. 46, pp. 1067-1071 (1993).

Bellini, et al., "Studi su 5beta-chetosteroidi—Nota VII. Derivati pirimidinici e pteridinici dell'acido 3,7,12-trichetocolanico", *Il Farmaco—Ed. Sc.*, vol. 25, fax. 3, pp. 226-233.

Bellini, et al., "Studi su 5β-cheto-steroidi.—Nota IV. Derivati eterociclici sugi anelli A e B dell'acido 3,7,12-tricheto-colanico", *Gazzetta Chimica Italiana*, vol. 99, fasc. XII, pp. 1243-1251 (1969).

Brouwer, et al., "An Efficient Synthesis of N-Protected β-Aminoethansulfonyl Chlorides", *Synthesis*, No. 11, pp. 1579-1584 (2000).

Clinton, et al., "Steroidal[3,2-c]pyrazoles. II. Androstanes, 19-Norandrostanes and their Unsaturated Analogs", *J. of American Chem. Soc.*, vol. 83, pp. 1478-1491 (1961).

Ho, et al., "Utilizing Bile Acid Carrier Mechanisms to Enahnce Liver and Small Intestine Absorption", *Ann. New York Acad. Sci.*, pp. 315-329 (1987).

Junjappa, H., et al., "α-Oxoketene-S,S-, N,S- And N,N-Acetals: Versatile Intermediates in Organic Synthesis", *Tetrahedron Report*, No. 278, pp. 5423-5506 (1990).

Kim, et al., "Evaluation of Bile Acid Transporter in Enhancing Intestinal Permeaility of Renin-Inhibitory Peptides", *J. Drug TargetingI*, vol. 1, pp. 347-359 (1993).

Kramer, et al., "Substrate Specificity of the Ileal and the Hepatic Na+/Bile Acid Cotransporters of the Rabbit. I. Transport Studies with Membrane Vesicles and Cell Lines Expressing the Cloned Transporters", *J. of Lipid Res.*, vol. 40, pp. 1604-1617 (1999).

Kramer, et al., "Liver-Specific Drug Targeting by Coupling to Bile Acids", *J. Biol. chem.*, vol. 267, pp. 18598-18604 (1992).

(Continued)

*Primary Examiner*—Barbara P. Badio
(74) *Attorney, Agent, or Firm*—Buchanan Ingersoll PC

(57) ABSTRACT

Disclosed are compounds that exhibit high transport across the intestinal wall of an animal. The compounds may optionally be linked to drugs that are poorly absorbed or poorly transported across the intestinal wall after oral administration to provide for enhanced therapeutic, and optionally prolonged therapeutic, systemic blood concentrations of the drugs upon oral administration of the drug-compound conjugate. Also disclosed are pharmaceutical compositions containing and methods of using such compounds.

21 Claims, 39 Drawing Sheets

OTHER PUBLICATIONS

Kramer, et al., "Intestinal Absorption of Peptides by Coupling to Bile Acids", *J. of Biol. Chem.*, vol. 269, No. 14, pp. 10621-10627 (1994).

Kramer, et al., "Bile Acid Derived HMG-CoA Reductase Inhibitors", *Biochim. Biophys. Acta*, vol. 1227, pp. 137-154 (1994).

Kullak-Ublick, et al., "Hepatobiliary Transport", *J. Hepatology*, vol. 32, pp. 3-18 (2000).

Navia, et al., "Design Principles for Orally Bioavailable Drugs", *Drug Discovery Today*, vol. 1, pp. 179-189 (1996).

Paquette, L.A., et al., "2-Chloro-1-Formyl-1-Cyclohexene", *Organic Syntheses*, vol. 5, pp. 215-232.

Petzinger, E., et al., "Hepatobiliary Transport of Hepatic 3-hydroxy-3-Methylglutaryl Coenzyme A Reductase Inhibitors Conjugated with Bile Acids", *Hepatology*, vol. 22, pp. 1801-1811 (1995).

Rocchi, R., et al., "Studi Su 5β-Cheto-Steroidi, Nota VI—Derivati Pirimidinici e pteridinici degli acidi 3,12-dicheto—e 7,12-dichetocolanici", *Il Farmaco. Ed. Sc.*, vol. 25, Fasc. 2, pp. 125-132 (1970).

Spivey, et al., "A New Germanium-Based Linker for Solid Phase Synthesis of Aromatics: Synthesis of a Pyrazole Library", *J. Org. Chem.*, vol. 65, pp. 5253-5263 (2000).

Swaan, P.W., et al., "Use of the Intestinal and Hepatic bile Acid Transporters for Drug Delivery", *Adv. Drug Delivery Rev.*, vol. 20, pp. 59-82 (1996).

Tserng, "A Convenient Synthesis of 3-Keto Bile Acids by Selective Oxidation of Bile Acids with Silver Carbonate-Celite", *J. of Lipid Res.*, vol. 19, pp. 501-504 (1978).

Tsuji, et al. "Carrier-Mediated Intestinal Transport of Drugs", *Pharmaceutical Res.*, vol. 13, No. 7, pp. 963-977 (1996).

Venepalli, B., et al., "Synthesis and Substance P Receptor Binding Activity of Androstano[3,2-b]pyrimido[1,2-a]benzimidazoles", *J. Med. Chem*, vol. 35, pp. 374-378 (1992).

Preparation of steroidal building blocks

Scheme 1. Preparation of 3-oxo steroidal building blocks 1

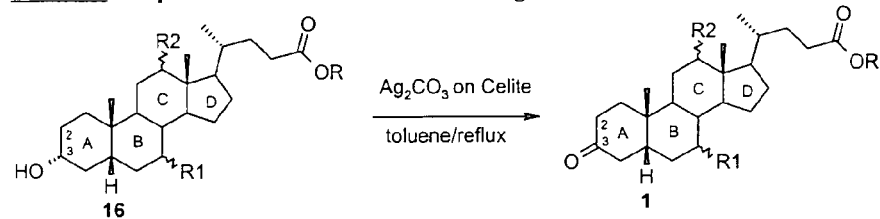

1, 16 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, $^tBu$, $CH_2Ph$ Scheme 2. Preparation of 2,3-dioxo steroidal building blocks 2

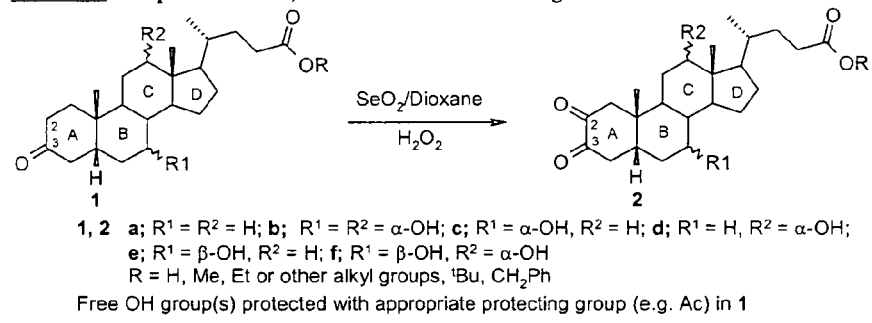

1, 2 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, $^tBu$, $CH_2Ph$
Free OH group(s) protected with appropriate protecting group (e.g. Ac) in 1

Scheme 3. Preparation of 3-chloro-2-formyl steroidal building blocks 3

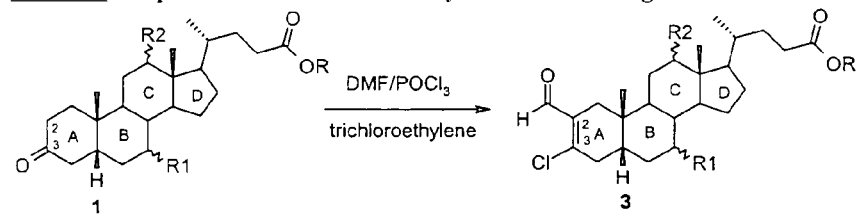

1, 3 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, $^tBu$, $CH_2Ph$
Free OH group(s) protected with appropriate protecting group (e.g. Ac) in 1

FIG. 1A

Scheme 4. Preparation of 2-hydroxymethylene-3-oxo steroidal building blocks 4

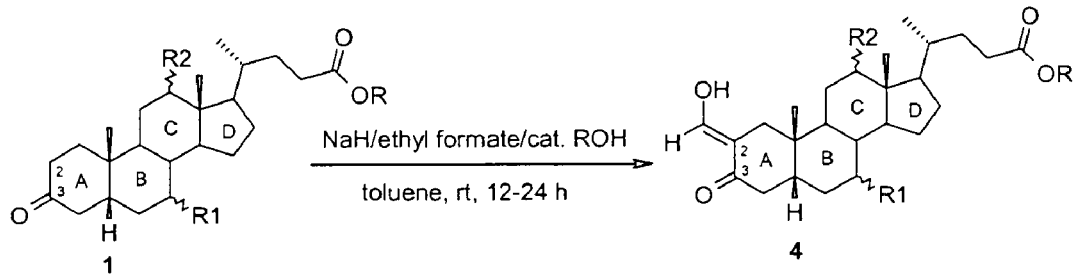

1, 4  a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
      e; $R^1 = \beta\text{-OH}, R^2 = H$; f; $R^1 = \beta\text{-OH}, R^2 = \alpha\text{-OH}$
      R = H, Me, Et or other alkyl groups, $^t$Bu, $CH_2Ph$ Scheme 5. Preparation of 2-dimethylaminomethylene-3-oxo steroidal building blocks 5

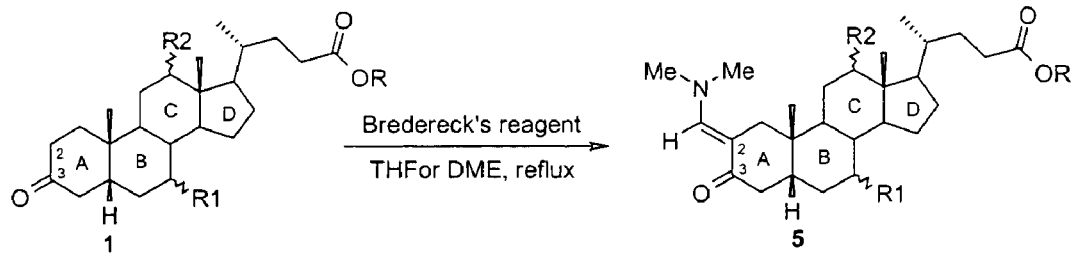

1, 5  a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
      e; $R^1 = \beta\text{-OH}, R^2 = H$; f; $R^1 = \beta\text{-OH}, R^2 = \alpha\text{-OH}$
      R = H, Me, Et or other alkyl groups, $^t$Bu, $CH_2Ph$
Free OH group(s) protected with appropriate protecting group (e.g. Ac, TMS, TBDMS) in 1

Scheme 6. Preparation of oxoketene S,S-acetal derivatives of bile acids 6

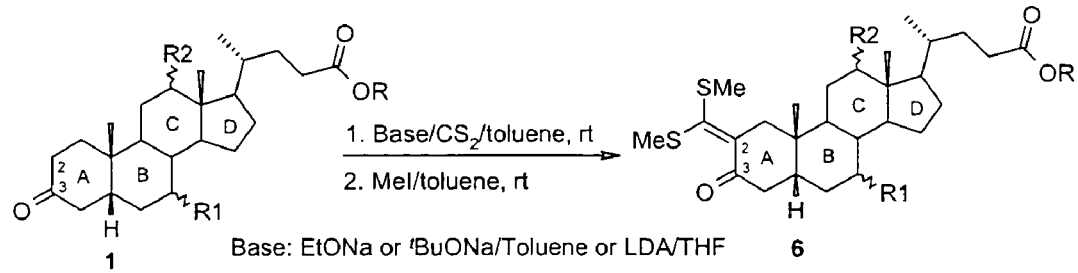

1, 6  a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
      e; $R^1 = \beta\text{-OH}, R^2 = H$; f; $R^1 = \beta\text{-OH}, R^2 = \alpha\text{-OH}$
      R = H, Me, Et or other alkyl groups, $^t$Bu, $CH_2Ph$
Free OH group(s) protected with appropriate protecting group (e.g. TES, TBDMS) in 1

FIG. 1B

Scheme 7. Preparation of oxoketene N,S-acetal derivatives of bile acids 7

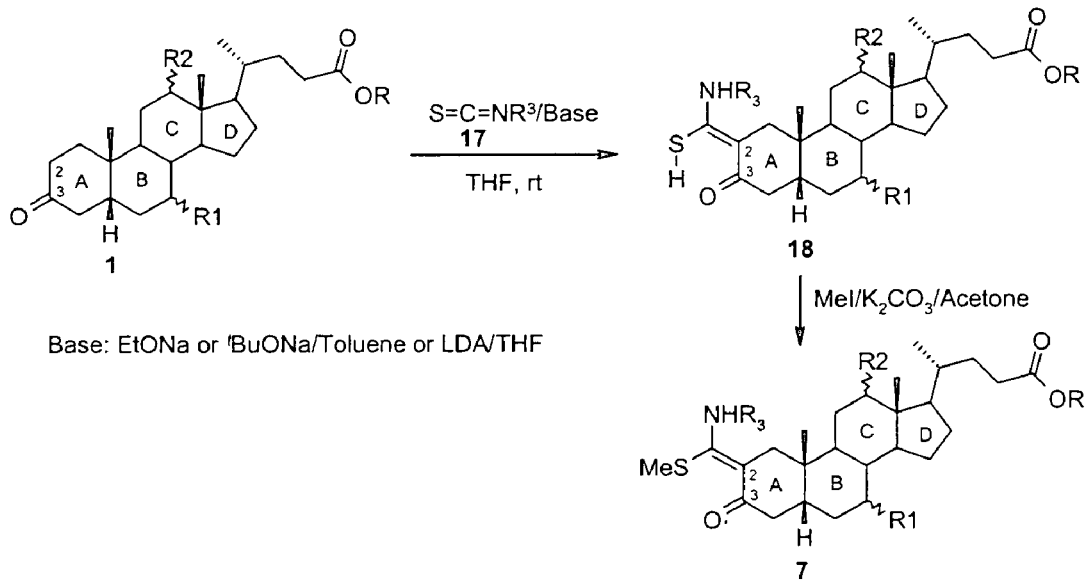

Base: EtONa or ᵗBuONa/Toluene or LDA/THF

1, 7, 18a a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, ᵗBu, $CH_2Ph$

7, 17-18, $R^3$ = alkyl, aryl, alkaryl substituents with or without functional groups
Free OH group(s) is protected with appropriate protecting group (e.g. TES, TBDMS) in 1

Scheme 8. Preparation of oxoketene N,S-acetal derivatives of bile acids 8

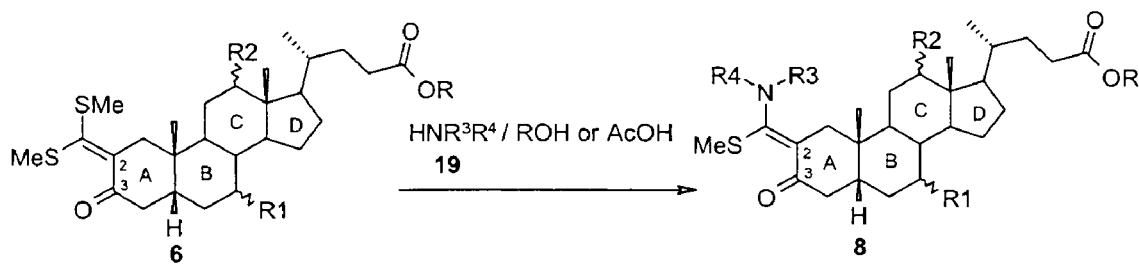

6, 8 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, ᵗBu, $CH_2Ph$

8, 19, $R^3$, $R^4$ = H, alkyl, aryl, alkaryl substituents with or without functional groups

FIG. 1C

Scheme 9: Preparation of 3-oxo-2-(β-oxomethyl)substituted bile acid building blocks 9 (1,4-dicarbonyl steroidal building blocks)

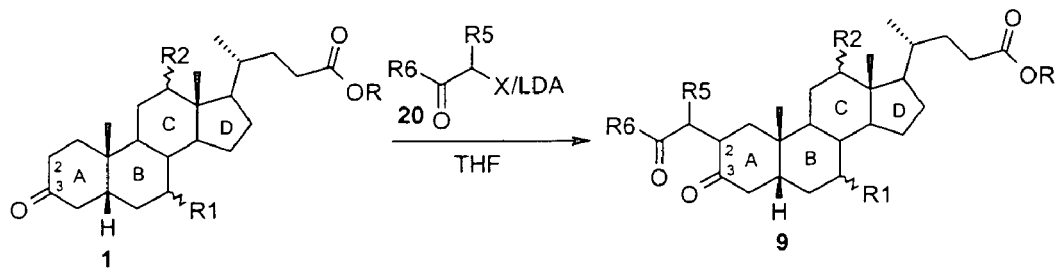

1, 9 a; $R^1 = R^2 = H$; b; $R^1 = R^2 = \alpha$-OH; c; $R^1 = \alpha$-OH, $R^2 = H$; d; $R^1 = H$, $R^2 = \alpha$-OH;
e; $R^1 = \beta$-OH, $R^2 = H$; f; $R^1 = \beta$-OH, $R^2 = \alpha$-OH
R = H, Me, Et or other alkyl groups, $^t$Bu, CH$_2$Ph 9, 20 $R^5$ = H, alkyl, aryl and alkaryl substituents with or without functional groups
$R^6$ = H, alkyl, aryl and alkaryl substituents with or without functional groups;
Alkoxide, aryloxide and alkaryloxide substituents with or without functional groups;
Thioalkoxide, thioaryloxide and thioalkaryloxide substituents with or without functional groups; 1° and 2° amines
20, X = Cl, Br, I, OTs, OMs, OTf
Free OH group(s) protected with appropriate protecting group (e.g. TES, TBDMS) in 1

Scheme 10: Preparation of 2-propargyl derivatives of bile acids 10

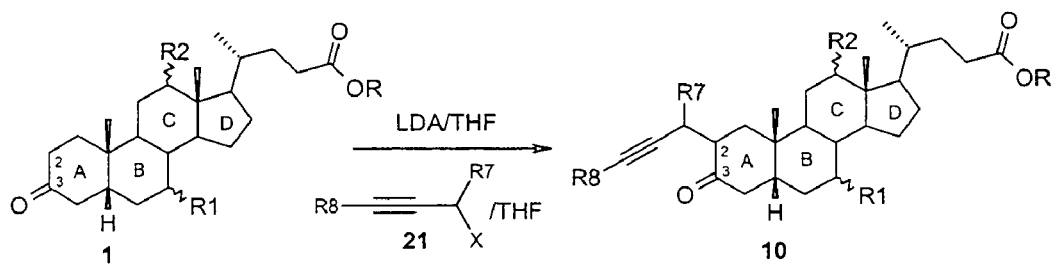

1, 10 a; $R^1 = R^2 = H$; b; $R^1 = R^2 = \alpha$-OH; c; $R^1 = \alpha$-OH, $R^2 = H$; d; $R^1 = H$, $R^2 = \alpha$-OH;
e; $R^1 = \beta$-OH, $R^2 = H$; f; $R^1 = \beta$-OH, $R^2 = \alpha$-OH
R = H, Me, Et or other alkyl groups, $^t$Bu, CH$_2$Ph 10, 21, $R^7$ = H, alkyl, aryl or alkaryl substituents with or without functional groups
$R^8$ = ether, amine, ester, amide functional groups; H, alkyl, aryl or alkaryl substituents with or without functional groups
21, X = Cl, Br, I, OTs, OMs, OTf
Free OH group(s) protected with appropriate protecting group (e.g. TES, TBDMS) in 1

FIG. 1D

Scheme 11: Preparation of vinyl ether or ester derivatives of bile acids 11

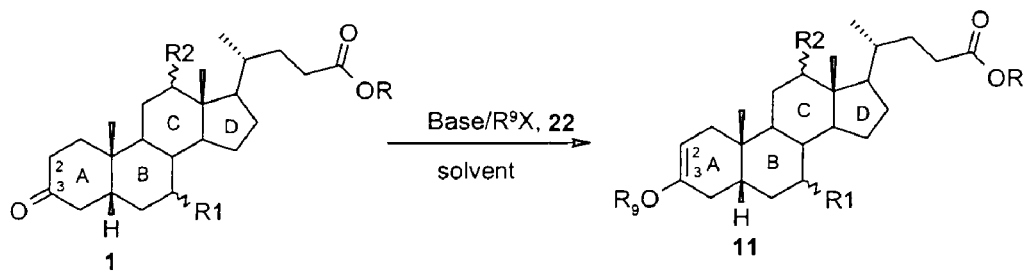

1, 11 a; $R^1 = R^2 = H$; b; $R^1 = R^2 = \alpha\text{-OH}$; c; $R^1 = \alpha\text{-OH}$, $R^2 = H$; d; $R^1 = H$, $R^2 = \alpha\text{-OH}$;
e; $R^1 = \beta\text{-OH}$, $R^2 = H$; f; $R^1 = \beta\text{-OH}$, $R^2 = \alpha\text{-OH}$
R = H, Me, Et or other alkyl groups, $^t$Bu, $CH_2Ph$
11, 22, $R^9$ = TMS, TES, TBDMS, alkyl, aryl, acetyl, tosyl, mesyl, triflyl groups
22, X = Cl, Br, I, OTs, OMs, OTf
Free OH group(s) protected with appropriate protecting group (e.g. Ac, TES, TBDMS) in 1
For $R^9$ = Ac: Reaction conditions-Isopropenyl acetate/cat. pTSA/toluene, reflux Scheme 12: Preparation of 2-methylene-3-oxo derivatives (enones) of bile acids 12

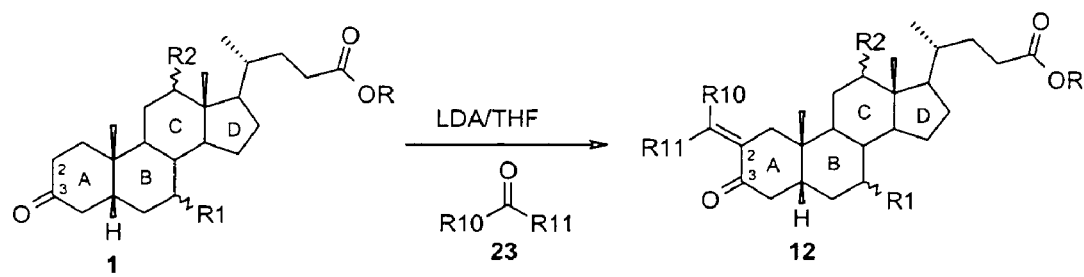

1, 12 a; $R^1 = R^2 = H$; b; $R^1 = R^2 = \alpha\text{-OH}$; c; $R^1 = \alpha\text{-OH}$, $R^2 = H$; d; $R^1 = H$, $R^2 = \alpha\text{-OH}$;
e; $R^1 = \beta\text{-OH}$, $R^2 = H$; f; $R^1 = \beta\text{-OH}$, $R^2 = \alpha\text{-OH}$
R = H, Me, Et or other alkyl groups, $^t$Bu, $CH_2Ph$
12, 23, $R^{10}$, $R^{11}$ = H, alkyl, aryl, alkaryl substituents with or without functional groups
Free OH group(s) protected with appropriate protecting group (e.g. TMS, TES, TBDMS) in 1

FIG. 1E

Preparation of Amino Acid Building Blocks

α-Amino acid derivatives 13 and taurine 14 are commercially available. The 2-aminoethylthioesters 15 are not commercially available and they can be easily prepared from the corresponding amino acids by the reported protocol in overall good yields.

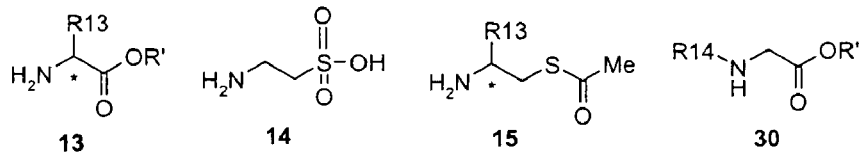

R' = H, Me, Et or other alkyl groups, $^t$Bu, CH$_2$Ph
R$^{13}$ = H, alkyl, aryl, alkaryl substituents with or without functional groups
R$^{14}$ = alkyl, aryl, alkaryl substituents with or without functional groups

Scheme 13. Preparation of 2-aminoethylthioacetate 15

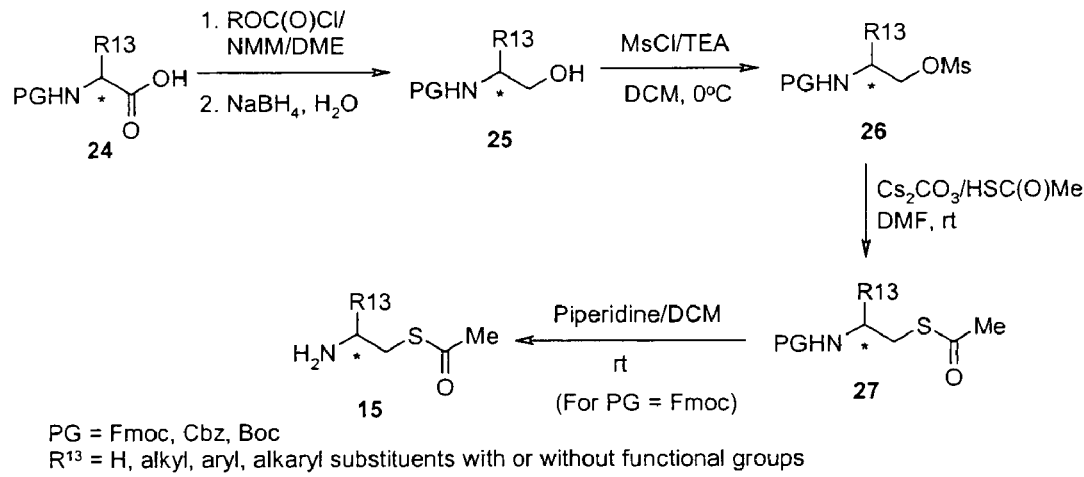

PG = Fmoc, Cbz, Boc
R$^{13}$ = H, alkyl, aryl, alkaryl substituents with or without functional groups

**Scheme 14. Preparation of *N*-substituted α-amino acid esters 30**

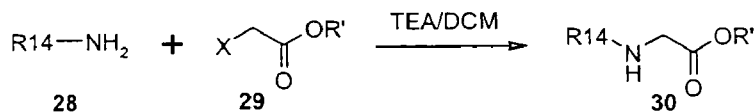

R' = Me, Et or other alkyl groups, $^t$Bu, CH$_2$Ph
R$^{14}$ = alkyl, aryl, alkaryl substituents with or without functional groups
X = Cl, Br, I, OTs, OMs, OTf

FIG. 2

Synthetic strategy for 5-membered 2,3-fused heterocycles

General structure:

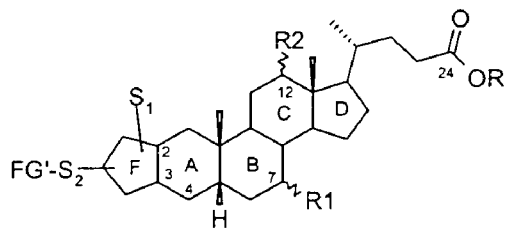

Template IVA a, $R^1 = R^2 = H$; b, $R^1 = R^2 = \alpha\text{-OH}$; c, $R^1 = \alpha\text{-OH}$, $R^2 = H$; d, $R^1 = H$, $R^2 = \alpha\text{-OH}$; e, $R^1 = \beta\text{-OH}$, $R^2 = H$; f, $R^1 = \beta\text{-OH}$, $R^2 = \alpha\text{-OH}$ R = H, Me, Et or other alkyl groups, $^t$Bu, $CH_2Ph$, $CPh_3$
F = Fused aromatic and non-aromatic carbocycles and heterocycles with one or more hetero atoms
$S^1$, $S^2$ = H, alkyl, aryl and alkaryl substituents with or without functional groups
FG = Functional Groups [e.g. OH, SH, $NH_2$, NHR, $CO_2H$, $CO_2R$, $CONH_2$, CONHR, C(=S)OR, C(=O)SR]

---

5-Membered core structures:

1. Furans
2. Pyrroles
3. Indoles
4. Dihydropyrroles
5. Pyrazoles
6. Dihydropyrazoles
7. Isoxazoles
8. Triazoles

FIG. 3A

Scheme 15: Synthetic strategy for 2,3-fused furan derivatives of bile acids 31

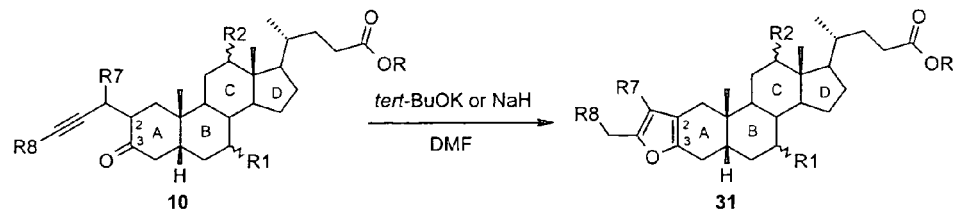

10, 31 a; $R^1 = R^2 = H$; b; $R^1 = R^2 = \alpha\text{-OH}$; c; $R^1 = \alpha\text{-OH}$, $R^2 = H$; d; $R^1 = H$, $R^2 = \alpha\text{-OH}$;
e; $R^1 = \beta\text{-OH}$, $R^2 = H$; f; $R^1 = \beta\text{-OH}$, $R^2 = \alpha\text{-OH}$
R = H, Me, Et or other alkyl groups, $^ت$Bu, $CH_2Ph$
10, $R^7$ = H, alkyl, aryl or alkaryl substituents with or without functional groups
$R^8$ = ether, amine, ester, amide functional groups; H, alkyl, aryl or alkaryl
substituents with or without functional groups
Free OH group(s) protected with appropriate protecting group (e.g. TES, TBDMS) in 10

Scheme 16: Synthetic strategy for 2,3-fused pyrrole derivatives of bile acids 33

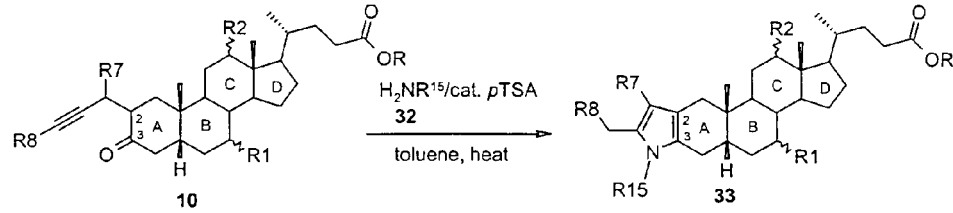

10, 33 a; $R^1 = R^2 = H$; b; $R^1 = R^2 = \alpha\text{-OH}$; c; $R^1 = \alpha\text{-OH}$, $R^2 = H$; d; $R^1 = H$, $R^2 = \alpha\text{-OH}$;
e; $R^1 = \beta\text{-OH}$, $R^2 = H$; f; $R^1 = \beta\text{-OH}$, $R^2 = \alpha\text{-OH}$
R = H, $^t$Bu, $CPh_3$
10, 32, 33 $R^7$ = H, alkyl, aryl or alkaryl substituents with or without functional groups
$R^8$ = ether, amine, ester, amide functional groups; H, alkyl, aryl or alkaryl
substituents with or without functional groups
$R^{15}$ = H, alkyl or aryl substituents with or without functional groups
Free OH group(s) protected with appropriate protecting group (e.g. TES, TBDMS) in 10

FIG. 3B

Scheme 17: Synthetic strategy for 2,3-fused pyrrole derivatives of bile acids 34

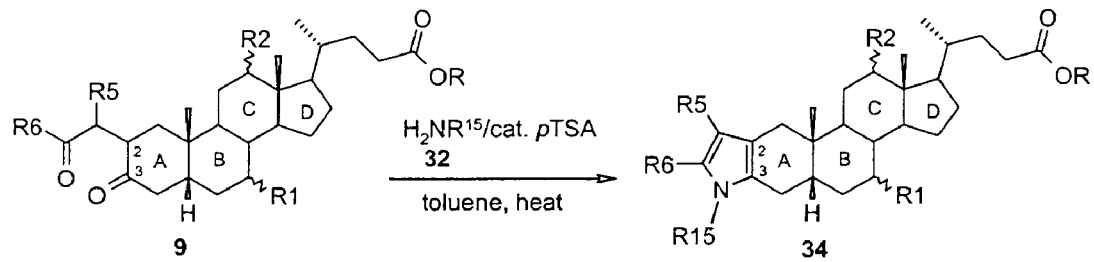

9, 34 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
$R = H$, $^tBu$, $CPh_3$ 32, 34  $R^5 = H$, alkyl, aryl and alkaryl substituents with or without functional groups
$R^{15} = H$, alkyl, aryl, alkaryl substituents with or without functional groups 9  $R^6 = H$, alkyl, aryl and alkaryl substituents with or without functional groups;
Alkoxide, aryloxide and alkaryloxide substituents with or without functional groups;
Thioalkoxide, thioaryloxide and thioalkaryloxide substituents with or without functional groups; 1° and 2° amines 34 $R^6 = OH$; H, alkyl, aryl, alkaryl substituents with or without functional groups Free OH group(s) may be protected with appropriate protecting group (e.g. TES, TBDMS) in 9

Scheme 18: Synthetic strategy for 2,3-fused pyrrole derivatives of bile acids 35.

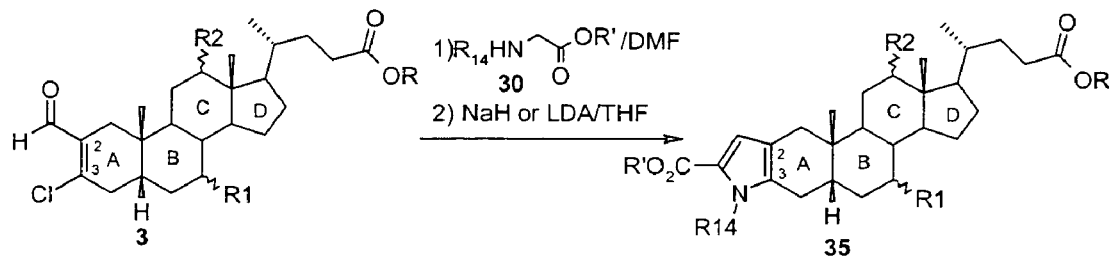

3, 35 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R, R' = H, Me, Et or other alkyl groups, $^tBu$, $CH_2Ph$ 30, 35 $R^{14} = H$, alkyl, aryl, alkaryl substitutions with or without functional groups

FIG. 3C

Scheme 19: Synthetic strategy for 2,3-fused pyrrole derivatives of bile acids 36.

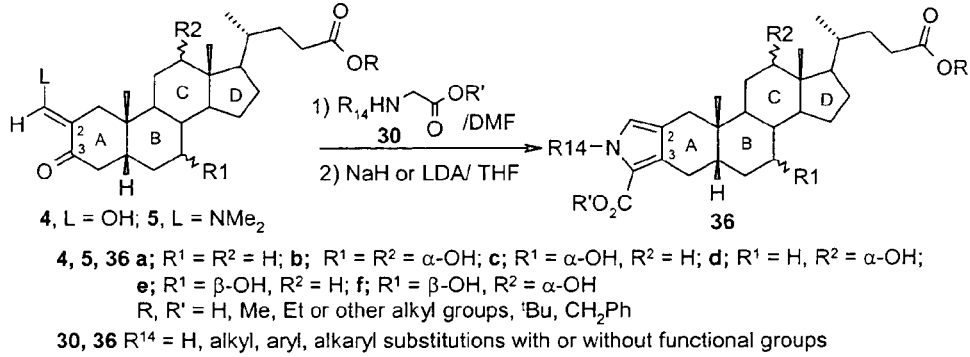

4, L = OH; 5, L = NMe$_2$ 4, 5, 36 a; R$^1$ = R$^2$ = H; b; R$^1$ = R$^2$ = α-OH; c; R$^1$ = α-OH, R$^2$ = H; d; R$^1$ = H, R$^2$ = α-OH;
e; R$^1$ = β-OH, R$^2$ = H; f; R$^1$ = β-OH, R$^2$ = α-OH
R, R' = H, Me, Et or other alkyl groups, $^t$Bu, CH$_2$Ph
30, 36 R$^{14}$ = H, alkyl, aryl, alkaryl substitutions with or without functional groups Scheme 20: Synthetic strategy for 2,3-fused pyrrole derivatives of bile acids 38.

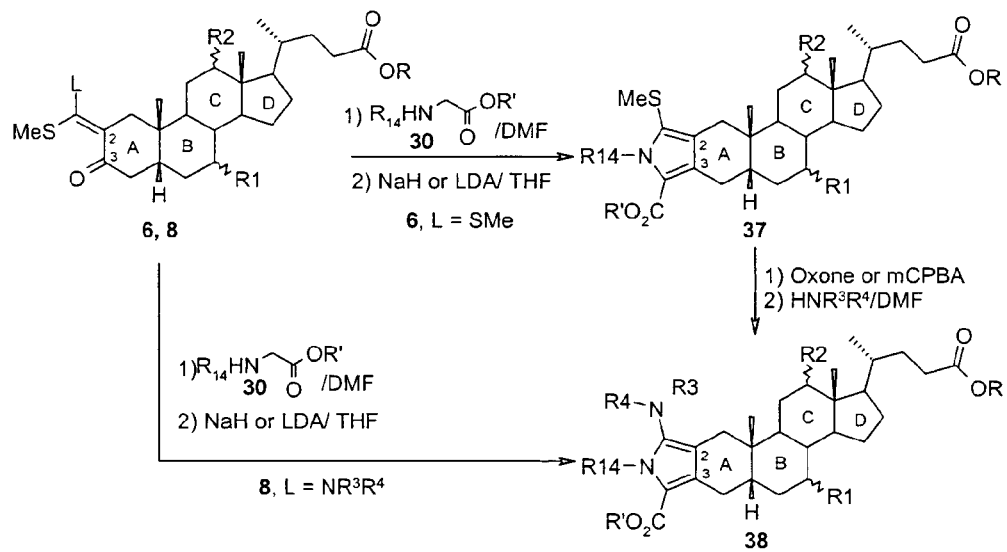

6, 8, 37, 38 a; R$^1$ = R$^2$ = H; b; R$^1$ = R$^2$ = α-OH; c; R$^1$ = α-OH, R$^2$ = H; d; R$^1$ = H, R$^2$ = α-OH;
e; R$^1$ = β-OH, R$^2$ = H; f; R$^1$ = β-OH, R$^2$ = α-OH
R, R' = H, Me, Et or other alkyl groups, $^t$Bu, CH$_2$Ph
30, 37, 38 R$^3$, R$^4$, R$^{14}$ = H, alkyl, aryl, alkaryl substitutions with or without functional groups

FIG. 3D

Scheme 21: Synthetic strategy for 2,3-fused pyrrole derivatives of bile acids 40.

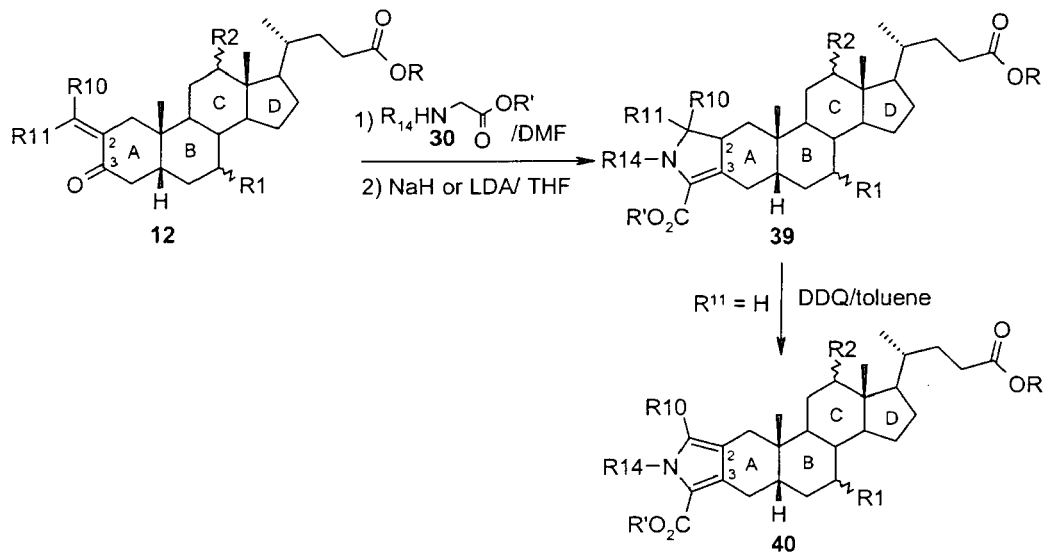

12, 39, 40  a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R, R' = H, Me, Et or other alkyl groups, $^t$Bu, $CH_2Ph$
12, 30, 39, 40  $R^{10}, R^{11}, R^{14}$ = H, alkyl, aryl, alkaryl substitutions with or without functional groups

FIG. 3E

Scheme 22: Synthetic strategy for 2,3-fused indole derivatives of bile acids 44.

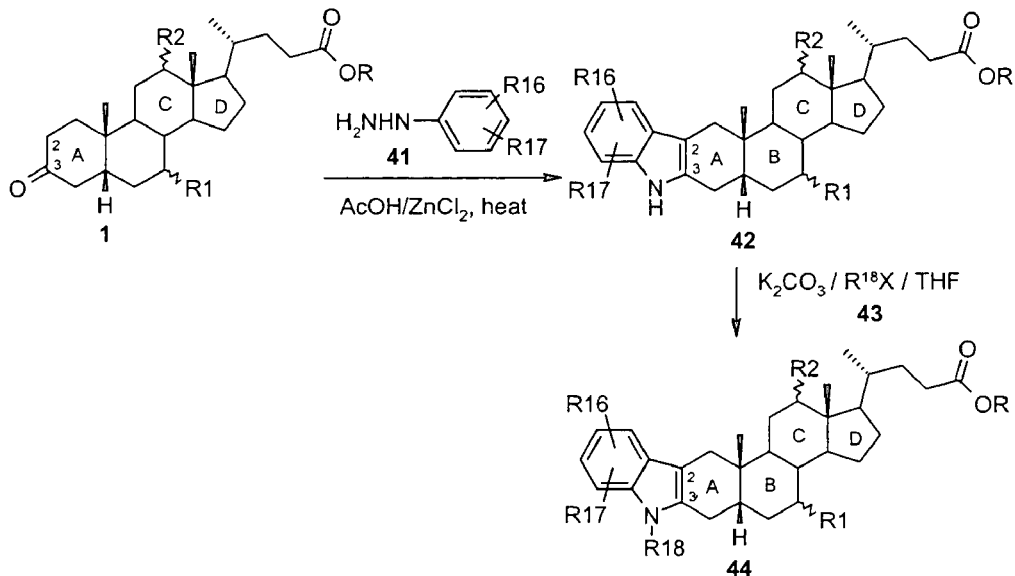

1, 42, 44 a; $R^1 = R^2 = H$; b; $R^1 = R^2 = \alpha\text{-OH}$; c; $R^1 = \alpha\text{-OH}$, $R^2 = H$; d; $R^1 = H$, $R^2 = \alpha\text{-OH}$;
  e; $R^1 = \beta\text{-OH}$, $R^2 = H$; f; $R^1 = \beta\text{-OH}$, $R^2 = \alpha\text{-OH}$
  R = H, $^t$Bu, CPh$_3$ 42, 44, $R^{16}$, $R^{17}$ = H, alkyl, aryl, alkaryl substituents with or without functional groups, OH, alkoxy, amino, acyl, CO$_2$R where R= H, alkyl, aryl, alkaryl substituents with or without functional groups 43, 44 $R^{18}$ = H, alkyl, aryl, alkaryl substituents with or without functional groups,
43 X = Cl, Br, I, OTs, OMs, OTf

FIG. 3F

Scheme 23: Synthetic strategy for 2,3-fused 2'(1')-substituted pyrazole derivatives of bile acids 46 and 47

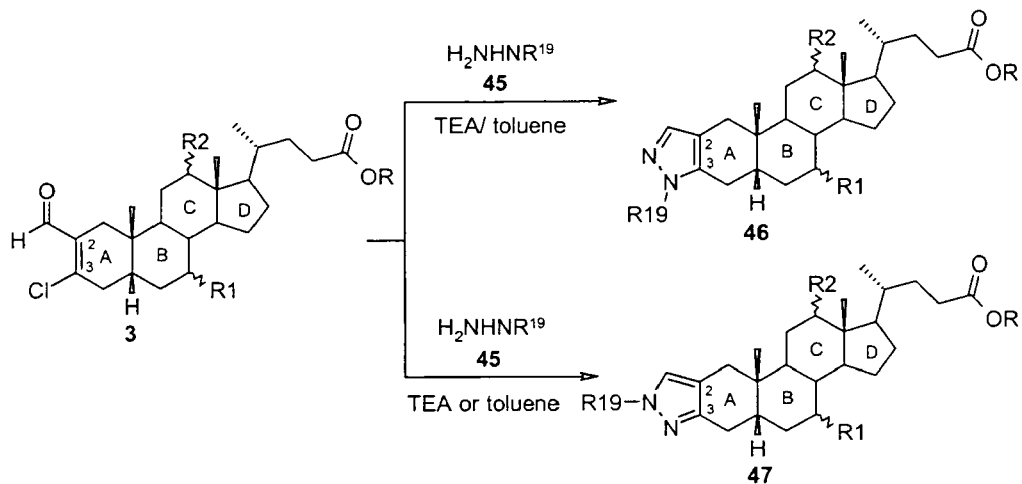

3, 46, 47 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
$R = H, {}^tBu, CPh_3$
46 $R^{19}$ = aryl or electron withdrawing substituents with or without functional groups
47 $R^{19}$ = H, alkyl substituents with or without functional groups

FIG. 3G

Scheme 24: Synthetic strategy for 2,3-fused 2'(1')-substituted pyrazole derivatives of bile acids 48 and 49.

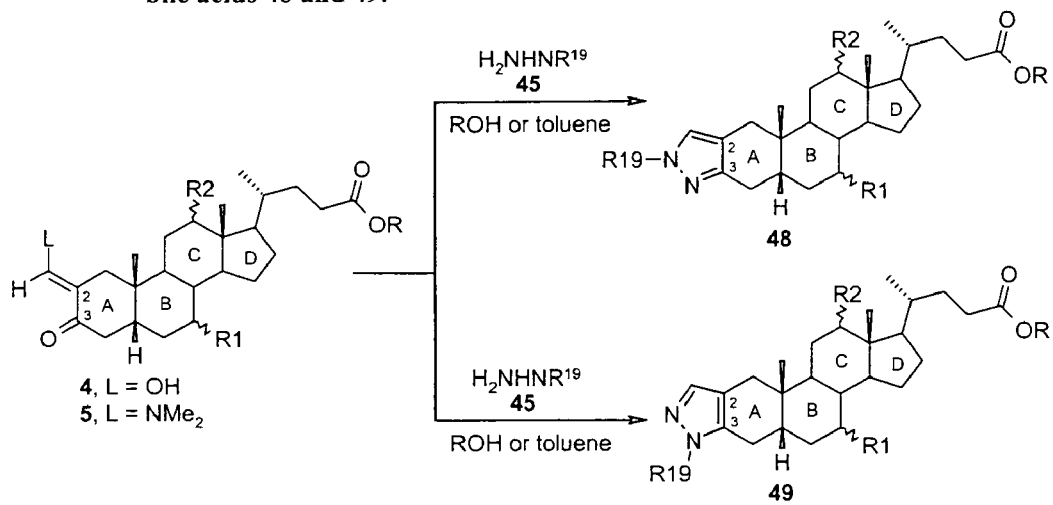

4, 5, 48, 49 a; $R^1 = R^2 = H$; b; $R^1 = R^2 = \alpha\text{-OH}$; c; $R^1 = \alpha\text{-OH}$, $R^2 = H$; d; $R^1 = H$, $R^2 = \alpha\text{-OH}$; e; $R^1 = \beta\text{-OH}$, $R^2 = H$; f; $R^1 = \beta\text{-OH}$, $R^2 = \alpha\text{-OH}$ R = H, Me, Et or other alkyl groups, $^t$Bu, $CH_2Ph$, $CPh_3$ 48 $R^{19}$ = H, alkyl substituents with or without functional groups
49 $R^{19}$ = aryl or electron withdrawing substituents with or without functional groups

FIG. 3H

Scheme 25: Synthetic strategy for 2,3-fused 3'-aminosubstituted pyrazole derivatives of bile acids 51.

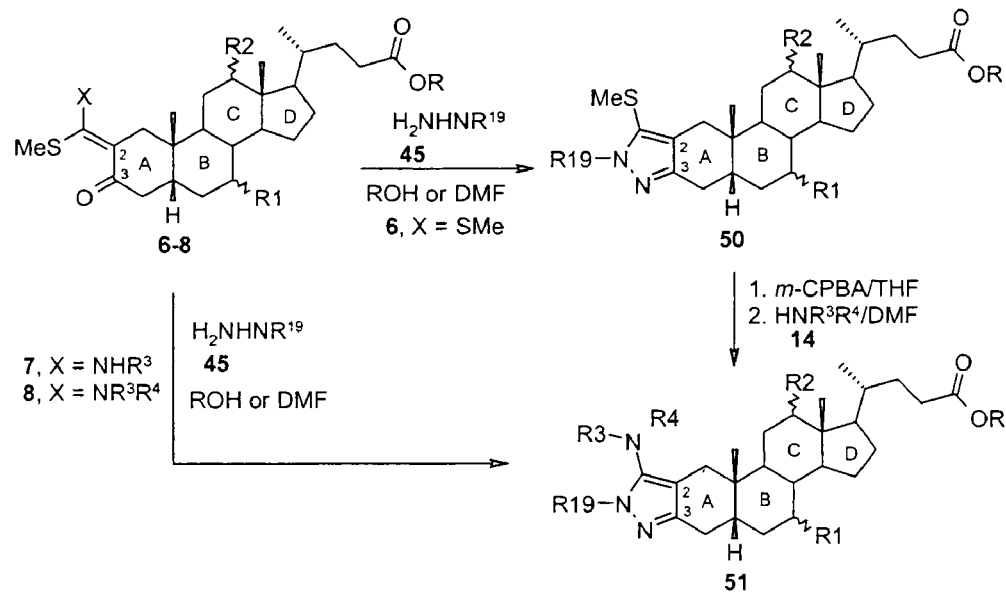

6-8, 50, 51 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, $^t$Bu, $CH_2Ph$, $CPh_3$
$R^3$, $R^4$ = H, alkyl, aryl, alkaryl substituents with or without functional groups
$R^{19}$ = H, alkyl substituents with or without functional groups

FIG. 31

Scheme 26: Synthetic strategy for 2,3-fused pyrazole derivatives of bile acids 53.

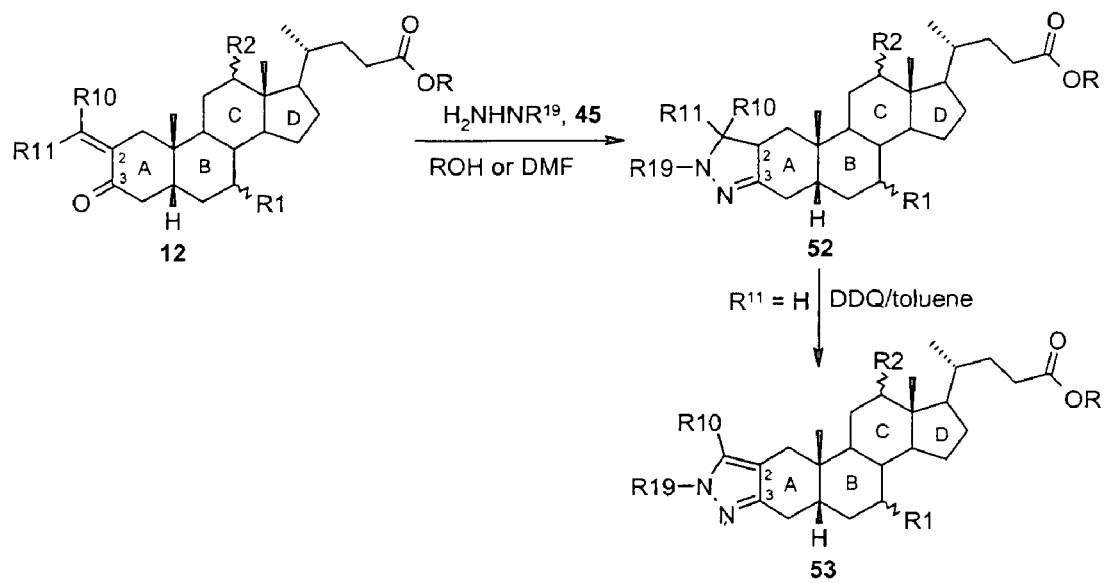

12, 52, 53 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, $^tBu$, $CH_2Ph$, $CPh_3$
$R^{10}$, $R^{11}$ = H, alkyl, aryl, alkaryl with or without functional groups
45, 52, 53 $R^{19}$ = H, alkyl, aryl, alkaryl with or without functional groups Scheme 27: Synthetic strategy for 2,3-fused isoxazole derivatives of bile acids 54.

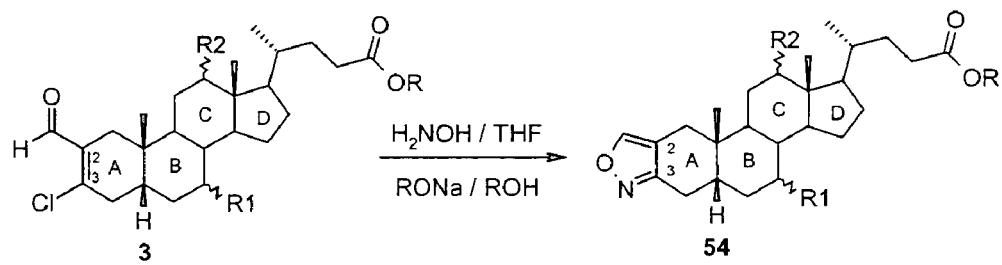

4, 54 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, $^tBu$, $CH_2Ph$, $CPh_3$

FIG. 3J

Scheme 28: Synthetic strategy for 2,3-fused isoxazole derivatives of bile acids 55.

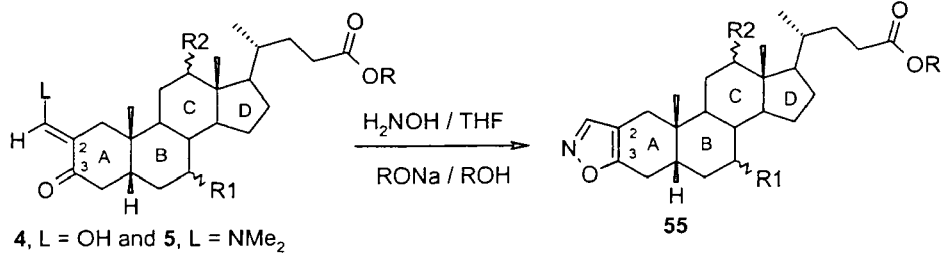

4, L = OH and 5, L = NMe₂

4, 5, 55 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, ᵗBu, CH₂Ph, CPh₃

Scheme 29: Synthetic strategy for 2,3-fused 3'-aminosubstituted isoxazole derivatives of bile acids 57.

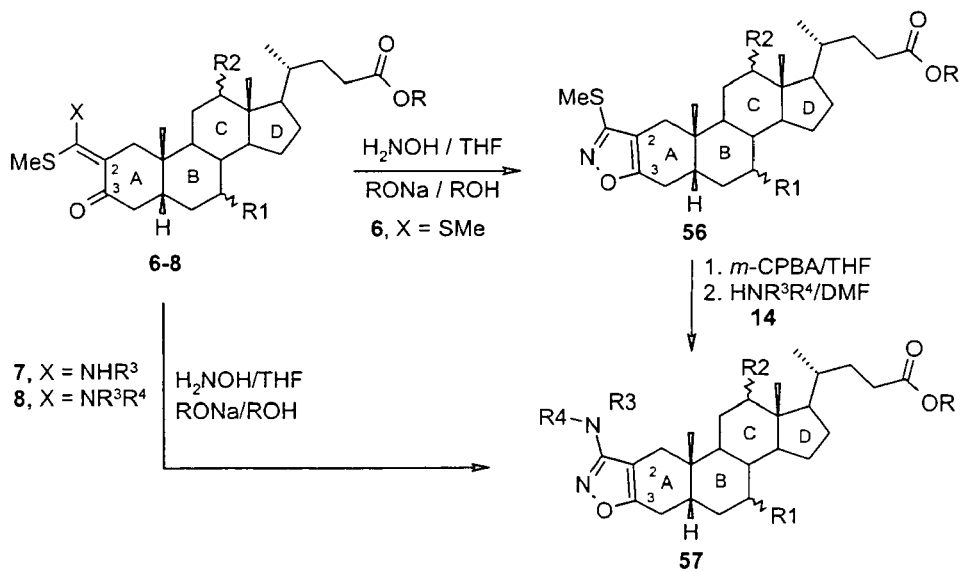

6-8, 56, 57 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, ᵗBu, CH₂Ph, CPh₃
$R^3, R^4$ = H, alkyl, aryl, alkaryl substituents with or without functional groups

FIG. 3K

Scheme 30: Synthetic strategy for 2,3-fused triazole derivatives of bile acids 58.

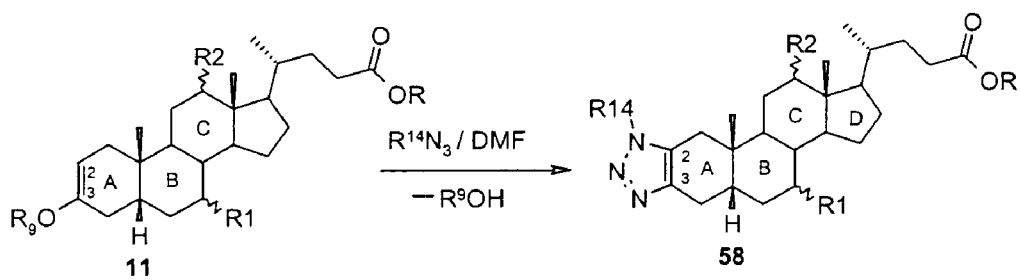

11, 58 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, $^t$Bu, $CH_2Ph$, $CPh_3$
$R^9$ = TMS, TES, TBDMS, alkyl, aryl, acetyl, tosyl, mesyl, triflyl groups
$R^{14}$ = alkyl, aryl, alkaryl substituents with or without functional groups

FIG. 3L

Synthetic strategy for 6-membered 2,3-fused heterocycles

General Structure:

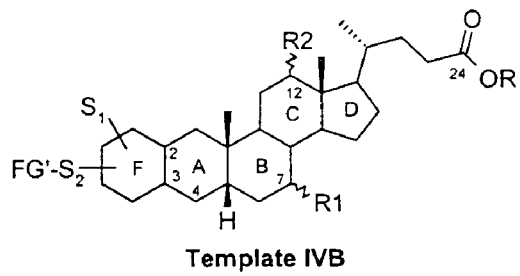

Template IVB a, $R^1 = R^2 = H$; b, $R^1 = R^2 = \alpha\text{-OH}$; c, $R^1 = \alpha\text{-OH}$, $R^2 = H$; d, $R^1 = H$, $R^2 = \alpha\text{-OH}$;
e, $R^1 = \beta\text{-OH}$, $R^2 = H$; f, $R^1 = \beta\text{-OH}$, $R^2 = \alpha\text{-OH}$
R = H, Me, Et or other alkyl groups, $^t$Bu, $CH_2Ph$, $CPh_3$
F = Fused aromatic and non-aromatic 6-membered carbocycles and heterocycles with one or more hetero atoms
$S^1$, $S^2$ = H, alkyl, aryl and alkaryl substituents with or without functional groups
FG = Functional Groups [e.g. OH, SH, $NH_2$, NHR, $CO_2H$, $CO_2R$, $CONH_2$, CONHR, C(=S)OR, C(=O)SR]

---

6-Membered core structures:

1. Six membered aromatic and non-aromatic rings
2. Pyran and dihydropyran
3. Pyridine
4. Pyrazine
5. Pyrimidine

FIG. 4A

Scheme 31: Synthetic strategy for 2,3-fused carbocyclic derivatives of bile acids 61

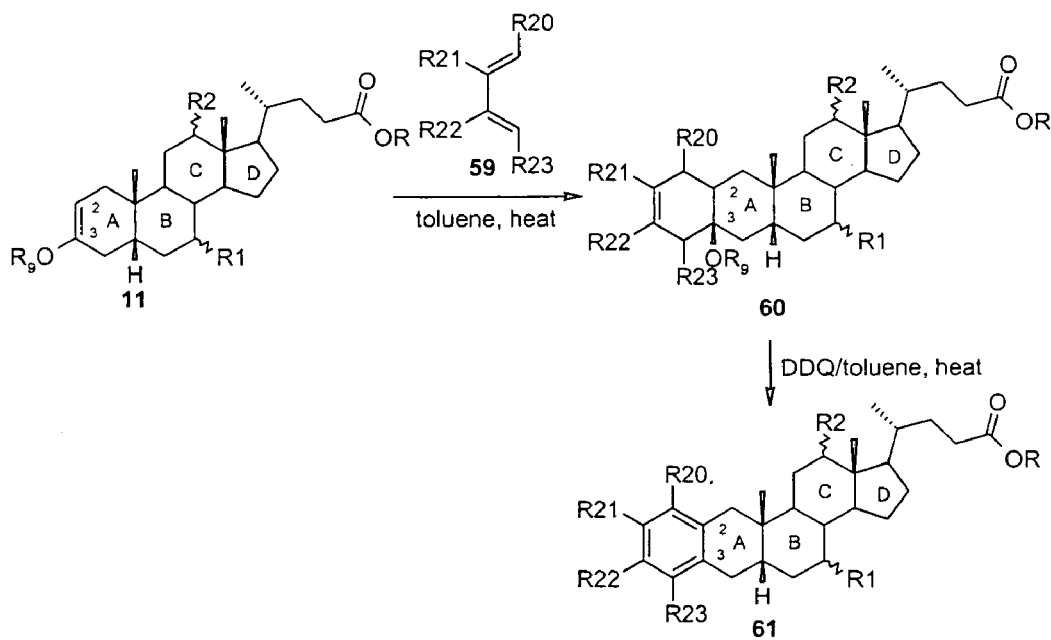

11, 60, 61 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, $^t$Bu, $CH_2Ph$
11, 60: $R^9$ = TMS, TES, TBDMS, alkyl, aryl, acetyl, tosyl, mesyl, triflyl groups
59-61: $R^{20}$-$R^{23}$ = H, alkyl, aryl and alkaryl substituents with or without functional groups
(functional groups e.g. OH, SH, OR, $NH_2$, $NR_2$, $CO_2H$, $CO_2R$, $CONH_2$, CONHR, etc)

FIG. 4B

Scheme 32: Synthetic strategy for 2,3-fused dihydropyran derivatives of bile acids 64

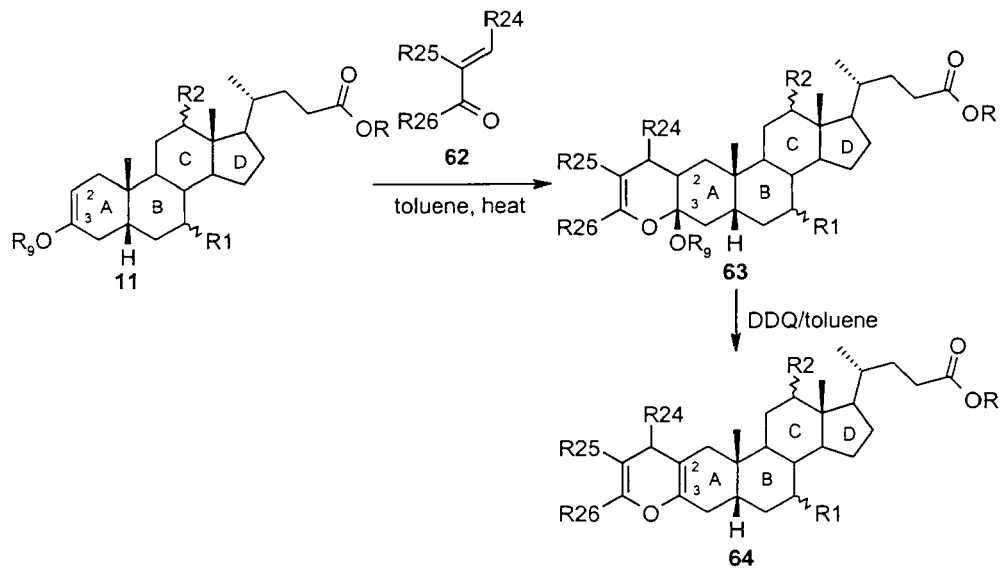

11, 63, 64 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, $^tBu$, $CH_2Ph$

11, 63: $R^9$ = TMS, TES, TBDMS, alkyl, aryl, acetyl, tosyl, mesyl, triflyl groups
62-64: $R^{24}\text{-}R^{26}$ = H, alkyl, aryl and alkaryl substituents with or without functional groups

FIG. 4C

Scheme 33: Synthetic strategy for 2,3-fused pyridine derivatives of bile acids 67

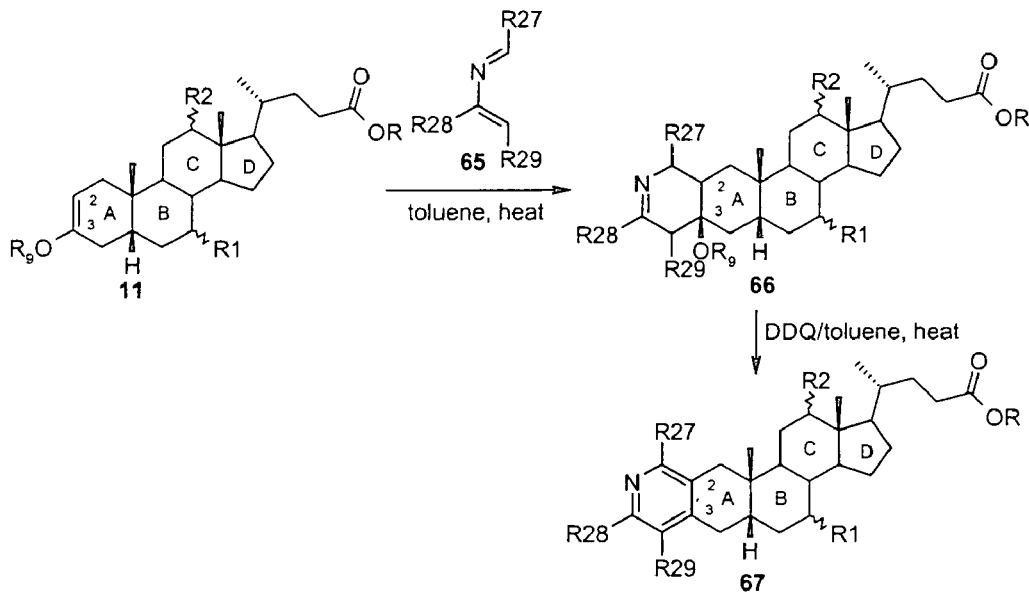

11, 66, 67 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, $^t$Bu, $CH_2Ph$ 11, 66: $R^9$ = TMS, TES, TBDMS, alkyl, aryl, acetyl, tosyl, mesyl, triflyl groups 65-67: $R^{27}$-$R^{29}$ = H, alkyl, aryl and alkaryl substituents with or without functional groups Scheme 34: Synthetic strategy for 2,3-fused pyrazine derivatives of bile acids 69

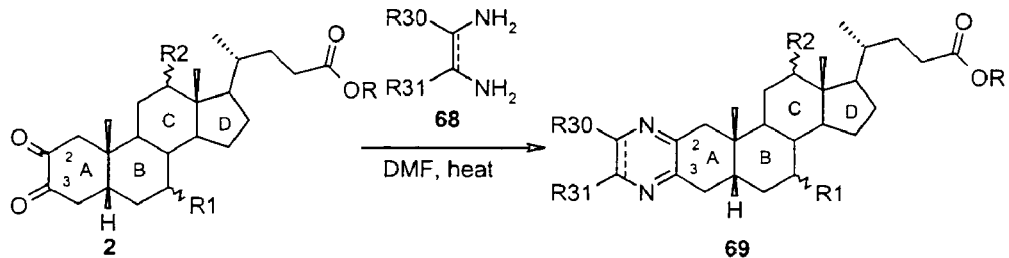

2, 69 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, $^t$Bu, $CPh_3$ 68, 69: $R^{30}$, $R^{31}$ = H, alkyl, aryl, alkaryl substituents with functional groups
(functional groups e.g. OH, OR, $CO_2R$ etc); Also $R^{30}$ and $R^{31}$
may be linked in a ring

FIG. 4D

Scheme 35: Synthetic strategy for 2,3-fused pyrimidine derivatives of bile acids 74-77

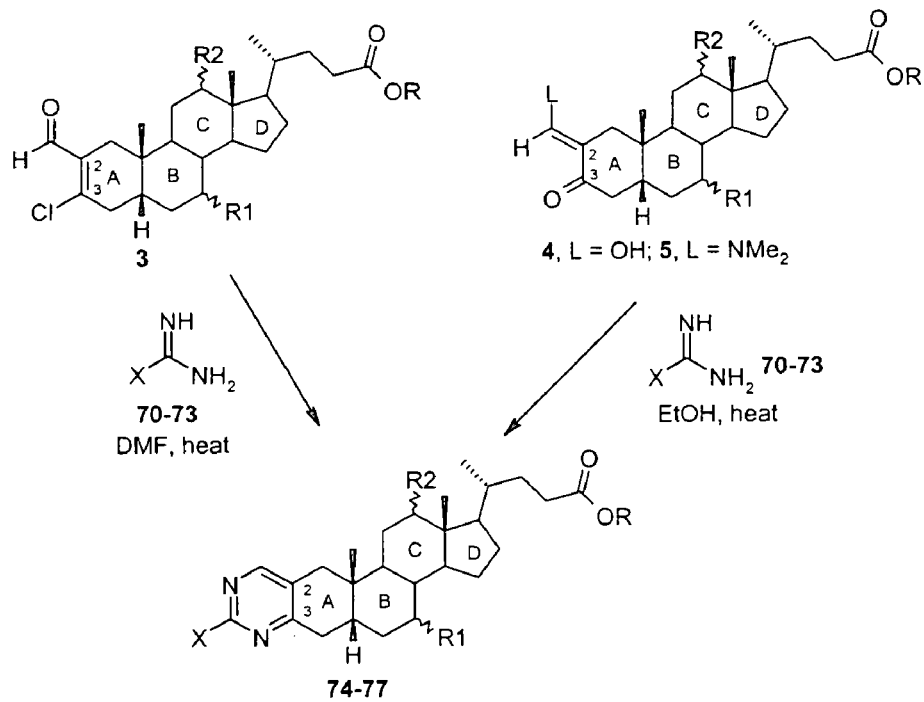

3-5, 74-77 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
R = H, Me, Et or other alkyl groups, $^t$Bu, $CH_2Ph$
70, 74: X = OH; 71, 75: X = SH; 72, 76: X = $NH_2$; 73, 77: X = $R^{32}$ = H, alkyl, aryl and alkaryl substituents with or without functional groups

| Pyrimidines synthesized from 4a |
|---|
| 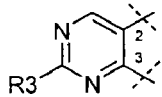 74a-1: R = Et and Me (~8:2)<br>$R^1 = R^2 = H, R^3 = OH$<br>75a-1: R = Et and Me (~8:2)<br>$R^1 = R^2 = H, R^3 = SH$<br>77a-1: R = Et and Me (~8:2)<br>$R^1 = R^2 = H, R^3 = p\text{-}C_6H_4CONH_2$ |

FIG. 4E

Scheme 36: Synthetic strategy for 2,3-fused 3'-aminosubstituted pyrimidine derivatives of bile acids 82-85

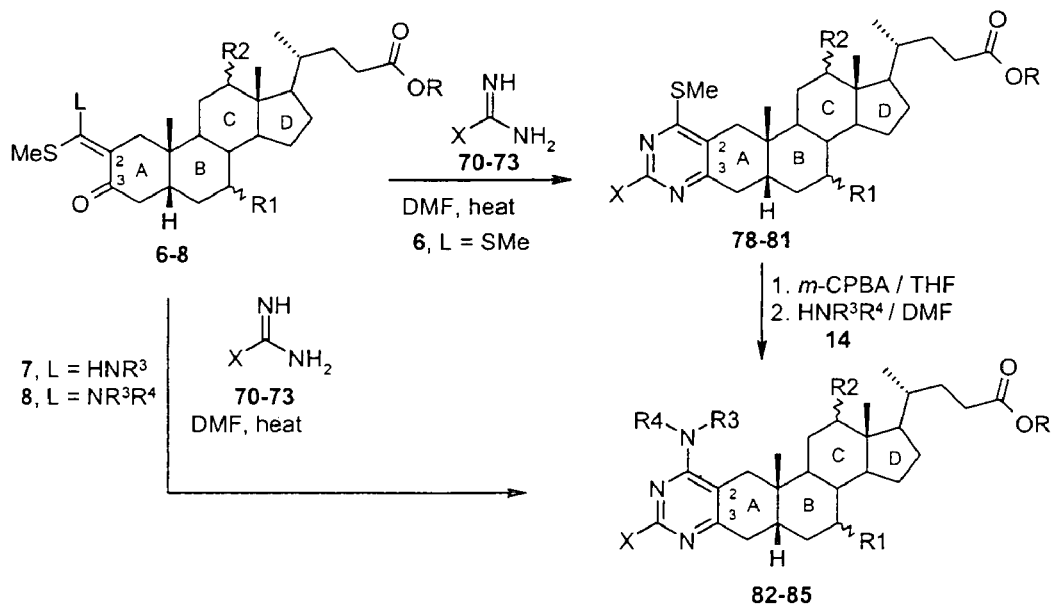

6-8, 78-85 a; R¹ = R² = H; b; R¹ = R² = α-OH; c; R¹ = α-OH, R² = H; d; R¹ = H, R² = α-OH;
e; R¹ = β-OH, R² = H; f; R¹ = β-OH, R² = α-OH
R = H, Me, Et or other alkyl groups, ᵗBu, CH$_2$Ph
R³, R⁴ = = H, alkyl, aryl and alkaryl substituents with or without functional groups
70, 78, 82: X = OH; 71, 79, 83: X = SH; 72, 80, 84: X = NH$_2$; 73, 81, 85: X = R³² = H, alkyl, aryl and alkaryl substituents with or without functional groups

FIG. 4F

Scheme 37: Synthetic strategy for 2,3-fused 3'-substituted pyrimidine derivatives of bile acids 90-93

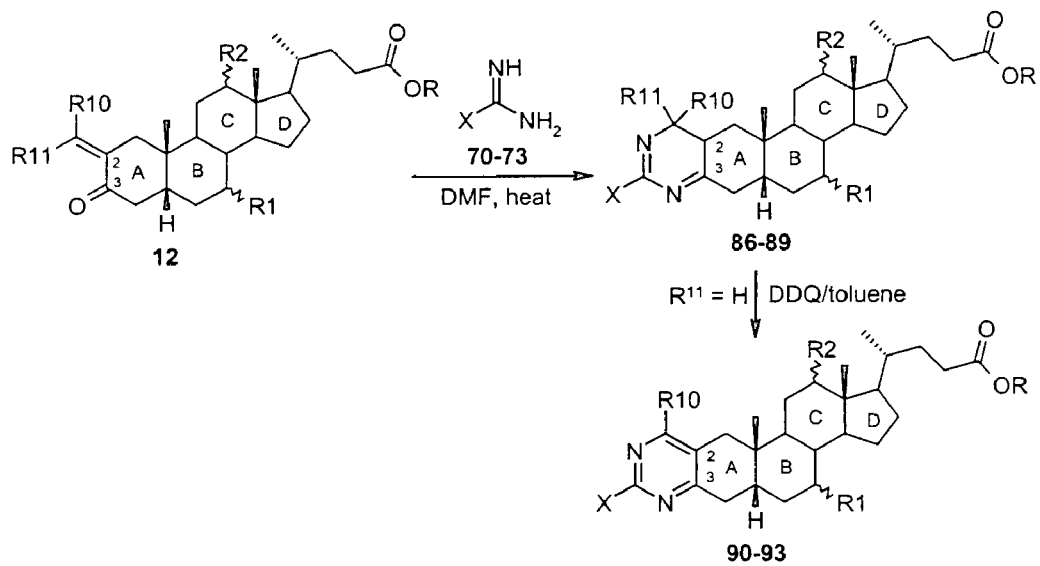

12, 86-93 a; $R^1 = R^2 = H$; b; $R^1 = R^2 = \alpha\text{-OH}$; c; $R^1 = \alpha\text{-OH}$, $R^2 = H$; d; $R^1 = H$, $R^2 = \alpha\text{-OH}$;
e; $R^1 = \beta\text{-OH}$, $R^2 = H$; f; $R^1 = \beta\text{-OH}$, $R^2 = \alpha\text{-OH}$
R = H, Me, Et or other alkyl groups, $^t$Bu, $CH_2Ph$
$R^{10}$, $R^{11}$ = H, alkyl, aryl and alkaryl substituents with or without functional groups
70, 86, 90: X = OH; 71, 87, 91: X = SH; 72, 88, 92: X = $NH_2$; 73, 89, 93: X = $R^{32}$ = H, alkyl, aryl and alkaryl substituents with or without functional groups

FIG. 4G

Synthetic strategy for 7- and 8-membered 2,3-fused heterocycles

General Structures:

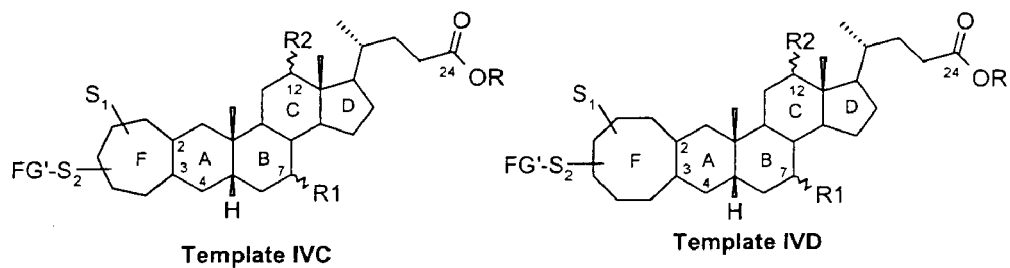

Template IVC  Template IVD a, $R^1 = R^2 = H$; b, $R^1 = R^2 = \alpha\text{-OH}$; c, $R^1 = \alpha\text{-OH}, R^2 = H$; d, $R^1 = H, R^2 = \alpha\text{-OH}$;
e, $R^1 = \beta\text{-OH}, R^2 = H$; f, $R^1 = \beta\text{-OH}, R^2 = \alpha\text{-OH}$
R = H, Me, Et or other alkyl groups, $^t$Bu, $CH_2Ph$, $CPh_3$
F = Fused aromatic and non-aromatic 7- and 8-membered carbocycles and heterocycles with one or more hetero atoms
$S^1$, $S^2$ = H, alkyl, aryl and alkaryl substituents with or without functional groups
FG = Functional Groups [e.g. OH, SH, $NH_2$, NHR, $CO_2H$, $CO_2R$, $CONH_2$, CONHR, C(=S)OR, C(=O)SR]

FIG. 5A

Scheme 38: Synthetic strategy for 2,3-fused diazepine derivatives of bile acids 95

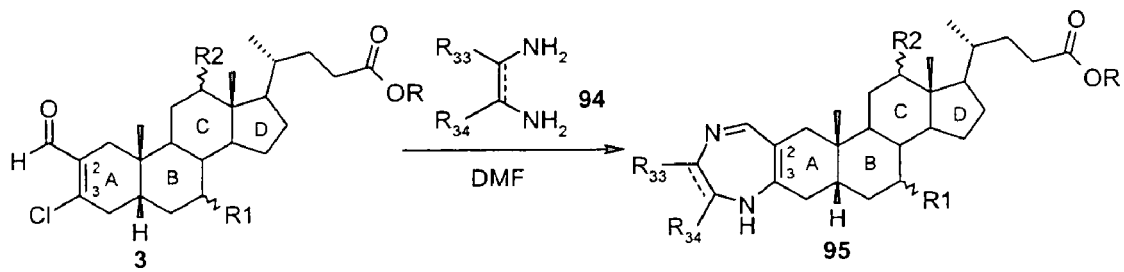

3, 95 a; $R^1 = R^2 = H$; b; $R^1 = R^2 = \alpha\text{-OH}$; c; $R^1 = \alpha\text{-OH}$, $R^2 = H$; d; $R^1 = H$, $R^2 = \alpha\text{-OH}$;
e; $R^1 = \beta\text{-OH}$, $R^2 = H$; f; $R^1 = \beta\text{-OH}$, $R^2 = \alpha\text{-OH}$
R = H, $^t$Bu, CPh$_3$ 94, 95: $R^{33}$, $R^{34}$ = H, alkyl, aryl, alkaryl substituents with functional groups
(functional groups e.g. OH, OR, CO$_2$R etc); Also $R^{33}$ and $R^{34}$
may be linked in a ring Scheme 39: Synthetic strategy for 2,3-fused diazepine derivatives of bile acids 96

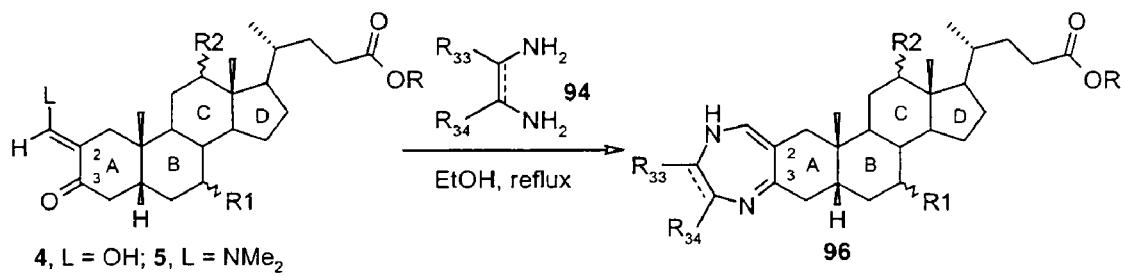

4, L = OH; 5, L = NMe$_2$ 4, 5, 96 a; $R^1 = R^2 = H$; b; $R^1 = R^2 = \alpha\text{-OH}$; c; $R^1 = \alpha\text{-OH}$, $R^2 = H$; d; $R^1 = H$, $R^2 = \alpha\text{-OH}$;
e; $R^1 = \beta\text{-OH}$, $R^2 = H$; f; $R^1 = \beta\text{-OH}$, $R^2 = \alpha\text{-OH}$
R = H, $^t$Bu, CPh$_3$ 94, 96: $R^{33}$, $R^{34}$ = H, alkyl, aryl, alkaryl substituents with functional groups
(functional groups e.g. OH, OR, CO$_2$R etc); Also $R^{33}$ and $R^{34}$
may be linked in a ring

| Diazepines prepared from 4a |
|---|
| 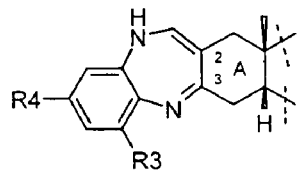 96a-1, R = Et and Me (~9:1)<br>$R^1 = R^2 = H$<br>$R^3 = OH$; $R^4 = H$<br>96a-2, R = Et; $R^1 = R^2 = H$<br>$R^3 = H$; $R^4 = CO_2Me$ |

FIG. 5B

Scheme 40: Synthetic strategy for 2,3-fused diazepine derivatives of bile acids 97

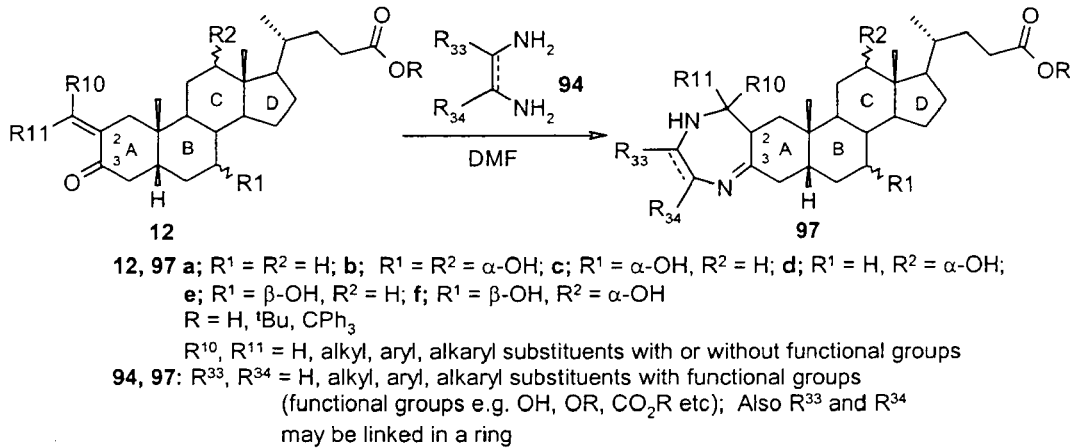

12, 97 a; $R^1 = R^2 = H$; b; $R^1 = R^2 = \alpha\text{-OH}$; c; $R^1 = \alpha\text{-OH}$, $R^2 = H$; d; $R^1 = H$, $R^2 = \alpha\text{-OH}$;
e; $R^1 = \beta\text{-OH}$, $R^2 = H$; f; $R^1 = \beta\text{-OH}$, $R^2 = \alpha\text{-OH}$
R = H, $^t$Bu, CPh$_3$
$R^{10}$, $R^{11}$ = H, alkyl, aryl, alkaryl substituents with or without functional groups
94, 97: $R^{33}$, $R^{34}$ = H, alkyl, aryl, alkaryl substituents with functional groups
(functional groups e.g. OH, OR, CO$_2$R etc); Also $R^{33}$ and $R^{34}$
may be linked in a ring

Scheme 41: Synthetic strategy for 2,3-fused diazepine derivatives of bile acids 99

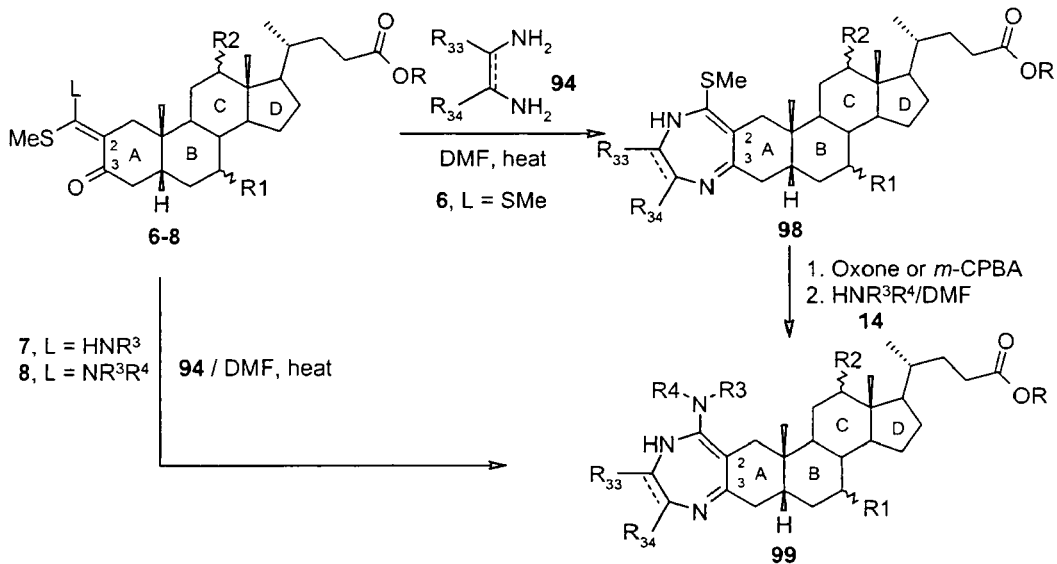

6-8, 98, 99 a; $R^1 = R^2 = H$; b; $R^1 = R^2 = \alpha\text{-OH}$; c; $R^1 = \alpha\text{-OH}$, $R^2 = H$; d; $R^1 = H$, $R^2 = \alpha\text{-OH}$;
e; $R^1 = \beta\text{-OH}$, $R^2 = H$; f; $R^1 = \beta\text{-OH}$, $R^2 = \alpha\text{-OH}$
R = H, $^t$Bu, CPh$_3$
$R^3$, $R^4$ = H, alkyl, aryl, alkaryl substituents with or without functional groups
98, 99: $R^{33}$, $R^{34}$ = H, alkyl, aryl, alkaryl substituents with functional groups
(functional groups e.g. OH, OR, CO$_2$R etc); Also $R^{33}$ and $R^{34}$
may be linked in a ring

FIG. 5C

Scheme 42: Synthetic strategy for 2,3-fused octadiazepine derivatives of bile acids 101

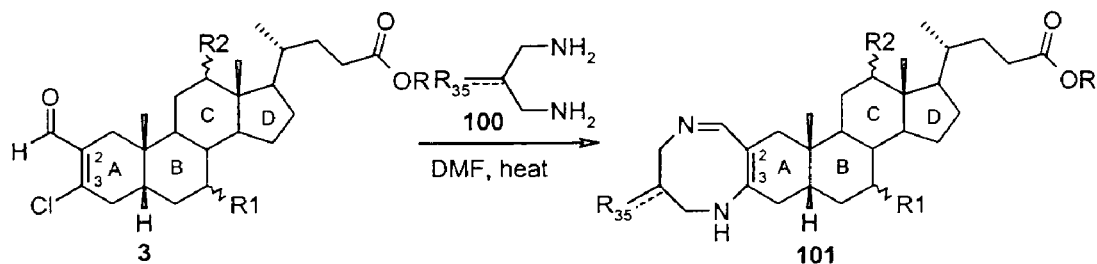

3, 101 a; $R^1 = R^2 = H$; b; $R^1 = R^2 = \alpha\text{-OH}$; c; $R^1 = \alpha\text{-OH}$, $R^2 = H$; d; $R^1 = H$, $R^2 = \alpha\text{-OH}$;
e; $R^1 = \beta\text{-OH}$, $R^2 = H$; f; $R^1 = \beta\text{-OH}$, $R^2 = \alpha\text{-OH}$
R = H, $^t$Bu, CPh$_3$
100, 101: $R^{35}$ = H, O, OH, alkyl, aryl, alkaryl alkoxy, aryloxy, alkaryloxy substituents with or without functional groups Scheme 43: Synthetic strategy for 2,3-fused diazepine derivatives of bile acids 102

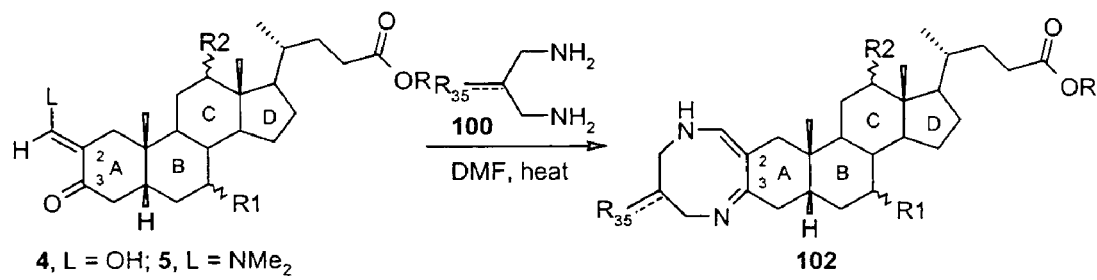

4, L = OH; 5, L = NMe$_2$                    102

4, 5, 102 a; $R^1 = R^2 = H$; b; $R^1 = R^2 = \alpha\text{-OH}$; c; $R^1 = \alpha\text{-OH}$, $R^2 = H$; d; $R^1 = H$, $R^2 = \alpha\text{-OH}$;
e; $R^1 = \beta\text{-OH}$, $R^2 = H$; f; $R^1 = \beta\text{-OH}$, $R^2 = \alpha\text{-OH}$
R = H, $^t$Bu, CPh$_3$
100, 102: $R^{35}$ = H, O, OH, alkyl, aryl, alkaryl alkoxy, aryloxy, alkaryloxy substituents with or without functional groups

FIG. 5D

Scheme 44: Synthetic strategy for 2,3-fused diazepine derivatives of bile acids 103

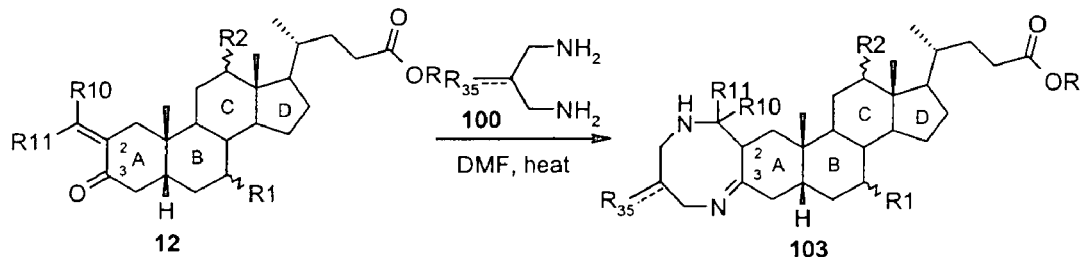

12, 103 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
$R = H, {}^tBu, CPh_3$
$R^{10}, R^{11}$ = H, alkyl, aryl, alkaryl substituents with or without functional groups
100, 103: $R^{35}$ = H, O, OH, alkyl, aryl, alkaryl alkoxy, aryloxy, alkaryloxy substituents with or without functional groups Scheme 45: Synthetic strategy for 2,3-fused diazepine derivatives of bile acids 105

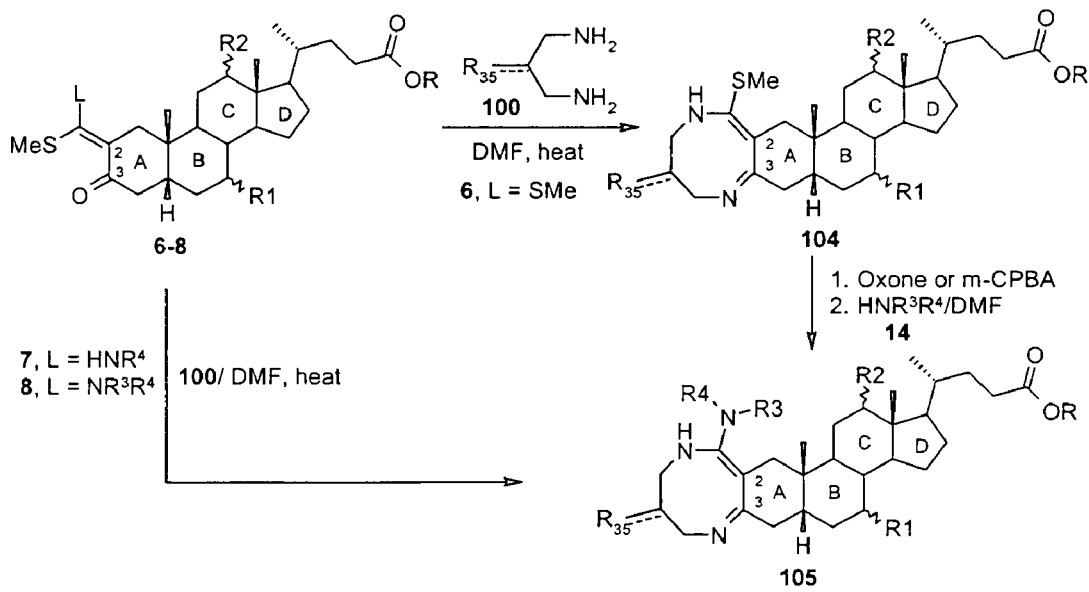

6-8, 104, 105 a; $R^1 = R^2 = H$; b; $R^1 = R^2 = \alpha\text{-OH}$; c; $R^1 = \alpha\text{-OH}, R^2 = H$; d; $R^1 = H, R^2 = \alpha\text{-OH}$;
e; $R^1 = \beta\text{-OH}, R^2 = H$; f; $R^1 = \beta\text{-OH}, R^2 = \alpha\text{-OH}$
$R = H, {}^tBu, CPh_3$
$R^3, R^4$ = H, alkyl, aryl, alkaryl substituents with or without functional groups
100, 104, 105: $R^{35}$ = H, O, OH, alkyl, aryl, alkaryl alkoxy, aryloxy, alkaryloxy substituents with or without functional groups

FIG. 5E

Synthesis of 2,3-fused carbocyclic and heterocyclic derivatives of glyco- and taurocholanoic acids

General Structure:

Template II

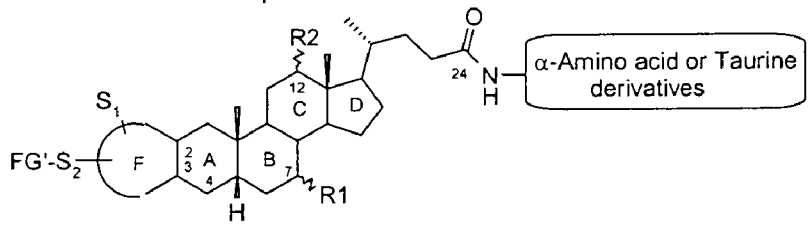

109-111, 113-114 a, $R^1 = R^2 = H$; b, $R^1 = R^2 = \alpha\text{-OH}$; c, $R^1 = \alpha\text{-OH}, R^2 = H$; d, $R^1 = H, R^2 = \alpha\text{-OH}$;
e, $R^1 = \beta\text{-OH}, R^2 = H$; f, $R^1 = \beta\text{-OH}, R^2 = \alpha\text{-OH}$
R = H, Me, Et or other alkyl groups, $^t$Bu, $CH_2Ph$, $CPh_3$
F = Fused aromatic and non-aromatic carbocycles and heterocycles with one or more hetero atoms
$S^1$, $S^2$ = H, alkyl, aryl and alkaryl substituents with or without functional groups
FG' = Functional Groups [e.g. OH, SH, $NH_2$, NHR, $CO_2H$, $CO_2R$, $CONH_2$, CONHR, C(=S)OR, C(=O)SR]

FIG. 6A

Scheme 46: Synthesis of 2,3-fused carbocyclic and heterocyclic derivatives of glycocholanoic acids having general formula 109

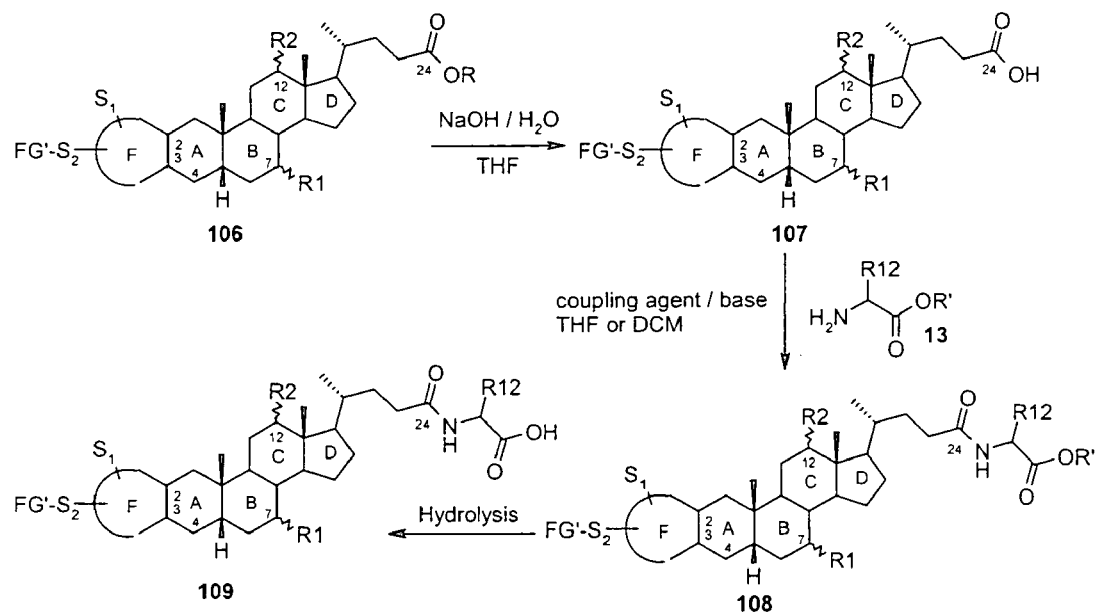

a, $R^1 = R^2 = H$; b, $R^1 = R^2 = \alpha\text{-OH}$; c, $R^1 = \alpha\text{-OH}$, $R^2 = H$; d, $R^1 = H$, $R^2 = \alpha\text{-OH}$;
e, $R^1 = \beta\text{-OH}$, $R^2 = H$; f, $R^1 = \beta\text{-OH}$, $R^2 = \alpha\text{-OH}$
R, R' = H, Me, Et or other alkyl groups, $^t$Bu, $CH_2Ph$, $CPh_3$
$R^{12}$ = H, alkyl, aryl, alkaryl substituents with or with out functional groups
F = Fused aromatic and non-aromatic carbocycles and heterocycles with one or more hetero atoms
$S^1$, $S^2$ = H, alkyl, aryl and alkaryl substituents with or without functional groups
FG' = Functional Groups [e.g. OH, SH, $NH_2$, NHR, $CO_2H$, $CO_2R$, $CONH_2$, CONHR, Deprotection condtions: R = Me, Et, other simple alkyl:- NaOH, $H_2O$, THF; R = $CH_2Ph$:- Pd/C, $H_2$, EtOAc;
R = $^t$Bu, $CPh_3$:- TFA or HCl, dioxane
Coupling conditions: DCC, DIC, EDAC, EDCI, ethyl chloroformate and base like TEA, DIEA, Pyridine
Hydrolysis conditions: TFA or HCl, dioxane (R' = $^t$Bu); NaOH, $H_2O$, THF (R' = alkyl)

FIG. 6B

Scheme 47: Synthesis of 2,3-fused carbocyclic and heterocyclic derivatives of taurocholanoic acid having the general structure 110.

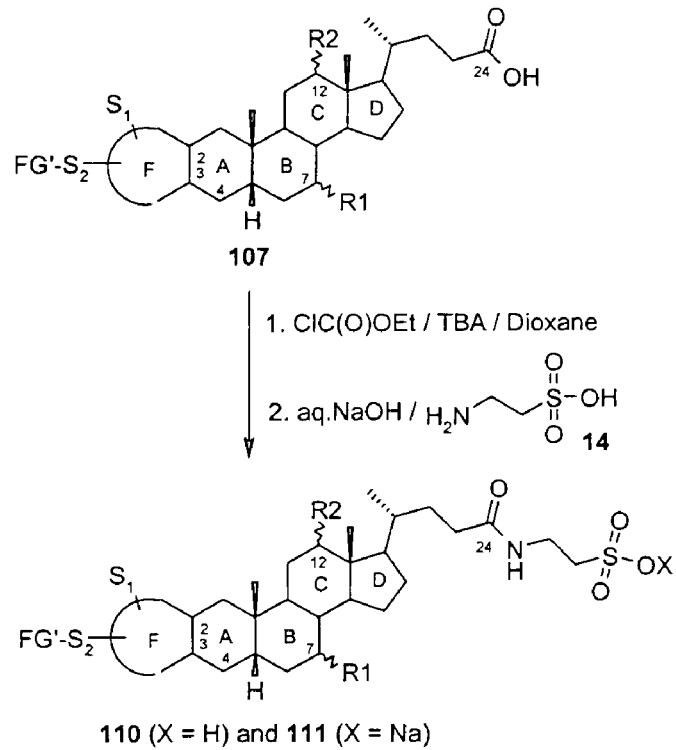

a, $R^1 = R^2 = H$; b, $R^1 = R^2 = \alpha\text{-OH}$; c, $R^1 = \alpha\text{-OH}$, $R^2 = H$; d, $R^1 = H$, $R^2 = \alpha\text{-OH}$;
e, $R^1 = \beta\text{-OH}$, $R^2 = H$; f, $R^1 = \beta\text{-OH}$, $R^2 = \alpha\text{-OH}$
F = Fused aromatic and non-aromatic carbocycles and heterocycles with one or more hetero atoms
$S^1$, $S^2$ = H, alkyl, aryl and alkaryl substituents with or without functional groups
FG' = Functional Groups [e.g. OH, SH, $NH_2$, NHR, $CO_2H$, $CO_2R$, $CONH_2$, CONHR, C(=S)OR, C(=O)SR]

FIG. 6C

Scheme 48: Synthesis of 2,3-fused carbocyclic and heterocyclic derivatives of taurocholanoic acids having the general structure 113.

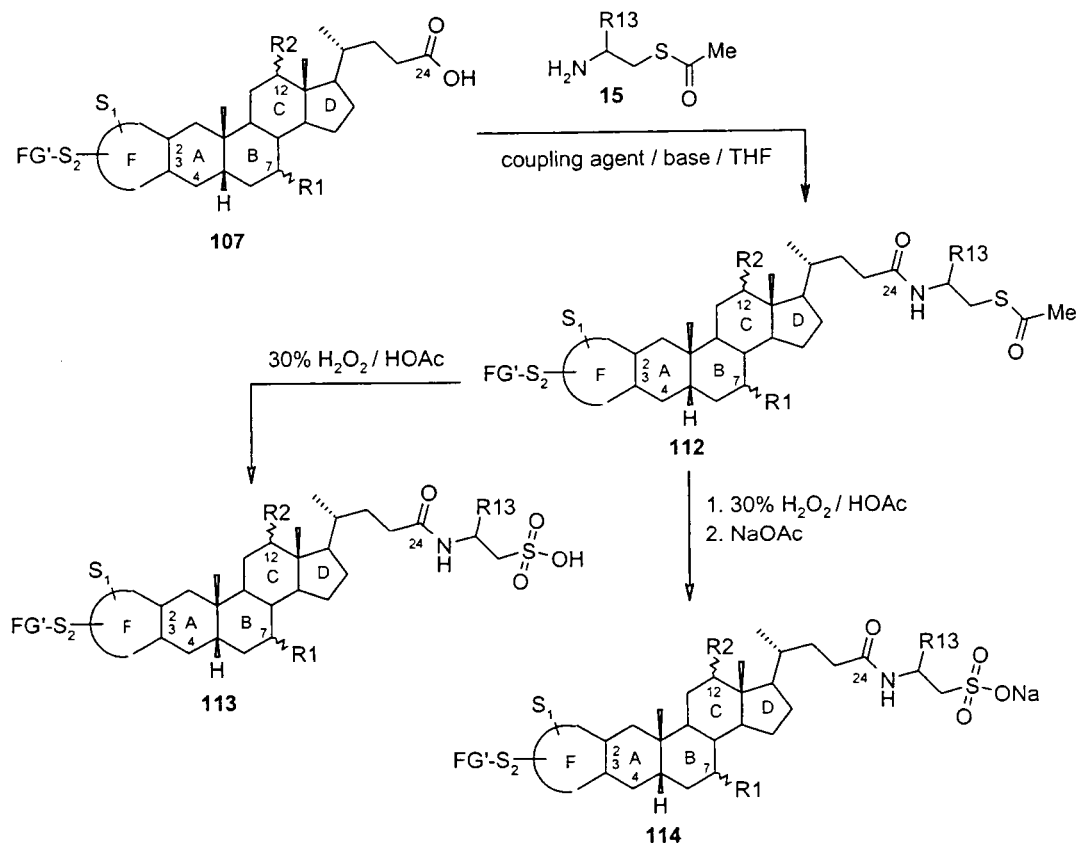

a, $R^1 = R^2 = H$; b, $R^1 = R^2 = \alpha\text{-OH}$; c, $R^1 = \alpha\text{-OH}, R^2 = H$; d, $R^1 = H, R^2 = \alpha\text{-OH}$;
e, $R^1 = \beta\text{-OH}, R^2 = H$; f, $R^1 = \beta\text{-OH}, R^2 = \alpha\text{-OH}$
R, R' = H, Me, Et or other alkyl groups, $^t$Bu, CH$_2$Ph, CPh$_3$
$R^{13}$ = H, alkyl, aryl, alkaryl substituents with or with out functional groups
F = Fused aromatic and non-aromatic carbocycles and heterocycles with one or more hetero atoms
S$^1$, S$^2$ = H, alkyl, aryl and alkaryl substituents with or without functional groups
FG' = Functional Groups [e.g. OH, SH, NH$_2$, NHR, CO$_2$H, CO$_2$R, CONH$_2$, CONHR, C(=S)OR, C(=O)SR]

Coupling conditions: DCC, DIC, EDAC, EDCI, ethyl chloroformate and base like TEA, DIEA, Pyridine

FIG. 6D

Conjugation of drug molecules or surrogates to carbocyclic and heterocyclic derivatives of glyco- and taurocholanoic acids

General structure:

Template III

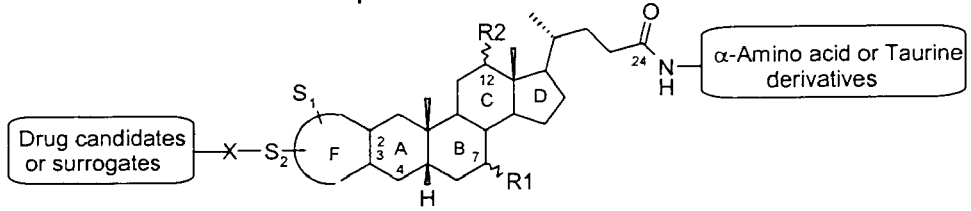

a, $R^1 = R^2 = H$; b, $R^1 = R^2 = \alpha\text{-OH}$; c, $R^1 = \alpha\text{-OH}$, $R^2 = H$; d, $R^1 = H$, $R^2 = \alpha\text{-OH}$;
e, $R^1 = \beta\text{-OH}$, $R^2 = H$; f, $R^1 = \beta\text{-OH}$, $R^2 = \alpha\text{-OH}$
F = Fused aromatic and non-aromatic carbocycles and heterocycles with one or more hetero atoms
$S^1$, $S^2$ = H, alkyl, aryl and alkaryl substituents with or without functional groups
X = Bond that connects drug candidates or surrogates to fused ring

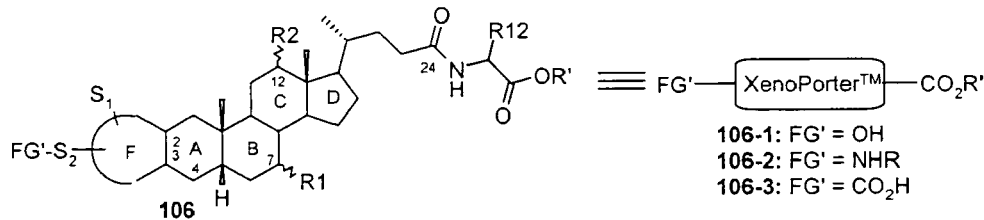

106-1: FG' = OH
106-2: FG' = NHR
106-3: FG' = $CO_2H$

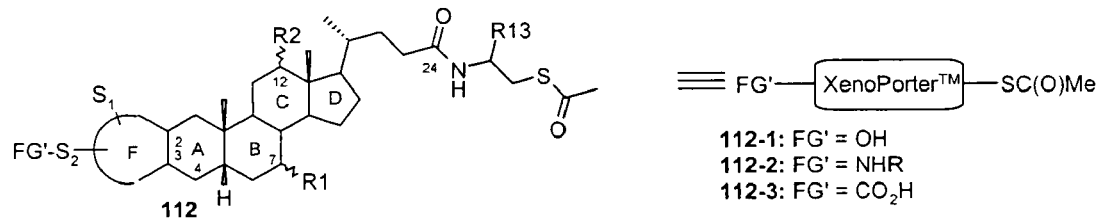

112-1: FG' = OH
112-2: FG' = NHR
112-3: FG' = $CO_2H$ 115-1: FG" = $CO_2H$
116-2: FG" = NHR
117-3: FG" = OH a, $R^1 = R^2 = H$; b, $R^1 = R^2 = \alpha\text{-OH}$; c, $R^1 = \alpha\text{-OH}$, $R^2 = H$; d, $R^1 = H$, $R^2 = \alpha\text{-OH}$;
e, $R^1 = \beta\text{-OH}$, $R^2 = H$; f, $R^1 = \beta\text{-OH}$, $R^2 = \alpha\text{-OH}$
R' = H, Me, Et or other alkyl groups, $^tBu$, $CH_2Ph$, $CPh_3$
R, $R^{12}$, $R^{13}$ = H, alkyl, aryl, alkaryl substituents with or with out functional groups
F = Fused aromatic and non-aromatic carbocycles and heterocycles with one or more hetero atoms
$S^1$, $S^2$ = H, alkyl, aryl and alkaryl substituents with or without functional groups
FG' and FG" = OH, $CO_2H$, NHR

FIG. 7A

Scheme 50: Conjugation of drug molecules to XenoPorter™ 106-2 (R' = <sup>t</sup>Bu) with an amine functional group on the fused ring
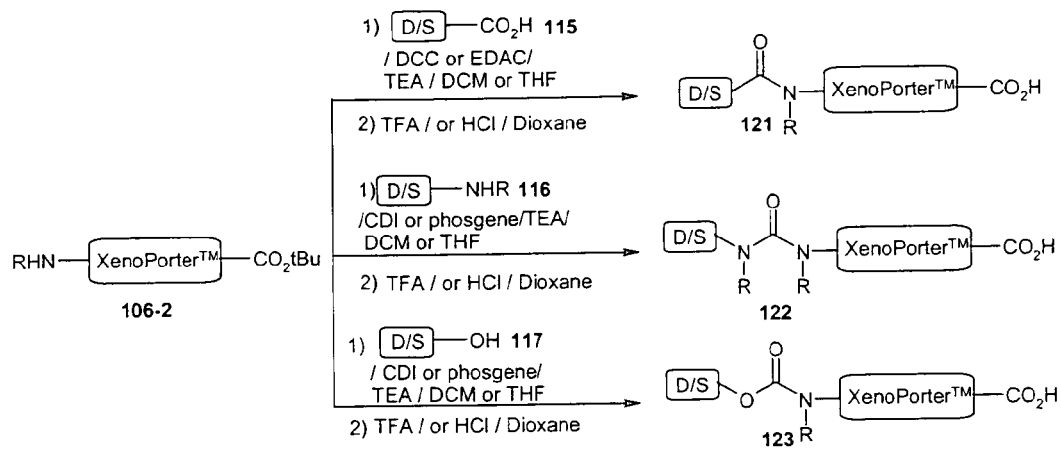
Scheme 51: Conjugation of drug molecules to XenoPorter™ 106-3 (R' = <sup>t</sup>Bu) with a carboxyl functional group on the fused ring
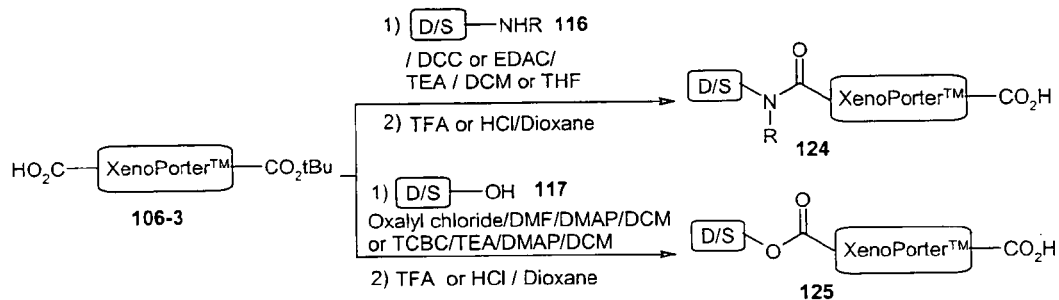
FIG. 7C

Scheme 52: Conjugation of drug molecules to XenoPorter™ 112-1 with a hydroxy functional group on the fused ring
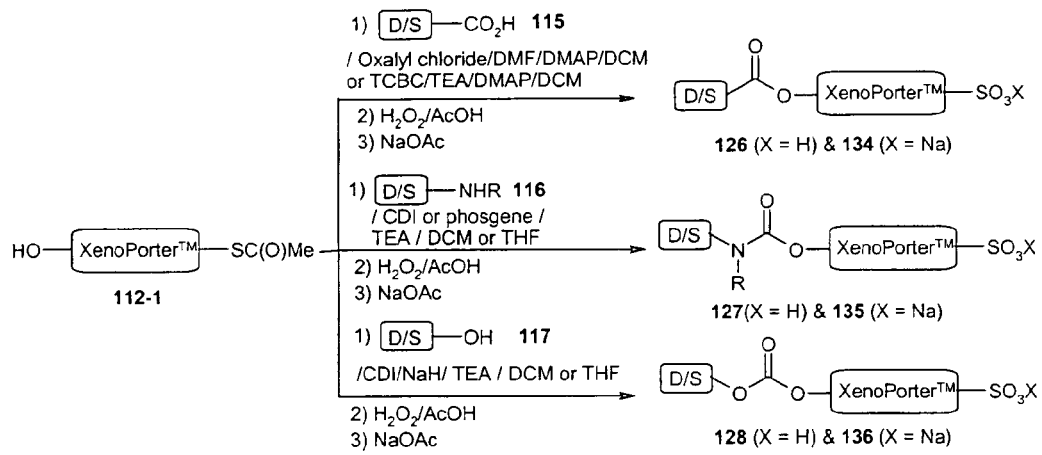
Scheme 53: Conjugation of drug molecules to XenoPorter™ 112-2 with an amine functional group on the fused ring
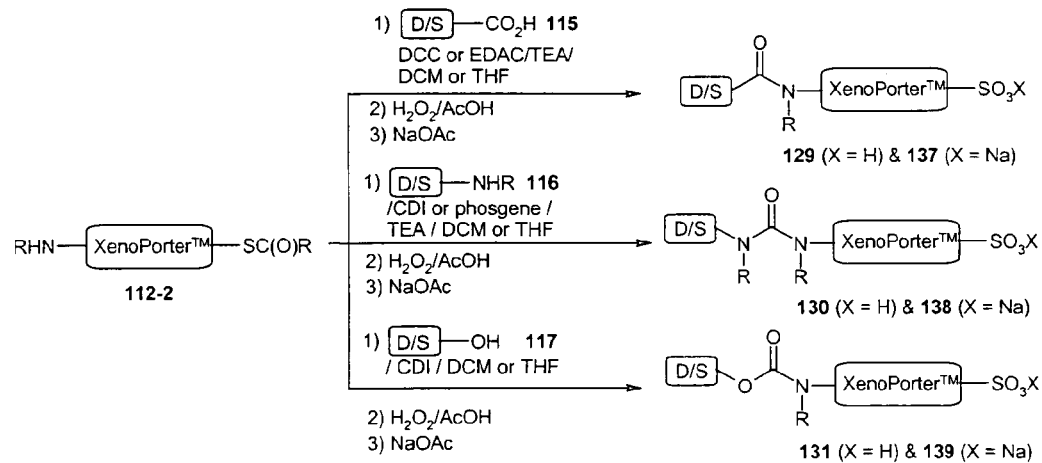
FIG. 7D

Scheme 54: Conjugation of drug molecules to XenoPorter™ 112-3 with a carboxyl functional group on the fused ring

BILE-ACID DERIVED COMPOUNDS FOR ENHANCING ORAL ABSORPTION AND SYSTEMIC BIOAVAILABILITY OF DRUGS

This application claims priority under 35 U.S.C. § 119 to U.S. Provisional Application No. 60/316,182, entitled Bile-acid Derived Compounds for Enhancing Oral Absorption and Systemic Bioavailability of Drugs, filed on Aug. 29, 2001, the entire content of which is hereby incorporated by reference.

BACKGROUND OF THE INVENTION

1. Field of the Invention

This invention is directed to compounds that provide for the enhanced and prolonged systemic blood concentrations of drugs that are incompletely translocated across the intestinal wall after oral delivery to animals. This invention is also directed to pharmaceutical compositions containing and methods using such compounds.

2. State of the Art

Incomplete or poor oral bioavailability of both existing and developmental stage therapeutic and/or prophylactic compounds represents a major impediment to effective pharmaceutical drug development. Though multiple factors influence the bioavailability of drugs (including solubility, dissolution rate, first-pass metabolism, p-glycoprotein and related efflux mechanisms, etc), low intestinal cell permeability is a particularly significant reason for the poor systemic absorption of many compounds.

Compound uptake from the gut is significantly curtailed by the network of tight junctions formed by the intestinal epithelial cell layer, and the majority of drugs that are orally absorbed traverse this epithelial barrier by passive diffusion across the apical and basolateral membranes of these cells.

The physicochemical features of a molecule that favor its passive uptake from the intestinal lumen into the systemic circulation include low molecular weight (e.g. <500 Da), adequate solubility, and a balance of hydrophobic and hydrophilic character (logP generally 1.5–4.0) (Navia and Chaturvedi, 1996). Polar or hydrophilic compounds are typically poorly absorbed through an animal's intestine as there is a substantial energetic penalty for passage of such compounds across the lipid bilayers that constitute cellular membranes. Many nutrients that result from the digestion of ingested foodstuffs in animals, such as amino acids, di- and tripeptides, monosaccharides, nucleosides and water-soluble vitamins, are polar compounds whose uptake is essential to the viability of the animal. For these substances there exist specific mechanisms for active transport of the solute molecules across the apical membrane of the intestinal epithelia. This transport is frequently energized by co-transport of ions down a concentration gradient. Solute transporter proteins are generally single sub-unit, multi-transmembrane spanning polypeptides, and upon binding of their substrates are believed to undergo conformational changes which result in movement of the substrate(s) across the membrane.

Over the past 10–15 years, it has been found that a number of orally administered drugs are recognized as substrates by some of these transporter proteins, and that this active transport may largely account for the oral absorption of these molecules (Tsuji and Tamai, 1996). While in most instances the transporter substrate properties of these drugs were unanticipated discoveries made through retrospective analysis, it has been appreciated that, in principle, one might achieve good intestinal permeability for a drug by designing in recognition and uptake by a nutrient transport system.

Incomplete bioavailability of drugs that, nevertheless, are orally delivered necessitates the administration of a larger dose of such drug to compensate for that amount of drug not delivered to the systemic blood circulation. Such larger doses of the drug, however, may result in greater variability in drug exposure, more frequent occurrence of side effects, decrease in patient compliance, or alternatively, require use of parenteral delivery routes.

One attractive pathway that might be exploitable for oral delivery of such drugs is the intestinal bile acid transport system (Swaan et al, 1996). Bile acids are hydroxylated steroids that play a key role in digestion and absorption of fat and lipophilic vitamins. After synthesis in the liver, they are secreted into bile and excreted by the gall bladder into the intestinal lumen where they emulsify and help solubilize lipophilic substances. Bile acids are conserved in the body by active uptake from the terminal ileum via the sodium-dependent transporter IBAT (or ASBT) and subsequent hepatic extraction by the transporter NTCP located in the sinusoidal membrane of hepatocytes. This efficient mechanism to preserve the bile acid pool is termed the enterohepatic circulation (see FIG. 1). In man, the total bile acid pool (3–5 g) recirculates 6–10 times per day giving rise to a daily uptake of approximately 20–30 g of bile acids.

The high transport capacity of the bile acid pathway has been a key reason for interest in this system for drug delivery purposes. Several papers have postulated that chemical conjugates of bile acids with drugs could be used to provide liver site-directed delivery of a drug to bring about high therapeutic concentrations in the diseased liver with minimization of general toxic reactions elsewhere in the body; and gallbladder-site delivery systems of cholecystographic agents and cholesterol gallstone dissolution accelerators" (Ho, 1987). Several groups have explored these concepts in some detail, using the C-24 carboxylic acid, C-3, C-7, and C-12 hydroxyl groups of cholic acid (and other bile acids) as handles for chemically conjugating drugs or drug surrogates. (Kramer, et al., 1992, Kim, et al., 1993).

The most rigorous drug targeting studies using the bile acid transport pathway to date relate to work with bile acid conjugates of HMG-CoA reductase inhibitors (Kramer et al, 1994b; Petzinger et al, 1995; Kramer and Wess, 1995; Kramer et al, 1997b). Coupling of the HMG-CoA reductase inhibitor HR 780 via an amide linkage to the C-3 position of cholate, taurocholate and glycocholate afforded substrates for both the ileal and liver bile acid transporter proteins (FIG. 2). Upon oral dosing of rats, the cholate conjugate S 3554 led to specific inhibition of HMG-CoA reductase in the liver, and in contrast to the parent compound HR 780, gave significantly reduced inhibition of the enzyme in extrahepatic organs. Companion studies that looked at the tissue distribution of radiolabeled drugs two hours after i.v., administration through the mesenteric vein of rats also showed dramatically lower systemic levels for the bile acid conjugate relative to the parent. Because inhibition of HMG-CoA reductase requires the presence of the free carboxylic acid moiety in HR 780 this data was taken to indicate that S 3554 served as a prodrug of HR 780, undergoing hydrolysis (and other uncharacterized metabolism) in the rat liver. Interestingly, uptake of S 3554 by liver did not appear to depend on the liver bile acid transporter NTCP (which prefers taurocholate conjugates), but may instead have involved another multispecific organic anion transport system on the sinusoidal hepatocyte membrane.

Syntheses of substituted steroids are well known in the art. By way of example, heterocyclic derivatives of 3,7,12-triketo-cholanic acid, including diaminopyriidine, diamino-, and diketopteridine derivatives, in which the heterorings are fused to both the A and B rings of steroidic compounds in positions 2, 3 and 6, 7 or 3, 4 and 6, 7, are known. (Bellini et al, 1969; Bellini et al; Rocchi et al). In addition, heterosteroids containing a dihydroethisterone skeleton have been prepared and have been shown to displace substance P in receptor binding assays. (Venepalli et al, 1992).

In summary, while the concept of harnessing the intestinal bile acid uptake pathway to enhance the absorption of poorly absorbed drugs is well appreciated, the existing art has merely demonstrated that bile acid-drug conjugates may be effectively trafficked to the liver and generally excreted into the bile, either unchanged or as some type of metabolite. The art gives no guidance as to how one prepares a composition that exploits the bile acid transport pathway and simultaneously provides therapeutically meaningful levels of a drug substance outside of the enterohepatic circulation. The art further gives no guidance as to bile acid derivatives that can be used in such a composition.

SUMMARY OF THE INVENTION

This invention is directed to the surprising discovery that the bile acid transport system can be utilized to enhance the systemic bioavailability of orally delivered drugs which are incompletely translocated across the intestinal wall of an animal. This invention, therefore, permits enhanced oral bioavailability in animals of such incompletely translocated drugs and, in addition, permits therapeutic or prophylactic systemic blood concentrations of orally delivered drugs which heretofore could not be achieved by oral administration.

In one aspect, the invention is directed to compounds of formula (I):

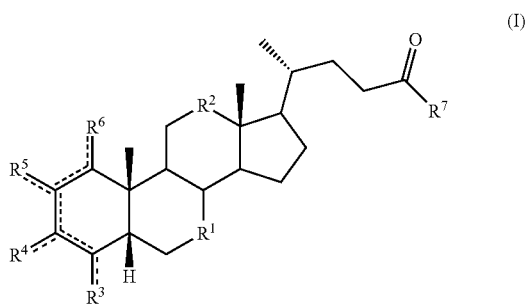

wherein
$R^1$ is $CH_2$, CHOH or $CR^{12}OH$;
$R^2$ is $CH_2$, CHOH or $CR^{12}OH$;
$R^3$ is H, OH, alkylene-$R^8$, substituted alkylene-$R^8$, cycloalkylene-$R^8$, substituted cycloalkylene-$R^8$, alkenylene-$R^8$, substituted alkenylene-$R^8$, cycloalkenylene-$R^8$, substituted cycloalkenylene-$R^8$, alkynylene-$R^8$, substituted alkynylene-$R^8$, arylene-$R^8$, substituted arylene-$R^8$, heteroarylene-$R^8$, substituted heteroarylene-$R^8$, heterocyclene-$R^8$, or substituted heterocyclene-$R^8$ or $R^3$ and $R^4$ together with the carbon atoms to which they are attached form a cycloalkyl-$R^8$, substituted cycloalkyl-$R^8$, cycloalkenyl-$R^8$, substituted cycloalkenyl-$R^8$, heterocycloalkyl-$R^8$, substituted heterocycloalkyl-$R^8$, heterocycloalkenyl-$R^8$, substituted heterocycloalkenyl-$R^8$, aryl-$R^8$, substituted aryl-$R^8$, heteroaryl-$R^8$ or substituted heteroaryl-$R^8$ ring;
$R^4$ is H, OH, alkylene-$R^9$, substituted alkylene-$R^9$, cycloalkylene-$R^9$, substituted cycloalkylene-$R^9$, alkenylene-$R^9$, substituted alkenylene-$R^9$, cycloalkenylene-$R^9$, substituted cycloalkenylene-$R^9$, alkynylene-$R^9$, substituted alkynylene-$R^9$, arylene-$R^9$, substituted arylene-$R^9$, heteroarylene-$R^9$, substituted heteroarylene-$R^9$, heterocyclene-$R^9$, or substituted heterocyclene-$R^9$ or $R^4$ and $R^5$ together with the carbon atoms to which they are attached form a cycloalkyl-$R^9$, substituted cycloalkyl-$R^9$, cycloalkenyl-$R^9$, substituted cycloalkenyl-$R^9$, heterocycloalkyl-$R^9$, substituted heterocycloalkyl-$R^9$, heterocycloalkenyl-$R^9$, substituted heterocycloalkenyl-$R^9$, aryl-$R^9$, substituted aryl-$R^9$, heteroaryl-$R^9$ or substituted heteroaryl-$R^9$ ring;
$R^5$ is H, OH, alkylene-$R^{10}$, substituted alkylene-$R^{10}$, cycloalkylene-$R^{10}$, substituted cycloalkylene-$R^{10}$, alkenylene-$R^{10}$, substituted alkenylene-$R^{10}$, cycloalkenylene-$R^{10}$, substituted cycloalkenylene-$R^{10}$, alkynylene-$R^{10}$, substituted alkynylene-$R^{10}$, arylene-$R^{10}$, substituted arylene-$R^{10}$, heteroarylene-$R^{10}$, substituted heteroarylene-$R^{10}$, heterocyclene-$R^{10}$, or substituted heterocyclene-$R^{10}$ or $R^5$ and $R^6$ together with the carbon atoms to which they are attached form a cycloalkyl-$R^{10}$, substituted cycloalkyl-$R^{10}$, cycloalkenyl-$R^{10}$, substituted cycloalkenyl-$R^{10}$, heterocycloalkyl-$R^{10}$, substituted heterocycloalkyl-$R^{10}$, heterocycloalkenyl-$R^{10}$, substituted heterocycloalkenyl-$R^{10}$, aryl-$R^{10}$, substituted aryl-$R^{10}$, heteroaryl-$R^{10}$ or substituted heteroaryl-$R^{10}$ ring;
$R^6$ is H, OH, alkylene-$R^{11}$, substituted alkylene-$R^{11}$, cycloalkylene-$R^{11}$, substituted cycloalkylene-$R^{11}$, alkenylene-$R^{11}$, substituted alkenylene-$R^{11}$, cycloalkenylene-$R^{11}$, substituted cycloalkenylene-$R^{11}$, alkynylene-$R^{11}$, substituted alkynylene-$R^{11}$, arylene-$R^{11}$, substituted arylene-$R^{11}$, heteroarylene-$R^{11}$, substituted heteroarylene-$R^{11}$, heterocyclene-$R^{11}$ or substituted heterocyclene-$R^{11}$; provided that one and only one of $R^3/R^4$, $R^4/R^5$ or $R^5/R^6$ form a ring;
$R^7$ is OH, an alkylamino group substituted with a moiety that is negatively charged at physiological pH and located 5 to 15 atoms from C-22 of the bile acid nucleus, a di-substituted alkylamino group substituted with L-D and a moiety that is negatively charged at physiological pH and located 5 to 15 atoms from C-22 of the bile acid nucleus, L-D or pharmaceutically acceptable salts thereof;
$R^8$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;
$R^9$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;
$R^{10}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;
$R^{11}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;

$R^{12}$ is alkyl, substituted alkyl, cycloalkyl, substituted cycloalkyl, aryl, substituted aryl, heteroaryl or substituted heteroaryl;

$R^{13}$ is alkyl, substituted alkyl, cycloalkyl, substituted cycloalkyl, aryl, substituted aryl, heteroaryl or substituted heteroaryl;

dashed lines represent possible sites of unsaturation;

L is a covalent bond or a linking group;

D is a drug;

or a pharmaceutically acceptable salt thereof;

provided that not more than one of the substituents $R^3$, $R^4$, $R^5$, $R^6$, and $R^7$ includes moiety L-D;

when $R^1$ and $R^2$ are CHOH, $R^5$ and $R^6$ are H, and $R^7$ is OH, then $R^3$ and $R^4$ together with the carbon atoms to which they are attached do not form

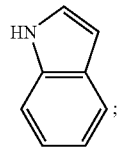

and when $R^1$ and $R^2$ are CHOH, $R^3$ and $R^6$ are H, and $R^7$ is OH, then $R^4$ and $R^5$ together with the carbon atoms to which they are attached do not form

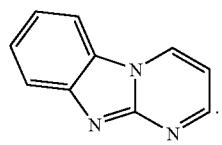

Preferably, the compound of formula (I) is one of the following compounds:

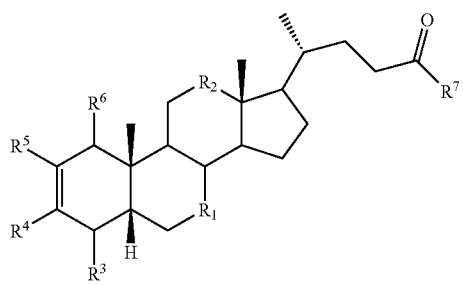

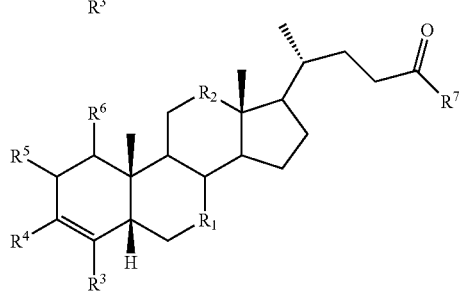

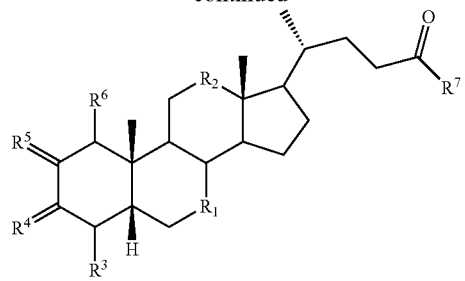

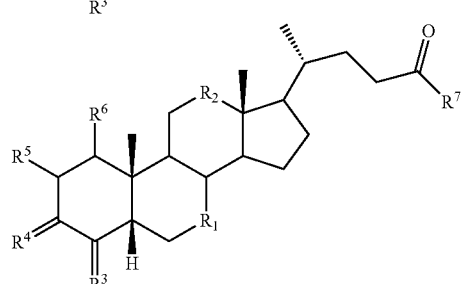

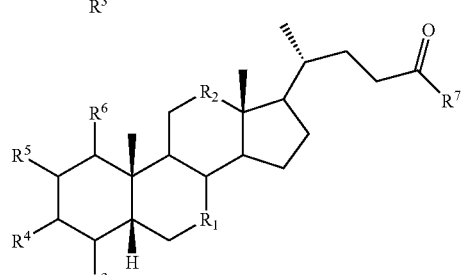

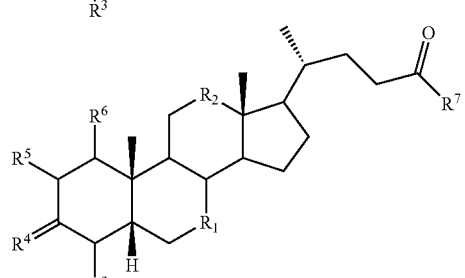

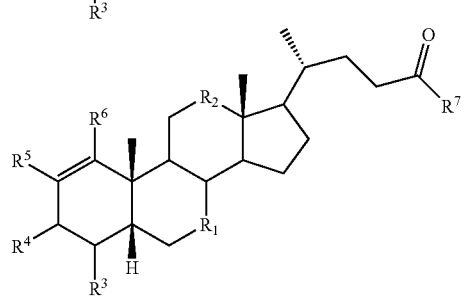

wherein the substituents are as defined above.

In one class of preferred compounds, $R^4$ and $R^5$ together with the carbon atoms to which they are attached form a 5-membered ring, wherein the ring is heterocycloalkyl-$R^9$, substituted heterocycloalkyl-$R^9$, heteroaryl-$R^9$ or substituted heteroaryl-$R^9$.

In another class of preferred compounds, $R^3$ and $R^4$ together with the carbon atoms to which they are attached form a 5-membered ring, wherein the ring is heterocycloalkyl-$R^9$, substituted heterocycloalkyl-$R^9$, heteroaryl-$R^9$ or substituted heteroaryl-$R^9$.

In another class of preferred compounds, $R^4$ and $R^5$ together with the carbon atoms to which they are attached form a 6-membered ring, wherein the ring is cycloalkyl-$R^9$, substituted cycloalkyl-$R^9$, cycloalkenyl-$R^9$, substituted cycloalkenyl-$R^9$, aryl-$R^9$, substituted aryl-$R^9$, heterocycloalkyl-$R^9$, substituted heterocycloalkyl-$R^9$, heteroaryl-$R^9$ or substituted heteroaryl-$R^9$.

In another class of preferred compounds, $R^3$ and $R^4$ together with the carbon atoms to which they are attached form a 6-membered ring, wherein the ring is cycloalkyl-$R^9$, substituted cycloalkyl-$R^9$, cycloakenyl-$R^9$, substituted cycloalkenyl-$R^9$, aryl-$R^9$, substituted aryl-$R^9$, heterocycloalkyl-$R^9$, substituted heterocycloalkyl-$R^9$, heteroaryl-$R^9$ or substituted heteroaryl-$R^9$.

In another class of preferred compounds, $R^4$ and $R^5$ together with the carbon atoms to which they are attached form a 7-membered ring, wherein the ring is heterocycloalkyl-$R^9$, substituted heterocycloalkyl-$R^9$, heterocycloalkenyl-$R^9$, substituted heterocycloalkenyl-$R^9$, heteroaryl-$R^9$ or substituted heteroaryl-$R^9$.

In another class of preferred compounds, $R^3$ and $R^4$ together with the carbon atoms to which they are attached form a 7-membered ring, wherein the ring is heterocycloalkyl-$R^9$, substituted heterocycloalkyl-$R^9$, heterocycloalkenyl-$R^9$, substituted heterocycloalkenyl-$R^9$, heteroaryl-$R^9$ or substituted heteroaryl-$R^9$.

In another class of preferred compounds, $R^4$ and $R^5$ together with the carbon atoms to which they are attached form an 8-membered ring, wherein the ring is heterocycloalkyl-$R^9$, substituted heterocycloalkyl-$R^9$, heterocycloalkenyl-$R^9$ or substituted heterocycloalkenyl-$R^9$.

In another class of preferred compounds, $R^3$ and $R^4$ together with the carbon atoms to which they are attached form an 8-membered ring, wherein the ring is heterocycloalkyl-$R^9$, substituted heterocycloalkyl-$R^9$, heterocycloalkenyl-$R^9$ or substituted heterocycloalkenyl-$R^9$.

In certain preferred compounds, $R^7$ is an alkylamino group substituted with a moiety that is negatively charged at physiological pH and located 5 to 15 atoms from C-22 of the bile acid nucleus, wherein the moiety is selected from the group consisting of —COOH, —SO$_3$H, —SO$_2$H, —PO$_3$H, —OPO$_3$H, —OSO$_3$H, —C(O)NHOH, -tetrazole, -catechol and pharmaceutically acceptable salts thereof.

In other preferred compounds, $R^7$ is a di-substituted alkylamino group substituted with L-D and a moiety that is negatively charged at physiological pH and located 5 to 15 atoms from C-22 of the bile acid nucleus, and wherein the moiety is selected from the group consisting of —COOH, —SO$_3$H, —SO$_2$H, —PO$_3$H, —OPO$_3$H, —OSO$_3$H, —C(O)NHOH, -tetrazole, -catechol and pharmaceutically acceptable salts thereof.

In other preferred compounds, $R^7$ is OH.

In other preferred compounds, $R^7$ is L-D.

Where in the compound $R^4$ and $R^5$ together with the carbon atoms to which they are attached form a 5-membered ring, the 5-membered ring is preferably one of the following 5-membered rings:

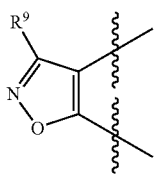 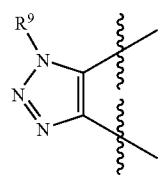 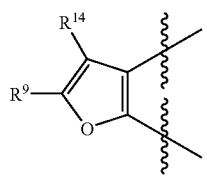

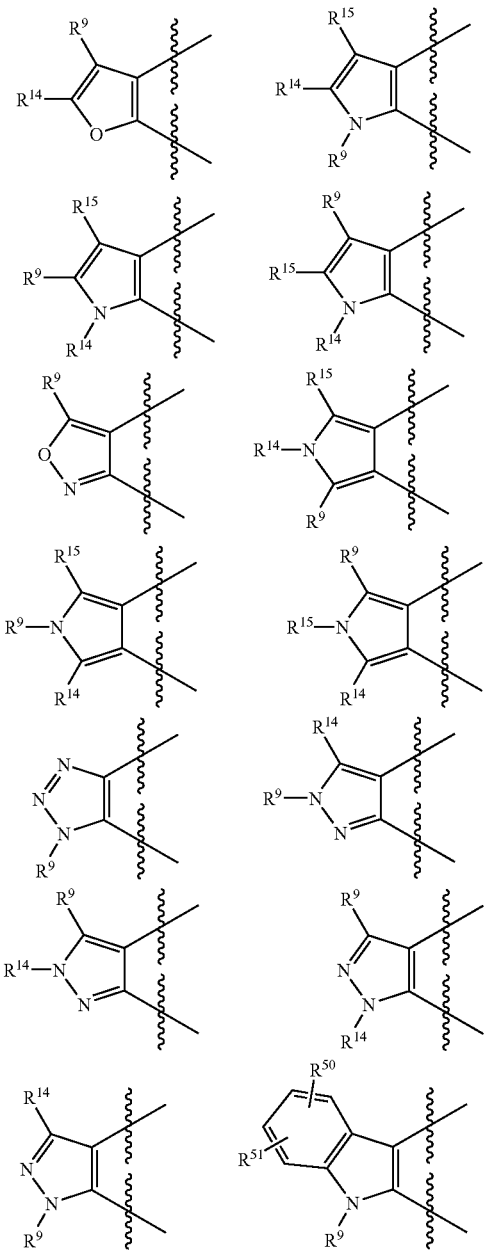

wherein $R^9$ is L-D;

$R^{14}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR$^{13}$, SH, SR$^{13}$, NH$_2$, NHR$^{13}$, N(R$^{13}$)$_2$, CO$_2$H, CO$_2$R$^{13}$, CONH$_2$, CONHR$^{13}$ or CON(R$^{13}$)$_2$;

$R^{15}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR$^{13}$, SH, SR$^{13}$, NH$_2$, NHR$^{13}$, N(R$^{13}$)$_2$, CO$_2$H, CO$_2$R$^{13}$, CONH$_2$, CONHR$^{13}$ or CON(R$^{13}$)$_2$; and $R^{50}$ and $R^{51}$ are independently H, halo, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$.

Where in the compound $R^3$ and $R^4$ together with the carbon atoms to which they are attached form a 5-membered ring, the 5-membered ring is preferably one of the following 5-membered rings:

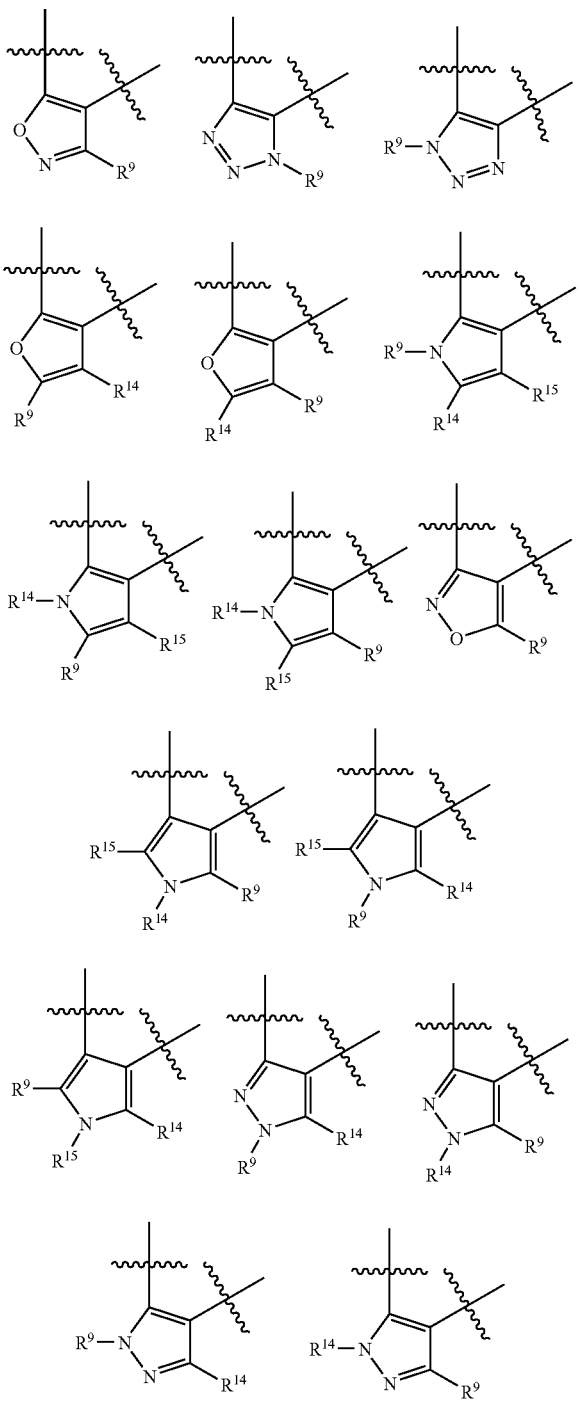

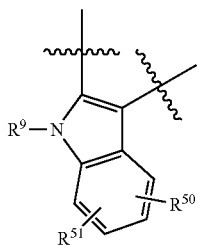

wherein $R^9$ is L-D;

$R^{14}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$;

$R^{15}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$; and $R^{50}$ and $R^{51}$ are independently H, halo, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$.

Where in the compound $R^4$ and $R^5$ together with the carbon atoms to which they are attached form a 6-membered ring, the 6-membered ring is preferably one of the following 6-membered rings:

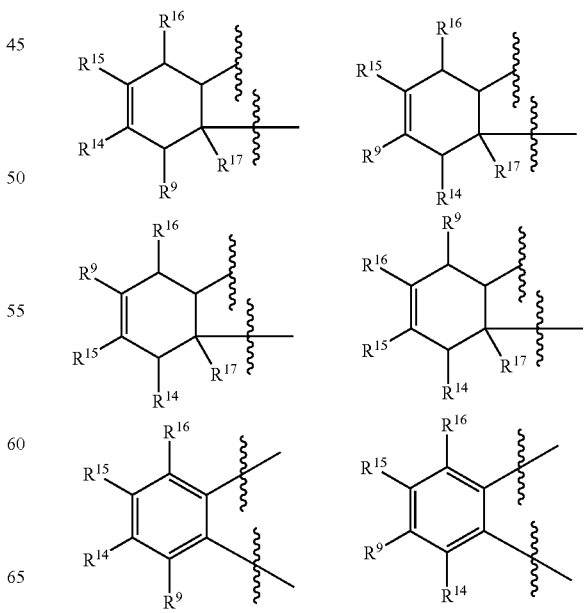

-continued

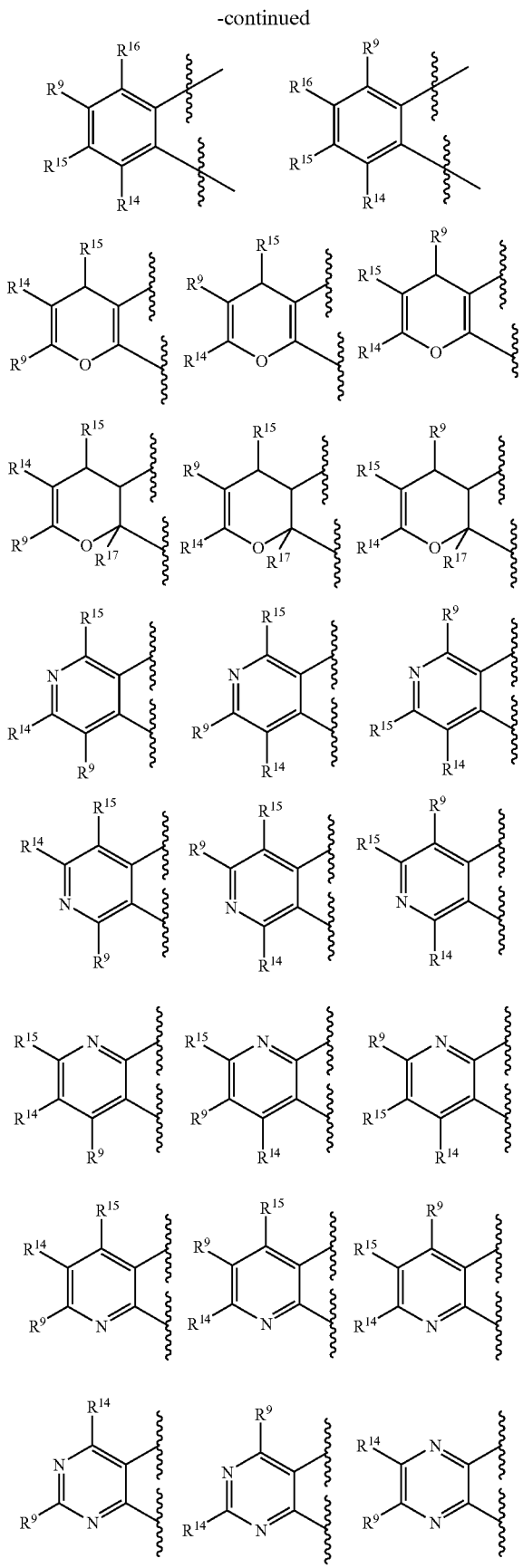
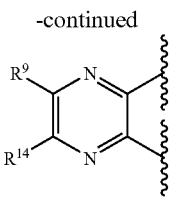

wherein

R[9] is L-D;

R[14] is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR[13], SH, SR[13], $NH_2$, NHR[13], $N(R^{13})_2$, $CO_2H$, $CO_2R^{13}$, $CONH_2$, CONHR[13] or $CON(R^{13})_2$;

R[15] is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR[13], SH, SR[13], $NH_2$, NHR[13], $N(R^{13})_2$, $CO_2H$, $CO_2R^{13}$, $CONH_2$, CONHR[13] or $CON(R^{13})_2$;

R[16] is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR[13], SH, SR[13], $NH_2$, NHR[13], $N(R^{13})_2$, $CO_2H$, $CO_2R^{13}$, $CONH_2$, CONHR[13] or $CON(R^{13})_2$; and, R[17] is OH, OP, NHP or $NR^{52}P$, wherein R[52] is alkyl or aryl and P is a protecting group.

Where in the compound R[3] and R[4] together with the carbon atoms to which they are attached form a 6-membered ring, the 6-membered ring is preferably one of the following 6-membered rings:

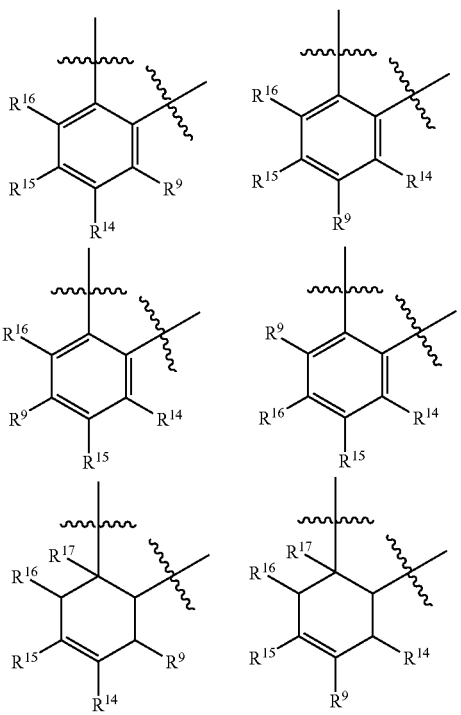

-continued

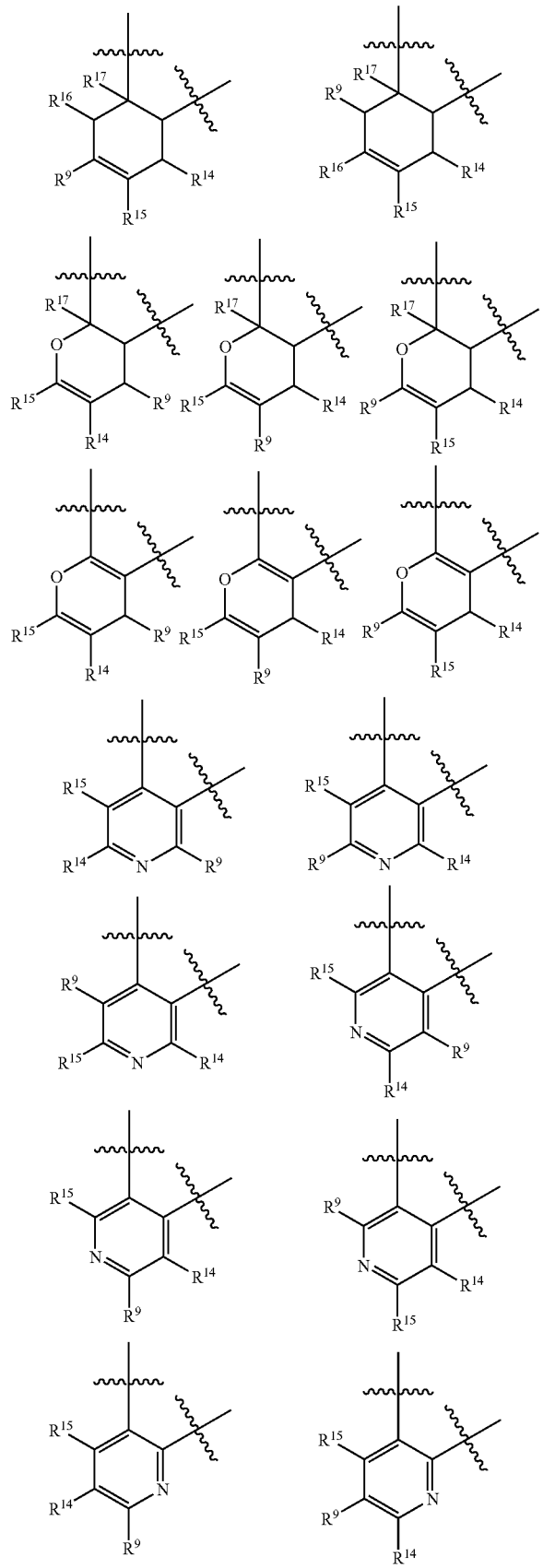

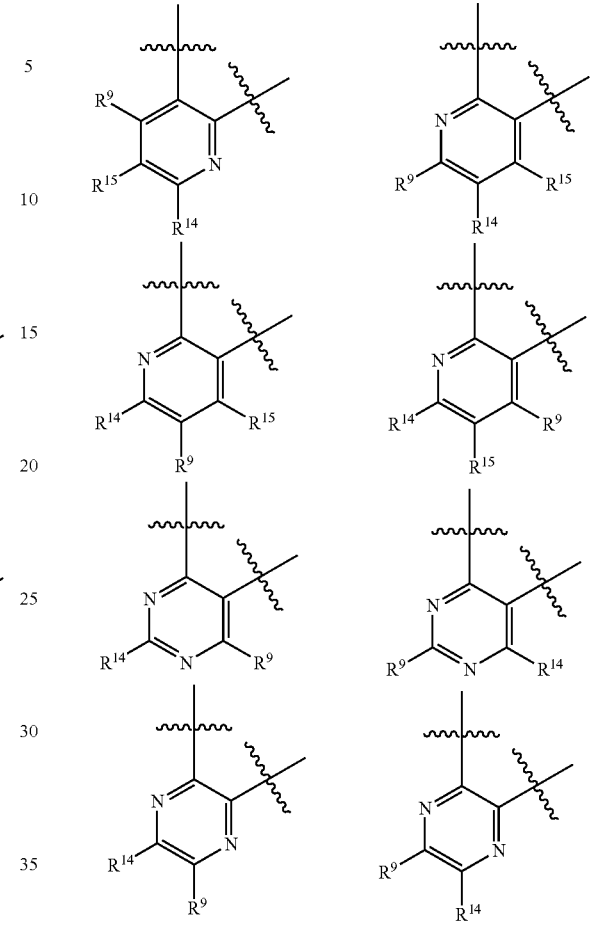

wherein

R⁹ is L-D;

R¹⁴ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂;

R¹⁵ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂;

R¹⁶ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂; and, R¹⁷ is OH, OP, NHP or NR⁵²P, wherein R⁵² is alkyl or aryl and P is a protecting group.

Where in the compound R⁴ and R⁵ together with the carbon atoms to which they are attached form a 7-membered ring, the 7-membered ring is preferably one of the following 7-membered rings:

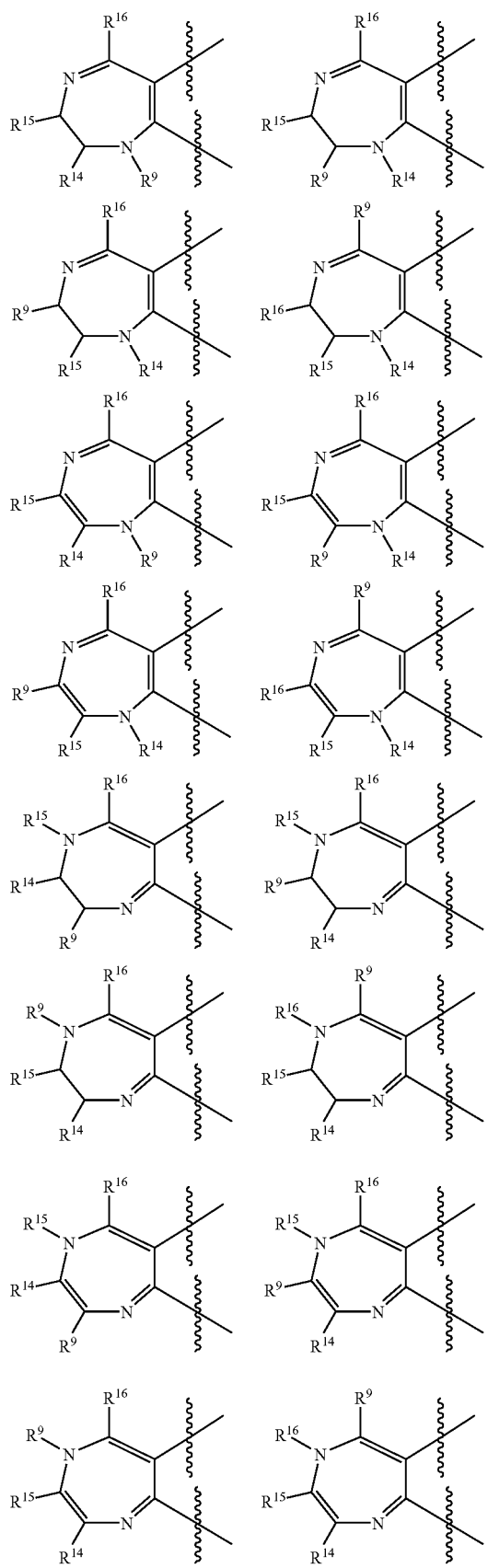
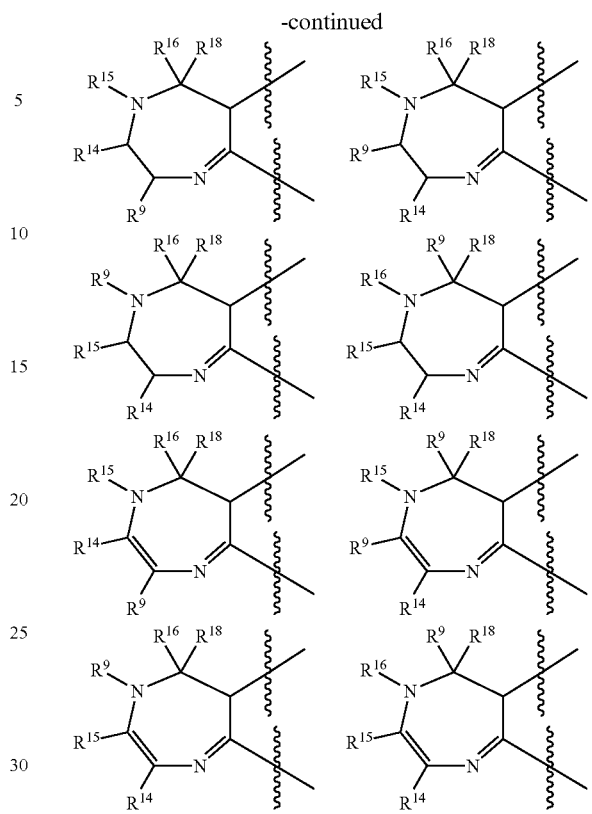

wherein $R^9$ is L-D;

$R^{14}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$;

$R^{15}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$;

$R^{16}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^3$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$; and, $R^{18}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$.

Where in the compound $R^3$ and $R^4$ together with the carbon atoms to which they are attached form a 7-membered ring, the 7-membered ring is preferably one of the following 7-membered rings:

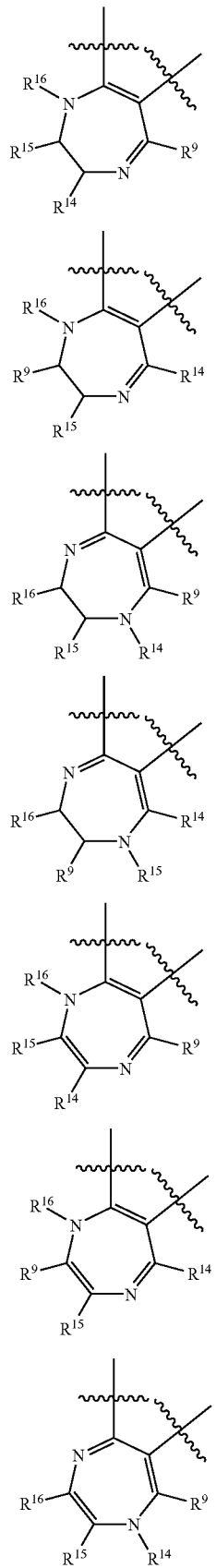
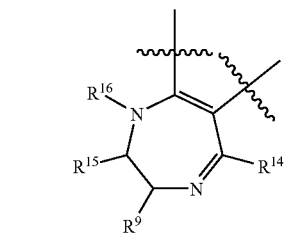
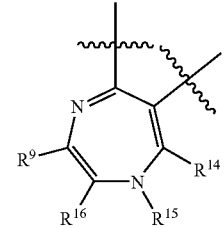
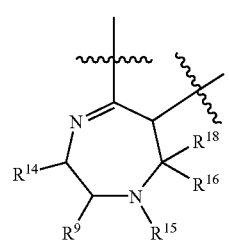
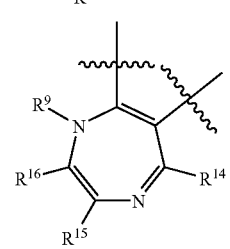
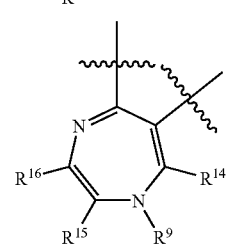

-continued wherein

R$^9$ is L-D;

R$^{14}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR$^{13}$, SH, SR$^{13}$, NH$_2$, NHR$^{13}$, N(R$^{13}$)$_2$, CO$_2$H, CO$_2$R$^{13}$, CONH$_2$, CONHR$^{13}$ or CON(R$^{13}$)$_2$;

R$^{15}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR$^{13}$, SH, SR$^{13}$, NH$_2$, NHR$^{13}$, N(R$^{13}$)$_2$, CO$_2$H, CO$_2$R$^{13}$, CONH$_2$, CONHR$^{13}$ or CON(R$^{13}$)$_2$;

R$^{16}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$; and, $R^{18}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$.

Where in the compound $R^4$ and $R^5$ together with the carbon atoms to which they are attached form a 8-membered ring, the 8-membered ring is preferably one of the following 8-membered rings:

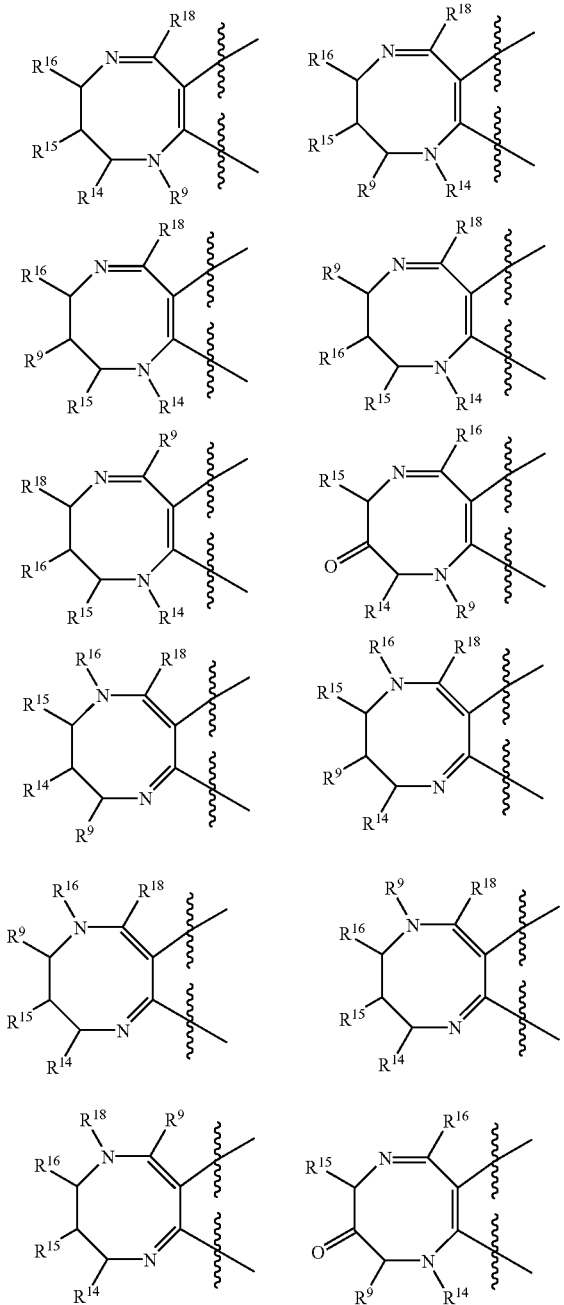

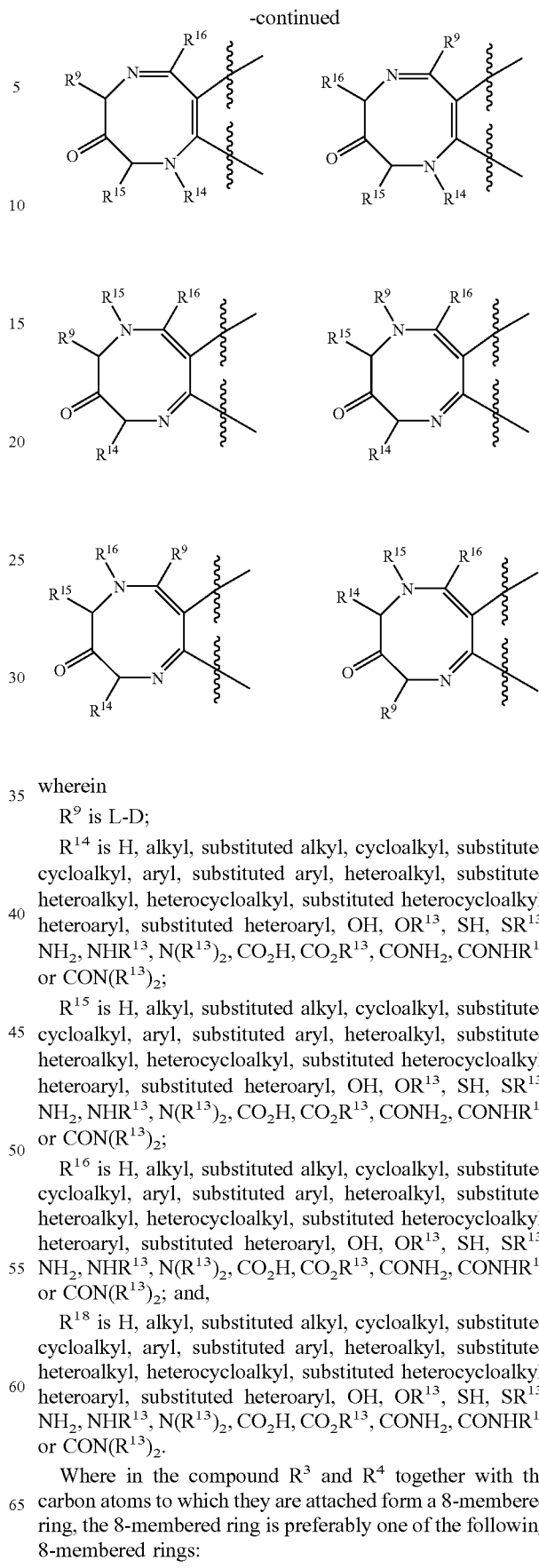

wherein $R^9$ is L-D;

$R^{14}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$;

$R^{15}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$;

$R^{16}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$; and, $R^{18}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$.

Where in the compound $R^3$ and $R^4$ together with the carbon atoms to which they are attached form a 8-membered ring, the 8-membered ring is preferably one of the following 8-membered rings:

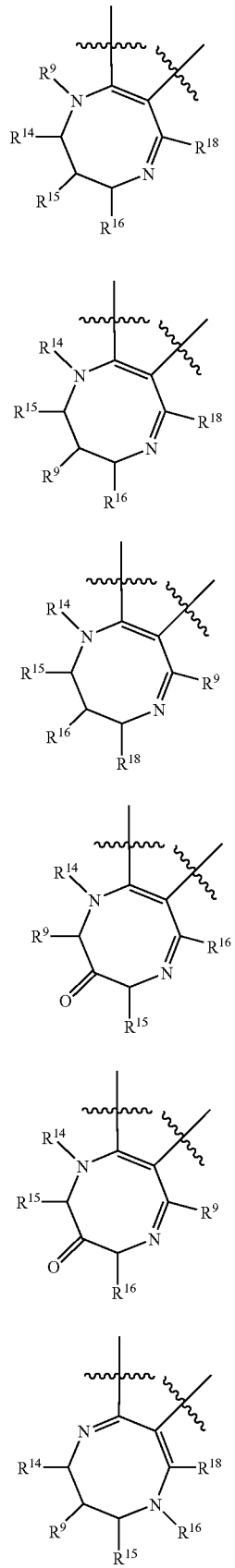
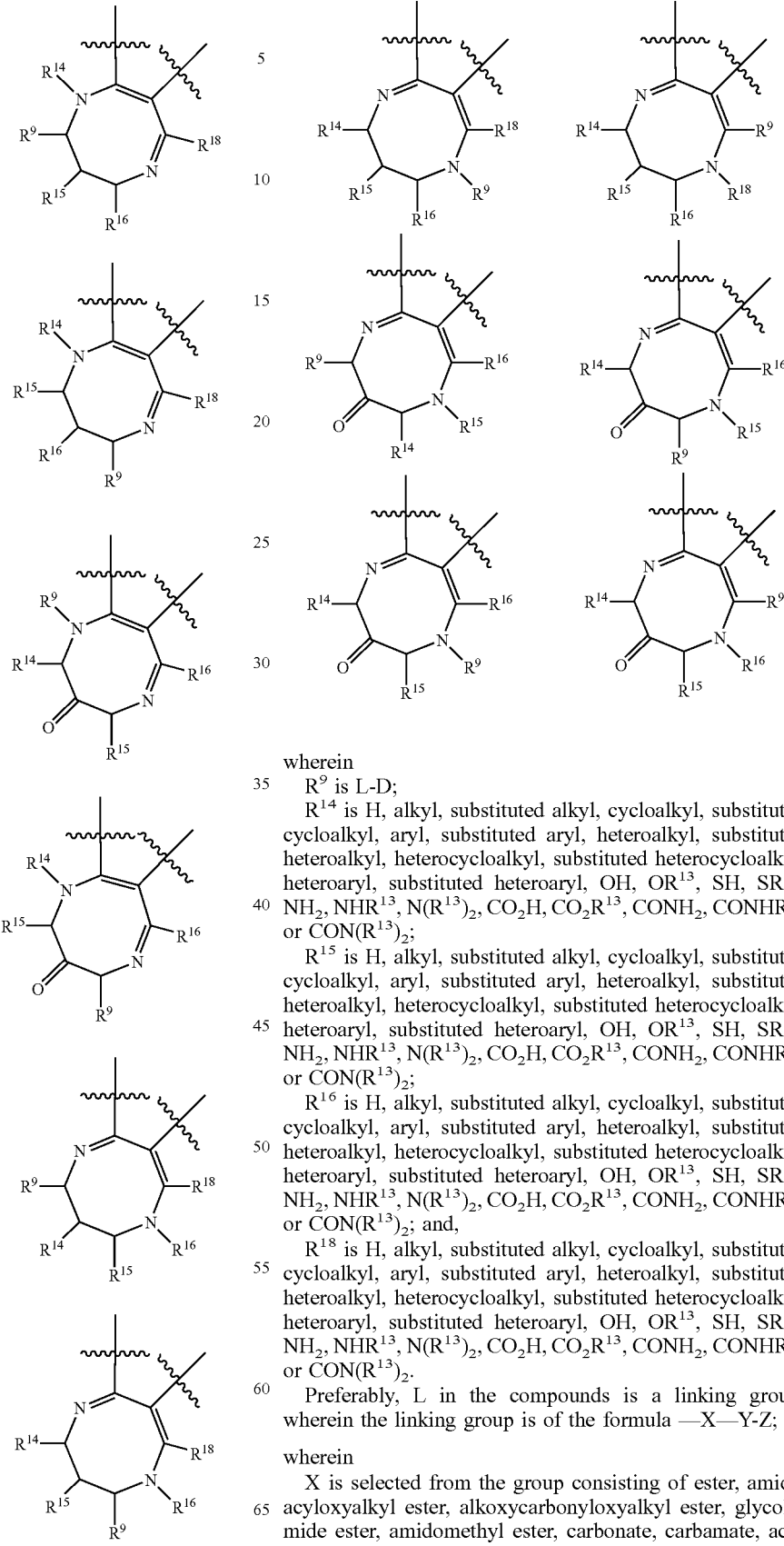

wherein

R⁹ is L-D;

R¹⁴ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂;

R¹⁵ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂;

R¹⁶ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂; and, R¹⁸ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂.

Preferably, L in the compounds is a linking group, wherein the linking group is of the formula —X—Y-Z;

wherein

X is selected from the group consisting of ester, amide, acyloxyalkyl ester, alkoxycarbonyloxyalkyl ester, glycolamide ester, amidomethyl ester, carbonate, carbamate, acyloxyalkyl ether, alkoxycarbonyloxyalkyl ether, acyloxyalkyl carbonate, acyloxyalkyl carbamate, alkoxycarbonyloxyalkyl carbamate, Mannich base, imide, N-acyloxyalkyl phosphoramidate, and N-alkoxycarbonyloxyalkyl phosphoramidate;

Y is of the formula —$(R^{100})m(R^{101})n(R^{102})p$-, wherein each of $R^{100}$, $R^{101}$ and $R^{102}$ are independently selected from the group consisting of alkylene, substituted alkylene, alkenylene, substituted alkenylene, alkynylene, substituted alkynylene, cycloalkylene, substituted cycloalkylene, cycloalkenylene, substituted cycloalkenylene, arylene, substituted arylene, heteroarylene, substituted heteroarylene, heterocyclene and substituted heterocyclene;

each of m, n and p are independently an integer from 0 to 3; and,

Z is selected from the group consisting of ether, thioether, ester, carbonate, carbamate, phosphate, phosphonate, phosphoramidate, amide, amine, urea, thiourea, sulfonamide, sulfoxide, sulfone, thioester, and disulfide.

In certain preferred compounds, L is a cleavable linking group.

In particularly preferred compounds, L is a linking group selected from —OC(O)$(CH_2)_q$NHC(O)—, —OC(O)(alkylene-O)$_q$-alkylene-, and —C(O)O(alkylene-O)$_q$-alkylene, wherein q is an integer of from 1 to 20.

In another aspect, the invention is directed to pharmaceutical compositions comprising a pharmaceutically acceptable excipient and a compound of formula (I):

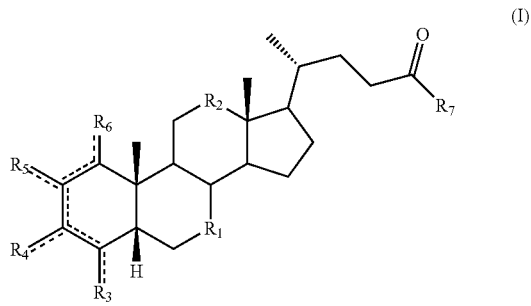

(I)

wherein
$R^1$ is $CH_2$, CHOH or $CR^{12}OH$;
$R^2$ is $CH_2$, CHOH or $CR^{12}OH$;
$R^3$ is H, OH, alkylene-$R^8$, substituted alkylene-$R^8$, cycloalkylene-$R^8$, substituted cycloalkylene-$R^8$, alkenylene-$R^8$, substituted alkenylene-$R^8$, cycloalkenylene-$R^8$, substituted cycloalkenylene-$R^8$, alkynylene-$R^8$, substituted alkynylene-$R^8$, arylene-$R^8$, substituted arylene-$R^8$, heteroarylene-$R^8$, substituted heteroarylene-$R^8$, heterocyclene-$R^8$, or substituted heterocyclene-$R^8$ or $R^3$ and $R^4$ together with the carbon atoms to which they are attached form a cycloalkyl-$R^8$, substituted cycloalkyl-$R^8$, cycloalkenyl-$R^8$, substituted cycloalkenyl-$R^8$, heterocycloalkyl-$R^8$, substituted heterocycloalkyl-$R^8$, heterocycloalkenyl-$R^8$, substituted heterocycloalkenyl-$R^8$, aryl-$R^8$, substituted aryl-$R^8$, heteroaryl-$R^8$ or substituted heteroaryl-$R^8$ ring;

$R^4$ is H, OH, alkylene-$R^9$, substituted alkylene-$R^9$, cycloalkylene-$R^9$, substituted cycloalkylene-$R^9$, alkenylene-$R^9$, substituted alkenylene-$R^9$, cycloalkenylene-$R^9$, substituted cycloalkenylene-$R^9$, alkynylene-$R^9$, substituted alkynylene-$R^9$, arylene-$R^9$, substituted arylene-$R^9$, heteroarylene-$R^9$, substituted heteroarylene-$R^9$, heterocyclene-$R^9$, or substituted heterocyclene-$R^9$ or $R^4$ and $R^5$ together with the carbon atoms to which they are attached form a cycloalkyl-$R^9$, substituted cycloalkyl-$R^9$, cycloalkenyl-$R^9$, substituted cycloalkenyl-$R^9$, heterocycloalkyl-$R^9$, substituted heterocycloalkyl-$R^9$, heterocycloalkenyl-$R^9$, substituted heterocycloalkenyl-$R^9$, aryl-$R^9$, substituted aryl-$R^9$, heteroaryl-$R^9$ or substituted heteroaryl-$R^9$ ring;

$R^5$ is H, OH, alkylene-$R^{10}$, substituted alkylene-$R^{10}$, cycloalkylene-$R^{10}$, substituted cycloalkylene-$R^{10}$, alkenylene-$R^{10}$, substituted alkenylene-$R^{10}$, cycloalkenylene-$R^{10}$, substituted cycloalkenylene-$R^{10}$, alkynylene-$R^{10}$, substituted alkynylene-$R^{10}$, arylene-$R^{10}$, substituted arylene-$R^{10}$, heteroarylene-$R^{10}$, substituted heteroarylene-$R^{10}$, heterocyclene-$R^{10}$, or substituted heterocyclene-$R^{10}$ or $R^5$ and $R^6$ together with the carbon atoms to which they are attached form a cycloalkyl-$R^{10}$, substituted cycloalkyl-$R^{10}$, cycloalkenyl-$R^{10}$, substituted cycloalkenyl-$R^{10}$, heterocycloalkyl-$R^{10}$, substituted heterocycloalkyl-$R^{10}$, heterocycloalkenyl-$R^{10}$, substituted heterocycloalkenyl-$R^{10}$, aryl-$R^{10}$, substituted aryl-$R^{10}$, heteroaryl-$R^{10}$ or substituted heteroaryl-$R^{10}$ ring;

$R^6$ is H, OH, alkylene-$R^{11}$, substituted alkylene-$R^{11}$, cycloalkylene-$R^{11}$, substituted cycloalkylene-$R^{11}$, alkenylene-$R^{11}$, substituted alkenylene-$R^{11}$, cycloalkenylene-$R^{11}$, substituted cycloalkenylene-$R^{11}$, alkynylene-$R^{11}$, substituted alkynylene-$R^{11}$, arylene-$R^{11}$, substituted arylene-$R^{11}$, heteroarylene-$R^{11}$, substituted heteroarylene-$R^{11}$, heterocyclene-$R^{11}$ or substituted heterocyclene-$R^{11}$;

with the proviso that only one of $R^3/R^4$, $R^4/R^5$ or $R^5/R^6$ form a ring;

$R^7$ is OH, an alkylamino group substituted with a moiety that is negatively charged at physiological pH and located 5 to 15 atoms from C-22 of the bile acid nucleus, a di-substituted alkylamino group substituted with L-D and a moiety that is negatively charged at physiological pH and located 5 to 15 atoms from C-22 of the bile acid nucleus, L-D or pharmaceutically acceptable salts thereof;

$R^8$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;

$R^9$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^3)_2$, $CO_2H$, $CO_2R^{13}$, $CONH_2$, $CONHR^{13}$, $CON(R^{13})_2$ or L-D;

$R^{10}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;

$R^{11}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;

$R^{12}$ is alkyl, substituted alkyl, cycloalkyl, substituted cycloalkyl, aryl, substituted aryl, heteroaryl or substituted heteroaryl;

$R^{13}$ is alkyl, substituted alkyl, cycloalkyl, substituted cycloalkyl, aryl, substituted aryl, heteroaryl or substituted heteroaryl;

dashed lines represent possible sites of unsaturation;
L is a covalent bond or a linking group;

D is a drug;
or a pharmaceutically acceptable salt thereof;
provided that
not more than one of the substituents $R^3$, $R^4$, $R^5$, $R^6$, and $R^7$ includes moiety L-D;
when $R^1$ and $R^2$ are CHOH, $R^5$ and $R^6$ are H, and $R^7$ is OH, then $R^3$ and $R^4$ together with the carbon atoms to which they are attached do not form

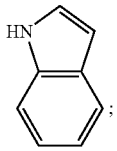

and when $R^1$ and $R^2$ are CHOH, $R^3$ and $R^6$ are H, and $R^7$ is OH, then $R^4$ and $R^5$ together with the carbon atoms to which they are attached do not form

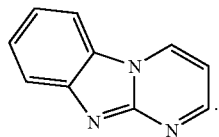

In another aspect, the invention is directed to methods for achieving prolonged therapeutic or prophylactic concentrations of a drug or active metabolite thereof in the systemic circulation of an animal comprising orally administering a compound of formula (I) to the animal:

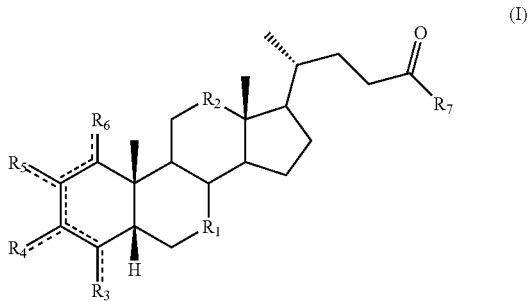

(I)

wherein
$R^1$ is $CH_2$, CHOH or $CR^{12}OH$;
$R^2$ is $CH_2$, CHOH or $CR^{12}OH$;
$R^3$ is H, OH, alkylene-$R^8$, substituted alkylene-$R^8$, cycloalkylene-$R^8$, substituted cycloalkylene-$R^8$, alkenylene-$R^8$, substituted alkenylene-$R^8$, cycloalkenylene-$R^8$, substituted cycloalkenylene-$R^8$, alkynylene-$R^8$, substituted alkynylene-$R^8$, arylene-$R^8$, substituted arylene-$R^8$, heteroarylene-$R^8$, substituted heteroarylene-$R^8$, heterocyclene-$R^8$, or substituted heterocyclene-$R^8$ or $R^3$ and $R^4$ together with the carbon atoms to which they are attached form a cycloalkyl-$R^8$, substituted cycloalkyl-$R^8$, cycloalkenyl-$R^8$, substituted cycloalkenyl-$R^8$, heterocycloalkyl-$R^8$, substituted heterocycloalkyl-$R^8$, heterocycloalkenyl-$R^8$, substituted heterocycloalkenyl-$R^8$, aryl-$R^8$, substituted aryl-$R^8$, heteroaryl-$R^8$ or substituted heteroaryl-$R^8$ ring;
$R^4$ is H, OH, alkylene-$R^9$, substituted alkylene-$R^9$, cycloalkylene-$R^9$, substituted cycloalkylene-$R^9$, alkenylene-$R^9$, substituted alkenylene-$R^9$, cycloalkenylene-$R^9$, substituted cycloalkenylene-$R^9$, alkynylene-$R^9$, substituted alkynylene-$R^9$, arylene-$R^9$, substituted arylene-$R^9$, heteroarylene-$R^9$, substituted heteroarylene-$R^9$, heterocyclene-$R^9$, or substituted heterocyclene-$R^9$ or $R^4$ and $R^5$ together with the carbon atoms to which they are attached form a cycloalkyl-$R^9$, substituted cycloalkyl-$R^9$, cycloalkenyl-$R^9$, substituted cycloalkenyl-$R^9$, heterocycloalkyl-$R^9$, substituted heterocycloalkyl-$R^9$, heterocycloalkenyl-$R^9$, substituted heterocycloalkenyl-$R^9$, aryl-$R^9$, substituted aryl-$R^9$, heteroaryl-$R^9$ or substituted heteroaryl-$R^9$ ring;
$R^5$ is H, OH, alkylene-$R^{10}$, substituted alkylene-$R^{10}$, cycloalkylene-$R^{10}$, substituted cycloalkylene-$R^{10}$, alkenylene-$R^{10}$, substituted alkenylene-$R^{10}$, cycloalkenylene-$R^{10}$, substituted cycloalkenylene-$R^{10}$, alkynylene-$R^{10}$, substituted alkynylene-$R^{10}$, arylene-$R^{10}$, substituted arylene-$R^{10}$, heteroarylene-$R^{10}$, substituted heteroarylene-$R^{10}$, heterocyclene-$R^{10}$, or substituted heterocyclene-$R^{10}$ or $R^5$ and $R^6$ together with the carbon atoms to which they are attached form a cycloalkyl-$R^{10}$, substituted cycloalkyl-$R^{10}$, cycloalkenyl-$R^{10}$, substituted cycloalkenyl-$R^{10}$, heterocycloalkyl-$R^{10}$, substituted heterocycloalkyl-$R^{10}$, heterocycloalkenyl-$R^{10}$, substituted heterocycloalkenyl-$R^{10}$, aryl-$R^{10}$, substituted aryl-$R^{10}$, heteroaryl-$R^{10}$ or substituted heteroaryl-$R^{10}$ ring;
$R^6$ is H, OH, alkylene-$R^{11}$, substituted alkylene-$R^{11}$, cycloalkylene-$R^{11}$, substituted cycloalkylene-$R^{11}$, alkenylene-$R^{11}$, substituted alkenylene-$R^{11}$, cycloalkenylene-$R^{11}$, substituted cycloalkenylene-$R^{11}$, alkynylene-$R^{11}$, substituted alkynylene-$R^{11}$, arylene-$R^{11}$, substituted arylene-$R^{11}$, heteroarylene-$R^{11}$, substituted heteroarylene-$R^{11}$, heterocyclene-$R^{11}$ or substituted heterocyclene-$R^{11}$;

with the proviso that only one of $R^3/R^4$, $R^4/R^5$ or $R^5/R^6$ form a ring;
$R^7$ is OH, an alkylamino group substituted with a moiety that is negatively charged at physiological pH and located 5 to 15 atoms from C-22 of the bile acid nucleus, a di-substituted alkylamino group substituted with L-D and a moiety that is negatively charged at physiological pH and located 5 to 15 atoms from C-22 of the bile acid nucleus, L-D or pharmaceutically acceptable salts thereof;
$R^8$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;
$R^9$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;
$R^{10}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;
$R^{11}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;
$R^{12}$ is alkyl, substituted alkyl, cycloalkyl, substituted cycloalkyl, aryl, substituted aryl, heteroaryl or substituted heteroaryl;

R[13] is alkyl, substituted alkyl, cycloalkyl, substituted cycloalkyl, aryl, substituted aryl, heteroaryl or substituted heteroaryl;

dashed lines represent possible sites of unsaturation;

D is a drug;

L is a cleavable linking group, wherein a sufficient amount of the linking group is cleaved to release D or an active metabolite thereof thereby providing a therapeutic or prophylactic systemic blood concentration in said animal;

or a pharmaceutically acceptable salt thereof;

provided that not more than one of the substituents $R^3$, $R^4$, $R^5$, $R^6$, and $R^7$ includes moiety L-D;

when $R^1$ and $R^2$ are CHOH, $R^5$ and $R^6$ are H, and $R^7$ is OH, then $R^3$ and $R^4$ together with the carbon atoms to which they are attached do not form

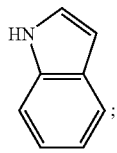

and when $R^1$ and $R^2$ are CHOH, $R^3$ and $R^6$ are H, and $R^7$ is OH, then $R^4$ and $R^5$ together with the carbon atoms to which they are attached do not form

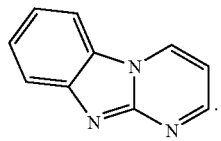

In a preferred method, at least a portion of the cleavable linker cleaves in the contents of the intestinal lumen of said animal.

In another preferred method, at least a portion of the cleavable linker cleaves in the intestinal cells of said animal.

In another preferred method, at least a portion of the cleavable linker cleaves in the blood of said animal.

In another preferred method, at least a portion of the cleavable linker cleaves in the liver cells of said animal.

In another preferred method, at least a portion of the cleavable linker cleaves in the biliary tract of said animal.

In another aspect, the invention is directed to methods for enhancing the systemic bioavailability of a drug or an active metabolite thereof in an animal by increasing the amount of drug translocated across the intestinal wall of said animal comprising orally administering a compound of formula (I) to said animal:

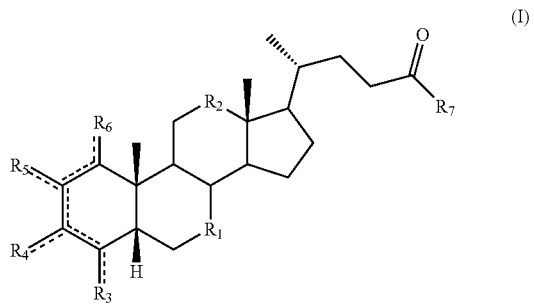

(I)

wherein $R^1$ is $CH_2$, CHOH or $CR^{12}OH$;

$R^2$ is $CH_2$, CHOH or $CR^{12}OH$;

$R^3$ is H, OH, alkylene-$R^8$, substituted alkylene-$R^8$, cycloalkylene-$R^8$, substituted cycloalkylene-$R^8$, alkenylene-$R^8$, substituted alkenylene-$R^8$, cycloalkenylene-$R^8$, substituted cycloalkenylene-$R^8$, alkynylene-$R^8$, substituted alkynylene-$R^8$, arylene-$R^8$, substituted arylene-$R^8$, heteroarylene-$R^8$, substituted heteroarylene-$R^8$, heterocyclene-$R^8$, or substituted heterocyclene-$R^8$ or $R^3$ and $R^4$ together with the carbon atoms to which they are attached form a cycloalkyl-$R^8$, substituted cycloalkyl-$R^8$, cycloalkenyl-$R^8$, substituted cycloalkenyl-$R^8$, heterocycloalkyl-$R^8$, substituted heterocycloalkyl-$R^8$, heterocycloalkenyl-$R^8$, substituted heterocycloalkenyl-$R^8$, aryl-$R^8$, substituted aryl-$R^8$, heteroaryl-$R^8$ or substituted heteroaryl-$R^8$ ring;

$R^4$ is H, OH, alkylene-$R^9$, substituted alkylene-$R^9$, cycloalkylene-$R^9$, substituted cycloalkylene-$R^9$, alkenylene-$R^9$, substituted alkenylene-$R^9$, cycloalkenylene-$R^9$, substituted cycloalkenylene-$R^9$, alkynylene-$R^9$, substituted alkynylene-$R^9$, arylene-$R^9$, substituted arylene-$R^9$, heteroarylene-$R^9$, substituted heteroarylene-$R^9$, heterocyclene-$R^9$, or substituted heterocyclene-$R^9$ or $R^4$ and $R^5$ together with the carbon atoms to which they are attached form a cycloalkyl-$R^9$, substituted cycloalkyl-$R^9$, cycloalkenyl-$R^9$, substituted cycloalkenyl-$R^9$, heterocycloalkyl-$R^9$, substituted heterocycloalkyl-$R^9$, heterocycloalkenyl-$R^9$, substituted heterocycloalkenyl-$R^9$, aryl-$R^9$, substituted aryl-$R^9$, heteroaryl-$R^9$ or substituted heteroaryl-$R^9$ ring;

$R^5$ is H, OH, alkylene-$R^{10}$, substituted alkylene-$R^{10}$, cycloalkylene-$R^{10}$, substituted cycloalkylene-$R^{10}$, alkenylene-$R^{10}$, substituted alkenylene-$R^{10}$, cycloalkenylene-$R^{10}$, substituted cycloalkenylene-$R^{10}$, alkynylene-$R^{10}$, substituted alkynylene-$R^{10}$, arylene-$R^{10}$, substituted arylene-$R^{10}$, heteroarylene-$R^{10}$, substituted heteroarylene-$R^{10}$, heterocyclene-$R^{10}$, or substituted heterocyclene-$R^{10}$ or $R^5$ and $R^6$ together with the carbon atoms to which they are attached form a cycloalkyl-$R^{10}$, substituted cycloalkyl-$R^{10}$, cycloalkenyl-$R^{10}$, substituted cycloalkenyl-$R^{10}$, heterocycloalkyl-$R^{10}$, substituted heterocycloalkyl-$R^{10}$, heterocycloalkenyl-$R^{10}$, substituted heterocycloalkenyl-$R^{10}$, aryl-$R^{10}$, substituted aryl-$R^{10}$, heteroaryl-$R^{10}$ or substituted heteroaryl-$R^{10}$ ring;

$R^6$ is H, OH, alkylene-$R^{11}$, substituted alkylene-$R^{11}$, cycloalkylene-$R^{11}$, substituted cycloalkylene-$R^{11}$, alkenylene-$R^{11}$, substituted alkenylene-$R^{11}$, cycloalkenylene-$R^{11}$, substituted cycloalkenylene-$R^{11}$, alkynylene-$R^{11}$, substituted alkynylene-$R^{11}$, arylene-$R^{11}$, substituted arylene-$R^{11}$, heteroarylene-$R^{11}$, substituted heteroarylene-$R^{11}$, heterocyclene-$R^{11}$ or substituted heterocyclene-$R^{11}$;

with the proviso that only one of $R^3/R^4$, $R^4/R^5$ or $R^5/R^6$ form a ring;

$R^7$ is OH, an alkylamino group substituted with a moiety that is negatively charged at physiological pH and located 5 to 15 atoms from C-22 of the bile acid nucleus, a di-substituted alkylamino group substituted with L-D and a moiety that is negatively charged at physiological pH and located 5 to 15 atoms from C-22 of the bile acid nucleus, L-D or pharmaceutically acceptable salts thereof;

$R^8$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;

$R^9$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR$^{13}$, SH, SR$^3$, NH$_2$, NHR$^{13}$, N(R$^{13}$)$_2$, CO$_2$H, CO$_2$R$^{13}$, CONH$_2$, CONHR$^{13}$, CON(R$_{13}$)$_2$ or L-D;

R$^{10}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR$^{13}$, SH, SR$^{13}$, NH$_2$, NHR$^{13}$, N(R$^{13}$)$_2$, CO$_2$H, CO$_2$R$^{13}$, CONH$_2$, CONHR$^{13}$, CON(R$^{13}$)$_2$ or L-D;

R$^{11}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR$^{13}$, SH, SR$^{13}$, NH$_2$, NHR$^{13}$, N(R$^{13}$)$_2$, CO$_2$H, CO$_2$R$^{13}$, CONH$_2$, CONHR$^{13}$, CON(R$^{13}$)$_2$ or L-D;

R$^{12}$ is alkyl, substituted alkyl, cycloalkyl, substituted cycloalkyl, aryl, substituted aryl, heteroaryl or substituted heteroaryl;

R$^{13}$ is alkyl, substituted alkyl, cycloalkyl, substituted cycloalkyl, aryl, substituted aryl, heteroaryl or substituted heteroaryl;

dashed lines represent possible sites of unsaturation;

D is a drug which is incompletely translocated across the intestinal wall of the animal;

L is a cleavable linking group, wherein a sufficient amount of the linking group is cleaved to release D or an active metabolite thereof thereby providing a therapeutic or prophylactic systemic blood concentration in the animal;

or a pharmaceutically acceptable salt thereof;

provided that not more than one of the substituents R$^3$, R$^4$, R$^5$, R$^6$, and R$^7$ includes moiety L-D;

when R$^1$ and R$^2$ are CHOH, R$^5$ and R$^6$ are H, and R$^7$ is OH, then R$^3$ and R$^4$ together with the carbon atoms to which they are attached do not form

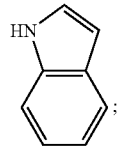

;

and when R$^1$ and R$^2$ are CHOH, R$^3$ and R$^6$ are H, and R$^7$ is OH, then R$^4$ and R$^5$ together with the carbon atoms to which they are attached do not form

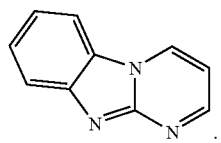

.

In a preferred method, at least a portion of the cleavable linker cleaves in the contents of the intestinal lumen of said animal.

In another preferred method, at least a portion of the cleavable linker cleaves in the intestinal cells of said animal.

In another preferred method, at least a portion of the cleavable linker cleaves in the blood of said animal.

In another preferred method, at least a portion of the cleavable linker cleaves in the liver cells of said animal.

In another preferred method, at least a portion of the cleavable linker cleaves in the biliary tract of said animal.

In another aspect, the invention is directed to methods for modulating cholesterol metabolism in an animal comprising orally administering to the animal a compound of formula (I).

In a further aspect, the invention is directed to a method of treating a condition in a mammal selected from the group consisting of gallstone, a gastrointestinal inflammatory disorder, colorectal cancer, a viral infection, and a fungal infection, comprising orally administering to the animal a compound of formula (I).

In an additional aspect, the invention is directed to a method for increasing oral or nasal mucosal permeability, comprising applying a compound of formula (I) to the oral or nasal mucosa of an animal.

In a further aspect, the invention is directed to a method of inhibiting apoptosis in an animal, comprising orally administering to the animal a compound of formula (I).

In an additional aspect, the invention is directed to a method of delivering a therapeutic drug to the liver of an animal comprising orally administering to the animal a compound of formula (I), wherein the compound contains L-D.

A further aspect of the invention is directed to a method of delivering a diagnostic agent to the liver of an animal comprising orally administering to the animal a compound of formula (I).

In another aspect, the invention is directed to compounds of formula (II), which are useful for the production of compounds of formula (I):

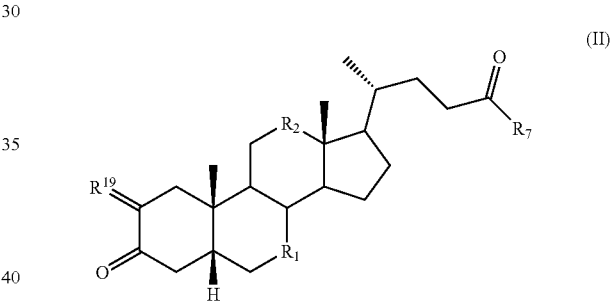

wherein

R$^1$ is CH$_2$, CHOH or CR$^{12}$OH;

R$^2$ is CH$_2$, CHOH or CR$^{12}$OH;

R$^7$ is OH, an alkylamino group substituted with a moiety that is negatively charged at physiological pH and located 5 to 15 atoms from C-22 of the bile acid nucleus, a di-substituted alkylamino group substituted with L-D and a moiety that is negatively charged at physiological pH and located 5 to 15 atoms from C-22 of the bile acid nucleus, L-D or pharmaceutically acceptable salts thereof;

R$^{12}$ is alkyl, aryl or substituted aryl;

R$^{19}$ is O, CH(OH), CHN(R$^{20}$)(R$^{21}$), C(SR$^{20}$)(SR$^{21}$), C(SR$^{20}$)NH(R$^{21}$), C(SR$^{20}$)N(R$^{21}$)(R$^{22}$) or C(R$^{21}$)(R$^{22}$);

R$^{20}$ is alkyl, substituted alkyl, cycloalkyl, substituted cycloalkyl, aryl, substituted aryl, heteroaryl or substituted heteroaryl;

R$^{21}$ is alkyl, substituted alkyl, cycloalkyl, substituted cycloalkyl, aryl, substituted aryl, heteroaryl or substituted heteroaryl;

R$^{22}$ is alkyl, substituted alkyl, cycloalkyl, substituted cycloalkyl, aryl, substituted aryl, heteroaryl or substituted heteroaryl;

L is a covalent bond or a linking group; and

D is a drug.

Preferably, R$^{20}$ is alkyl, R$^{21}$ is alkyl and R$^{22}$ is alkyl.

In a particularly preferred compound, $R^{20}$ is methyl, $R^{21}$ is methyl and $R^{22}$ is methyl.

In another aspect, the invention is directed to compounds of formula (III), which are useful for the production of compounds of formula (I):

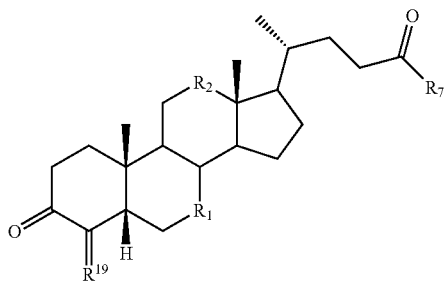

(III)

wherein $R^1$ is $CH_2$, CHOH or $CR^{12}OH$;

$R^2$ is $CH_2$, CHOH or $CR^{12}OH$;

$R^7$ is OH, an alkylamino group substituted with a moiety that is negatively charged at physiological pH and located 5 to 15 atoms from C-22 of the bile acid nucleus, a di-substituted alkylamino group substituted with L-D and a moiety that is negatively charged at physiological pH and located 5 to 15 atoms from C-22 of the bile acid nucleus, L-D or pharmaceutically acceptable salts thereof;

$R^{12}$ is alkyl, aryl or substituted aryl;

$R^{19}$ is O, CH(OH), $CHN(R^{20})(R^{21})$, $C(SR^{20})(SR^{21})$, $C(SR^{20})NH(R^{21})$, $C(SR^{20})N(R^{21})(R^{22})$ or $C(R^{21})(R^{22})$;

$R^{20}$ is alkyl, substituted alkyl, cycloalkyl, substituted cycloalkyl, aryl, substituted aryl, heteroaryl or substituted heteroaryl;

$R^{21}$ is alkyl, substituted alkyl, cycloalkyl, substituted cycloalkyl, aryl, substituted aryl, heteroaryl or substituted heteroaryl;

$R^{22}$ is alkyl, substituted alkyl, cycloalkyl, substituted cycloalkyl, aryl, substituted aryl, heteroaryl or substituted heteroaryl;

L is a covalent bond or a linking group; and

D is a drug.

Preferably, $R^{20}$ is alkyl, $R^{21}$ is alkyl and $R^{22}$ is alkyl.

In a particularly preferred compound, $R^{20}$ is methyl, $R^{21}$ is methyl and $R^{22}$ is methyl.

In another aspect, the invention is directed to compounds of formula (IV), which are useful for the production of compounds of formula (I):

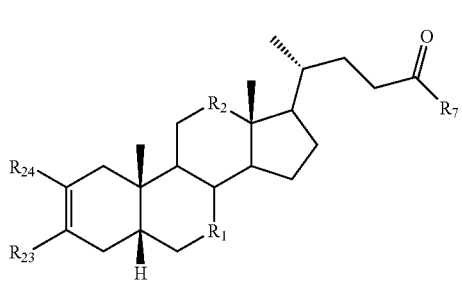

(IV)

wherein $R^1$ is $CH_2$, CHOH or $CR^{12}OH$;

R2 is CH2, CHOH or CR12OH;

$R^7$ is OH, an alkylamino group substituted with a moiety that is negatively charged at physiological pH and located 5 to 15 atoms from C-22 of the bile acid nucleus, a di-substituted alkylamino group substituted with L-D and a moiety that is negatively charged at physiological pH and located 5 to 15 atoms from C-22 of the bile acid nucleus, L-D or pharmaceutically acceptable salts thereof;

$R^{12}$ is alkyl, aryl or substituted aryl;

$R^{23}$ is halo or $OR^{25}$;

$R^{24}$ is H, alkyl or substituted alkyl;

$R^{25}$ is a protecting group;

L is a covalent bond or a linking group; and

D is a drug.

Preferably, $R^{25}$ is TMS, TBDMS, acetyl, tosyl, mesyl or triflyl.

In another aspect, the invention is directed to compounds of formula (V), which are useful for the production of compounds of formula (I):

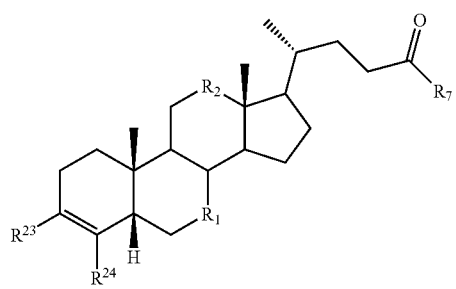

(V)

wherein $R^1$ is $CH_2$, CHOH or $CR^{12}OH$;

$R^2$ is $CH_2$, CHOH or $CR^{12}OH$;

$R^7$ is OH, an alkylamino group substituted with a moiety that is negatively charged at physiological pH and located 5 to 15 atoms from C-22 of the bile acid nucleus, a di-substituted alkylamino group substituted with L-D and a moiety that is negatively charged at physiological pH and located 5 to 15 atoms from C-22 of the bile acid nucleus, L-D or pharmaceutically acceptable salts thereof;

$R^{12}$ is alkyl, aryl or substituted aryl;

$R^{23}$ is halo or $OR^{25}$;

$R^{24}$ is H, alkyl or substituted alkyl;

$R^{25}$ is a protecting group;

L is a covalent bond or a linking group; and

D is a drug.

Preferably, $R^{25}$ is TMS, TBDMS, acetyl, tosyl, mesyl or triflyl.

In another aspect, the invention is directed to compounds of formula (VI), which are useful for the production of compounds of formula (I):

(VI)

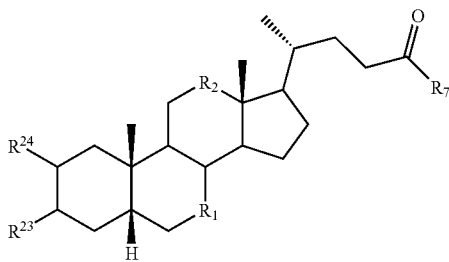

wherein
$R^1$ is $CH_2$, CHOH or $CR^{12}OH$;
$R^2$ is $CH_2$, CHOH or $CR^{12}OH$;
$R^7$ is OH, an alkylamino group substituted with a moiety that is negatively charged at physiological pH and located 5 to 15 atoms from C-22 of the bile acid nucleus, a di-substituted alkylamino group substituted with L-D and a moiety that is negatively charged at physiological pH and located 5 to 15 atoms from C-22 of the bile acid nucleus, L-D or pharmaceutically acceptable salts thereof;
$R^{12}$ is alkyl, aryl or substituted aryl;
$R^{23}$ is halo or $OR^{25}$;
$R^{24}$ is H, alkyl or substituted alkyl;
$R^{25}$ is a protecting group;
L is a covalent bond or a linking group; and
D is a drug.
Preferably, $R^{25}$ is TMS, TBDMS, acetyl, tosyl, mesyl or triflyl.

In another aspect, the invention is directed to compounds of formula (VII), which are useful for the production of compounds of formula (I):

(VII)

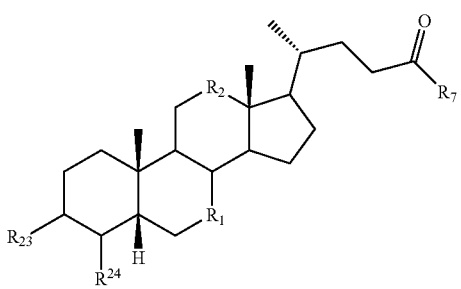

wherein
$R^1$ is $CH_2$, CHOH or $CR^{12}OH$;
$R^2$ is $CH_2$, CHOH or $CR^{12}OH$;
$R^7$ is OH, an alkylamino group substituted with a moiety that is negatively charged at physiological pH and located 5 to 15 atoms from C-22 of the bile acid nucleus, a di-substituted alkylamino group substituted with L-D and a moiety that is negatively charged at physiological pH and located 5 to 15 atoms from C-22 of the bile acid nucleus, L-D or pharmaceutically acceptable salts thereof;
$R^{12}$ is alkyl, aryl or substituted aryl;
$R^{23}$ is halo or $OR^{25}$;
$R^{24}$ is H, alkyl or substituted alkyl;
$R^{25}$ is a protecting group;

L is a covalent bond or a linking group; and
D is a drug.
Preferably, $R^{25}$ is TMS, TBDMS, acetyl, tosyl, mesyl or triflyl.

In another aspect, the invention is directed to compounds of formula (VIII), which are useful for the production of compounds of formula (I):

(VIII)

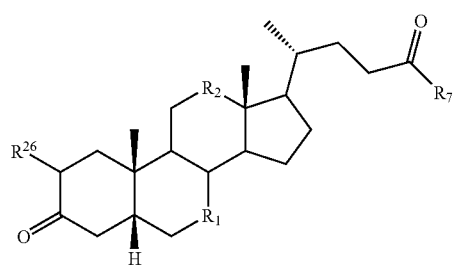

wherein
$R^1$ is $CH_2$, CHOH or $CR^{12}OH$;
$R^2$ is $CH_2$, CHOH or $CR^{12}OH$;
$R^7$ is OH, an alkylamino group substituted with a moiety that is negatively charged at physiological pH and located 5 to 15 atoms from C-22 of the bile acid nucleus, a di-substituted alkylamino group substituted with L-D and a moiety that is negatively charged at physiological pH and located 5 to 15 atoms from C-22 of the bile acid nucleus, L-D or pharmaceutically acceptable salts thereof;
$R^{12}$ is alkyl, aryl or substituted aryl;
$R^{26}$ is alkyl or substituted alkyl;
L is a covalent bond or a linking group; and
D is a drug.
Preferably, substituents $R^{26}$–$R^{32}$ are as follows:
$R^{26}$ is $CH(R^{27})C(O)R^{28}$ or $CH(R^{29})CCR^{30}$;
$R^{27}$ is H, alkyl, substituted alkyl, aryl or substituted aryl;
$R^{28}$ is H, alkyl, substituted alkyl, aryl, substituted aryl, $OR^{31}$, $SR^{31}$ or $NR^{31}R^{32}$;
$R^{29}$ is H, alkyl, substituted alkyl aryl or substituted aryl;
$R^{30}$ is H, alkyl, substituted alkyl, aryl or substituted aryl;
$R^{31}$ is H, alkyl, substituted alkyl, aryl or substituted aryl;
$R^{32}$ is H, alkyl, substituted alkyl, aryl or substituted aryl.

In another aspect, the invention is directed to compounds of formula (IX), which are useful for the production of compounds of formula (I):

(IX)

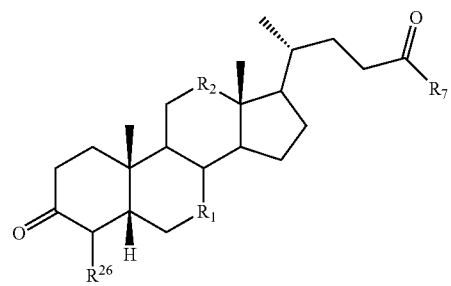

wherein
$R^1$ is $CH_2$, CHOH or $CR^{12}OH$;
$R^2$ is $CH_2$, CHOH or $CR^{12}OH$;

$R^7$ is OH, an alkylamino group substituted with a moiety that is negatively charged at physiological pH and located 5 to 15 atoms from C-22 of the bile acid nucleus, a di-substituted alkylamino group substituted with L-D and a moiety that is negatively charged at physiological pH and located 5 to 15 atoms from C-22 of the bile acid nucleus, L-D or pharmaceutically acceptable salts thereof;

$R^{12}$ is alkyl, aryl or substituted aryl;

$R^{26}$ is alkyl or substituted alkyl;

L is a covalent bond or a linking group; and

D is a drug.

Preferably, substituents $R^{26}$–$R^{32}$ are as follows:

$R^{26}$ is $CH(R^{27})C(O)R^{28}$ or $CH(R^{29})CCR^{30}$;

$R^{27}$ is H, alkyl, substituted alkyl, aryl or substituted aryl;

$R^{28}$ is H, alkyl, substituted alkyl, aryl, substituted aryl, $OR^{31}$, $SR^{31}$ or $NR^{31}R^{32}$;

$R^{29}$ is H, alkyl, substituted alkyl, aryl or substituted aryl;

$R^{30}$ is H, alkyl, substituted alkyl, aryl or substituted aryl;

$R^{31}$ is H, alkyl, substituted alkyl, aryl or substituted aryl;

$R^{32}$ is H, alkyl, substituted alkyl, aryl or substituted aryl.

BRIEF DESCRIPTION OF THE DRAWINGS

FIGS. 1A–1E illustrate the preparation of steroidal building blocks that are used in the preparation of compounds of formula (I).

FIG. 2 illustrates the preparation of amino acid building blocks that are used in the preparation of compounds of formula (I).

FIGS. 3A–3L illustrate synthetic strategies for obtaining compounds of formula (I), wherein the compounds have a 5-membered fused heterocycle.

FIGS. 4A–4G illustrate synthetic strategies for obtaining compounds of formula (I), wherein the compounds have a 6-membered fused heterocycle.

FIGS. 5A–5E illustrate synthetic strategies for obtaining compounds of formula (I), wherein the compounds have either a 7-membered or 8-membered fused heterocycle.

FIGS. 6A–6D illustrate synthetic strategies for obtaining compounds of formula (I), wherein the compounds are derivatives of either glyco- or taurocholanic acids.

FIGS. 7A–7E illustrate synthetic strategies for conjugating drug molecules or surrogates to derivatives of either glyco- or taurocholanic acids.

DETAILED DESCRIPTION OF THE INVENTION

Figure 7B:
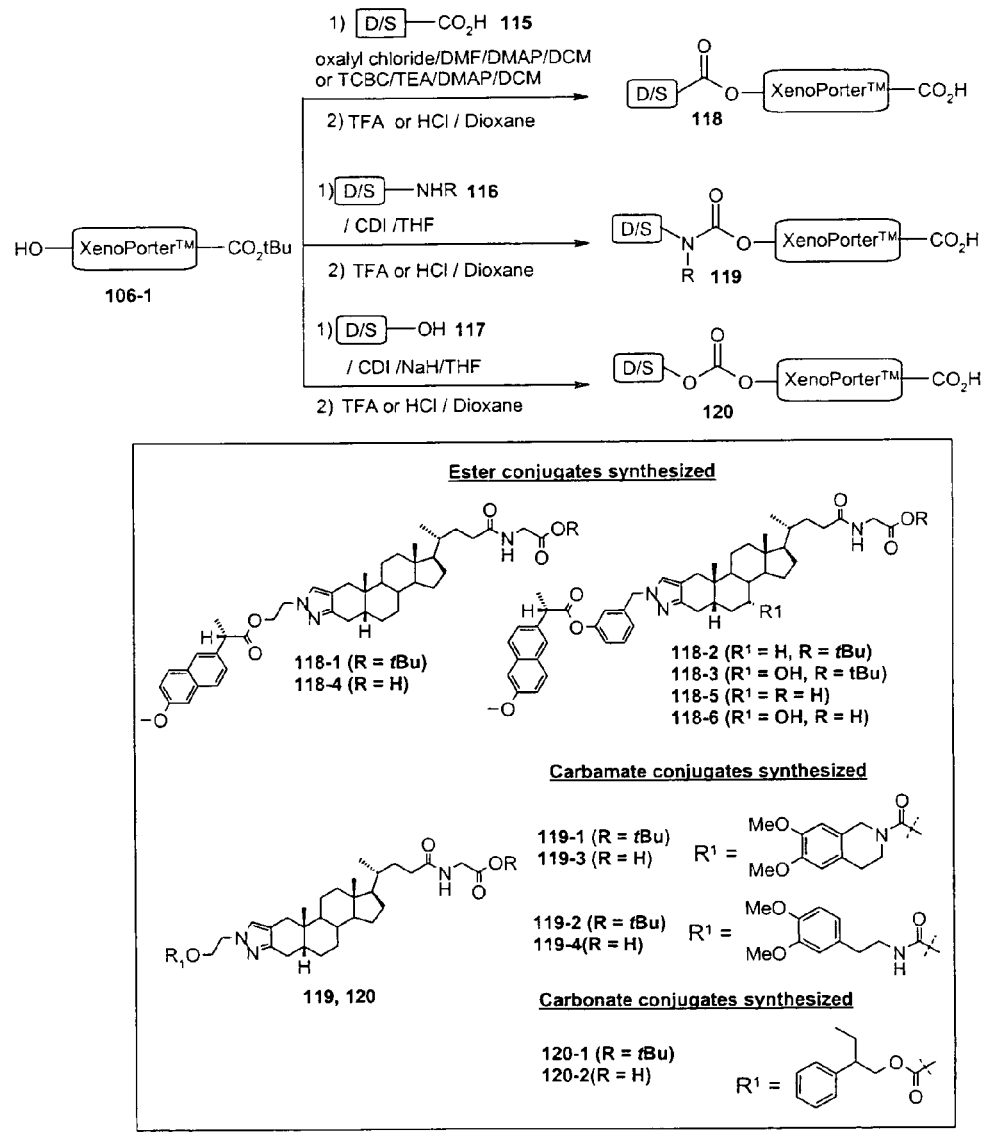

This invention provides compositions and methods for providing enhanced systemic blood concentrations of orally delivered drugs that are incompletely translocated across the intestinal wall of an animal. This invention also provides methods and compositions for the sustained release of drugs, whether poorly or readily bioavailable via oral delivery to animals. This invention further provides methods and compositions for modulating cholesterol metabolism. However, prior to describing this invention in further detail, the following terms will first be defined:

Definitions

As used herein, the term "animal" refers to various species such as mammalian and avian species including, by way of example, humans, cattle, sheep, horses, dogs, cats, turkeys, chicken, and the like. Preferably, the animal is a mammal and even more preferably is a human.

"Active metabolite of a drug" refers to products of in vivo modification of a compound of formula (I) which have therapeutic or prophylactic effect.

"Active transport or active transport mechanism" refers to the movement of molecules across cellular membranes that:
 a) is directly or indirectly dependent on an energy mediated process (i.e. driven by ATP hydrolysis, ion gradient, etc);
 b) occurs by facilitated diffusion mediated by interaction with specific transporter proteins; or
 c) occurs through a modulated solute channel.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 20 carbon atoms and more preferably 2 to 6 carbon atoms and having at least 1 and preferably from 1–2 sites of alkenyl unsaturation.

"Alkenylene" refers to a divalent alkenylene group preferably having from 2 to 20 carbon atoms and more preferably 1 to 6 carbon atoms and having from 1 to 2 sites of alkenyl unsaturation. This term is exemplified by groups such as ethenylene (—CH=CH—), propenylene (—CH$_2$CH=CH—), and the like.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkyl" refers to alkyl groups preferably having from 1 to 20 carbon atoms and more preferably 1 to 6 carbon atoms. This term is exemplified by groups such as methyl, t-butyl, n-heptyl, octyl, dodecyl and the like.

"Alkylene" refers to a divalent alkylene group preferably having from 1 to 20 carbon atoms and more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkynyl" refers to alkynyl group preferably having from 2 to 20 carbon atoms and more preferably 3 to 6 carbon atoms and having at least 1 and preferably from 1–2 sites of alkynyl unsaturation.

"Alkynylene" refers to a divalent alkynylene group preferably having from 2 to 20 carbon atoms and more preferably 1 to 6 carbon atoms and having from 1 to 2 sites of alkynyl unsaturation. This term is exemplified by groups such as ethynylene, propynylene and the like.

"Amidino" refers to the group H$_2$NC(=NH)— and the term "alkylamidino" refers to compounds having 1 to 3 alkyl groups (e.g., alkylHNC(=NH)—).

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like). Preferred aryls include phenyl and naphthyl.

"Arylene" refers to a divalent unsaturated aromatic carbocyclic group of from 6 to 14 carbon atoms having a single ring (e.g., phenylene) or multiple condensed rings (e.g., naphthylene or anthrylene) which condensed rings may or may not be aromatic. Preferred arylenes include phenylene and naphthylene.

"Aryloxy" refers to the group aryl-O— which includes, by way of example, phenoxy, naphthoxy, and the like.

"Aryloxyaryl" refers to the group -aryl-O-aryl.

"Bile acid transport system" refers to any membrane transporter protein capable of causing a bile acid or a derivative thereof to be translocated across a membrane of a cell of the gastrointestinal tract or liver.

"Cleavable linker or cleavable linking group" refers to linkers that contain one or more functional groups which permit cleavage of such groups in vivo by, for example, endogenous enzymes. Preferably, the functional group subject to cleavage in the cleavable linker is attached adjacent the drug moiety, D, such that upon cleavage, the free drug is released. The cleavable linker preferably comprises one or more functional groups such as ester groups, amide groups, glycolamide ester groups, amidomethyl esters, acyloxyalkyl esters, alkoxycarbonyloxyalkyl esters, and the like. FIGS. 7A through 7D illustrate suitable cleavable linker functionality which can be used.

"Conjugating" refers to the formation of a covalent bond.

"Cycloalkenyl" refers to cyclic alkenyl groups of from 3 to 8 carbon atoms having a single cyclic ring.

"Cycloalkenylene" refers to a divalent cyclic alkenylene groups of from 3 to 8 carbon atoms having a single cyclic ring.

"Cycloalkoxy" refers to —O-cycloalkyl groups.

"Cycloalkyl" refers to cyclic alkyl groups of from 3 to 8 carbon atoms having a single cyclic ring including, by way of example, cyclopropyl, cyclobutyl, cyclopentyl, cyclooctyl and the like. Excluded from this definition are multi-ring alkyl groups such as adamantanyl, etc.

"Cycloalkylene" refers to divalent cyclic alkylene groups of from 3 to 8 carbon atoms having a single cyclic ring including, by way of example, cyclopropylene, cyclobutylene, cyclopentylene, cyclooctylene and the like.

"N,N-Dimethylcarbamyloxy" refers to the group —OC(O)N(CH$_3$)$_2$.

"Drug/cleavable linker/transporter compound" (which sometimes is referred to as the "drug-transporter compound", "drug/linker/transporter compound" and "drug/cleavable linker/transporter conjugate" refers to a compound of formula (I).

"Drugs that are either completely or incompletely translocated across the intestinal wall into the systemic blood circulation of an animal" refer to any of the well known orally delivered drugs currently delivered by oral administration as well as drugs which cannot be orally administered because such drugs are insufficiently translocated across the intestinal wall of an animal to provide therapeutic or prophylactic blood concentrations in said animal.

Preferably, drugs that fall into the following categories:
i) drugs which are insufficiently translocated across the intestinal wall to provide therapeutic or prophylactic blood concentrations;
ii) incompletely translocated drugs; or
iii) drugs that are either completely or incompletely translocated across the intestinal wall into the systemic blood circulation of an animal contain suitable functionality to provide points of linkage in forming a compound of formula (I) above. Such functionality includes, by way of example, carboxyl groups, amine groups and hydroxyl groups.

Examples of drugs containing carboxyl groups include, for instance, angiotensin-converting enzyme inhibitors such as alecapril, captopril, 1-[4-carboxy-2-methyl-2R,4R-pentanoyl]-2,3-dihydro-2S-indole-2-carboxylic acid, enalaprilic acid, lisinopril, N-cyclopentyl-N-[3-[(2,2-dimethyl-1-oxopropyl)thio]-2-methyl-1-oxopropyl]glycine, pivopril, (2R, 4R)-2-hydroxyphenyl)-3-(3-mercaptopropionyl)-4-thiazolidinecarboxylic acid, (S)benzamido-4-oxo-6-phenylhexenoyl-2-carboxypyrrolidine, [2S-1[R*(R*))]]2α,3αβ,7αβ]-1[2-[[1-carboxy-3-phenylpropyl]-amino]-1-oxopropyl]octahydro-1H-indole-2-carboxylic acid, [3S-1[R*(R*))]], 3R*]-2-[2-[[1-carboxy-3-phenylpropyl]-amino]-1-oxopropyl]- 1,2,3,4-tetrahydro-3-isoquinolone carboxylic acid and tiopronin; cephalosporin antibiotics such as cefaclor, cefadroxil, cefamandole, cefatrizine, cefazedone, cefazuflur, cefazolin, cefbuperazone, cefmenoxime, cefmetazole, cefodizime, cefonicid, cefoperazone, ceforanide, cefotaxime, cefotefan, cefotiam, cefoxitin, cefpimizole, cefpirome, cefroxadine, cefsulodin, cefpiramide, ceftazidime, ceftezole, ceftizoxime, ceftriaxone, cefuroxime, cephacetrile, cephalexin, cephaloglycin, cephaloridine, cephalosporin, cephanone, cephradine and latamoxef; penicillins such as amoxycillin, ampicillin, apalcillin, azidocillin, azlocillin, benzylpencillin, carbenicillin, carfecillin, carindacillin, cloxacillin, cyclacillin, dicloxacillin, epicillin, flucloxacillin, hetacillin, methicillin, mezlocillin, nafcillin, oxacillin, phenethicillin, piperazillin, sulbenicllin, temocillin and ticarcillin; non-steroidal antiinflammatory agents such as acametacin, alclofenac, alminoprofen, aspirin (acetylsalicylic acid), 4-biphenylacetic acid, bucloxic acid, carprofen, cinchofen, cinmetacin, clometacin, clonixin, diclenofac, diflunisal, etodolac, fenbufen, fenclofenac, fenclosic acid, fenoprofen, ferobufen, flufenamic acid, flufenisal, flurbiprofin, fluprofen, flutiazin, ibufenac, ibuprofen, indomethacin, indoprofen, ketoprofen, ketorolac, lonazolac, loxoprofen, meclofenamic acid, mefenamic acid, 2-(8-methyl-10,11-dihydro-11-oxodibenz[b,f] oxepin-2-yl)propionic acid, naproxen, nifluminic acid, O-(carbamoylphenoxy)acetic acid, oxoprozin, pirprofen, prodolic acid, salicylic acid, salicylsalicylic acid, sulindac, suprofen, tiaprofenic acid, tolfenamic acid, tolmetin and zopemirac; prostaglandins such as ciprostene, 16-deoxy-16-hydroxy-16-vinyl prostaglandin $E_2$, 6,16-dimethylprostaglandin $E_2$, epoprostostenol, meteneprost, nileprost, prostacyclin, prostaglandins $E_1$, $E_2$, or $F_{2\alpha}$ and thromboxane $A_2$; quinolone antibiotics such as acrosoxacin, cinoxacin, ciprofloxacin, enoxacin, flumequine, naladixic acid, norfloxacin, ofloxacin, oxolinic acid, pefloxacin, pipemidic acid and piromidic acid.

Representative drugs containing amine groups include: acebutalol, albuterol, alprenolol, atenolol, bunolol, butopamine, butoxamine, carbuterol, cartelolol, colterol, deterenol, dexpropanolol, diacetolol, dobutamine, exaprolol, exprenolol, fenoterol, fenyripol, labotolol, levobunolol, metolol, metaproterenol, metoprolol, nadolol, pamatolol, penbutalol, pindolol, pirbuterol, practolol, prenalterol, primidolol, prizidilol, procaterol, propanolol, quinterenol, rimiterol, ritodrine, solotol, soterenol, sulfiniolol, sulfinterol, sulictidil, tazaolol, terbutaline, timolol, tiprenolol, tipridil, tolamolol, thiabendazole, albendazole, albutoin, alinidine, alizapride, amiloride, aminorex, aprinocid, cambendazole, cimetidine, clonidine, cyclobenzadole, etintidine, fenbendazole, fenmetazole, flubendazole, fludorex, lobendazole, mebendazole, metazoline, nocodazole, oxfendazole, oxibendazole, oxmetidine, parbendazole, ranitidine, tetrahydrazoline, tiamenidine, tinazoline, tiotidine, tolazoline, tramazoline, xylometazoline, dimethoxyphenethylamine, N-[3 (R)-[2-piperidin-4-yl)ethyl]-2-piperidone-1-yl]acetyl-3(R)-methyl-β-alanine, adrenolone, aletamine, amidephrine, amphetamine, aspartame, bamethan, betahistine, clorprenaline, chlortermine, dopamine, ephrinephrine etryptamine, fenfluramine, methyldopamine, norepinephrine, tocainide, enviroxime, nifedipine, nimodipine, triamterene, norfloxacin and similar compounds such as pipedemic acid, 1-ethyl-6-fluoro-1,4-dihydro-4-oxo-7-(1-piperazinyl)-1,8-napthyridine-3-carboxylic acid, 1-cyclopropyl-6-fluoro-1,4-dihydro-4-oxo-7-(piperazinyl)-3-quinolinecarboxylic acid.

Representative drugs containing hydroxy groups include: steroidal hormones such as allylestrenol, cingestol, dehydroepiandrosteron, dienostrol, diethylstilbestrol, dimethisteron, ethyneron, ethynodiol, estradiol, estron, ethinyl estradiol, ethisteron, lynestrenol, mestranol, methyl testosterone, norethindron, norgestrel, norvinsteron, oxogeston, quinestrol, testosteron and tigestol; tranquilizers such as dofexazepam, hydroxyzin, lorazepam and oxazepam; neuroleptics such as acetophenazine, carphenazine, fluphenazine, perphenyzine and piperaetazine; cytostatics such as aclarubicin, daunorubicin, dihydro-5-azacytidine, doxorubicin, epirubicin, estramustin, etoposide, 7-hydroxychlorpromazin, neplanocin A, pentostatin, podophyllotoxin, vinblastin, vincristin, vindesin; hormones and hormone antagonists such as buserilin, gonadoliberin, icatibrant and leuprorelin acetate; antihistamines such as terphenadine; analgesics such as diflunisal, naproxol, paracetamol, salicylamide and salicyclic acid; antibiotics such as azidamphenicol, cefamandol, chloramphenicol, clavulanic acid, clindamycin, comptothecin, demeclocyclin, doxycyclin, imipenem, latamoxef, novobiocin, oleandomycin, oxytetracyclin, tetracyclin and thiamenicol; prostaglandins such as arbaprostil, carboprost and prostacydin; antidepressives such as 8-hydroxychlorimipramine and 2-hydroxyimipramine; antihypertonics such as sotarol and fenoldopam; anticholinerogenics such as biperidine, carbidopa, procyclidin and trihexyphenidal; antiallergenics such as cromolyn; glucocorticoids such as betamethasone, budenosid, chlorprednison, clobetasol, clobetasone, corticosteron, cortisone, cortodexon, dexamethason, flucortolon, fludrocortisone, flumethasone, flunisolid, fluprednisolon, flurandrenolide, flurandrenolon acetonide, hydrocortisone, meprednisone, methylpresnisolon, paramethasone, prednisolon, prednisol, triamcinolon and triamcinolon acetonide; narcotic agonists and antagonists such as apomorphine, buprenorphine, butorphanol, codein, cyclazocin, hydromorphon, ketobemidon, levallorphan, levorphanol, metazocin, morphine, nalbuphin, nalmefen, naloxon, nalorphine, naltrexon, oxycodon, oxymorphon and pentazocin; stimulants such asmazindol and pseudoephidrine; anaesthetics such as hydroxydion and propofol; β-receptor blockers such as acebutolol, albuterol, alprenolol, atenolol, betazolol, bucindolol, cartelolol, celiprolol, cetamolol, labetalol, levobunelol, metoprolol, metipranolol, nadolol, oxyprenolol, pindolol, propanolol and timolol; α-sympathomimetics such as adrenalin, metaraminol, midodrin, norfenefrin, octapamine, oxedrin, oxilofrin, oximetazolin and phenylefrin; β-sympathomimetics such as bamethan, clenbuterol, fenoterol, hexoprenalin, isoprenalin, isoxsuprin, orciprenalin, reproterol, salbutamol and terbutalin; bronchodilators such as carbuterol, dyphillin, etophyllin, fenoterol, pirbuterol, rimiterol and terbutalin; cardiotonics such as digitoxin, dobutamin, etilefrin and prenalterol; antimycotics such as amphotericin B, chlorphenesin, nystatin and perimycin; anticoagulants such as acenocoumarol, dicoumarol, phenprocoumon and warfarin; vasodilators such as bamethan, dipyrimadol, diprophyllin, isoxsuprin, vincamin and xantinol nicotinate; antihypocholesteremics such as compactin, eptastatin, mevinolin and simvastatin; miscellaneous drugs such as bromperidol (antipsychotic), dithranol (psoriasis) ergotamine (migraine) ivermectin (antihelminthic), metronidazole and secnizadole (antiprotozoals), nandrolon (anabolic), propafenon and quinadine (antiarythmics), serotonin (neurotransmitter) and silybin (hepatic disturbance).

"Drugs which are insufficiently translocated across the intestinal wall to provide therapeutic or prophylactic blood concentrations" refers to drugs which, when administered orally at tolerable doses or using a practical dosage regimen, cannot provide blood concentrations of the drug or active metabolite thereof sufficient to effect either disease therapy or prophylaxis. Examples of such drugs include, for instance:

(i) the antibiotics, cefepime, ceftazidime, ceftriaxone, aztreonam, meropenem, imipenem;
  (ii) the anticancer agents, paclitaxel, docetaxel, doxorubicin, fludarabine, gemcitabine, pentostatin, camptothecin;
  (iii) the thrombin inhibitors, argatroban, melagatran, napsagatran;
  (iv) the renin inhibitors, enalkiren, ciprokiren, terlakiren;
  (v) the HIV protease inhibitors, kynostatin, A-77003, SB-206343, XM-323;
  (vi) the gpIIb/IIIa inhibitors, lamifiban; orbofiban; fradafiban, FK-633; and
  (vii) the influenza neuraminidase inhibitors, zanamivir, BCX-1812.

"Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alkynyl, —NRC(=NR)NR-substituted alkynyl, —NRC(=NR)NR-aryl, —NRC(=NR)NR-substituted aryl, —NRC(=NR)NR-cycloalkyl, —NRC(=NR)NR-heteroaryl, —NRC(=NR)NR-substituted heteroaryl, —NRC(=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl,aryl, substituted aryl, heteroaryl, substituted heteroaryl, heterocyclic and substituted heterocyclic are as defined herein.

"Guanidinosulfone" refers to the groups —NRC(=NR)NRSO$_2$-alkyl, —NRC(=NR)NRSO$_2$-substituted alkyl, —NRC(=NR)NRSO$_2$-alkenyl, —NRC(=NR)NRSO$_2$-substituted alkenyl, —NRC(=NR)NRSO$_2$-alkynyl, —NRC(=NR)NRSO$_2$-substituted alkynyl, —NRC(=NR)NRSO$_2$-aryl, —NRC(=NR)NRSO$_2$-substituted aryl, —NRC(=NR)NRSO$_2$-cycloalkyl, —NRC(=NR)NRSO$_2$-substituted cycloalkyl, —NRC(=NR)NRSO$_2$-heteroaryl, and —NRC(=NR)NRSO$_2$-substituted heteroaryl, —NRC(=NR)NRSO$_2$-heterocyclic, and —NRC(=NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from the group consisting of oxygen, nitrogen and sulfur within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heteroarylene" refers to a divalent aromatic carbocyclic group of from 2 to 10 carbon atoms and 1 to 4 heteroatoms selected from the group consisting of oxygen, nitrogen and sulfur within the ring. Such heteroarylene groups can have a single ring (e.g., pyridylene or furylene) or multiple condensed rings (e.g., indolizinylene or benzothienylene). Preferred heteroarylenes include pyridylene, pyrrolylene, indolylene and furylene.

"Heteroaryloxy" refers to the group —O-heteroaryl and "substituted heteroaryloxy" refers to the group —O-substituted heteroaryl.

"Heterocyclene" refers to a divalent saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Heterocyclyloxy" refers to the group —O-heterocyclic and "substituted heterocyclyloxy" refers to the group —O-substituted heterocyclic.

"Incompletely translocated drugs" refer to those drugs wherein less than 90%, typically less than 75%, and more typically less than 50% of the drug delivered orally to an animal is absorbed into the systemic blood circulation of the animal as the drug itself or as an active metabolite thereof, wherein incomplete absorption is due, at least in part, to incomplete translocation of the drug or active metabolite thereof across the intestinal wall of the animal. Examples of incompletely translocated drugs include, for instance, bisphosphonates such as alendronate, clondronate, ibandronate, incadronate, pamidronate, risedronate, tiludronate, zoledronate.

"Leaving group" refers to a chemical moiety that can either be displaced by a nucleophile (SN2 reaction) or eliminated in the presence of a base (E2 reaction). Examples of leaving groups include, without limitation, the following: tosyl, mesyl and triflyl.

"A moiety selected to permit a compound of formula (I) to be translocated across the intestinal wall of an animal via the bile acid transport system" refers to compounds which, when conjugated to the drug/cleavable linker moiety, are translocated across the intestinal wall via the bile acid transport system. Evaluation of which candidate compounds can be so translocated across the intestinal wall can be conducted by the in vitro assay set forth in Examples 50 and 51 below.

"Orally delivered drugs" refer to drugs which are administered to an animal in an oral form, preferably, in a pharmaceutically acceptable diluent. Oral delivery includes ingestion of the drug as well as oral gavage of the drug.

"Oxycarbonylamino" refers to the groups —OC(O)NH$_2$, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH$_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Pharmaceutically acceptable excipient" refers to an excipient that is useful in preparing a pharmaceutical composition that is generally safe, non-toxic and neither biologically nor otherwise undesirable, and includes an excipient that is acceptable for veterniary use as well as human pharmaceutical use. "A pharmaceutically acceptable excipient" as used in the specification and claims includes both one and more than one such excipient.

"Pharmaceutically acceptable salt" refers to pharmaceutically acceptable salts of a compound of the present invention which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Practical dosage regimen" refers to a schedule of drug administration that is practical for a patient to comply with. For human patients, a practical dosage regimen for an orally administered drug is likely to be an aggregate dose of less than 10 g/day.

"Protecting group" refers to a chemical moiety used to prevent certain functional groups from undergoing undesired reactions. Examples of protecting groups include, without limitation, the following: TMS, TBDMS and acetyl.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OS$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, -NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted alkenylene" refers to alkenylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted alkoxy" refers to the group "substituted alkyl-O—".

"Substituted alkyl" refers to an alkyl group, preferably of from 1 to 20 carbon atoms, having from 1 to 5 substituents selected from the group consisting of alkoxy, substituted alkoxy, acyl, acylamino, thiocarbonylamino, acyloxy, amino, amidino, alkyl amidino,thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-

"Substituted alkylene" refers to alkylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$- heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted alkynylene" refers to alkynylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted aryl" refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylhetcroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thiobeterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Substituted arylene" refers to arylene groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Substituted aryloxy" refers to substituted aryl-O— groups.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Substituted cycloalkoxy" refers to —O-substituted cycloalkyl groups.

"Substituted cycloalkyl" and "substituted cycloalkenyl" refers to an cycloalkyl or cycloalkenyl group, preferably of from 3 to 8 carbon atoms, having from 1 to 5 substituents selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted cycloalkylene" and "substituted cycloalkenylene" refers to a cycloalkylene or cycloalkenylene group, preferably of from 3 to 8 carbon atoms, having from 1 to 5 substituents selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Substituted heteroarylene" refers to heteroarylene groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Substituted heterocyclene" refers to heterocyclene groups which are substituted with from 1 to 3 substituents selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O-aryl, —C(O)O-substituted aryl, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O-aryl, —C(O)O-substituted aryl, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted thioalkyl" refers to the group —S-substituted alkyl.

"Substituted thiocycloalkyl" refers to the group —S-substituted cycloalkyl.

"Sustained release" refers to release of a compound of the invention (i.e., a compound whether or not linked to a drug D) into the gut lumen over a prolonged period of time relative to that achieved by administration of a conventional orally administered formulation of the compound. A number of known sustained release oral dosage forms can be used to achieve sustained release of the compounds of the present invention including compound-releasing beads, tablets, erodible and non-erodible polymers, enteric-coated materials, lipid matrices, wax matrices, osmotic delivery systems such as the OROS® systems made by ALZA Corporation of Mountain View, Calif., and tiny timed-release pills. Regardless of the specific form of sustained release oral dosage form used, the compound is preferably released from the oral sustained release dosage form over a period of at least 6 hours, more preferably over a period of at least about 8 hours, and most preferably over a period of at least about 12 hours. Further the dosage form preferably releases from 0 to 20% of the compound in 0 to 2 hours, from 20 to 50% of the compound in 2 to 12 hours, from 50 to 85% of the compound in 3 to 20 hours and greater than 75% of the compound in 5 to 18 hours. Preferably, the dosage forms are administered no more frequently than twice per day, more preferably no more frequently than once per day.

"Systemic bioavailability" refers to the rate and extent of systemic exposure to a drug or a metabolite thereof as reflected by the area under the systemic blood concentration versus time curve.

"Therapeutic or prophylactic blood concentrations" refers to systemic exposure to a sufficient concentration of a drug or an active metabolite thereof over a sufficient period of time to effect disease therapy or to prevent the onset or reduce the severity of a disease in the treated animal.

"Thioalkyl" refers to the groups —S-alkyl.

"Thioamidino" refers to the group RSC(=NH)— where R is hydrogen or alkyl.

"Thioaryl" refers to the group —S-aryl and "substituted thioaryl" refers to the group —S-substituted aryl.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alky, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocycloalkyl" refers to the groups —S-cycloalkyl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Thiol" refers to the group —SH.

"Tissue of the enterohepatic circulation" refers to the blood, plasma, intestinal contents, intestinal cells, liver cells, biliary tract or any fraction, suspension, homogenate, extract or preparation thereof.

"Translocation across the intestinal wall" refers to movement of a drug or drug conjugate by a passive or active mechanism, or both, across an epithelial cell membrane of any region of the gastrointestinal tract.

Compound Preparation

Figure 7E:
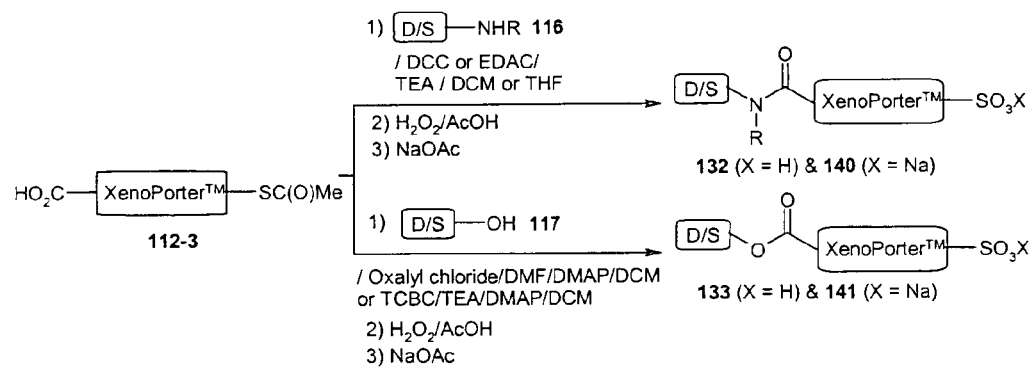

The compounds of this invention can be prepared from readily available starting materials using the following general methods and procedures. (See Examples 1–49 and FIGS. 1–7.) It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, N.Y., 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Utility

In one embodiment of the present invention, the compounds and methods described herein permit significant increases in systemic blood levels of drugs or active metabolites thereof upon oral dosing of animals with the drug/linker/transporter compounds (relative to blood levels achieved with the parent compounds). In addition, the selection of cleavable linker also permits the drug/linker/transporter compounds described herein to provide sustained release of the drug or active metabolite thereof relative to oral dosing with the parent drug itself. In this regard, the enterohepatic recycling of the bile acid conjugates creates a reservoir for the active agent. The above are molar comparisons, i.e., they are based on molar amounts of compounds of the present invention and parent drugs. The above comparisons are also based on approximately the same oral dosage forms, which release at approximately the same location in the gastrointestinal tract of the animal being dosed.

In another embodiment of the present invention, the compounds described herein are inhibitors of the intestinal bile acid transporter and have utility as anti-hypercholesterolemic and anti-atherogenic agents (for example, see Stenglelin et al, International Publication No. WO 00/20437; Wess et al, European Patent Application No. EP 702026 A2; Wess et al, European Patent Application No. EP 624593 A2).

In another embodiment of the present invention, the compounds described herein are anticholestatic agents and are useful in the treatment of biliary calculosis (i.e. gallstone dissolution) (for example, see Gilat et al, International Publication No. WO 99/52932; Marchi et al, European Patent Application No. EP 676410 A2; Kramer et al, Ger. Offen. DE 98-19824123). In a preferred embodiment of this method, the compounds described herein do not contain L-D.

In another embodiment of the present invention, the compounds described herein modulate cholesterol metabolism via interaction with nuclear hormone receptors selected from the group consisting of FXR and LXR (for example, see Forman et al, International Publication No. WO 00/57915; Shan et al, International Publication No. WO 00/40965; Mangelsdorf et al, International Publication No. WO 00/34461; Liao et al, International Publication No. WO 00/66611). In a preferred embodiment of this method, the compounds described herein do not contain L-D.

In another embodiment of the present invention, the compounds described herein are mucosal permeability enhancers useful in oral or nasal drug delivery systems (for example, see Illum et al, International Publication No. WO 98/01159; Takahashi et al, Jpn. Kokai Tokkyo Koho JP 10286453 A2; Okada, Jpn. Kokai Tokkyo Koho JP 11060594). In a preferred embodiment of this method, the compounds described herein do not contain L-D.

In another embodiment of the present invention, the compounds described herein are inhibitors of gastrointestinal inflammatory disorders (for example, see Setchell et al, International Publication No. WO 97/18816). In a preferred embodiment of this method, the compounds described herein do not contain L-D.

In another embodiment of the present invention, the compounds described herein are useful in the prevention and treatment of colorectal cancer (for example, see Gibson et al, International Publication No. WO 97/44043). In a preferred embodiment of this method, the compounds described herein do not contain L-D.

In another embodiment of the present invention, the compounds described herein are useful as antiviral agents (for example, see Ozeki, International Publication No. WO 95/03056; Berlati et al, International Publication No. WO 94/00126; Atkinson et al, European Patent Application No. EP 285285 A2). In a preferred embodiment of this method, the compounds described herein do not contain L-D.

In another embodiment of the present invention, the compounds described herein are useful as antifungal agents (for example, see Stretton, International Publication No. WO 90/13298). In a preferred embodiment of this method, the compounds described herein do not contain L-D.

In another embodiment of the present invention, the compounds described herein are inhibitors of apoptosis (for example, see Steer et al, International Publication No. WO 99/15179). In a preferred embodiment of this method, the compounds described herein do not contain L-D.

In another embodiment of the present invention, the compounds described herein are useful for the liver-specific delivery of therapeutic (e.g. antineoplastics) or diagnostic agents (e.g. MRI contrast agents, etc) (for example, see Anelli et al, International Publication No. WO 00/38738; Sherman et al, U.S. Pat. No. 4,848,349). In an embodiment of this method, the compounds described herein contain L-D. In an additional embodiment of this method, the compounds described herein do not contain L-D.

Pharmaceutical Formulations

When employed as pharmaceuticals, the compounds of the present invention are usually administered in the form of pharmaceutical compositions that are administered by oral routes. Such compositions are prepared in a manner well known in the pharmaceutical art and comprise at least one active compound.

This invention also includes pharmaceutical compositions that contain, as the active ingredient, one or more of the compounds of the present invention associated with a pharmaceutically acceptable excipient. In making the compositions of this invention, the active ingredient is usually mixed with an excipient, diluted by an excipient, and optionally enclosed within a pharmaceutically acceptable carrier, which carrier can be in the form of a capsule, sachet, paper or other container. When the excipient serves as a diluent, it can be a solid, semi-solid, or liquid material, which acts as a vehicle or medium for the active ingredient. Thus, the compositions can be in the form of tablets, pills, powders, lozenges, sachets, cachets, elixirs, suspensions, emulsions, solutions, syrups, etc. containing, for example, up to 10% by weight of the active compound using, for example, soft and hard gelatin capsules.

In preparing a formulation, it may be necessary to mill the active compound to provide the appropriate particle size prior to combining with other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. ~40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.1 to about 500 mg, more usually about 10 to about 100 mg, of the active ingredient. The term "unit dosage forms" refers to physically discrete units suitable as unitary dosages for human subjects and other animals, each unit containing a predetermined quantity of active material calculated to produce the desired therapeutic effect, in association with a suitable pharmaceutical excipient.

In therapeutic use in warm-blooded animals, the compounds or pharmaceutical compositions thereof will be administered orally at a dosage and at a frequency per day to obtain and maintain a concentration, that is, an amount or blood-level of active component in the animal undergoing treatment, that will be therapeutically effective. Generally, such therapeutically effective amount of dosage of active component (i.e., an effective dosage) will be in the range of about 0.1 to about 100, more preferably about 0.1 to about 10 mg/kg of body weight/day.

The frequency of administration may be varied or adjusted widely depending upon the dosage of active component, that is, the compound according to the subject invention, in the pharmaceutical composition, the particular application, the potency of the particular compound, and the desired concentration. The frequency of administration may be in the range of about once to three times per 24 hours, preferably once per 24 hours.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 mg to about 2 g of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

Tablets, each containing 30 mg of active ingredient, are prepared as follows

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 4

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

FORMULATION EXAMPLE 5

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 6

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Other suitable formulations for use in the present invention can be found in Remington's Pharmaceutical Sciences, Mace Publishing Company, Philadelphia, Pa., 17th ed. (1985).

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

Toxicity and therapeutic efficacy of such compounds can be determined by standard pharmaceutical procedures in cell cultures or experimental animals, e.g., for determining the L-$D_{50}$ (the dose lethal to 50% of the population) and the $ED_{50}$ (the dose therapeutically effective in 50% of the population). The dose ratio between toxic and therapeutic effects is the therapeutic index and it can be expressed as the ratio L-$D_{50}$/$ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range which includes the $IC_{50}$ (the concentration of the test compound which achieves a half-maximal inhibition of symptoms) as determined in cell culture. Such information can be used to more accurately determine useful doses in humans. Levels in plasma may be measured, for example, by high performance liquid chromatography.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| Atm = | atmosphere |
| Cbz = | carbobenzyloxy |
| CPM = | counts per minute |
| DCM = | dichloromethane |
| DMAP = | 4-N,N-dimethylaminopyridine |
| DMEM = | Dulbecco's minimun eagle medium |
| DMF = | N,N-dimethylformamide |
| DMSO = | dimethylsulfoxide |
| FMOC = | 9-fluorenylmethyloxycarbonyl |
| g = | gram |
| h = | hour |
| HBSS = | Hank's buffered saline solution |
| IBAT = | intestinal bile acid transporter |
| kg = | kilograms |
| LBAT = | liver bile acid transporter |
| L = | liter |
| LC/MS = | liquid chromatography/mass spectroscopy |
| M = | molar |
| min = | minute |
| mL = | milliliter |
| mmol = | millimols |
| NTCP = | Na + taurocholate cotransporting polypeptide |
| PBS = | phosphate buffered saline |
| TBDMS = | tert-butyldimethylsilyl |
| TEOC-Cl = | trimethylsilylethyl chloroformate |
| TEA = | triethylamine |
| TES = | triethylsilyl |
| THF = | tetrahydrofuran |
| TFA = | trifluoroacetic acid |
| TMS = | trimethylsilyl |
| μL = | microliter |
| μM = | micromolar |
| v/v = | volume to volume |

EXPERIMENTAL METHODS

I. General Procedures for the Preparation of Steroidal Building Blocks 1–12

Example 1

Preparation of 3-oxocholanoic acid alkyl esters 1 (Scheme 1)

The 3-oxocholanoic acid methyl esters were prepared according to the protocol reported by Tserang, K-Y (*J. Lipid Res.* 1978, 32, 977–983). To a solution of the appropriate cholanoic acid methyl ester 16 (25 mmol) in 250 mL of anhydrous toluene was added silver carbonate, ~50 wt. % on Celite (28.5 g, 50 mmol). The reaction flask was then attached to a Dean-Stark apparatus and refluxed for 2–10 h. The reaction mixture was filtered, the precipitate washed with hot toluene (25 mL×3) and then the combined filtrate was evaporated. The residue was passed through a short silica gel column using 10–25% ethyl acetate and hexane as eluents to give the corresponding pure 3-oxocholanoic acid methyl esters 1a–d in 70–92% overall yields (Table 1). Similarly, other 3-oxocholanoic acid alkyl esters are prepared from the corresponding alkyl esters following this protocol.

Example 2

Preparation of 2,3-dioxocholanoic acid acids and their alkyl esters 2 (Scheme 2)

A stirred suspension of selenium dioxide (15 mmol) in dioxane (50 mL) and few drops of water is stirred at 50–55° C. for 10–20 min to give a clear solution. Then, a solution of the appropriate 3-oxocholanoic acid or its ester 1 (10 mmol) in 50 mL of dioxane is introduced into the flask and the mixture is heated at 50–85° C. for 4–10 h (monitored by TLC or LC/MS). Prior to oxidation, any free C-7 and/or C-12 hydroxy groups on the cholanoic acid derivative 1 are protected with an appropriate protecting group, preferably with acetyl or trialkylsilyl group. The reaction mixture is filtered through a sintered funnel, the precipitate washed with dioxane (15 mL×2) and the combined filtrate is evaporated on a rotavapor under reduced pressure. The residue is purified by silica gel column chromatography using 10–25% gradient of ethyl acetate and hexane as eluents to give the pure 2.

Example 3

Preparation of 3-chloro-2-formyl derivatives of cholenoic acid alkyl esters 3 (Scheme 3)

To a stirred solution of anhydrous N,N-dimethylformamide (15 mmol) in 50 mL of trichloroethane under nitrogen atmosphere at 0° C. is added dropwise phosphorous oxychloride (12 mmol). The reaction mixture is slowly warmed to room temperature. Then, a solution of the appropriate 3-oxocholanoic acid ester 1 (10 mmol) in 50 mL of trichloroethylene is added to the reaction mixture at such a rate that the temperature does not rise above 60° C. Prior to chloroformylation, any free C-7 and/or C-12 hydroxy groups on the cholanoic acid derivative 1 are protected with an appropriate protecting group, preferably with acetyl or trialkylsilyl group. When the addition is completed, the reaction mixture is heated at 55–60° C. for 3–12 h (monitored by TLC or LC/MS). The reaction mixture is cooled to room temperature and then a solution of sodium acetate (400 g) in water (500 mL) is cautiously added dropwise through a dropping funnel. The organic layer is separated, washed with brine (15 mL×2) and dried over anhydrous sodium sulfate. After evaporating the solvent under reduced pressure, the residue is purified by passing through a short silica gel column using a gradient of ethyl acetate and hexane as eluents to give the corresponding pure 3-chloro-2-formyl cholenoic acid ester 3.

Example 4

Preparation of 2-hydroxymethylene-3-oxocholanoic acid esters 4 (Scheme 4)

To a stirred suspension of sodium hydride (11 mmol) in anhydrous toluene (25 mL) under nitrogen atmosphere at room temperature was added dropwise a solution of the appropriate 3-oxocholanoic acid ester (R=Me) 1 (10 mmol) and ethyl formate (30 mmol) in anhydrous toluene (25 mL). After having stirred for 30 min, 2–3 drops of anhydrous ethanol was introduced into the reaction mixture. The mixture was further stirred at room temperature for 18–24 h (monitored by TLC). Then, the reaction mixture was cautiously poured onto crushed ice and acidified with 5% HCl. The organic layer was separated and the aqueous layer was extracted with ethyl acetate (25 mL×2). The combined extract was washed with brine (50 mL), dried over anhydrous sodium sulfate and evaporated to give a mixture of 2-hydroxymethylene-3-oxocholanoic acid ethyl and methyl esters, 4a–d in ~3:1 to 5:1 ratios. The crude 4a–d gave satisfactory $^1$H NMR and LS/MS spectra (Table 2).

Similarly, the compounds 4e–f (R=Et/Me) are prepared from the corresponding 3-oxocholanoic acids 1e–f. The crude 2-hydroxymethylene derivatives 4a–d were used for the synthesis of corresponding fused pyrazoles and pyrimidine derivatives without any further purification.

Example 5

Preparation of 2-dimethylaminomethylene-3-oxocholanoic acid methyl esters 5a–c (Scheme 5)

To a stirred solution of the appropriate 3-oxocholanoic acid ester 1 (10 mmol) in anhydrous THF or dioxane (30 mL) under nitrogen atmosphere was added Bredereck's reagent, tert-butoxybis(dimethylamino)methane (22 mmol) and the mixture was refluxed for 3–24 h (monitored by TLC or LC/MS). After concentrating the reaction mixture under reduced pressure the residue was diluted with ethyl acetate (50 mL). Then, it was washed with water (25 mL) and brine (25 mL). Solvent was evaporated after drying over anhydrous sodium sulfate. The crude 5a–c gave satisfactory $^1$H NMR and LS/MS spectra. (Table 3).

Similarly, the compounds 5d–f (R=Me) are prepared from the corresponding 3-oxocholanoic acids 1d–f. The crude 2-hydroxymethylene derivatives 5a–c were used for the synthesis of fused pyrazoles derivatives 48 without any further purification.

Example 6

Preparation of 2-bis(thiomethyl)methylene-3-oxocholanoic acid esters 6 (Scheme 6)

To a stirred solution of sodium ethoxide or tert-butoxide (22 mmol) in anhydrous toluene (100 mL) under nitrogen atmosphere at 0–5° C. is dropwise added a solution of the appropriate 3-oxocholanoic acid ester 1 (10 mmol) and carbon disulfide (10 mmol) in anhydrous toluene (50 mL). Any free C-7 and/or C-12 hydroxy groups on the cholanoic acid derivative 1 are protected with an appropriate protecting group, preferably with a trialkylsilyl group. The reaction mixture is slowly warmed to room temperature and stirring is continued further at room temperature for 12–15 h. Then, a solution of iodomethane (25 mmol) in anhydrous toluene (25 mL) is added dropwise at 0–5° C. and stirred further for 12–15 h at room temperature. The reaction mixture is poured onto crushed ice and the organic layer is separated. The aqueous layer is extracted with ethyl acetate (25 mL) and the combined extract is washed with water (25 mL) then dried over anhydrous sodium sulfate. The solvent is evaporated under reduced pressure and the residue is purified by silica gel column chromatography using 0–25% gradient of ethyl acetate and hexane as eluents.

Example 7

Preparation of Oxoketene N,S-acetal Derivatives of Cholanoic Acid Esters 7 (Scheme 7)

To a stirred solution of sodium ethoxide or tert-butoxide (12 mmol) in anhydrous toluene (50 mL) under nitrogen atmosphere at 0–5° C. is added dropwise a solution of the appropriate 3-oxocholanoic acid ester 1 (10 mmol) and isothiocyanate 17 (10 mmol) in anhydrous toluene (50 mL). Any free C-7 and/or C-12 hydroxy groups on the cholanoic acid derivative 1 are protected with an appropriate protecting group, preferably with a trialkylsilyl group. After having stirred at room temperature for 12–18 h, the reaction mixture is poured onto crushed ice. The organic phase is separated and the aqueous layer is extracted with ethyl acetate (25 mL×2). The combined extract is washed with water (50 mL), dried over anhydrous sodium sulfate and evaporated under reduced pressure. The crude β-ketothioamide 18 is purified by silica gel column chromatography using 0–25% gradient of ethyl acetate and hexane as eluents. The pure thioamide 18 is added to a stirred suspension of potassium carbonate (10 mmol) in anhydrous acetone (100 mL) and refluxed for 3–4 h. After cooling the reaction mixture to 0° C., a solution of iodomethane (15 mmol) in anhydrous acetone (25 mL) is added dropwise and stirred at room temperature for 12–18 h. Then, the mixture is filtered through a sintered funnel and the precipitate is washed with acetone (25 mL×2). The combined filtrate is concentrated on a rotavopor under reduced pressure. The residue is diluted with ethyl acetate (200 mL) and washed with water (25 mL×2), dried over anhydrous sodium sulfate, and the solvent evaporated. The crude product is passed through a short silica gel column using 0–25% gradient of ethyl acetate and hexane as eluents to give the corresponding pure oxoketene N,S-acetal 7.

Following this protocol, the N,S-acetal 7a-1 (R=Et, $R^1=R^2=H$ and $R^3=C_6H_5$) was prepared in 25% yield using sodium ethoxide as a base (Scheme 7). The 7a-1 gave satisfactory $^1H$ NMR spectral data. The Electrospray mass spectrometry showed the expected molecular ion at m/z=552 (M+H).

Example 8

Preparation of Oxoketene N,S-acetal Derivatives of Cholanoic Acid Esters 8 (Scheme 8)

A solution of the appropriate oxoketene S,S-acetal 6 (10 mmol) and aliphatic amine 19 (10 mmol) in methanol or ethanol (50 mL) is refluxed for 12–18 h (monitored by TLC). Acetic acid is used as solvent if 19 is an aromatic amine. After completion of the reaction, the solvent is evaporated on a rotavapor under reduced pressure and the residue is diluted with ethyl acetate (100 mL). The organic layer is washed with water (25 mL×2), dried over anhydrous sodium sulfate, and evaporated. The crude product is purified by silica gel chromatography using 10–25% gradient of ethyl acetate and hexane as eluents to give the pure N,S-acetal 8.

Example 9

Preparation of 3-oxo-2-(β-oxomethyl) substituted bile acid building blocks 9 (Scheme 9)

To a stirred solution of the appropriate 3-oxocholanoic acid ester derivative 1 (10 mmol) in anhydrous THF (50 mL) under nitrogen atmosphere at −78° C. is added dropwise a solution of freshly prepared L-DA (10.5 mmol) in THF. The reaction mixture is slowly warmed to 0° C. After having stirred at 0° C. for 1 h, the reaction mixture is cooled to −78° C. and a solution of the appropriate 20 (10 mmol) in anhydrous THF (25 mL) added dropwise. The reaction mixture is slowly warmed to room temperature and further stirred at room temperature for 12–18 h. The mixture is poured into saturated ammonium chloride solution (250 mL) and extracted with ethyl acetate (50 mL×3). The combined extract is washed with water (25 mL), dried over anhydrous sodium sulfate, and finally the solvent evaporated under reduced pressure. The residue is purified by silica gel column chromatography using 5–25% gradient of ethyl acetate and hexane as eluents to give the pure 9.

Example 10

Preparation of 3-oxo-2-propargyl substituted bile acid building blocks 10 (Scheme 10)

To a stirred, solution of the appropriate 3-oxocholanoic acid ester derivative 1 (10 mmol) in anhydrous THF (50 mL) under nitrogen atmosphere at −78° C. is added dropwise a solution of freshly prepared L-DA (10.5 mmol) in THF. The reaction mixture is slowly warmed to 0° C. After having stirred at 0° C. for 1 h, the reaction mixture is cooled to −78° C. and a solution of appropriate propargyl halide or tosylate 21 (10 mmol) in anhydrous THF (25 mL) added dropwise. The reaction mixture is slowly warmed to room temperature and further stirred at room temperature for 12–18 h. The mixture is poured into saturated ammonium chloride solution (250 mL) and extracted with ethyl acetate (50 mL×3). The combined extract is washed with water, dried over anhydrous sodium sulfate, and finally evaporated the solvent under reduced pressure. The residue is purified by silica gel column chromatography using 5–25% gradient of ethyl acetate and hexane as eluents to give the pure 10.

Example 11

Preparation of Vinyl Ether or Ester Derivatives of Bile Acid Building Blocks 11 (Scheme 11)

To a stirred solution of the appropriate 3-oxocholanoic acid ester derivative 1 (10 mmol) in anhydrous THF (50 mL) under nitrogen atmosphere at −78° C. is added dropwise a solution of freshly prepared L-DA (10.5 mmol) in THF. The reaction mixture is slowly warmed to 0° C. After having stirred at 0° C. for 1 h, the reaction mixture is cooled to −78° C. and a solution of the appropriate alkylating or silylating agent 22 (10 mmol) in anhydrous THF (25 mL) added dropwise. The reaction mixture is slowly warmed to room temperature and further stirred at room temperature for 12–18 h. The mixture is poured into saturated ammonium chloride solution (250 mL) and extracted with ethyl acetate (50 mL×3). The combined extract is washed with brine (25 mL), dried over anhydrous sodium sulfate, and finally evaporated the solvent under reduced pressure. The crude product 11 is carried further for the synthesis of various 2,3-fused carbocyclic and heterocyclic derivatives without purification. The corresponding vinyl acetate derivatives ($R^9$=Ac) are prepared by refluxing the appropriate 1 with excess of isopropenyl acetate in anhydrous toluene in the presence of catalytic amounts of p-toluenesulfonic acid.

Example 12

Preparation of 2-methylene-3-oxo derivatives of bile acid building blocks 12 (Scheme 12)

To a stirred solution of the appropriate 3-oxocholanoic acid ester derivative 1 (10 mmol) in anhydrous THF (50 mL) under nitrogen atmosphere at −78° C. is added dropwise a solution of freshly prepared L-DA (10.5 mmol) in THF. The reaction mixture is slowly warmed to 0° C. After having stirred at 0° C. for 1 h, the reaction mixture is cooled to −78° C. and a solution of the appropriate aldehyde or ketone 23 (10 mmol) in anhydrous THF (25 mL) added dropwise. The reaction mixture is slowly warmed to room temperature and further stirred at room temperature for 12–18 h. The mixture is poured into saturated ammonium chloride solution (250 mL) and extracted with ethyl acetate (50 mL×3). The combined extract is washed with water (25 mL), dried over anhydrous sodium sulfate, and finally the solvent evaporated under reduced pressure. The residue is purified by silica gel column chromatography using 5–25% gradient of ethyl acetate and hexane as eluents to give pure 12.

II. General Procedures for the Preparation of Amino Acid Building Blocks 15 and 30

Example 13

Preparation of 2-aminoethylthioacetate 15 (Scheme 13)

The N-protected amino acid alcohols 25 are either purchased from commercial sources or prepared in high yield according to the protocol reported by Rodriguez et al. To a stirred solution of the appropriate alcohol 25 (10 mmol) in anhydrous DCM (50 mL) is added triethylamine (12 mmol) at room temperature. After cooling to 0° C. methanesulfonyl chloride (12 mmol) is added dropwise. Stirring is continued for 1–5 h at room temperature followed by addition of DCM (50 mL). The mixture is washed with a $KHSO_4$ (1M, 50 mL), water (50 mL), and brine (50 mL). After drying over anhydrous sodium sulfate the solvent is evaporated under vacuum. The residue is crystallized from DCM/hexane to give the pure mesylates 26.

To a stirred suspension of cesium carbonate (4 mmol) in anhydrous DMF (25 mL) is added thioacetic acid (6 mmol) followed by the appropriate mesylate 26 (5 mmol) in one portion and the reaction mixture stirred at room temperature for 18 h. The mixture is poured into cold water and extracted with ethyl acetate (50 mL×3). The combined extract is washed with water (200 mL), sodium bicarbonate solution (55 w/w, 200 mL) and finally with brine (100 mL). The organic layer is dried over anhydrous sodium sulfate and concentrated under reduced pressure to give the crude product 15, which is purified by silica gel column chromatography using DCM as eluent.

Example 14

Preparation of N-substituted α-amino Acid Esters 30 (Scheme 14)

To a stirred solution of the appropriate primary amine 28 (10 mmol) in anhydrous DCM (50 mL) at room temperature is added TEA (11 mmol). The reaction mixture is cooled to 0° C. and then a solution of an appropriate α-activated acetate ester 29 (10 mmol) in anhydrous DCM (25 mL) is added dropwise. The reaction mixture is stirred at 0° C. for 3 h and at room temperature for 12–18 h. After completion of the reaction, the mixture is filtered and the precipitate washed with DCM (15 mL). The combined filtrate is concentrated on a rotavapor under reduced pressure and the residue is purified by column chromatography on silica gel using a gradient of ethyl acetate and hexane as eluents to give the pure product 30.

III. General Procedures for the Synthesis of 5-membered Heterocycles

Example 15

Synthesis of Fused Furan Derivatives of Cholanoic Acid Esters 31 (Scheme 15)

To a stirred solution of potassium tert-butoxide or sodium hydride (6 mmol) in anhydrous DMF (10 mL) under nitrogen atmosphere at room temperature is added a solution of the appropriate 3-oxo-2-propargylcholanoic acid ester 10 (5 mmol) in anhydrous DMF (15 mL). The reaction mixture is stirred at room temperature to reflux temperature for 5–24 h depending upon the substituents on the propargyl side chain. After completion of the reaction as judged by TLC or LC/MS, the reaction mixture is poured onto crushed ice and extracted with ethyl acetate (25 mL×3), dried over anhydrous sodium sulfate and finally the solvent evaporated under reduced pressure using a rotavapor. The crude product 31 is purified by silica gel chromatography using a gradient of ethyl acetate and hexane as eluents.

Example 16

Synthesis of Fused Pyrrole Derivatives of Cholanoic Acid Esters 33 (Scheme 16) and 34 (Scheme 17)

To a solution of the appropriate 3-oxo-2-propargylcholanoic acid ester 10 (e.g. R=$^t$Bu) (5 mmol) and an amine 32 (6 mmol) in anhydrous toluene (25 mL) is added catalytic amounts of p-toluenesulfonic acid and the mixture refluxed for 5–24 h. The progress of the reaction is monitored by TLC. The mixture is poured into cold water (100 mL) and extracted with ethyl acetate (25 mL×2). The combined extract is washed with brine (25 mL), dried over anhydrous sodium sulfate and finally the solvent evaporated under reduced pressure using a rotavapor. The residue is passed through a short silica gel column using a gradient of ethyl acetate and hexane to give the pure pyrrole 33 (Scheme 16).

Treatment of the appropriate cholanoic acid esters 9 (e.g. R=$^t$Bu) with amines 32 under identical conditions affords the corresponding 2,3-fused pyrrole derivatives 34 (Scheme 17).

Example 17

Synthesis of Fused Pyrrole Derivatives of Cholanoic Acid Esters 35 (Scheme 18) and 36 (Scheme 19)

To a stirred solution of the appropriate 3-chloro-2-formyl-2-cholenoic acid ester 3 (5 mmol) in anhydrous THF (15 mL) at 0° C. under nitrogen atmosphere is added dropwise a solution of an N-substituted amino acid ester 30 (5 mmol) and triethylamine (6 mmol) in THF (15 mL). The reaction mixture is warmed to room temperature and further stirred for 5–18 h (monitored by TLC or LC/MS). Once the reaction is complete, the reaction mixture is filtered to remove the triethylamine hydrochloride salt and the filtrate is concentrated on a rotavapor under reduced pressure. The residue is diluted with ethyl acetate (50 mL), washed with water (25 mL×2), dried over anhydrous sodium sulfate, and the solvent evaporated under reduced pressure to afford the corresponding enaminal cholanoic acid ester derivative. The crude enaminal is then dissolved in anhydrous THF (15 mL) and added dropwise to a stirred suspension of sodium hydride (5 mmol) in THF (15 mL) at 0° C. under nitrogen atmosphere. The reaction mixture is warmed to room temperature. If L-DA is used as the base, a freshly prepared solution of L-DA (5 mmol) in THF (15 mL) is added to stirred solution of crude enaminal at −78° C. and slowly warmed to room temperature. The mixture is stirred further at room temperature for 2–15 h. The mixture is poured into crushed ice, acidified with 5% HCl solution, and then extracted with ethyl acetate (25 mL×3). The combined extract is washed with water (25 mL), brine (25 mL), dried over anhydrous sodium sulfate and evaporated. The crude pyrrole 35 is purified by silica gel column chromatography using a gradient of ethyl acetate and hexane as eluents.

The pyrrole derivatives 36 are also prepared under identical reaction conditions by treating 2-hydroxymethylene-3- oxocholanoic acid esters 4 or 2-dimethylamino-methylene-3-oxocholanoic acid esters 5 with amine 30 (Scheme 19).

Example 18

Synthesis of Fused Pyrrole Derivatives of Cholanoic Acid Esters 38 (Scheme 20)

A solution of the appropriate α-oxoketene S,S-acetal 6 (5 mmol) and amino acid ester 30 (5 mmol) in anhydrous DMF (25 mL) is heated at 80–90° C. for 5–12 h. The progress of the reaction is monitored by TLC. The reaction mixture is poured into cold water (25 mL), extracted with ethyl acetate (25 mL×3), and dried over anhydrous sodium sulfate. The solvent is evaporated under reduced pressure to give the corresponding N,S-acetal. The crude N,S-acetal is dissolved in anhydrous THF (15 mL) and added dropwise to a stirred suspension of sodium hydride (5 mmol) in THF (15 mL) under nitrogen atmosphere at 0° C. If L-DA is used as the base, a solution of L-DA (5 mmol) in THF is added to a solution of N,S-acetal (5 mmol) in THF (15 mL) under nitrogen atmosphere at –78° C. The reaction mixture is slowly warmed to room temperature and further stirred at room temperature for 12–18 h. Then, the mixture is poured onto crushed ice, acidified with 5% HCl, and extracted with ethyl acetate (25 mL×3). The combined extract is washed with water (25 mL), brine (25 mL), and dried over anhydrous sodium sulfate. After evaporation of the solvent, the residue is purified by silica gel column chromatography using a gradient of ethyl acetate and hexane as eluents to give the pure pyrrole 37.

The pyrrole 37 (3 mmol) is treated with m-chloroperbenzoic acid (7 mmol) in THF (25 mL) at room temperature for 12–24 h (monitored by TLC or LC/MS). The reaction mixture is filtered, the filtrate is diluted with water (25 mL), and extracted with ethyl acetate (25 mL×3). The combined extract is washed with saturated sodium bicarbonate (15 ml×2), water (25 mL), dried over anhydrous sodium sulfate, and cautiously evaporated under reduced pressure. The crude sulfone is then heated at ~70° C. with the appropriate amine (3 mmol) in DMF (25 mL) for 12–24 h (monitored by TLC). The solvent is evaporated and the residue chromatographed on silica gel column using a gradient of ethyl acetate and hexane as eluents to give the pure aminopyrrole 38 (Scheme 20).

The aminopyrroles 38 can also be prepared from the corresponding N,S-acetals 8 ($R^3$ and $R^4 \neq H$) in two steps under identical reaction conditions as described for the synthesis of pyrrole 37. Initial treatment of N,S-acetals 8 (5 mmol) with amines 30 gives the corresponding N,N-acetals, which after aqueous workup and purification as described above, are cyclized by treating with a suitable base (e.g. NaH or L-DA) to give the corresponding aminopyrroles 38 in good yields (Scheme 20).

Example 19

Synthesis of Fused Pyrrole Derivatives of Cholanoic Acid Esters 40 (Scheme 21)

A solution of enone 12 (5 mmol) and amino acid ester 30 (5 mmol) in anhydrous DMF or ethanol (25 mL) is heated at 70–90° C. (monitored by TLC). The mixture is cooled to room temperature, poured into cold water (50 mL), extracted with ethyl acetate (25 mL×3), and dried over anhydrous sodium sulfate. After evaporating the solvent, the residue is dissolved in anhydrous THF (15 mL) and added dropwise to a suspension of sodium hydride (5 mmol) in THF (15 mL) at 0° C. If L-DA is used instead as the base, a freshly prepared solution of L-DA (5 mmol) in THF is added to the corresponding amino acid ester adduct solution in THF (15 mL) at –78° C. The reaction mixture is slowly warmed to room temperature and further stirred for 12–15 h. The mixture is poured onto crushed ice and extracted with ethyl acetate (25 mL×3). The combined extract is washed with water (25 mL), brine (25 mL) and dried over anhydrous sodium sulfate. After evaporation of the solvent, the crude product 37 is treated with DDQ (6 mmol) in toluene at reflux temperature for 12–24 h (monitored by TLC). The reaction mixture is evaporated and the residue is chromatographed on silica gel column using a gradient of ethyl acetate and hexane as eluents to give the pure pyrrole 40 (Scheme 21).

Example 20

Synthesis of Fused Indole Derivatives of Cholanoic Acid Esters 42 and 44 (Scheme 22)

To a solution of the appropriate 3-oxocholanoic acid ester 1 (e.g. R=$^t$Bu) (5 mmol) in glacial acetic acid (50 mL) is added phenylhydrazine 41 (6 mmol) followed by anhydrous zinc chloride (10 mmol). The mixture is refluxed for 12–24 h (monitored by TLC). The reaction mixture is cooled to room temperature and poured into cold water (50 mL), extracted with ethyl acetate (25 mL×3). The combined extract is washed with saturated sodium bicarbonate (25 mL), water (25 mL), dried over anhydrous sodium sulfate, and evaporated to dryness. The residue is purified by silica gel column chromatography using a gradient of ethyl acetate and hexane as eluents to give the pure indole derivative 42 (Scheme 22).

The indole 42 may be alkylated with various alkylating agents under mild reaction conditions (Scheme 22). To a stirred suspension of potassium carbonate (3 mmol) in anhydrous THF (25 mL) is added the appropriate indole 42 (3 mmol) and then the mixture refluxed for 3 h. The reaction mixture is cooled to 0° C. and added dropwise a solution of the appropriate alkyl or acyl halide 43 (4 mmol) in THF (10 mL). The cooling bath is removed and the mixture is stirred at room temperature for 12–18 h. The reaction mixture is filtered and the filtrate is evaporated. The residue is dissolved in ethyl acetate (100 mL) and washed with water (25 mL×2). The organic phase is dried over anhydrous sodium sulfate and the solvent evaporated. The residue is passed through a short silica gel column using a gradient of ethyl acetate and hexane as eluents to give the corresponding pure N-alkylated or acylated indole 44 (Scheme 22).

Example 21

Synthesis of Fused Pyrazole Derivatives of Cholanoic Acid Esters 46 and 47 (Scheme 23)

To a solution of the appropriate 3-chloro-2-formyl cholenoic acid ester 3 (e.g. R=$^t$Bu) (5 mmol) and hydrazine 45 (5 mmol) in anhydrous toluene (25 mL) is added triethylamine (6 mmol). The mixture is refluxed for 5–24 h (monitored by TLC). After cooling to room temperature, the reaction mixture is poured into cold water (50 mL) and extracted with ethyl acetate (25 mL×3). The combined extract is washed with water (25 mL), dried over anhydrous sodium sulfate, and evaporated. The residue is purified by silica gel column chromatography using a gradient of ethyl acetate and hexane as eluents to give the pure pyrazole derivative 46 or 47. The N-alkyl substituted hydrazines 45 afford the 2'-substituted pyrazole 47 whereas N-aryl or electron withdrawing substituted hydrazines 45 afford the corresponding 1'-substituted pyrazoles 46 (Scheme 23).

Example 22

Synthesis of Fused Pyrazole Derivatives of Cholanoic Acid Esters 48 and 49 (Scheme 24)

A solution of appropriate 2-hydroxymethylene-3-oxocholanoic acid ester 4 (5 mmol) and hydrazine 45 (5 mmol) in absolute ethanol (25 mL) was refluxed for 5–24 h (monitored by TLC). The reaction mixture was evaporated on a rotavapor under reduced pressure, and the residue was diluted with ethyl acetate (50 mL). It was washed with water (15 mL×2), dried over anhydrous sodium sulfate and evaporated. The residue was purified by silica gel column chromatography using a 10–50% gradient of ethyl acetate and hexane as eluents to give the pure 2'-substituted pyrazole 48 in good yield. Similarly, the N-aryl or electron withdrawing substituted hydrazines afforded the corresponding 1'-substituted pyrazoles 49 in good yields (Scheme 24). The pyrazole derivatives 48 and 49 prepared by this method and their corresponding analytical data are given in Table 4.

Similarly, pyrazole derivatives 48 were also synthesized from the corresponding. 2-dimethylaminomethylene-3-oxocholanoic acid esters 5 and hydrazines 45 under identical reaction conditions (Scheme 24).

Example 23

Synthesis of Fused Pyrazole Derivatives of Cholanoic Acid Esters 50 and 51 (Scheme 25)

A solution of the appropriate α-oxoketene S,S-acetal 6 (5 mmol) and hydrazine 45 (5 mmol) in absolute alcohol or anhydrous DMF (25 mL) is heated at 80–90° C. for 5–12 h. The progress of the reaction is monitored by TLC. The reaction mixture is poured into cold water (50 mL), extracted with ethyl acetate (25 mL×3) and dried over anhydrous sodium sulfate. After evaporating the solvent, the residue is purified by column chromatography on silica gel using a gradient of ethyl acetate and hexane as eluents to give the pure thiomethylpyrazole derivative 50. Under identical reaction conditions N,S-acetals 7 and 8 afford the corresponding aminopyrazole derivatives 51.

The amino pyrazoles 51 can also be prepared from the corresponding pyrazoles 50 (Scheme 25). The pyrazole 50 (3 mmol) is treated with m-chloroperbenzoic acid (7 mmol) in THF (25 mL) at room temperature for 12–24 h (monitored by TLC or LC/MS). The reaction mixture is filtered, the filtrate is diluted with water (25 mL) and extracted with ethyl acetate (25 mL×3). The combined extract is washed with saturated sodium bicarbonate (15 mL×2), water (25 mL), dried over anhydrous sodium sulfate, and cautiously evaporated under reduced pressure. The crude sulfone thus obtained is heated at ~70° C. with the appropriate amine 14 (3 mmol) in DMF (25 mL) for 12–24 h (monitored by TLC). The solvent is evaporated and the residue chromatographed on silica gel column using a gradient of ethyl acetate and hexane as eluents to give the corresponding pure aminopyrazole 51 (Scheme 25).

Example 24

Synthesis of Fused Dihydropyrazole and Pyrazole Derivatives of Cholanoic Acid Esters 52 and 53 (Scheme 26)

A solution of enone 12 (5 mmol) and hydrazine 45 in absolute ethanol or anhydrous DMF (25 mL) is heated at 70–90° C. (monitored by TLC). The mixture is cooled to room temperature, poured into cold water (50 mL), extracted with ethyl acetate (25 mL×3) and dried over anhydrous sodium sulfate. After evaporating the solvent, the residue is purified by silica gel column chromatography on silica gel using a gradient of ethyl acetate and hexane as eluents to give the pure dihydropyrazole derivative 52.

The purified or crude 52 ($R^{11}$=H) (2 mmol) is refluxed with DDQ (3 mmol) in anhydrous toluene (25 mL) for 12–24 h (monitored by TLC). After evaporation of the solvent, the residue is purified by silica gel column chromatography using a gradient of ethyl acetate and hexane as eluents to give the pure pyrazole derivative 53.

Example 25

Synthesis of Fused Isoxazole Derivatives of Cholanoic Acid Esters 54 (Scheme 27) and 55 (Scheme 28)

To a stirred suspension of hydroxylamine hydrochloride (6 mmol) in anhydrous THF (15 mL) is added freshly prepared sodium ethoxide (15 mmol) followed by the appropriate 3-chloro-2-formyl derivative of cholenoic acid ester 3 (5 mmol) in THF (25 mL). The reaction mixture is refluxed for 12–24 h (monitored by TLC). The mixture is cooled to room temperature, diluted with water (50 mL) and extracted with ethyl acetate (25 mL×3). The combined extract is washed with water (25 mL), dried over anhydrous sodium sulfate and evaporated. The residue is purified by silica gel column chromatography using a gradient of ethyl acetate and hexane as eluents to give the corresponding pure isoxazole derivative 54 (Scheme 27).

The isoxazole derivatives 55 are synthesized from the 2-hydroxymethylene 4, or 2-dimethylaminomethylene-3-oxocholanoic acid ester 5 with hydroxylamine hydrochloride under identical reaction conditions (Scheme 28).

Example 26

Synthesis of Fused Isoxazole Derivatives of Cholanoic Acid Esters 57 (Scheme 29)

To a stirred suspension of hydroxylamine hydrochloride (6 mmol) in anhydrous THF (25 mL) is added sodium ethoxide or methoxide (15 mmol) followed by a solution of the appropriate α-oxoketene S,S-acetal 6 (5 mmol). Then, the mixture is refluxed for 8–24 h (monitored by TLC). The reaction mixture is poured into cold water (50 mL), extracted with ethyl acetate (25 mL×3) and dried over anhydrous sodium sulfate. After evaporating the solvent, the residue is purified by column chromatography on silica gel using a gradient of ethyl acetate and hexane as eluents to give the pure thiomethylisoxazole derivative 56. Under identical reaction conditions N,S-acetals 7 and 8 afford the corresponding aminoisoxazole derivatives 57.

The aminoisoxazoles 57 can also be prepared from the corresponding isoxazole 56 (Scheme 29). The appropriate isoxazole 56 (3 mmol) is treated with m-chloroperbenzoic acid (7 mmol) in THF (25 mL) at room temperature for 12–24 h (monitored by TLC or LC/MS). The reaction mixture is filtered, the filtrate is diluted with water (25 mL) and extracted with ethyl acetate (25 mL×3). The combined extract is washed with saturated sodium bicarbonate (15 mL×2), water (25 mL), dried over anhydrous sodium sulfate, and cautiously evaporated under reduced pressure. Then, a solution the crude sulfone and the appropriate amine 14 (3 mmol) is heated at ~70° C. in DMF (25 mL) for 12–24 h (monitored by TLC). The solvent is evaporated under reduced pressure and the residue is chromatographed on silica gel column using a gradient of ethyl acetate and hexane as eluents to give the corresponding pure aminoisoxazole 57 (Scheme 29).

Example 27

Synthesis of Fused Triazole Derivatives of Cholanoic Acid Esters 58 (Scheme 30)

To a stirred solution of the appropriate vinyl acetate or ether 11 (5 mmol) in anhydrous DMF (15 mL) in a wide mouth reaction vessel is added a solution of alkyl or arylazide (5 mmol) in DMF (15 mL). The reaction mixture is heated at 100–120° C. for 8–24 h (monitored by TLC). After cooling, the reaction mixture is poured into ice-cold water and extracted with ethyl acetate (25 mL×3). The combined extract is washed with water (25 mL), dried over anhydrous sodium sulfate, and evaporated. The residue is purified by silica gel column chromatography using a gradient of ethyl acetate and hexane as eluents to give the pure triazole 58.

IV. General Procedures for the Synthesis of Fused 6-membered Carbocyclic and Heterocyclic Derivatives of Bile Acids Example 28

Synthesis of 2,3-benzofused cholanoic acid esters 61 (Scheme 31)

A solution of the appropriate vinyl ester or ether 11 (5 mmol) and diene 59 (5 mmol) in anhydrous toluene (25 mL) is heated in a sealed tube at 110–115° C. for 8–14 h (monitored by TLC). After evaporation of the solvent under reduced pressure the residue is purified by silica gel chromatography using a gradient of ethyl acetate and hexane as eluents to give the pure adduct 60 (Scheme 31).

The cycloadduct 60 is treated with DDQ (6 mmol) in anhydrous toluene (25 mL) at reflux temperature for 12–24 h (monitored by TLC). The solvent is evaporated under reduced pressure and the residue is purified by silica gel column chromatography using a gradient of ethyl acetate and hexane as eluents to give the pure benzofused cholanoic acid ester 61 (Scheme 31).

Example 29

Synthesis of Fused Dihydropyran Derivatives of Cholanoic Acid Esters 64 (Scheme 32)

Following the protocol described above for the synthesis of benzofused derivatives 61 (Scheme 31), the fused dihydropyran derivatives of cholanoic acid esters 64 are prepared by treating the appropriate vinyl ester or ether 11 with α,β-unsaturated carbonyl compounds 62 (Scheme 32).

Example 30

Synthesis of Fused Pyridine Derivatives of Cholanoic Acid Esters 67 (Scheme 33)

Following the protocol described above for the synthesis of benzofused derivatives 61 (Scheme 31), the fused pyridine derivatives of cholanoic acid esters 64 are prepared by treating the appropriate vinyl ester or ether 11 with α,β-unsaturated imines 65 (Scheme 33).

Example 31

Synthesis of Fused Pyrazine Derivatives of Cholanoic Acid Esters 69 (Scheme 34)

A solution of the appropriate 2,3-dioxocholanoic acid ester 2 (e.g. R=$^t$Bu) (5 mmol) and 1,2-diamine 68 (5 mmol) in DMF is heated at 100–120° C. for 5–24 h (monitored by TLC). After cooling to room temperature, the mixture is diluted with water (50 mL) and extracted with ethyl acetate (25 mL×3). The combined extract is washed with water (25 mL), dried over anhydrous sodium sulfate, and evaporated under reduced pressure. The residue is purified by silica gel chromatography using a gradient of ethyl acetate and hexane as eluents to give the corresponding pure fused pyrazine 69.

Example 32

Synthesis of Fused Pyrimidine Derivatives of Cholanoic Acid Esters 74–77 (Scheme 35)

A solution of the appropriate cholanoic acid ester building block 4 (5 mmol) and urea 70 (6 mmol) in ethanol (25 mL) was refluxed for 5–24 h (monitored by TLC). The reaction mixture was concentrated under reduced pressure. The residue was diluted with ethyl acetate (50 mL), washed with water (25 mL×2) and dried over dried over anhydrous sodium sulfate. After evaporation of the solvent the residue was purified by silica gel chromatography using a gradient of ethyl acetate and hexane as eluents to give the corresponding pure fused pyrimidone derivative 74 (Scheme 35).

Under identical reaction conditions, treatment of steroidal building blocks 4 with thiourea 71 afforded the corresponding fused 2-thiopyrimidones 75 and the amidine 73 ($X=C_6H_4CONH_2$) afforded the corresponding fused pyrimidine 77 (Scheme 35). Representative pyrimidine derivatives synthesized and their analytical data are given Table 5.

Similarly, other pyrimidine derivatives having the general structure 74–77 are prepared by reacting the steroidal building blocks 3, 4, and 5 with various 70–73 either in ethanol or DMF (Scheme 35).

Example 33

Synthesis of Fused Pyrimidine Derivatives of Cholanoic Acid Esters 82–85 (Scheme 36)

A solution of the appropriate oxoketene S,S-acetal derivative 6 (5 mmol) and urea (70) (5 mmol) in DMF (25 mL) is heated at 100–120° C. for 5–24 h (monitored by TLC). After cooling to room temperature, the mixture is diluted with water (50 mL) and extracted with ethyl acetate (25 mL×3). The combined extract is washed with water (25 mL), dried over anhydrous sodium sulfate and evaporated under reduced pressure. The residue is purified by silica gel chromatography using a gradient of ethyl acetate and hexane as eluents to give the corresponding pure fused thiomethylpyrimidone 78. Under identical reaction conditions, treatment of 6 with thiourea (71) affords the corresponding thiomethyl 2-thiopyrimidone 79; guanidine (72) affords 2-aminopyrimidine 80; and the amidine 73 affords pyrimidine 81 (Scheme 36). Following the same protocol, the treatment of N,S-acetals 7 and 8, with urea 70 affords the corresponding fused aminopyrimidones 82; thiourea 71 affords the fused amino 2-thiopyrimidones 83; guanidine 72 affords the fused diaminopyrimidines 84; and the amidines 73 afford the corresponding aminopyrimidines 85 (Scheme 36).

The amino substituted pyrimidine derivatives 82–85 are also prepared by the nucleophilic displacement of the thiomethyl moiety on the pyrimidines 78–81 with various amines 14 (Scheme 36). The appropriate pyrimidine 78–81 (3 mmol) is treated with m-chloroperbenzoic acid (7 mmol) in THF (25 mL) at room temperature for 12–24 h (monitored by TLC or LC/MS). The reaction mixture is filtered and the the filtrate is diluted with water (25 mL) followed by extraction with ethyl acetate (25 mL×3). The combined extract is washed with saturated sodium bicarbonate (15 ml×2), water (25 mL), dried over anhydrous sodium sulfate, and cautiously evaporated under reduced pressure. The crude sulfone is heated at ~70° C. with the appropriate amine 14 (3 mmol) in DMF (25 mL) for 12–24 h (monitored by TLC). The solvent is evaporated and the residue is chromatographed on silica gel column using a gradient of ethyl acetate and hexane as eluents to give the corresponding pure aminopyrimidines 82–85 (Scheme 36).

Example 34

Synthesis of Fused Pyrimidine Derivatives of Cholanoic Acid Esters 90–93 (Scheme 37)

A solution of enone 12 (5 mmol) and urea (70) in anhydrous DMF (25 mL) is heated at 100–120° C. for 8–24 h (monitored by TLC). The mixture is cooled to room temperature, diluted with cold water (50 mL), extracted with ethyl acetate (25 mL×3) and dried over anhydrous sodium sulfate. After evaporating the solvent, the residue is purified by silica gel column chromatography using a gradient of ethyl acetate and hexane as eluents to give the pure dihydropyrimidone 86. Similarly, the reaction of 12 with thiourea (71) affords the corresponding dihydrothiopyrimidone 87; reaction with guanidine (72) affords dihydroaminopyrimidine 88; and reaction with amidine 73 affords the dihydropyrimidine 89 (Scheme 37).

The purified or crude dihydropyrimidines 86–89 ($R^{11}$=H) (2 mmol) are refluxed with DDQ (3 mmol) in anhydrous toluene (25 mL) for 12–24 h (monitored by TLC). After evaporation of the solvent, the residues are purified by silica gel column chromatography using a gradient of ethyl acetate and hexane as eluents to give the pure pyrimidine derivatives 90–93 (Scheme 37).

V. General Procedures for the Synthesis of Fused Diazepine Derivative of Bile Acids Example 35

Synthesis of Fused Diazepine Derivatives of Cholanoic Acid Esters 95 and 97 (Schemes 38 and 40)

A solution of the appropriate 3-chloro-2-formyl cholanoic acid ester 3 (e.g. R=$^t$Bu) (5 mmol) and 1,2-diamine 94 (5 mmol) in DMF is heated at 100–120° C. for 5–24 h (monitored by TLC). After cooling to room temperature, the mixture is diluted with water (50 mL) and extracted with ethyl acetate (25 mL×3). The combined extract is washed with water (25 mL), dried over anhydrous sodium sulfate, and evaporated under reduced pressure. The residue is purified by silica gel chromatography using a gradient of ethyl acetate and hexane as eluents to give the corresponding pure fused diazepine 95 (Scheme 38).

Under identical reaction conditions, the reaction of 2-dimethylaminomethylene-3-oxocholanoic acid esters 5 with appropriate 1,2-diamines 94 affords the corresponding diazepines 96 (Scheme 39). Similarly, treatment of enones 12 with 1,2-diamines 94 affords the corresponding diazepines 97 (Scheme 40).

Example 36

Synthesis of Fused Diazepine Derivatives of Cholanoic Acid Esters 96 (Scheme 39)

A solution of the appropriate 2-hydroxymethylenecholenoic acid ester 4 (5 mmol) and 1,2-diamine 94 (5 mmol) in absolute ethanol was refluxed for 24 h (monitored by TLC). The reaction mixture was concentrated under reduced pressure. The residue was diluted with ethyl acetate (50 mL), washed with water (25 mL×2) and dried over dried over anhydrous sodium sulfate. After evaporation of the solvent the residue was purified by silica gel chromatography using a gradient of ethyl acetate and hexane as eluents to give the corresponding pure fused diazepine derivative 96 (Scheme 39).

Two representative diazepine derivative 96a-1 and 96a-2 were synthesized by treating 4a with 2,3-diaminophenol and methyl 3,4-diaminobenzoate respectively (Scheme 39).

Diazepine 96a-1: Yield, 24%. LC/MS (m/z): 519 (M+H, R=Et) and 505 (M+H, R=Me). Calcd. 518 ($C_{33}H_{46}N_2O_3$, R=Et) and 504 ($C_{32}H_{44}N_2O_3$, R=Me).

Diazepine 96a-2: Yield, 35%. LC/MS (m/z): 561 (M+H). Calcd. 560 ($C_{35}H_{48}N_2O_4$).

Example 37

Synthesis of Fused Diazepine Derivatives of Cholanoic Acid Esters 98 and 99 (Scheme 41)

A solution of the appropriate oxoketene S,S-acetal 6 (e.g. R=$^t$Bu) (5 mmol) and 1,2-diamine 94 (5 mmol) in anhydrous DMF is heated at 100–120° C. for 8–24 h (monitored by TLC). After cooling to room temperature, the reaction mixture is poured into cold water (50 mL), extracted with ethyl acetate (25 mL×3) and dried over anhydrous sodium sulfate. The solvent is evaporated and the residue is purified by column chromatography on silica gel using a gradient of ethyl acetate and hexane as eluents to give the pure thiomethyldiazepine derivative 98. Under identical reaction conditions N,S-acetals 7 and 8 afford the corresponding aminodiazepine derivatives 99.

The aminodiazepines 99 can also be prepared from the corresponding diazepines 98 (Scheme 41). The appropriate diazepine 98 (3 mmol) is treated with m-chloroperbenzoic acid (7 mmol) in THF (25 mL) at room temperature for 12–24 h (monitored by TLC or LC/MS). The reaction mixture is filtered and the filtrate is diluted with water (25 mL) and extracted with ethyl acetate (25 mL×3). The combined extract is washed with saturated sodium bicarbonate (15 mL×2), water (25 mL), dried over anhydrous sodium sulfate, and cautiously evaporated under reduced pressure. The crude sulfone is heated with the appropriate amine 14 (3 mmol) in DMF (25 mL) at ~70° C. for 12–24 h (monitored by TLC). The solvent is evaporated and the residue is chromatographed on silica gel column using a gradient of ethyl acetate and hexane as eluents to give the corresponding pure aminodiazepine 99 (Scheme 41).

VI. General Procedures for the Synthesis of Fused Octadiazepine Derivatives of Bile Acids Example 38

Synthesis of Fused Octadiazepine Derivatives of Cholanoic Acid Esters 101–103 (Schemes 42–44)

Following the protocol described for the synthesis of fused diazepine derivatives 95–97 (Schemes 38–40) the reaction of the appropriate 3-chloro-2-formyl cholenoic acid esters 3 with 1,3-diamines 100 affords the corresponding octadiazepines 101 (Scheme 42), the 2-hydroxymethylene 4, and 2-dimethylaminomethylene-3-oxocholanoic acid esters 5 with 100 affords the corresponding octadiazepines 102 (Scheme 43), and the enones 12 afford the corresponding octadiazepines 103 (Scheme 44).

Example 39

Synthesis of Fused Amino-substituted Octadiazeyine Derivatives of Cholanoic Acid Esters 105 (Scheme 45)

Following the protocol described for the synthesis of fused diazepine derivatives 98 (Scheme 41) the reaction of the appropriate oxoketene S,S-acetals 6 with 1,3-diamines 100 affords the corresponding thiomethyloctadiazepine derivatives 104. Similarly, the N,S-acetals 7 and 8 afford the corresponding amino-substituted octadiazepines 105 (Scheme 45).

The amino-substituted octadiazepines 105 (Scheme 45) are also prepared from the corresponding thiomethyl-substituted octadiazepines 104 by the nucleophilic displacement of the sulfone group with appropriate amines 14 following the procedure described for the synthesis of aminodiazepines 99 from the diazepines 98 (Scheme 41).

VII. General Procedure for the Synthesis of Fused Carbocyclic and Heterocyclic Derivatives of Glycocholanic Acid Esters Having the General Structure 10 (Scheme 46)

Example 40

Synthesis of Fused Cholanoic Acids Having the General Structure 107 (Scheme 46

Method 1. For R=Me, Et and other simple alkyl:
To a solution of a fused carbocyclic or heterocyclic derivative of cholanoic acid ester having the general structure 106 (5 mmol) in THF (25 mL) was added 2 equivalents of 2M NaOH and the reaction stirred 12–24 h (monitored by TLC). The reaction mixture was diluted with ice-cold water (25 mL) and acidified with 5% HCl. Then, the reaction mixture was extracted with ethyl acetate (20 mL×3) and the combined extract was washed with brine (20 mL), dried over anhydrous sodium sulfate and the solvent evaporated under reduced pressure. The crude product was purified by silica gel column chromatography using a 0–50% gradient of methanol and ethyl acetate as eluents to give the corresponding free fused cholanoic acid 107 (Scheme 46). The yields and analytical data for representative fused heterocyclic derivatives of bile acids having the general structure 107 are given in Table 6.

Method 2. For R=$^t$Bu
A fused carbocyclic or heterocyclic derivative of cholanoic acid ester having the general structure 106 (5 mmol) is treated with 15 mL of TFA or 4M HCl in dioxane at room temperature for 3–12 h (monitored by TLC). The reaction mixture is concentrated under reduced pressure and diluted with ethyl acetate (50 mL). Then, it is washed with water, dried over anhydrous sodium sulfate. The solvent is evaporated under reduced pressure. The crude product is purified by silica gel column chromatography using a 0–50% gradient of methanol and ethyl acetate as eluents to give the corresponding free fused cholanoic acid 107 (Scheme 46).

Method 3. For R=CH$_2$Ph
A fused carbocyclic or heterocyclic derivative of cholanoic acid ester having the general structure 106 (5 mmol) is dissolved in 25 mL of ethyl acetate and stirred with 10% Pd—C (50 mg) under 1 atm hydrogen gas for 4 h (monitored by TLC). The reaction is worked-up and purified as described above in Method 2.

Example 41

Synthesis of Fused Glycocholanic Acid Esters Having the General Structure 108 (R'=tert-butyl) (Scheme 46)

To a stirred suspension containing fused cholanoic acid derivative 107 (5 mmol), EDAC (15 mmol), and glycine tert-butyl ester (10 mmol) in anhydrous THF (25 mL) was added DIEA (50 mmol) at room temperature under a nitrogen atmosphere. The reaction mixture was stirred for 12–24 h (monitored by TLC). Then, the mixture was diluted with cold water (50 mL) and extracted with ethyl acetate (25 mL×3). The combined extract was washed with water (25 mL), brine (25 mL) and dried over anhydrous sodium sulfate. After evaporation of the solvent, the residue was purified by silica gel column chromatography using 25–100% gradient ethyl acetate and hexane as eluents to give the corresponding glycine tert-butyl ester 108. Representative glycocholanic acid esters 108 synthesized and their analytical data are given in Table 7.

Example 42

Synthesis of Fused Glycocholanoic Acids Having the General Structure 109 (Scheme 46)

The ester 108 was treated with 25 mL of 4M HCl in dioxane at room temperature for 3–12 h to cleave off the tert-butyl group. After completion, the reaction mixture was diluted with water (50 mL) and extracted with ethyl acetate (25 mL×3). The combined extract was washed with brine (25 mL), dried over anhydrous sodium sulfate and evaporated. The residue was purified by silica gel column chromatography using a gradient of 0–20% methanol and ethyl acetate as eluents to give the corresponding pure fused glycocholanoic acid derivative 109 in good yield. Trifluoroacetic acid was also used in some reactions instead of 4M HCl to cleave the tert-butyl group. Representative glycocholanoic acids 109 synthesized and the analytical data are given in Table 8.

VIII. General Procedure for the Synthesis of Fused Carbocyclic and Heterocyclic Derivatives of Taurocholanic Acid Having the General Structure 110 (Scheme 47)

Example 43

To a stirred solution of a fused carbocyclic or heterocyclic derivative of cholanoic acid 107 (5 mmol) and tributylamine (7 mmol) in anhydrous dioxane (15 mL) at 0° C. is added ethyl chloroformate (6 mmol). After stirring for 30 min, a solution of taurine (5 mmol) in 1M NaOH (5 mL) and dioxane (10 mL) is added in one portion. The mixture is stirred 3–5 h at room temperature (monitored by TLC). The reaction mixture is diluted with water (25 mL), acidified with 5% HCl and extracted with ethyl acetate (25 mL×4). The combined extract is washed with brine (20 mL), dried over anhydrous sodium sulfate and evaporated. The crude product is purified by silica gel column chromatography using 25–100% gradient of methanol and chloroform as eluents to give the pure taurocholanoic acid derivative 110. The treatment of 110 with one equivalent of NaOH followed by evaporation affords the corresponding sodium salt 111.

IX. General Procedure for the Synthesis of Fused Carbocyclic and Heterocyclic Derivatives of Taurocholanic Acid Having the General Structure 113 (Scheme 48)

Example 44

To a stirred suspension containing fused cholanoic acid derivative 107 (5 mmol), EDAC (15 mmol), and thioacetate 15 (10 mmol) in anhydrous THF (25 mL) is added DIEA (50 mmol) at room temperature under nitrogen atmosphere. The reaction mixture is stirred for 12–24 h (monitored by TLC). Then, the mixture is diluted with cold water (50 mL) and extracted with ethyl acetate (25 mL×3). The combined extract is washed with water (25 mL), brine (25 mL) and dried over anhydrous sodium sulfate. After evaporation of the solvent, the residue is chromatographed on silica gel column using 25–100% gradient ethyl acetate and hexane as eluents to give the corresponding thioacetate 112. Then, a mixture of $H_2O_2$ [30% w/w in $H_2O$ (5 mL)] and acetic acid (10 mL) is added to a solution of thioacetate 112 dissolved in acetic acid (5 mL). After stirring 12–18 h at room temperature 10% Pd/C (25 mg) is added to destroy the excess peroxide. For synthesis of the corresponding sodium sulfonate 114, sodium acetate (1.1 equiv) is added before adding the Pd/C, followed by stirring at room temperature for 1 h. Then the reaction mixture is filtered and the filtrate is concentrated. The crude taurocholanoic acid derivative 113 is purified by silica gel column chromatography using 25–100% methanol and chloroform as eluents. However, for the sodium salt of 114 ion-exchange resins are used instead of silica gel for the purification.

X. General Procedures for the Conjugation of Drug Molecules to Fused Carbocyclic and Heterocyclic Derivative of Glyco- and Taurocholanoic Acids Example 45

Conjugation of Drug Molecules or Surrogates to the Fused Ring of the Glycocholanoic Acids via an Ester Bond Synthesis of 118 (Scheme 49), 125 (Scheme 51), 126 (Scheme 52), and 133 (Scheme 54)

Method 1. Synthesis of conjugate ester 118-1 using oxalyl chloride and DMF as coupling agents (Scheme 49).

To a stirred solution of naproxen (1.0 mmol, 230.3 mg) in anhydrous benzene under nitrogen atmosphere at room temperature was added a catalytic amount of DMF (10–20 μL) followed by oxalyl chloride (3.0 mmol, 380.8 mg). The reaction mixture was stirred at room temperature until all solids were dissolved, the gas evolution stopped and the reaction mixture turned yellow. The benzene was evaporated under reduced pressure using a rotary evaporator and the residue was diluted in anhydrous dichloromethane (DCM) to a total volume of 5 mL (stock solution). The acid chloride stock solution (0.60 mL) was added dropwise to a stirred solution of pyrazole 108-48a-2 (0.01 to 0.005 mmol) and DMAP (5–10 mol %) in dichloromethane (2 mL) under nitrogen atmosphere at room temperature. The reaction mixture was stirred at room temperature for 18 h (monitored by TLC). The reaction was quenched with a saturated solution of sodium bicarbonate (5 mL) and diluted with ethyl acetate (40 mL). After separating the organic layer the aqueous layer was extracted with ethyl acetate (40 mL×2). The combined extracts were successively washed with an aqueous solution of potassium hydrogen sulfate, water, brine and finally dried over anhydrous $MgSO_4$. After evaporation of the solvent the crude product was purified by flash chromatography on silica gel using a gradient of hexane and ethyl acetate to give the pure products as white solids (Scheme 49).

Method 2. Synthesis of ester conjugates 118-2 and 118-3 using trichlorobenzoyl chloride (TCBC) as coupling agent (Scheme 49).

To a stirred solution of naproxen (0.12 mmol) in anhydrous dichloromethane (2 mL) under nitrogen atmosphere at room temperature was added trichlorobenzoyl chloride (0.12 mmol, 29.2 mg) followed by triethylamine (0.12 mmol, 12.2 mg). The reaction mixture was stirred at room temperature for 1 h. The resulting mixed anhydride intermediate was added to a stirred solution of the appropriate pyrazole (i.e. 108-48a-3 or 108-48c-3) (0.01 to 0.005 mmol) and DMAP (5–10 mol %) in anhydrous dichloromethane (2 mL) under nitrogen atmosphere at room temperature. The reaction mixture was stirred at room temperature for 18 h (monitored by TLC). The reaction was quenched with saturated solution of sodium bicarbonate (5 mL) and diluted with ethyl acetate (40 mL). After separating the organic layer the aqueous layer was extracted with ethyl acetate (40 mL×2). The combined extracts were successively washed with an aqueous solution of potassium hydrogen sulfate, water, brine and finally dried over anhydrous $MgSO_4$. After evaporation of the solvent the crude product was purified by flash chromatography on silica gel using a gradient of methanol and ethyl acetate to give the pure ester conjugate tert-butyl esters 118-2 and 118-3 (Scheme 49).

The tert-butyl group was cleaved by treating the appropriate drug and/or drug surrogate conjugated pyrazole derivative of glycocholanoic acid tert-butyl ester (0.1 mmol) with 5 mL of neat TFA (for conjugates derived from gly-colithocholic acid derivatives) or with a 4N solution of HCl in 1,4-dioxane (for conjugates derived from hydroxyl group-bearing bile acids such as glycocholic-, glycochenodeoxy-, or glycodeoxy acid derivatives). The reaction mixture was stirred for 5–24 h at room temperature and course of the reaction was monitored by TLC and/or LC/MS. Upon complete consumption of the starting materials, the TFA or the HCl/1,4-dioxane solution was concentrated under reduced pressure using a rotary evaporator. The residue was subjected to purification by preparative HPLC.

Similarly other drug and drug surrogates conjugated via an ester bond linkage: i.e. 118 (Scheme 49), 125 (Scheme 51), 126 (Scheme 52), and 133 (Scheme 54) are synthesized by following above described methods or by using standard protocols reported in the literature (vide infra). In the case of taurocholanoic acid derivatives, after conjugation of drug molecules or drug surrogates to 112, the oxidation of the thioacetate group to the corresponding sulfonic acid derivatives 126 and 133, and conversion to their sodium salts 134 and 141 are performed according to the procedures described for the synthesis of 113 and 114 (Scheme 48).

Ester Conjugate 118-1 ($R^1$=H, R=tBu) (Method 1)

Yield: 64–69%. $^1$H NMR (CDCl$_3$, 400 MHz, characteristic signals, dr ca. 3:1, de ca. 50%) δ 0.58 (3H, s, CH$_3$-19, minor diastereoisomer); 0.60 (3H, s, CH$_3$-19, major diastereoisomer); 0.80 (3H, d, J=6.4 Hz, CH$_3$-21, minor diastereoisomer); 0.84 (3H, d, J=6.4 Hz, CH$_3$-21, major diastercoisomer); 0.97 (3H, s, CH$_3$-18, major diastereoisomer); 0.98 (3H, s, CH$_3$-18, minor diastereoisomer); 1.44 (9H, s, C(CH$_3$)$_3$, both diastereoisomers); 1.51 [3H, d, J=7.6 Hz, CHCH$_3$C(=O), minor diastercoisomer]; 1.52 [3H, d, J=7.6 Hz, CHCH$_3$C(=O), major diastereoisomer]; 3.78 [1H, q, J=7.2 Hz, CHCH$_3$C(=O), minor diastereoisomer]; 3.82 [1H, q, J=7.2 Hz, CHCH$_3$C(=O),), major diastereoisomer]; 3.86–3.92 (5H, m, OCH$_3$, NHCH$_2$C(=O), both diastereoisomers]; 4.04–4.20 (2H, m, OCH$_2$CH$_2$N, both diastereoisomers); 4.26–4.50 (2H, m, OCH$_2$CH$_2$N, both diastereoisomers); 5.83 (1H, br. t, J=5.2 Hz, NHCH$_2$C(=O), minor diastereoisomer]; 5.88 (1H, br. t, J=4.8 Hz, NHCH$_2$C(=O), major diastereoisomer]; 7.06–7.36 (4H, m, Ar—H, Pyrazole-H); 7.52–7.70 (3H, m, Ar—H, both diastereoisomers) ppm. $^{13}$C NMR (CDCl$_3$, 100 MHz, major diastereoisomer) δ 12.04; 18.12; 18.30; 21.32; 23.02; 23.81; 24.01; 25.41; 25.89; 27.99; 29.67; 31.21; 31.54; 33.24; 35.18; 35.28; 35.44; 39.76; 40.14; 41.94; 42.64; 45.38; 50.39; 55.25; 55.80; 56.14; 63.60; 82.23; 105.52; 114.52; 119.10; 126.00; 126.17; 126.52; 127.20; 128.86; 129.22; 129.26; 133.69; 135.29; 137.08; 137.83; 148.64; 157.68; 169.30; 173.46; 174.09. LC/MS (m/z): found, 768 (M+H). Calcd.: 767 (C$_{47}$H$_{65}$N$_3$O$_6$).

Ester Conjugate 118-2 ($R^1$=H, R=tBu) (Method 2)

Yield: 68–79%. $^1$H NMR (CDCl$_3$, 400 MHz, characteristic signals) δ 0.60 (3H, s, CH$_3$-19); 0.85 (3H, d, J=6.4 Hz, CH$_3$-21); 1.03 (3H, s, CH$_3$-18); 1.44 [9H, s, C(CH$_3$)$_3$]; 1.65 [3H, d, J=7.2 Hz, CHCH$_3$C(=O)]; 3.89 [2H, d, J=5.2 Hz, NHCH$_2$C(=O)]; 3.90 (3H, s, OCH$_3$); 4.04 [1H, q, J=7.2 Hz, CHCH$_3$C(=O)]; 5.10 (1H, d, J=16.0 Hz, NCHHAr); 5.17 (1H, d, J=16.0 Hz, NCHHAr); 5.88 (1H, br. t, J=5.2 Hz, NHCH$_2$C(=O)]; 6.72–7.02 (3H, m, Ar—H); 7.10–7.30 (4H, m, Ar—H, Pyrazole-H); 7.43–7.48 (1H, dd, J=8.4, 1.2 Hz, Ar—H); 7.69–7.76 (3H, m, Ar—H) ppm; $^{13}$C NMR (CDCl$_3$, 100 MHz) δ 8.57; 12.31; 18.55; 18.78; 21.37; 22.55; 22.98; 24.03; 25.50; 25.68; 27.99; 29.66; 31.54; 31.87; 33.26; 35.10; 35.40; 35.73; 39.48; 39.80; 40.35; 41.94; 42.65; 45.49; 45.70; 52.23; 55.29; 55.89; 56.32; 82.23; 105.54; 114.81; 119.08; 119.95; 120.54; 124.07; 126.04; 126.09; 127.35; 128.92; 129.29; 129.59; 133.76; 135.01; 136.80; 137.59; 138.93; 151.01; 157.71; 169.29; 172.98; 173.45. LC/MS (m/z): found, 830 (M+H). Calcd.: 829 (C$_{52}$H$_{67}$N$_3$O$_6$).

Ester Conjugate 118-3 ($R^1$=OH, R=tBu) (Method 2)

Yield: 73%. $^1$H NMR (CDCl$_3$, 400 MHz, characteristic signals) δ 0.64 (3H, s, CH$_3$-19); 0.87 (3H, d, J=6.4 Hz, CH$_3$-21); 1.01 (3H, s, CH$_3$-18); 1.44 [9H, s, C(CH$_3$)$_3$]; 1.65 [3H, d, J=7.2 Hz, CHCH$_3$C(=O)]; 3.55 (1H, m, CHOH); 3.87 [2H, d, J=5.2 Hz, NHCH$_2$C(=O)]; 3.89 (3H, s, OCH$_3$); 3.67 [1H, q, J=7.2 Hz, CHCH$_3$C(=O)]; 4.04 [1H, q, J=7.2 Hz, CHCH$_3$C(=O)]; 5.07 (1H, d, J=14.8 Hz, NCHHAr); 5.17 (1H, d, J=14.8 Hz, NCHHAr); 5.92 (1H, br. t, J=5.2 Hz, NHCH$_2$C(=O)]; 6.83–6.92 (2H, m, Ar—H); 6.99 (1H, br. d, J=8.0 Hz, Ar—H); 7.09–7.16 (2H, m, Ar—H); 7.20 (1H, s, Pyrazole-H); 7.25 (1H, t, J=8.0 Hz, Ar—H); 7.31 (1H, dd, J=8.8, 2.0 Hz, Ar—H); 7.63–7.76 (3H, m, Ar—H) ppm. $^{13}$C NMR (CDCl$_3$, 100 MHz) δ 8.57; 12.04; 18.28; 18.51; 21.37; 22.55; 22.98; 24.03; 25.50; 25.68; 27.99; 28.17; 29.66; 31.54; 31.81; 33.26; 35.10; 35.40; 35.73; 39.48; 39.80; 40.35; 41.94; 42.65; 45.49; 52.23; 55.29; 55.89; 56.32; 82.23; 105.54; 114.81; 119.08; 119.95; 120.54; 124.07; 126.04; 126.09; 127.35; 128.93; 129.29; 129.59; 133.76; 135.01; 136.80; 137.59; 138.93; 151.01; 157.71; 169.29; 127.98; 173.45. LC/MS (m/z): found, 846 (M+H). Calcd.: 845 (C$_{52}$H$_{67}$N$_3$O$_7$).

Ester Conjugate 118-4 ($R^1$=H, R=H)

Yield: 60–80%. $^1$H NMR (CDCl$_3$, 400 MHz, dr ca. 3:1, de ca. 50%): δ 0.56 (3H, s, CH$_3$-19, minor diastereoisomer); 0.60 (3H, s, CH$_3$-19, major diastereoisomer); 0.78 (3H, d, J=6.4 Hz, CH$_3$-21, minor diastereoisomer); 0.84 (3H, d, J=6.8 Hz, CH$_3$-21, major diastereoisomer); 0.92 (3H, s, CH$_3$-18, major diastereoisomer); 0.94 (3H, s, CH$_3$-18, minor diastereoisomer); 1.49 [3H, d, J=6.8 Hz, CHCH$_3$C(=O), minor diastereoisomer]; 1.53 [3H, d, J=6.8 Hz, CHCH$_3$C(=O), major diastereoisomer]; 3.75 [1H, q, J=6.8 Hz, CHCH$_3$C(=O), minor diastereoisomer]; 3.83 [1H, q, J=6.8 Hz, CHCH$_3$C(=O),), major diastereoisomer]; 3.88 (3H, m, OCH$_3$, minor diastereoisomer) 3.89 (3H, m, OCH$_3$, major diastereoisomer); 3.97 (2H, br. m, HCH$_2$C(=O), both diastereoisomers); 4.20–4.40 (2H, br. m, OCH$_2$CH$_2$N, both diastereoisomers); 4.40–4.60 (2H, br. m, OCH$_2$CH$_2$N, both diastereoisomers); 6.57–6.72 (1H, br. m, NHCH$_2$C(=O), both diastereoisomers]; 7.06–7.21 (2H, m, Ar—H, both diastereoisomers); 7.26 (1H, dd, J=8.4, 1.6 Hz, Ar—H, minor diastereoisomer); 7.31 (1H, dd, J=8.4, 1.6 Hz, Ar—H, major diastereoisomer); 7.53 (1H, s, Pyrrazole-H, minor diastereoisomer); 7.60 (1H, s, Pyrazole-H, major diastereoisomer); 7.61–7.73 (3H, m, Ar—H, both diastereoisomers) ppm. $^{13}$C NMR (CDCl$_3$, 100 MHz, major diastereoisomer) δ 11.95; 17.65; 18.06; 18.14; 21.25; 21.50; 22.52; 23.85; 25.06; 27.97; 29.56; 29.67; 31.56; 32.73; 35.03; 35.28; 38.42; 39.48; 40.23; 41.54; 42.45; 42.54; 45.24; 49.91; 55.26; 55.32; 55.47; 55.95; 62.17; 105.55; 116.58; 119.25; 119.53; 125.97; 126.09; 127.40; 128.82; 129.28; 130.72; 146.44; 157.97; 173.63; 176.00.

Ester Conjugate 118-5 ($R^1$=H, R=H)

Yield: 60–80%. $^1$H NMR (CDCl$_3$, 400 MHz) δ 0.61 (3H, s, CH$_3$-19); 0.86 (3H, d, J=6.4 Hz, CH$_3$-21); 1.09 (3H, s, CH$_3$-18); 1.65 [3H, d, J=7.6 Hz CHCH$_3$C(=O)]; 3.91 (3H, s, OCH$_3$); 4.04 [2H, d, J=5.2 Hz, NHCH$_2$C(=O)]; 4.07 [1H, q, J=7.2 Hz, CHCH$_3$C(=O)]; 5.35 (1H, d, J=16.4 Hz, NCHHAr); 5.49 (1H, d, J=16.4 Hz, NCHHAr); 6.37 (1H, br. t, J=5.2 Hz, NHCH$_2$C(=O)]; 6.86–6.90 (1H, m, Ar—H); 6.92–7.00 (2H, m, Ar—H); 7.10–7.18 (2H, m, Ar—H); 7.31 (1H, t, J=8.0 Hz, Ar—H); 7.46 (1H, dd, J=8.4, 2.0 Hz, Ar—H); 7.62 (1H, s, Pyrazole-H); 7.69–7.76 (3H, br. m, Ar—H). LC/MS (m/z): found, 774 (M+H); 772 (M−H). Calcd.: 773 (C$_{48}$H$_{59}$N$_3$O$_6$).

Ester Conjugate 118-6 ($R^1$=OH, R=H)

Yield: 81%. $^1$H NMR (CDCl$_{3, 400}$ MHz): δ 0.60 (3H, s, CH$_3$-19); 0.85 (3H, d, J=6.4 Hz, CH$_3$-21); 1.02 (3H, s, CH$_3$-18); 1.65 [3H, d, J=7.6 Hz, CHCH$_3$C(=O)]; 3.77 (1H, br. m, CHOH); 3.89 (3H, s, OCH$_3$); 3.95 [2H, d, J=5.6 Hz, NHCH$_2$C(=O)]; 4.06 [1H, q, J=7.6 Hz, CHCH$_3$C(=O)]; 5.28 (2H, br. m, NCH$_2$Ar); 6.67 (1H, br. t, J=5.2 Hz, NHCH$_2$C(=O)]; 6.89–7.01 (2H, m, Ar—H); 7.07–7.17 (3H, m, Ar—H); 7.31 (1H, t, J=8.0 Hz, Ar—H); 7.36 (1H, s, Pyrazole-H); 7.43 (1H, dd, J=8.4, 2.0 Hz, Ar—H); 7.67–7.73 (3H, br. m, Ar—H). LC/MS (m/z): found, 790 (M+H); 788 (M−H). Calcd.: 789 (C$_{48}$H$_{59}$N$_3$O$_7$).

Example 46

Conjugation of Drug Molecules or Surrogates to the Fused Ring of Glycocholanoic Acid Derivatives via a Carbamate Bond Synthesis of 119 (Scheme 49), 123 (Scheme 50), 127 and 135 (Scheme 52), and 131 and 139 (Scheme 53)

Synthesis of Carbamate Conjugates 119 (Scheme 49)

To a stirred solution of pyrazole 108-48a-3 (1.0 mmol) in anhydrous THF (1 mL) under nitrogen atmosphere at room temperature was added a solution of N,N'-carbonyldiimidazole (162.2 mg, 1.0 mmol) in THF (4.8 mL). The reaction mixture was heated at 65° C. till the starting pyrazole was completely converted to the corresponding N-imidazolyl carbamate intermediate (~12 h, monitored by TLC). Then, a solution of appropriate amine drug or drug surrogate (0.2 mmol) in THF (1 mL) was added at room temperature. The reaction mixture was stirred at room temperature for 24 h (monitored by TLC). The reaction mixture was diluted with ethyl acetate (40 mL). After separating the organic layer the aqueous layer was extracted with ethyl acetate (40 mL×2). The combined extracts were successively washed with an aqueous solution of potassium hydrogen sulfate, water, brine and finally dried over anhydrous MgSO$_4$. After evaporation of the solvent the crude product was purified by flash chromatography on silica gel using a gradient of hexane and ethyl acetate to give the pure carbamate tert-butyl esters conjugates 119 (Scheme 49).

The tert-butyl group was cleaved by treating the appropriate drug and/or drug surrogate conjugated pyrazole glycocholanoic acid tert-butyl ester derivative (0.1 mmol) with 5 mL of neat TFA (for conjugates derived from glycolithocholic acid derivatives) or with a 4N solution of HCl in 1,4-dioxane (for conjugates derived from hydroxyl group-bearing bile acids such as glycocholic-, glycochenodeoxy-, or glycodeoxy acid derivatives). The reaction mixture was stirred for 5–24 h at room temperature and course of the reaction was monitored by TLC and/or LC/MS. Upon complete consumption of the starting materials, the TFA or the HCl/1,4-dioxane solution was concentrated under reduced pressure on rotary evaporator. The residue was subjected to purification by preparative HPLC.

Similarly other drug and drug surrogates conjugated via a carbamate bond linkage: 119 (Scheme 49), 123 (Scheme 50), 127 (Scheme 52), and 131 (Scheme 53) are synthesized by following above described method or by using standard protocols reported in the literature (vide infra). In the case of taurocholanoic acid derivatives, after conjugation of drug molecules or drug surrogates to 112, the oxidation of the thioacetate group to the corresponding sulfonic acid derivatives 127 and 131 and conversion to their sodium salts 135 and 139 are performed according to the procedures described for the synthesis of 113 and 114 (Scheme 48).

Carbamate Conjugate 119-1 (R=tBu)

Yield: 81%-quant. $^1$H NMR (CDCl$_3$, 400 MHz, characteristic signals, line broadening): δ 0.59 (3H, s, CH$_3$-19); 0.81 (3H, br. d, CH$_3$-21); 1.03 (3H, br. s, CH$_3$-18); 1.43 [9H, br. s, C(CH$_3$)$_3$]; 3.50–3.68 (2H, br. m, ArCH$_2$CH$_2$NH); 3.81 (6H, br. s, OCH$_3$); 3.88 [2H, d, J=5.2 Hz, NHCH$_2$C(=O)]; 4.20–4.32 (2H, br. m, OCH$_2$CH$_2$N); 4.33–4.45 (4H, br. m, OCH$_2$CH$_2$N, ArCH$_2$N); 5.92 (1H, br. t, NHCH$_2$C(=O)]; 7.00 (2H, br. s, Ar—H); 7.20 (1H, br. s, Pyrazole-H) ppm. $^{13}$C NMR (CDCl$_3$, 100 MHz) δ 12.01; 18.26; 21.38; 23.05; 23.09; 23.89; 23.97; 25.42; 25.90; 27.97; 28.11; 31.50; 31.60; 33.19; 35.18; 35.30; 35.62; 39.82; 40.20; 41.91; 42.63; 45.30; 50.89; 55.81; 55.87; 56.18; 66.11; 77.20; 82.18; 108.78; 109.02; 109.23; 111.33; 111.43; 113.92; 114.60; 125.01; 124.50; 125.97; 126.41; 147.60; 148.88; 155.03; 169.26; 173.44. LC/MS (m/z): found, 776 (M+H). Calcd.: 775 (C$_{45}$H$_{66}$N$_4$O$_7$).

Carbamate Conjugate 119-2 (R=tBu)

Yield: 67%. $^1$H NMR (CDCl$_3$, 400 MHz, characteristic signals, line broadening): δ 0.59 (3H, s, CH$_3$-19); 0.81 (3H, d, J=6.0 Hz, CH$_3$-21); 1.02 (3H, s, CH$_3$-18); 1.42 [9H, s, C(CH$_3$)$_3$]; 3.36 (2H, br. quint., J=6.4 Hz, ArCH$_2$CH$_2$NH); 3.81 (3H, s, OCH$_3$); 3.82 (3H, s, OCH$_3$); 3.87 [2H, d, J=4.8 Hz, NHCH$_2$C(=O)]; 4.12–4.27 (2H, m, OCH$_2$CH$_2$N); 4.28–4.45 (2H, m, OCH$_2$CH$_2$N); 4.86 (1H, br. t, J=4.0 Hz, ArCH$_2$CH$_2$NH), 5.96 (1H, br. t, NHCH$_2$C(=O)]; 6.67 (1H, br. d, J=7.2 Hz, Ar—H); 6.75 (1H, br. d, J=8.0 Hz, Ar—H); 6.95 (1H, br. s, Ar—H); 7.17 (1H, br. s, Pyrazole-H) ppm. $^{13}$C NMR (CDCl$_3$, 100 MHz) δ 11.99; 18.23; 23.05; 23.11; 23.30; 23.89; 25.39; 25.89; 27.94; 28.10; 31.49; 31.53; 33.16; 35.18; 35.31; 35.59; 35.73; 39.76; 39.80; 40.16; 41.88; 42.20; 42.62; 50.93; 55.76; 55.82; 55.90; 56.15; 63.46; 82.13; 111.23; 111.77; 114.57; 120.59; 126.39; 130.99; 131.04; 136.90; 147.60; 148.85; 148.91; 155.87; 169.25; 173.45. LC/MS (m/z): found: 764 (M+H). Calcd.: 763 (C$_{44}$H$_{66}$N$_5$O$_7$).

Carbamate Conjugate 119-3 (R=H)

Yield: 45% unoptimized. LC/MS (m/z): found, 719 (M+H); 717 (M–H). Calcd.: 718 (C$_{41}$H$_{58}$N$_4$O$_7$).

Carbamate Conjugate 119-4 (R=H)

Yield: 60%. $^1$H NMR (CDCl$_3$, 400 MHz, characteristic signals, line broadening): δ 0.60 (3H, s, CH$_3$-19); 0.82 (3H, br. d, CH$_3$-21); 1.09 (3H, s, CH$_3$-18); 3.20–3.40 (2H, br. m, ArCH$_2$CH$_2$NH); 3.76–3.88 (8H, m, 2×OCH$_3$, NHCH$_2$C(=O)]; 3.92–4.04 (2H, br. m, ArCH$_2$CH$_2$N); 4.30–4.60 (4H, br. m, OCH$_2$CH$_2$N, OCH$_2$CH$_2$N); 5.52–5.75 (1H, br. m, ArCH$_2$CH$_2$NH); 6.55–6.80 (4H, br. m, Ar—H, NHCH$_2$C(=O)]; 7.27 (1H, br. s, Pyrazole-H). LC/MS (m/z): found, 707 (M+H); 705 (M–H). Calcd.: 706 (C$_{40}$H$_{58}$N$_4$O$_7$).

Example 47

Conjugation of Drug Molecules or Surrogates to the Fused Ring of Glycocholanoic Acid Derivatives via a Carbonate Bond Synthesis of 120 (Scheme 49) and 128 and 136 (Scheme 52)

Synthesis of Carbonate Conjugate 120-1 (Scheme 49)

To a stirred solution of β-ethylphenylethylalcohol (150.2 mg, 1.0 mmol) in anhydrous THF (3 mL) under nitrogen atmosphere at 0° C. was added a solution of N,N'-carbonyldiimidazole (162.2 mg, 1.0 mmol) in THF (1.6 mL). After having stirred at 0° C. for 10 min the reaction mixture was further stirred at room temperature for 2 h to give the N-imidazolylcarbamate intermediate. The carbamate intermediate was added dropwise to a stirred solution of pyrazole 108-48a-3 (0.1 mmol) and catalytic amounts of sodium hydride (2–3 mg) in THF (1 mL) at 0° C. The reaction mixture was stirred at 0° C. for 30 min and then at room temperature for 18 h (monitored by TLC). The reaction was diluted with ethyl acetate (40 mL). After separating the organic layer the aqueous layer was extracted with ethyl acetate (40 mL×2). The combined extracts were successively washed with an aqueous solution of potassium hydrogen sulfate, water, brine and finally dried over anhydrous MgSO$_4$. After evaporation of the solvent the crude product was purified by flash chromatography on silica gel using a gradient of hexane and ethyl acetate to give the pure carbonate tert-butyl ester conjugate 120-1 (Scheme 49).

The tert-butyl group was cleaved by treating the appropriate drug and/or drug surrogate conjugated pyrazole glycocholanoic acid tert-butyl ester derivative (0.1 mmol) with 5 mL of neat TFA (for conjugates derived from glycolithocholic acid derivatives) or with a 4N solution of HCl in 1,4-dioxane (for conjugates derived from hydroxyl group-bearing bile acids such as glycocholic-, glycochenodeoxy-, or glycodeoxy acid derivatives). The reaction mixture was stirred for 5–24 h at room temperature and course of the reaction was monitored by TLC and/or LC/MS. Upon complete consumption of the starting materials, the TFA or the HCl/1,4-dioxane solution was concentrated under reduced pressure on rotary evaporator. The residue was subjected to purification by preparative HPLC.

Similarly other drug and drug surrogates conjugated via a carbonate bond linkage: 121 (Scheme 49), 128 (Scheme 52) are synthesized by following above described method or by using standard protocols reported in the literature (vide infra). In case of taurocholanoic acid derivatives, after conjugation of drug molecules or drug surrogates to 112, the oxidation of the thioacetate group to the corresponding sulfonic acid derivatives 128 and conversion to their sodium salts 136 are performed according to the procedures described for the synthesis of 113 and 114 (Scheme 48).

Carbonate Conjugate 120-1 (R=tBu)

Yield: 57%. $^1$H NMR (CDCl$_3$, 400 MHz, characteristic signals, both diastereoisomers, dr ca. 2:1, de ca. 33%): δ 0.61 (3H, s, CH$_3$-19, both diastereoisomers); 0.78 (3H, t, J=7.6 Hz, CH(CH$_2$CH$_3$), minor diastereoisomer), 0.79 (3H, t, J=7.6 Hz, CH(CH$_2$CH$_3$), major diastereoisomer); 0.84 (3H, d, J=6.4 Hz, CH$_3$-21, major diastercoisomier); 0.86 (3H, d, J=6.4 Hz, CH$_3$-21, minor diastereoisomer); 1.04 (3H, s, CH$_3$-18, major diastereoisomer); 1.05 (3H, s, CH$_3$-18, minor diastereoisomer); 1.43 [9H, s, C(CH$_3$)$_3$, major diastereoisomer]; 1.44 [9H, s, C(CH$_3$)$_3$, minor diastereoisomer]; 2.74–2.88 (1H, m, CH(CH$_2$CH$_3$), both diastereoisomers); 3.89 [2H, d, J=5.2 Hz, NHCH$_2$C(=O), both diastereoisomers]; 4.1–4.26 (4H, m, CH(CH$_2$O), OCH$_2$CH$_2$N, both diastereoisomers); 4.32–4.44 (2H, m, OCH$_2$CH$_2$N, both diastereoisomers); 5.91 (1H, br. t, J=4.4 Hz, NHCH$_2$C(=O)]; 7.10–7.31 (6H, m, Pyrazole-H, Ar—H, both diastereoisomers) ppm. $^{13}$C NMR (CDCl$_3$, 100 MHz, major diastereoisomer) δ 11.66; 12.04; 18.28; 21.39; 23.12; 23.88; 24.02; 25.10; 25.43; 25.91; 27.98; 28.15; 29.64; 31.55; 33.23; 35.23; 35.35; 35.62; 39.78; 39.82; 40.19; 41.93; 42.67; 46.63; 50.35; 55.82; 56.18; 66.37; 71.79; 82.20; 114.73; 126.64; 126.79; 127.86; 128.45; 137.13; 141.02; 149.08; 154.73; 169.28; 173.47. LC/MS (m/z): found: 733 (M+H). Calcd.: 732 (C$_{44}$H$_{65}$N$_3$O$_6$).

Carbonate Conjugate 120-2

Yield: ca. quant. $^1$H NMR (CDCl$_3$, 400 MHz, both diastereoisomers, characteristic signals, line broadening, dr ca. 2:1, de ca. 33%): δ 0.62 (3H, s, CH$_3$-19, both diastereoisomers); 0.77 (3H, t, J=7.6 Hz, CH(CH$_2$CH$_3$), minor diastereoisomer), 0.79 (3H, t, J=7.6 Hz, CH(CH$_2$CH$_3$), major diastereoisomer); 0.84 (3H, br. d, J=6.4 Hz, CH$_3$-21, both diastereoisomers); 1.15 (3H, s, CH$_3$-18, both diastereoisomers); 4.03 [2H, d, J=4.4 Hz, NHCH$_2$C(=O), both diastereoisomers]; 4.16–4.32 (4H, m, CH(CH$_2$O), OCH$_2$CH$_2$N, both diastereoisomers); 4.32–4.70 (2H, m, OCH$_2$CH$_2$N, both diastereoisomers); 6.86 (1H, br. t, NHCH$_2$C(=O), both diastercoisomers]; 7.10–7.40 (6H, m, Pyrazole-H, Ar—H, both diastercoisomers). LC/MS (m/z): found, 676 (M+H). Calcd.: 675 (C$_{40}$H$_{57}$N$_3$O$_6$).

Example 48

Conjugation of Drug Molecules or Surrogates to the Fused Ring of Glycocholanoic Acid Derivatives via an Amide Bond Synthesis of 121 (Scheme 50), 124 (Scheme 51), 129 and 137 (Scheme 53), and 132 and 140 (Scheme 54)

To a stirred suspension containing 106-2 (5 mmol), bearing a free amino group on the fused ring, EDAC or an equivalent coupling agent such as DCC, DIC (15 mmol), and a drug molecule or surrogate bearing a carboxyl group 115 (5 mmol) in anhydrous THF (25 mL) is added DIEA (50 mmol) at room temperature under a nitrogen atmosphere. The reaction mixture is stirred for 12–24 h (monitored by TLC). Then, the mixture is diluted with cold water (50 mL) and extracted with ethyl acetate (25 mL×3). The combined extract is washed with water (25 mL), brine (25 mL) and dried over anhydrous sodium sulfate. After evaporation of the solvent, the residue is purified by silica gel column chromatography using 25–100% gradient ethyl acetate and hexane as eluents to give the corresponding amide conjugate tert-butyl esters (Scheme 50).

The tert-butyl group was cleaved by treating the appropriate drug and/or drug surrogate conjugated pyrazole derivative of glycocholanoic acid tert-butyl ester (0.1 mmol) with 5 mL of neat TFA (for conjugates derived from glycolithocholic acid derivatives) or with a 4N solution of HCl in 1,4-dioxane (for conjugates derived from hydroxyl group-bearing bile acids such as glycocholic-, glycochenodeoxy-, or glycodeoxy acid derivatives). The reaction mixture was stirred for 5–24 h at room temperature and course of the reaction was monitored by TLC and/or LC/MS. Upon complete consumption of the starting materials, the TFA or the HCl/1,4-dioxane solution was concentrated under reduced pressure on rotary evaporator. The crude residue was subjected to purification by preparative HPLC.

Similarly other drug and drug surrogate conjugated via an amide bond linkage: 121 (Scheme 50), 124 (Scheme 51), 129 (Scheme 53) and 132 (Scheme 54) are synthesized by following above described method or by using standard protocols reported in the literature (vide infra). In case of taurocholanoic acid derivatives, after conjugation of drug molecules or drug surrogates to 112, the oxidation of the thioacetate group to the corresponding sulfonic acid derivatives 129 and 132 and conversion to their sodium salts 137 and 140 are performed according to the procedures described for the synthesis of 113 and 114 (Scheme 48).

Example 49

Conjugation of Drug Molecules or Surrogates to the Fused Ring of Glycocholanoic Acid Derivatives via a Urea Bond Synthesis of 122 (Scheme 50) and 130, 138 (Scheme 53)

To a stirred solution of 106-2 (1.0 mmol) in anhydrous THF (1 mL) under nitrogen atmosphere at room temperature was added a solution of N,N'-carbonyldiimidazole (162.2 mg, 1.0 mmol) in THF (4.8 mL). The reaction mixture was heated at 65° C. till complete conversion of the starting 106-2 to the corresponding N-imidazolyl carbamate intermediate (~12 h, monitored by TLC). Then, a solution of appropriate amine drug or drug surrogate 116 (0.2 mmol) in THF (1 mL) was added at room temperature. The reaction mixture was stirred at room temperature for 24 h (monitored by tlc). The reaction mixture was diluted with ethyl acetate (40 mL). After separating the organic layer the aqueous layer was extracted with ethyl acetate (40 mL×2). The combined extracts were successively washed with an aqueous solution of potassium hydrogen sulfate, water, brine and finally dried over anhydrous $MgSO_4$. After evaporation of the solvent the crude product was purified by flash chromatography on silica gel using a gradient of hexane and ethyl acetate to give the pure urea tert-butyl ester conjugates (Scheme 50).

The tert-butyl group was cleaved by treating the appropriate drug and/or drug surrogate conjugated pyrazole glycocholanoic acid tert-butyl ester derivative (0.1 mmol) with 5 mL of neat TFA (for conjugates derived from glycolithocholic acid derivatives) or with a 4N solution of HCl in 1,4-dioxane (for conjugates derived from hydroxyl group-bearing bile acids such as glycocholic-, glycochenodeoxy-, or glycodeoxy acid derivatives). The reaction mixture was stirred for 5–24 h at room temperature and course of the reaction was monitored by TLC and/or LC/MS. Upon complete consumption of the starting materials, the TFA or the HCl/1,4-dioxane solution was concentrated under reduced pressure on rotary evaporator. The crude residue was subjected to purification by preparative HPLC.

Similarly other drug and drug surrogate conjugates via urea bond linkage are synthesized by following above described method or by using standard protocols reported in the literature (vide infra). In case of taurocholanoic acid derivatives, after conjugation of drug molecules or drug surrogates to 112, the oxidation of the thioacetate group to the corresponding sulfonic acid derivatives 130 and conversion to their sodium salts 138 are performed according to the procedures described for the synthesis of 113 and 114 (Scheme 48).

XI. Analytical Data

TABLE 1

3-Oxocholanoic acid methyl esters 1a–d prepared (Scheme 1)

| Compound | Yield (%) | Mol. Formula (Calcd. exact M. Wt.) | LC-MS Data |
|---|---|---|---|
| 1a | 92 | $C_{25}H_{40}O_3$ (388) | 389 (M + H); 777 (2M + H) |
| 1b | 79 | $C_{25}H_{40}O_5$ (420) | 841 (2M + H) |
| 1c | 85 | $C_{25}H_{40}O_4$ (404) | 387 (M − OH); 809 (2M + H) |
| 1d | 70 | $C_{25}H_{40}O_4$ (404) | 387 (M − OH); 809 (2M + H) |

TABLE 2

2-Hydroxymethylene-3-oxocholanoic acid ethyl/methyl esters 4a–c prepared (Scheme 4)

| Compound | % Yield, NMR[a] and LC-MS Data |
|---|---|
| 4a<br>$R^1$ = H<br>$R^2$ = H | Yield, 94%. $^1$H NMR (CDCl$_3$, 400MHz):δ 0.65 (3H, s, CH$_3$-19); 0.93 (3H, d, J=6.4Hz, CH$_3$-21); 1.01 (3H, s, CH$_3$-18), 1.10–2.80 (CH$_2$ & CH-steroidal and OCH$_2$CH$_3$), 4.10 (2H, q, J=6.8Hz, OCH$_2$); 8.24 (1H, s, =CH). LC/MS (m/z): found, 431 (M+H, R=Et); 417 (M+H, R=Me) and calcd., 430 ($C_{27}H_{42}O_4$, R=Et), 416 ($C_{26}H_{40}O_4$, R=Me). |
| 4b<br>$R^1$ = OH<br>$R^2$ = OH | Yield, 81%. $^1$H NMR (CDCl$_3$, 400MHz):δ 0.68 (3H, s, CH$_3$-19); 0.91 (3H, d, J=6.0Hz, CH$_3$-21); 1.01 (3H, s, CH$_3$-18), 1.10–2.80 (CH$_2$ & CH-steroidal and OCH$_2$CH$_3$), 3.80 (1H, bs, CH-12); 3.88 (1H, bs, CH-7); 4.12 (2H, q, J=6.8Hz, OCH$_2$); 9.12 (1H, s, =CH). LC/MS (m/z): found, 925 (2M+H, R=Et); 461 (M−H, R=Et); 447 (M−H, R=Me). Calcd., 462 ($C_{27}H_{42}O_6$, R=Et) and 448 ($C_{26}H_{40}O_6$, R=Me). |
| 4c<br>$R^1$ = OH,<br>$R^2$ = H | Yield, 93%. $^1$H NMR (CDCl$_3$, 400MHz):δ 0.66 (3H, s, CH$_3$-19); 0.91 (3H, d, J=6.4Hz, CH$_3$-21); 1.02 (3H, s, CH$_3$-18), 1.10–2.80 (CH$_2$ & CH-steroidal and OCH$_2$CH$_3$), 3.82 (1H, m, CH-7); 4.12 (2H, q, J=6.8Hz, OCH$_2$); 9.13 (1H, s, =CH). LC/MS (m/z): found, 447 (M+H, R=Et); 445 (M−H, R=Et); 431 (M−H, R=Me). Calcd., 446 ($C_{27}H_{42}O_5$, R=Et) and 432 ($C_{26}H_{40}O_5$, R=Me). |
| 4d<br>$R^1$ = H,<br>$R^2$ = OH | Yield, %. LC/MS (m/z): found, 447 (M+H, R=Et); 445 (M−H, R=Et); 431 (M−H, R=Me). Calcd., 446 ($C_{27}H_{42}O_5$, R=Et) and 432 ($C_{26}H_{40}O_5$, R=Me). |

[a]The products 4a–d were obtained as a mixture of ethyl and methyl esters (R=Et and Me) in a ~3:1 to 5:1 ratio and their ratios were determined by $^1$H NMR spectral data. $^1$H NMR data of the major isomers (R=Et) are reported herein.

TABLE 3

3-Dimethylaminomethylene-3-oxocholanoic acid methyl esters 5a–c prepared (Scheme 5)

| Compound | Yield (%) | Mol. Formula (Calcd. exact M. Wt.) | LC-MS Data |
|---|---|---|---|
| 5a | 79 | $C_{28}H_{45}NO_3$ (443) | m/z=444 (M+H) |
| 5b | 55 | $C_{28}H_{45}NO_5$ (475) | m/z=476 (M+H), 457 (M−H$_2$O) |
| 5c | 66 | $C_{28}H_{45}NO_4$ (459) | m/z=460 (M+H) |

TABLE 4

2,3-Fused pyrazole derivative cholanoic acid ethyl/methyl esters having general structures 48 and 49 synthesized (Scheme 24)

| Compound | % Yield, NMR[a] and LC-MS Data |
|---|---|
| 48a-1<br>$R^1$ = H,<br>$R^2$ = H<br>$R^{19}$ = H | Yield, 84%. $^1$H NMR (CDCl$_3$, 400 MHz):δ 0.65 (3H, s, CH$_3$-19); 0.86 (3H, bd, J=6.0Hz, CH$_3$-21); 1.10 (3H, s, CH$_3$-18), 1.12–2.89 (CH$_2$ & CH-steroidal and OCH$_2$CH$_3$), 4.12 (2H, q, J=6.8Hz, OCH$_2$); 7.27 (1H, bs, H-Pyrazole). LC/MS (m/z): found, 399 (M-OEt, R=Et). Calcd., 426 ($C_{27}H_{42}N_2O_2$, R=Et). |
| 48a-2<br>$R^1$ = H,<br>$R^2$ = H,<br>$R^{19}$ = A | Yield, 75%. $^1$H NMR (CDCl$_3$, 400 MHz):δ 0.63 (3H, s, CH$_3$-19); 0.85 (3H, bd, J=6.4Hz, CH$_3$-21); 1.06 (3H, s, CH$_3$-18), 1.12–2.85 (CH$_2$ & CH-steroidal and OCH$_2$CH$_3$), 3.95 (2H, m, CH$_2$); 4.10 (4H, m, CH$_2$); 7.03 (1H, s, H-Pyrazole). LC/MS (m/z): found, 471 (M+H, R=Et). Calcd., 470 ($C_{29}H_{46}N_2O_3$, R=Et). |
| 48a-3<br>$R^1$ = H,<br>$R^2$ = H<br>$R^{19}$ = B | Yield, 69%. $^1$H NMR (CDCl$_3$, 400 MHz):δ 0.63 (3H, s, CH$_3$-19); 0.86 (31, bd, J=6.0Hz, CH$_3$-21); 1.07 (3H, s, CH$_3$-18), 1.12–2.85 (CH$_2$& CH-steroidal and OCH$_2$CH$_3$), 4.11 (2H, q, J=7.2Hz, OCH$_2$); 5.13 (2H, m, CH$_2$Ar); 6.57–6.71 (3H, m, H—Ar); 7.03–7.20 (2H, m, H-Pyrazole and H—Ar). LC/MS (m/z): found, 533 (M+H, R=Et); 531 (M−H, R=Et); 519 (M+H, R=Me). Calcd., 532 ($C_{34}H_{48}N_2O_3$, R=Et) and 518 ($C_{33}H_{46}N_2O_3$, R=Me). |

TABLE 4-continued 2,3-Fused pyrazole derivative cholanoic acid ethyl/methyl esters having general structures 48 and 49 synthesized (Scheme 24)

| Compound | % Yield, NMR[a] and LC-MS Data |
|---|---|
| 48a-4<br>$R^1$ = H,<br>$R^2$ = H,<br>$R^{19}$ = C | Yield, 78%. $^1$H NMR (CDCl$_3$, 400 MHz, mixture of two regioisomers, ~6;4):δ 0.63 (3H, s, CH$_3$-19); 0.85 (3H, bd, J= 6.0 Hz, CH$_3$-21); 1.11 (3H, bs, CH$_3$-18), 1.12–3.02 (CH$_2$ & CH-steroidal and OCH$_2$CH$_3$), 4.10 (2H, q, J=6.8Hz, OCH$_2$); 4.22 (2H, q, J=7.2Hz, OCH$_2$); 4.79 (2H, m, CH$_2$); 7.07 and 7.24 (1H, s, H-Pyrazole). LC/MS (m/z): found, 513 (M+H, R=Et); 511 (M−H, R=Et); 499 (M+H, R=Me). Calcd., 512 (C$_{31}$H$_{48}$N$_2$O$_4$, R=Et) and 498 (C$_{30}$H$_{46}$N$_2$O$_4$, R=Me). |
| 48b-1<br>$R^1$ = OH,<br>$R^2$ = OH<br>$R^{19}$ = B | Yield, 63%. $^1$H NMR (CDCl$_3$, 400 MHz):δ 0.68 (3H, s, CH$_3$-19); 0.86 (3H, bd, J=6.4Hz, CH$_3$-21); 1.02 (3H, s, CH$_3$-18), 1.12–2.85 (CH$_2$ & CH-steroidal and OCH$_2$CH$_3$), 3.97 (1H, bs, CH-7); 3.78 (1H, bs, CH-12); 4.10 (2H, q, J=7.2Hz, OCH$_2$); 5.04 (2H, m, CH$_2$Ar); 6.48 (1H, bs, H—Ar); 6.64 (2H, m, H—Ar); 7.07 (1H, m, H—Ar); 7.27 (1H, s, H-Pyrazole). $^{13}$C NMR (CDCl$_3$, 100 MHz): δ 13.06, 14.70, 17.73, 19.40, 21.81, 23.50, 27.02, 27.77, 29.58, 31.27, 31.40, 31.48, 31.77, 32.79, 35.11, 35.57, 38.23, 39.68, 42.36, 47.45, 51.85, 55.94, 60.55, 69.47, 73.12, 114.65, 115.66, 121.50, 129.3, 131.01, 138.00, 148.2, 158.72, 175.95. LC/MS (m/z): found, 565 (M+H, R=Et); 563 (M-1, R=Et); 551 (M+H, R=Me); 549 (M−H, R=Me). Calcd., 564 (C$_{34}$H$_{48}$N$_2$O$_5$, R=Et) and 550 (C$_{33}$H$_{46}$N$_2$O$_5$, R=Me). |
| 48c-1<br>$R^1$ = OH,<br>$R^2$ = H,<br>$R^{19}$ = H | Yield, 99%. $^1$H NMR (CDCl$_3$, 400 MHz):δ 0.67 (3H, s, CH$_3$-19); 0.86 (3H, bd, J=6.4Hz, CH$_3$-21); 1.10 (3H, s, CH$_3$-18), 1.12–2.80 (CH$_2$ & CH-steroidal and OCH$_2$CH$_3$), 3.86 (1H, m, CH-7); 4.12 (2H, q, J=7.2Hz, OCH$_2$); 7.62 (1H, bs, H-Pyrazole). LC/MS (m/z): found, 443 (M+H, R=Et). Calcd., 442 (C$_{27}$H$_{42}$N$_2$O$_3$, R=Et). |
| 48c-2<br>$R^1$ = OH,<br>$R^2$ = H,<br>$R^{19}$ = A | Yield, 88%. $^1$H NMR (CDCl$_3$, 400 MHz):δ 0.66 (3H, s, CH$_3$-19); 0.89 (3H, bd, J=6.4Hz, CH$_3$-21); 1.08 (3H, s, CH$_3$-18), 1.12–2.85 (CH$_2$ & CH-steroidal and OCH$_2$CH$_3$), 3.82 (1H, m, CH-7); 3.98 (2H, m, CH$_2$); 4.19 (4H, m, CH$_2$); 7.03 (1H, s, H-Pyrazole). LC/MS (m/z): found, 487 (M+H, R=Et); 473 (M+H, R=Me). Calcd., 486 (C$_{29}$H$_{46}$N$_2$O$_4$, R=Et) and 472 (C$_{28}$H$_{44}$N$_2$O$_4$, R=Me), |
| 48c-3<br>$R^1$ = OH,<br>$R^2$ = H,<br>$R^{19}$ = B | Yield, 93%. $^1$H NMR (CDCl$_3$, 400 MHz):δ 0.64 (3H, s, CH$_3$-19); 0.86 (3H, bd, J=7.2Hz, CH$_3$-21); 1.05 (3H, s, CH$_3$-18), 1.12–2.72 (CH$_2$ & CH-steroidal and OCH$_2$CH$_3$), 3.81 (1H, bs, CH-7), 4.11 (2H, q, J=7.2Hz, OCH$_2$); 5.10 (2H, m, CH$_2$Ar); 6.61 (1H, s, H—Ar); 6.68 (2H, m, H—Ar); 7.11 (1H, m, H—Ar); 7.40 (1H, s, H-Pyrazole). LC/MS (m/z): found, 549 (M+H, R=Et); 547 (M−H, R=Et); 535 (M+H, R=Me). Calcd., 548 (C$_{34}$H$_{48}$N$_2$O$_4$, R=Et) and 534 (C$_{33}$H$_{46}$N$_2$O$_4$, R=Me). |
| 49a-1<br>$R^1$ = H,<br>$R^2$ = H,<br>$R^{19}$ = D | Yield, 71%. $^1$H NMR (CDCl$_3$, 400 MHz):δ 0.65 (3H, s, CH$_3$-19); 0.86 (3H, d, J=6.8Hz, CH$_3$-21); 1.11 (3H, s, CH$_3$-18), 1.12–3.02 (CH$_2$ & CH-steroidal and OCH$_2$CH$_3$), 4.10 (2H, q, J=6.8Hz, OCH$_2$); 7.20 (1H, m, H—Ar); 7.39 (2H, m, H—Ar); 7.58 (1H, m, H—Ar); 7.65 (2H, m, H—Ar). $^{13}$C NMR (CDCl$_3$, 100 MHz):δ 12.51, 14.67, 18.63, 21.84, 23.52, 24.48, 25.87, 26.38, 28.52, 30.08, 31.35, 31.68, 32.14, 35.66, 35.67, 40.17, 40.21, 40.75, 43.08, 56.17, 56.58, 60.46, 117.24, 118.53, 118.57, 123.39, 123.48, 125.58, 125.63, 129.42, 151.09, 174.35. LC/MS (m/z): found, 503 (M+H, R=Et). Calcd., 502 (C$_{33}$H$_{46}$N$_2$O$_2$, R=Et). |

A = HOCH$_2$CH$_2$—; B = m-HOC$_6$H$_4$CH$_2$—; C = EtOC(O)CH$_2$—; D = C$_6$H$_5$

[a]The pyrazoles 48–49 were obtained as a mixture of ethyl and methyl esters (R=Et and Me) in a ~5:1 to 8:1 ratio and their ratios were determined by $^1$H NMR spectral data. $^1$H NMR data of the major isomers (R = Et) are reported herein.

TABLE 5

2,3-Fused pyrimidine derivative cholanoic acid ethyl/methyl esters 74a-1, 75a-1, and 77a-1 synthesized (Scheme 35)

| Compound | % Yield, NM[a] and LC-MS Data |
|---|---|
| 74a-1<br>$R^1$ = H<br>$R^2$ = H<br>X = OH | Yield, 54%. $^1$H NMR (CDCl$_3$): LC/MS (m/z): found: 455 (M+H, R=Et); 441 (M+H, R=Me) and calcd., 454 (C$_{28}$H$_{42}$N$_2$O$_3$, R=Et); 440 (C$_{27}$H$_{40}$N$_2$O$_3$, R=Me),. |
| 75a-1<br>$R^1$ = H,<br>$R^2$ = H<br>X = SH | Yield, 41%. LC/MS (m/z): found: 471 (M+H, R=Et); 469 (M−H, R=Et); 455 (M−H, R=Me) and calcd., 470 (C$_{28}$H$_{42}$N$_2$O$_2$S, R=Et); 456 (C$_{27}$H$_{40}$N$_2$O$_2$S, R=Me),. |
| 77a-1<br>$R^1$ = H,<br>$R^2$ = H<br>X = p-C$_6$H$_4$—CONH$_2$ | Yield, 63%. $^1$H NMR (CDCl$_3$, 400 MHz):δ 0.642 (3H, s, CH$_3$-19); 0.84 (3H, d, J=6.4, CH$_3$-21); 1.15 (3H, s, CH$_3$-18), 1.25–3.15 (26H, m, CH$_2$ & CH-steroidal and OCH$_2$CH$_3$), 3.89 (2H, q, J=7.2 Hz, OCH$_2$CH$_3$); 7.91 (2H, d, J=8.4 Hz, H—Ar); 8.41 (1H, s, H-Pyrimidine); 8.48 (2H, d, J=8.4, H—Ar); LC/MS (m/z): found: 558 (M+H, R=Et); 544 (M+H, R=Me). Calcd., 557 (C$_{35}$H$_{47}$N$_3$O$_3$, R=Et) and 543 (C$_{34}$H$_{45}$N$_3$O$_3$, R=Me); |

[a]The pyrimidines 74–75, and 77 were obtained as a mixture of ethyl and methyl esters (R=Et and Me) in a ~5:1 to 8:1 ratio and their ratios were determined by $^1$H NMR spectral data. $^1$H NMR data of the major isomers (R=Et) are reported herein.

TABLE 6

2,3-Fused pyrazole and pyrimidine derivatives of cholanoic acids 107 synthesized (Scheme 46)

| Compound | % Yield, NMR and LC-MS Data |
|---|---|
| 107-48a-1<br>$R^1$ = H,<br>$R^2$ = H<br>$R^{19}$ = H | Yield, 98%. $^1$H NMR (DMSO-d$_6$, 400 MHz):δ 0.59 (3H, s, CH$_3$-19); 0.80 (3H, bd, J=6.4Hz, CH$_3$-21); 1.02 (3H, s, CH$_3$-18), 1.12–2.80 (CH$_2$ & CH-steroidal), 7.19 (1H, bs, H-Pyrazole). LC/MS (m/z): found, 399 (M+H), 397 (M−H). Calcd., 398 (C$_{25}$H$_{38}$N$_2$O$_2$). |
| 107-48a-2<br>$R^1$ = H,<br>$R^2$ = H<br>$R^{19}$ = A | Yield, 93%. $^1$H NMR (CDCl$_3$, 400 MHz):δ 0.64 (3H, s, CH$_3$-19); 0.87 (3H, bd, J=6.4Hz, CH$_3$-21); 1.08 (3H, s, CH$_3$-18), 1.12–2.85 (CH$_2$ & CH-steroidal), 3.99 (2H, m, CH$_2$); 4.07 (2H, m, CH$_2$); 7.03 (1H, s, H-Pyrazole). LC/MS (m/z): found, 443 (M+H), 441 (M−H). Calcd., 442 (C$_{27}$H$_{42}$N$_2$O$_3$). |
| 107-48a-3<br>$R^1$ = H,<br>$R^2$ = H<br>$R^{19}$ = B | Yield, 95%. $^1$H NMR (CDCl$_3$, 400 MHz):δ 0.64 (3H, s, CH$_3$-19); 0.88 (3H, bd, J=6.4Hz, CH$_3$-21); 1.07 (3H, s, CH$_3$-18); 1.12–2.85 (CH$_2$ & CH-steroidal), 5.12 (2H, m, CH$_2$Ar); 6.45–6.72 (3H, m, H—Ar); 7.01–7.30 (2H, m, H-Pyrazole and H—Ar). LC/MS (m/z): found, 505 (M+H); 503 (M−H). Calcd., 504 (C$_{32}$H$_{44}$N$_2$O$_3$). |
| 107-48c-1<br>$R^1$ = OH,<br>$R^2$ = H<br>$R^{19}$ = H | Yield, 98%. $^1$H NMR (MeOH-d$_4$, 400 MHz):δ 0.72 (3H, s, CH$_3$-19); 0.94 (3H, bd, J=6.4Hz, CH$_3$-21); 1.12 (3H, s, CH$_3$-18), 1.12–2.80 (CH$_2$ & CH-steroidal), 3.82 (1H, m, CH-7); 7.97 (1H, bs, H-Pyrazole). LC/MS (m/z): found, 415 (M+H); 413 (M−H). Calcd., 414 (C$_{25}$H$_{38}$N$_2$O$_3$). |
| 107-48c-2<br>$R^1$ = OH,<br>$R^2$ = H,<br>$R^{19}$ = A | Yield, 95%. $^1$H NMR (MeOH-d$_4$, 400 MHz):δ 0.71 (3H, s, CH$_3$-19); 0.94 (3H, bd, J=6.4Hz, CH$_3$-21); 1.07 (3H, s, CH$_3$-18), 1.12–2.85 (CH$_2$ & CH-steroidal), 3.78 (1H, m, CH-7); 3.87 (2H, m, CH$_2$); 4.09 (4H, m, CH$_2$); 7.37 (1H, s, H-Pyrazole). LC/MS (m/z): found, 459 (M+H); 457 (M−H). Calcd., 458 (C$_{27}$H$_{42}$N$_2$O$_4$). |
| 107-48c-3<br>$R^1$ = OH,<br>$R^2$ = H,<br>$R^{19}$ = B | Yield, 91%. $^1$H NMR (CDCl$_3$, 400 MHz):δ 0.66 (3H, s, CH$_3$-19); 0.90 (3H, bd, J=6.4Hz, CH$_3$-21); 1.05 (3H, s, CH$_3$-18), 1.12–2.72 (CH$_2$ & CH-steroidal), 3.82 (1H, bs, CH-7), 5.13 (2H, m, CH$_2$Ar); 6.57 (1H, s, H—Ar); 6.75 (2H, m, H—Ar); 7.17 (1H, m, H—Ar); 7.32 (1H, s, H-Pyrazole). LC/MS (m/z): found, 521 (M+H); 519 (M−H). Calcd., 520 (C$_{32}$H$_{44}$N$_2$O$_4$) |

TABLE 6-continued 2,3-Fused pyrazole and pyrimidine derivatives of cholanoic acids 107 synthesized (Scheme 46)

| Compound | % Yield, NMR and LC-MS Data |
|---|---|
| 107-74a-1<br>$R^1 = H$<br>$R^2 = H$<br>X = O | Yield, 25%. LC/MS (m/z): found: 427 (M+H). Calcd., 426 ($C_{26}H_{38}N_2O_3$). |
| 107-75a-1<br>$R^1 = H$<br>$R^2 = H$<br>X = S | Yield, 17%. LC/MS (m/z): found: 443 (M+H). Calcd., 442 ($C_{26}H_{38}N_2O_2S$). |
| 107-77a-1<br>$R^1 = H$,<br>$R^2 = H$<br>X =<br>p-$C_6H_4$—<br>$CONH_2$ | Yield, 79%. LC/MS (m/z): found: 530(M+H); 528 (M−H). Calcd., 529 ($C_{33}H_{43}N_3O_3$). |

A = $HOCH_2CH_2$—; B = m-$HOC_6H_4CH_2$—

TABLE 7

2,3-Fused pyrazole 108-48 and pyrimidine 108-74, 108-77 cholanoic acid tert-butyl ester derivatives synthesized (Scheme 46)

| Compound | % Yield, NMR and LC-MS Data |
|---|---|
| 108-48a-1<br>$R^1 = H$,<br>$R^2 = H$<br>$R^{19} = H$ | Yield, 89%. $^1$H NMR (CDCl$_3$): LC/MS (m/z): found: 512 (M+1). Calcd., 511 ($C_{31}H_{49}N_3O_3$). |
| 108-48a-2<br>$R^1 = H$,<br>$R^2 = H$<br>$R^{19} = A$ | Yield, 86%. $^1$H NMR (CDCl$_3$, 400 MHz):δ 0.59 (3H, s, CH$_3$-19); 0.83 (3H, bd, J=6.8Hz, CH$_3$-21); 1.01 (3H, s, CH$_3$-18), 1.42 (9H, s, tBu); 1.12–2.85 (CH$_2$ & CH-steroidal), 3.86–3.91 (4H, m, CH$_2$); 4.11 (2H, m, CH$_2$); 6.03 (1H, bs, NHC=O); 7.01 (1H, s, H-Pyrazole). LC/MS (m/z): found 556 (M+H). Calcd., 555 ($C_{33}H_{53}N_3O_4$). |
| 108-48a-3<br>$R^1 = H$,<br>$R^2 = H$<br>$R^{19} = B$ | Yield, 87%. $^1$H NMR (CDCl$_3$, 400 MHz):δ 0.62 (3H, s, CH$_3$-19); 0.87 (3H, bd, J=6.4Hz, CH$_3$-21); 1.06 (3H, s, CH$_3$-18), 1.46 (9H, s, tBu); 1.12–2.80 (CH$_2$ & CH-steroidal), 3.92 (2H, m, CH$_2$); 5.12 (2H, m, CH$_2$Ar); 5.98 (1H, bs, NHC=O); 6.40 (1H, bs, HO—Ar); 6.59 (1H, m, H—Ar); 6.70 (2H, m, H—Ar); 7.09 (1H, t, J=7.6 Hz, H—Ar); 7.16 (1H, s, H-Pyrazole). LC/MS (m/z): found: 616 (M−H), 618 (M+H). Calcd., 617 ($C_{38}H_{55}N_3O_4$). |
| 108-48b-1<br>$R^1 = OH$,<br>$R^2 = OH$<br>$R^{19} = B$ | Yield, 71%. $^1$H NMR (CDCl$_3$, 400 MHz):δ 0.67 (3H, s, CH$_3$-19); 0.93 (3H, bd, J=6.4Hz, CH$_3$-21); 1.02 (3H, s, CH$_3$-18), 1.45 (9H, s, tBu); 1.12–2.85 (CH$_2$ & CH-steroidal), 3.76 (1H, bs, CH-12); 3.90 (2H, d, J=5.2 Hz, CH$_2$); 3.95(1H, bs, CH-7); 5.10 (2H, m, CH$_2$Ar); 6.22 (1H, t, J=5.2 Hz, NHCO); 6.51 (1H, bs, H—Ar); 6.65 (2H, m, H—Ar); 7.08 (1H, t, J=8 Hz, H—Ar); 7.24 (1H, s, H-Pyrazole). LC/MS (m/z): found: 650 (M+H) and 648 (M−H). Calcd., 649 ($C_{38}H_{55}N_3O_6$). |
| 108-48c-1<br>$R^1 = OH$,<br>$R^2 = H$,<br>$R^{19} = H$ | Yield, 97%. $^1$H NMR (CDCl$_3$, 400 MHz):δ 0.65 (3H, s, CH$_3$-19); 0.91 (3H, d, J=6.4Hz, CH$_3$-21); 1.12 (3H, s, CH$_3$-18), 1.42 (9H, s, tBu); 1.12–2.85 (26H, m, CH$_2$ & CH-steroidal), 3.74 (1H, m, CH-7); 3.90 (2H, m, CH$_2$); 6.11 (1H, m, NHCO); 7.46 (1H, bs, H-Pyrazole). LC/MS (m/z): found: 528 (M+H). Calcd., 527 ($C_{31_5}H_{49}N_3O_4$). |
| 108-48c-2<br>$R^1 = OH$,<br>$R^2 = H$<br>$R^{19} = A$ | Yield, 95%. $^1$H NMR (CDCl$_3$, 400 MHz):δ 0.64 (3H, s, CH$_3$-19); 0.89 (3H, bd, J=6.4Hz, CH$_3$-21); 1.02 (3H, s, CH$_3$-18), 1.44 (9H, s, tBu); 1.12–2.85 (CH$_2$ & CH-steroidal), 3.71 (1H, m, CH-7), 3.89 (4H, m, CH$_2$); 4.11 (2H, m, CH$_2$); 6.00 (1H, bs, NHC=O); 7.31 (1H, s, H-Pyrazole). LC/MS (m/z): found: 572 (M+H). Calcd., 571 ($C_{33}H_{53}N_3O_5$). |
| 108-48c-3<br>$R^1 = OH$,<br>$R^2 = H$<br>$R^{19} = B$ | Yield, 96%. $^1$H NMR (CDCl$_3$, 400 MHz):δ 0.61 (3H, s, CH$_3$-19); 0.84 (3H, bd, J=6.4Hz, CH$_3$-21); 1.00 (3H, s, CH$_3$-18), 1.42 (9H, s, tBu); 1.12–2.80 (CH$_2$ & CH-steroidal), 3.71 (1H, bs, CH-7), 3.86 (2H, m, CH$_2$); 5.00 (2H, m, CH$_2$Ar); 6.27 (1H, bs, NHC=O); 6.58 (1H, bs, H—Ar); 6.64 (2H, m, H—Ar); 7.06 (1H, m, H—Ar); 7.25 (1H, s, H-Pyrazole). LC/MS (m/z): found: 632 (M−H), 634 (M+H). Calcd., 633 ($C_{38}H_{55}N_3O_5$). |

TABLE 7-continued 2,3-Fused pyrazole 108-48 and pyrimidine 108-74, 108-77 cholanoic acid tert-butyl ester derivatives synthesized (Scheme 46)

| Compound | % Yield, NMR and LC-MS Data |
|---|---|
| 108-74a-1<br>$R^1 = H$<br>$R^2 = H$<br>X = O | Yield, 15%. LC/MS (m/z): found: 538 (M−H), 484(M-tBu). Calcd., 539 ($C_{32}H_{49}N_3O_4$). |
| 108-77a-1<br>$R^1 = H$<br>$R^2 = H$<br>X =<br>p-$C_6H_4$—<br>$CONH_2$ | Yield, 63%. $^1$H NMR (CDCl$_3$, 400 MHz):δ 0.65 (3H, s, CH$_3$-19); 0.88 (3H, bd, CH$_3$-21); 1.22 (3H, s, CH$_3$-18), 1.45 (9H, bs, tBu): 1.25–3.00 (CH$_2$ & CH-steroidal), 3.90 (2H, m, CH$_2$); 5.94 (1H, m, HNCOCH$_2$); 7.92 (2H, m, H—Ar); 8.48 (2H, m, H—Ar); 8.71 (1H, m, H-Pyrazole). LC/MS (m/z): found: 643 (M+H), 587 (M-tBu). Calcd., 642 ($C_{39}H_{54}N_4O_4$). |

A = $HOCH_2CH_2$—; B = m-$HOC_6H_4CH_2$—

TABLE 8

2,3-Fused pyrazole 109-48 and pyrimidine 109-77 derivatives of glycocholanoic acids synthesized (Scheme 46)

| Compound | % Yield, NMR and LC-MS data |
|---|---|
| 109-48a-1<br>$R^1 = H$,<br>$R^2 = H$<br>$R^{19} = H$ | Yield, 92%. $^1$H NMR (MeOH-d$_4$, 400 MHz):δ 0.69 (3H, s, CH$_3$-19); 0.92 (3H, d, J=6.8Hz, CH$_3$-21); 1.15 (3H, s, CH$_3$-18), 1.12–2.90 (CH$_2$ & CH-steroidal), 3.86 (2H, bs, CH$_2$); 7.59 (1H, bs, H-Pyrazole). LC/MS (m/z): found: 454(M−H), 456 (M+H). Calcd., 455 ($C_{27}H_{41}N_3O_3$). |
| 109-48a-2<br>$R^1 = H$,<br>$R^2 = H$<br>$R^{19} = A$ | Yield, 87%. $^1$H NMR (MeOH-d$_4$, 400 MHz):δ 0.69 (3H, s, CH$_3$-19); 0.91 (3H, bd, J=6.4Hz, CH$_3$-21); 1.12 (3H, s, CH$_3$-18), 1.12–2.90 (26H, m, CH$_2$ & CH-steroidal), 3.835 (2H, m, CH$_2$); 3.87 (2H, m, CH$_2$); 4.14 (2H, m, CH$_2$); 7.03 and 7.30 (1H, s, H-Pyrazole). LC/MS (m/z): found: 498 (M−H), 500 (M+H). Calcd., 499 ($C_{29}H_{45}N_3O_4$. |
| 109-48a-3<br>$R^1 = H$,<br>$R^2 = H$<br>$R^{19} = B$ | Yield, 89%. $^1$H NMR (MeOH-d$_4$, 400 MHz):δ 0.66 (3H, s, CH$_3$-19); 0.92 (3H, bd, J=6.4Hz, CH$_3$-21); 1.08 (3H, s, CH$_3$-18); 1.12–2.90 (26H, m, CH$_2$ & CH-steroidal); 3.75 (2H, bs, CH$_2$); 5.15 (2H, m, CH$_2$Ar); 6.37 (1H, bs, NHCO); 6.48–6.68 (3H, m, H—Ar); 7.09 (1H, t, J=7.6 Hz, H—Ar); 7.2 (1H, m, H-Pyrazole). LC/MS (m/z): found: 560 (M−H), 562 (M+H). Calcd., 561 ($C_{34}H_{47}N_3O_4$). |
| 109-48b-1<br>$R^1 = OH$,<br>$R^2 = OH$<br>$R^{19} = B$ | Yield 58%. LC/MS (m/z): found: 592 (M−H), 594 (M+H). Calcd., 593 ($C_{34}H_{47}N_3O_6$). |
| 109-48c-1<br>$R^1 = OH$,<br>$R^2 = H$,<br>$R^{19} = H$ | Yield, 98%. LC/MS (m/z): found: 470 (M−H), 472 (M+H). Calcd., 471 ($C_{27}H_{41}N_3O_4$). |
| 109-48c-2<br>$R^1 = OH$,<br>$R^2 = H$,<br>$R^{19} = A$ | Yield, 95%. LC/MS (m/z): found: 514 (M−H), 516 (M+H). Calcd., 515 ($C_{29}H_{45}N_3O_5$). |
| 109-48c-3<br>$R^1 = OH$,<br>$R^2 = H$,<br>$R^{19} = B$ | Yield, 92%. LC/MS (m/z): found: 576 (M−H), 578 (M+H). Calcd., 577 ($C_{34}H_{47}N_3O_5$). |
| 109-77a-1<br>$R^1 = H$<br>$R^2 = H$<br>X =<br>p-$C_6H_4$—<br>$CONH_2$ | Yield, 56%. $^1$H NMR (MeOH-d$_4$, 400 MHz):δ 0.74 (3H, s, CH$_3$-19); 0.92 (3H, bd, CH$_3$-21); 1.22 (3H, s, CH$_3$-18), 1.25–3.00 (CH$_2$ & CH-steroidal), 3.89 (2H, m, CH$_2$); 8.46 (2H, m, H—Ar); 8.46 (2H, m, H—Ar); 8.80 (1H, m, H-Pyrazole ); LC/MS (m/z): found: 587 (M+H), 585 (M−H). Calcd., 586 ($C_{35}H_{46}N_4O_4$). |

A = $HOCH_2CH_2$—; B = m-$HOC_6H_4CH_2$—

XII. In Vitro Compound Transport Assays with hIBAT and hLBAT-Expressing Cell Lines

Example 50

Inhibition of Radiolabeled Taurocholate Uptake

CHO cells transfected with either the hIBAT or hLBAT transporter were seeded into 96-well microtiter plates at 100,000 cells/well in 100 µL DMEM containing 10% serum, glutamine and Penstrep. After overnight incubation the media was removed and test compound (25 µL) added at 2× the final desired concentration. Tritiated taurocholate (50,000 CPM/well) was diluted with cold substrate to a final concentration of 5 µM and 25 µL/well of this mixture was added to the plate. After incubating for 1 h at room temperature the solution was removed and the plate washed 4× with PBS at 4° C. 200 µL/well of scintillant is added and the plate then read in a Wallac microbeta counter. The inhibition data is processed by standard methods to calculate an inhibition constant $IC_{50}$ for the test compound.

Example 51

Analysis of Electrogenic Transport in *Xenopus* Oocytes

RNA preparation: Human IBAT and LBAT Transporter cDNAs were subcloned into a modified pGEM plasmid that contains 5' and 3' untranslated sequences from the *Xenopus* β-actin gene. These sequences increase RNA stability and protein expression. Plasmid cDNA was linearized and used as template for in vitro transcription (Epicentre Technologies transcription kit, 4:1 methylated:non-methylated GTP).

*Xenopus* oocyte isolation. *Xenopus laevis* frogs were anesthetized by immersion in Tricaine (1.5 g/mL in deionized water) for 15 min. Oocytes were removed and digested in frog ringer solution (90 mM NaCl, 2 mM KCl, 1 mM $MgCl_2$, 10 mM NaHEPES, pH 7.45, no $CaCl_2$) with 1 mg/mL collagenase (Worthington Type 3) for 80–100 min with shaking. The oocytes were washed 6 times, and the buffer changed to frog ringer solution containing $CaCl_2$ (1.8 mM). Remaining follicle cells were removed if necessary. Cells were incubated at 16° C., and each oocyte injected with 10–20 µg RNA in 45 µL solution.

Electrophysiology measurements. Transport currents were measured 2–14 days after injection, using a standard two-electrode electrophysiology set-up (Geneclamp 500 amplifier, Digidata 1320/PCLAMP software and ADInstruments hardware and software were used for signal acquisition). Electrodes (2–4 mΩ) were microfabricated using a Sutter Instrument puller and filled with 3M KCl. The bath was directly grounded (transporter currents were less than 0.3 µA). Bath flow was controlled by an automated perfusion system (ALA Scientific Instruments, solenoid valves).

For transporter pharmacology, oocytes were clamped at −60 to −90 mV, and continuous current measurements acquired using PowerLab Software and an ADInstruments digitizer. Current signals were lowpass filtered at 20 Hz and acquired at 4–8 Hz. All bath and compound-containing solutions were frog ringers solution containing $CaCl_2$. Compounds were applied for 10–30 seconds until the induced current reached a new steady-state level, followed by a control solution until baseline currents returned to levels that preceded compound application. The difference current (baseline subtracted from peak current during compound application) reflected the net movement of charge resulting from electrogenic transport and was directly proportional to tranport rate. Recordings were made from a single oocyte for up to 60 min, enabling 30–40 separate compounds to be tested per oocyte. To compare results between oocytes expressing different levels of transport activity, a saturating concentration of glycodeoxycholate (300 µM) was used as a common reference to normalize results from test compounds. Using this normalization procedure $V_{max}$ (i.e. maximal induced current) for different compounds tested on different oocytes could be compared.

TABLE 9

In vitro transport (inhibition of tritiated taurocholate uptake) data for 2,3-fused pyrazole and pyrimidine derivatives of cholanoic acids 107 and glycocholanoic acids 109 on hIBAT and hLBAT expressing cells[a]

| Compound | hIBAT, $IC_{50}$ (µM) | hLBAT, $IC_{50}$ (µM) |
|---|---|---|
| 107-48a-1<br>$R^1 = R^2 = R^{19} = H$ | >300 | 26 |
| 107-48a-2<br>$R^1 = R^2 = H; R^{19} = HOCH_2CH_2—$ | >300 | 110 |
| 107-48a-3<br>$R^1 = R^2 = H; R^{19} = m-HOC_6H_4CH_2—$ | 240 | 0.7 |
| 107-48c-1<br>$R^1 = OH; R^2 = R^{19} = H$ | 2.5 | 0.6 |
| 107-48c-2<br>$R^1 = OH; R^2 = H; R^{19} = HOCH_2CH_2—$ | >300 | 4 |
| 107-48c-3<br>$R^1 = OH; R^2 = H; R^{19} = m-HOC_6H_4CH_2—$ | 4.5 | 0.7 |
| 107-74a-1<br>$R^1 = R^2 = H; X = O$ | 70 | 41 |
| 109-77a-1<br>$R^1 = R^2 = H; X = p-C_6H_4CONH_2$ | >300 | 20 |
| 109-48a-1<br>$R^1 = R^2 = R^{19} = H$ | 62 | 1.6 |
| 109-48a-2<br>$R^1 = R^2 = H; R^{19} = HOCH_2CH_2—$ | >300 | 0.7 |
| 109-48a-3<br>$R^1 = R^2 = H; R^{19} = m-HOC_6H_4CH_2—$ | 0.9 | 0.3 |
| 109-48b-1<br>$R^1 = R^2 = OH; R^{19} = m-HOC_6H_4CH_2—$ | >300 | 8.6 |
| 109-48c-1<br>$R^1 = OH, R^2 = R^{19} = H$ | 1.6 | 0.3 |
| 109-48c-2<br>$R^1 = OH, R^2 = H, R^{19} = HOCH_2CH_2—$ | 22 | 0.2 |
| 109-48c-3<br>$R^1 = OH, R^2 = H; R^{19} = m-HOC_6H_4CH_2—$ | 1.5 | 0.3 |
| 109-77a-1<br>$R^1 = R^2 = H; X = p-C_6H_4CONH_2$ | 140 | 2 |

[a]$IC_{50}$ values from radiolabelled competition assay in transporter-expressing CHO cells

TABLE 10

In vitro transport (oocyte assay) data for 2,3-fused pyrazole and pyrimidine derivatives of cholanoic acids 107 and glycocholanoic acids 109 on hIBAT expressing cells[a]

| Compound | % Max GDC |
|---|---|
| 107-48a-2<br>$R^1 = R^2 = H; R^{19} = HOCH_2CH_2—$ | 40 |
| 107-48c-1<br>$R^1 = OH; R^2 = R^{19} = H$ | 18 |
| 107-48c-2<br>$R^1 = OH; R^2 = H; R^{19} = HOCH_2CH_2—$ | 7 |
| 107-74a-1<br>$R^1 = R^2 = H; X = O$ | 40 |
| 109-48a-1<br>$R^1 = R^2 = R^{19} = H$ | 26 |
| 109-48a-3<br>$R^1 = R^2 = H; R^{19} = m-HOC_6H_4CH_2—$ | 27 |

TABLE 10-continued

In vitro transport (oocyte assay) data for 2,3-fused pyrazole and pyrimidine derivatives of cholanoic acids 107 and glycocholanoic acids 109 on hIBAT expressing cells[a]

| Compound | % Max GDC |
|---|---|
| 109-48b-1<br>$R^1 = R^2 = OH; R^{19} = m\text{-HOC}_6H_4CH_2-$ | 8 |
| 109-48c-1<br>$R^1 = O; R^2 = R^{19} = H$ | 21 |
| 109-48c-2<br>$R^1 = OH; R^2 = H; R^{19} = HOCH_2CH_2-$ | 13 |
| 109-48c-1<br>$R^1 = OH; R^2 = H; R^{19} =$<br>$m\text{-HOC}_6H_4CH_2-$ | 8 |
| 109-77a-1<br>$R^1 = R^2 = H; X = p\text{-}C_6H_4CONH_2$ | 8 |

[a]% Max values are relative to glycodeoxycholic acid (GDC) in transporter-expressing oocytes at a test sample concentration of 100 µM

TABLE 11

In vitro transport (inhibition of tritiated taurocholate uptake) data for the drug and drug surrogates conjugated to 2,3-fused pyrazole derivatives of glycocholanoic acids 118–120 on hIBAT and hLBAT expressing cells[a]

| Compound | hIBAT, $IC_{50}$ (µM) | hLBAT, $IC_{50}$ (µM) |
|---|---|---|
| 118-4 | 143 | 0.4 |
| 118-5 | >300 | 63 |
| 118-6 | >300 | 3.4 |
| 119-3 | 32 | 0.22 |
| 119-4 | 57 | 0.28 |
| 120-2 | >300 | 3.2 |

[a]$IC_{50}$ values from radiolabelled competition assay in transporter-expressing CHO cells

TABLE 12

In vitro transport (oocyte assay) data for the drug and drug surrogates conjugated to 2,3-fused pyrazole and derivatives of glycocholanoic acids 118–120 on hIBAT expressing cells[a]

| Compound | % Max GDC |
|---|---|
| 118-4 | 12 |
| 118-5 | 0 |
| 118-6 | 12 |
| 119-3 | 59 |
| 119-4 | 18 |
| 120-2 | 0 |

[a]% Max values are relative to glycodeoxycholic acid (GDC) in transporter-expressing oocytes at a test sample concentration of 100 µM

REFERENCES

Baringhaus, K.-H.; Matter, H.; Stengelin, S.; Kramer, W. Substrate specificity of the ileal and hepatic Na+/bile acid cotransporters of the rabbit. II. A reliable 3D QSAR pharmacophore model for the ileal Na+/bile acid cotransporter. *J. Lipid Res.* 1999, 40, 2158–2168.

Begum, S.; Adil, Q.; Siddiqui, B. S.; Siddiqui, S. Synthesis of 2β-hydroxyursolic acid and other ursane analogues from ursonic acid. *Aust. J. Chem.* 1993, 46, 1067–1071.

Bellini, A. M.; Rocchi, R.; Benassi, C. A. Studi su 5β cheto-steroidi.—Nota IV. Derivati eterociclici sugli anelli A e B dell'acido 3,7,12-tricheto-colanico. *Gazzetta Chimica Italiana*, 1969, vol. 99, fasc. 12, 1243–1251.

Bellini, A. M.; Rocchi, R.; Fornasini, G.; Benassi, C. A. Studi su 5β-chetosteroidi.—Nota VII. Derivati pirimidinici e pteridinici dell'acido 3,7,12-trichetocolanico. *Il Farmaco-Ed. Sc.*, vol. 25, fasc. 3, 226–233.

Brouwer, A.; Monnee, M. C. F.; Liskamp, R. M. J. A efficient synthesis of N-protected β-aminoethanesolfonyl chlorides: Versatile building blocks for the synthesis of oligopeptidosulfonamides. Synthesis 2000, 1579–1584.

Clinton, R. O.; Manson, A. J.; Stonner, F. W.; Neumann, H. C.; Christiansen, R. G.; Clarke, R. L.; Ackerman, J. H.; Page, D. F.; Dean, J. W.; Dickison, W. B.; Carabateas, C. Steroidal[3,2-c]pyrazoles II. Androstanes, 19-norandrastanes and their Unsaturated Analogs. *J. Am. Chem. Soc.* 1961, 83, 1478–1491.

Ho, N. F. H. Utilizing bile acid carrier mechanisms to enhance liver and small intestine absorption. *Ann. N. Y. Acad. Sci.* 1987, 507, 315–329.

Kim, D.-C.; Harrison, A. W.; Ruwart, M. J.; Wilkinson, K. F.; Fisher, J. F.; Hidalgo, I. J.; Borchardt, R. T. Evaluation of bile acid transporter in enhancing intestinal permeability of renin-inhibitory peptides. *J. Drug Targeting* 1993, 1, 347–359.

Kramer, W.; Wess, G.; Schubert, G.; Bickel, M.; Girbig, F.; Gutjahr, U.; Kowalewski, S.; Baringhaus, K.-H.; Enhsen, A.; Glombik, H.; Mullner, S.; Neckermann, G.; Schulz, S.; Petzinger, E. Liver-specific drug targeting by coupling to bile acids. *J. Biol. Chem.* 1992, 267, 18598–18604.

Kramer, W.; Wess, G.; Neckermann, G.; Schubert, G.; Fink, J.; Girbig, F.; Gutjahr, U.; Kowalewski, S.; Baringhaus, K.-H.; Boger, G.; Enhsen, A.; Falk, E.; Friedrich, M.; Glombik, H.; Hoffmann, A.; Pittius, C.; Urmann, M. Intestinal absorption of peptides by coupling to bile acids. *J. Biol. Chem.* 1994a, 269, 10621–10627.

Kramer, W.; Wess, G.; Enhsen, A.; Bock, K.; Falk, E.; Hoffmann, A.; Neckermann, G.; Gantz, D.; Schulz, S.; Nickau, L.; Petzinger, E.; Turley, S.; Dietschy, J. M. Bile acid derived HMG-CoA reductase inhibitors. *Biochim. Biophys. Acta* 1994b, 1227, 137–154.

Kramer, W.; Wess, G. Modified bile acid conjugates, and their use as pharmaceuticals. U.S. Pat. No. 5,462,933, 1995.

Kramer, W.; Wess, G. Bile acid conjugates of proline hydroxylase inhibitors. U.S. Pat. No. 5,646,272, 1997a.

Kramer, W.; Wess, G. Bile acid derivatives, processes for their preparation, and use as pharmaceuticals. U.S. Pat. No. 5,668,126, 1997b.

Kramer, W.; Stengelin, S.; Baringhaus, K.-H.; Enhsen, A.; Heuer, H.; Becker, W.; Corsiero, D.; Girbig, F.; Noll, R.; Weyland, C. Substrate specificity of the ileal and hepatic Na+/bile acid cotransporters of the rabbit. I. Transport studies with membrane vesicles and cell lines expressing the cloned transporters. *J. Lipid Res.* 1999, 40, 1604–1617.

Kullak-Ublick, G. A.; Beuers, U.; Paumgartner, G. Hepatobiliary transport. *J. Hepatology* 2000, 32 (Suppl. 1), 3–18.

Navia, M. A.; Chaturvedi, P. R. Design principles for orally bioavailable drugs. *Drug Discovery Today* 1996, 1, 179–189.

Paquette, L. A.; Johnson, B. A.; Hinga, F. M. 2-Chloro-1-formyl-1-cyclohexene. *Organic synth. Col.* Vol. Xx, 215–232, xxx.

Petzinger, E.; Nickau, L.; Horz, J. A.; Schulz, S.; Wess, G.; Enhsen, A.; Falk, E.; Baringhaus, K.-H.; Glombik, H.; Hoffmann, A.; Mullner, S.; Neckermann, G.; Kramer, W. Hepatobiliary transport of hepatic 3-hydroxy-3-methylglutaryl coenzyme A reductase inhibitors conjugated with bile acids. *Hepatology* 1995, 22, 1801–1811.

Rocchi, R.; Bellini, A. M.; Fornasini, G.; Benassi, C. A. Studi su 5β-cheto-steroidi.—Nota VI. Derivati pirimidinici e pteridinici degli acidi 3,12-dicheto- e 7,12-dichetocolanici. *Il Farmaco-Ed. Sc.*, vol. 25, fasc. 2, 125–132.

Spivey, S. C.; Diaper, C. M.; Adams, H. A new germanium-based linker for solid phase synthesis of aromatics: Synthesis of a pyrazole library. *J. Org. Chem.* 2000, 65, 5253–5263 and the references cited therein.

Swaan, P. W.; Szoka, F. C.; Oie, S. Use of the intestinal and hepatic bile acid transporters for drug delivery. *Adv. Drug Delivery Rev.* 1996, 20, 59–82.

Tserng, K-Y. A convenient synthesis of 3-keto bile acids by selective oxidation of bile acids with silver carbonate-Celite. *J. Lipid. Res.* 1978, 19, 501–504.

Tsuji, A.; Tamai, I. Carrier-mediated intestinal transport of drugs. *Pharm. Res.* 1996, 13, 963–977.

Venepalli, B. P.; Aimone, L. D.; Appell, K. C.; Bell, M. R.; Dority, J. A.; Goswami, R.; Hall, P. L.; Kumar, V.; Lawrence, K. B.; Logan, M. E.; Scensny, P. M.; Seelye, J. A.; Tomczuk, B. E.; Yanni, J. M. Synthesis and Substance P Receptor Binding Activiy of Androstano[3,2-b]pyrimio[1,2-a]benzimidazoles. *J. Med. Chem.* 1992. 35. 374–378.

For a review of chemistry of oxoketene S,S-, N,S- and N,N-acetals preparation and their chemistry see: Junjappa, H.; Ila, H.; and Asokan, C. V. α-Oxoketene S,S-, N,S- and N,N-acetals: Versatile intermediates in organic synthesis. *Tetrahedron* 1990, 46, 5423–5506.

What is claimed is:

1. A compound of formula (I):

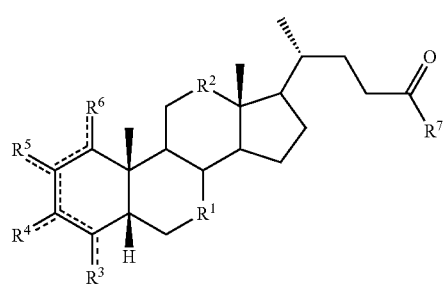

(I)

wherein $R^1$ is $CH_2$, CHOH or $CR^{12}OH$;

$R^2$ is $CH_2$, CHOH or $CR^{12}OH$;

$R^3$ is H, OH, alkylene-$R^8$, substituted alkylene-$R^8$, cycloalkylene-$R^8$, substituted cycloalkylene-$R^8$, alkenylene-$R^8$, substituted alkenylene-$R^8$, cycloalkenylene-$R^8$, substituted cycloalkenylene-$R^8$, alkynylene-$R^8$, substituted alkynylene-$R^8$, arylene-$R^8$, substituted arylene-$R^8$, heteroarylene-$R^8$, substituted heteroarylene-$R^8$, heterocyclene-$R^8$, or substituted heterocyclene-$R^8$;

$R^4$ and $R^5$ together with the carbon atoms to which they are attached form a heterocycloalkyl-$R^9$, substituted heterocycloalkyl-$R^9$, heterocycloalkenyl-$R^9$, substituted heterocycloalkenyl-$R^9$, heteroaryl-$R^9$ or substituted heteroaryl-$R^9$ ring;

$R^6$ is H, OH, alkylene-$R^{11}$, substituted alkylene-$R^{11}$, cycloalkylene-$R^{11}$, substituted cycloalkylene-$R^{11}$, alkenylene-$R^{11}$, substituted alkenylene-$R^{11}$, cycloalkenylene-$R^{11}$, substituted cycloalkenylene-$R^{11}$, alkynylene-$R^{11}$, substituted alkynylene-$R^{11}$, arylene-$R^{11}$, substituted arylene-$R^{11}$, heteroarylene-$R^{11}$, substituted heteroarylene-$R^{11}$, heterocyclene-$R^{11}$, or substituted heterocyclene-$R^{11}$;

$R^7$ is an alkylamino group substituted with a moiety that is negatively charged at physiological pH and located 5 to 15 atoms from C-22 of the bile acid nucleus, a di-substituted alkylamino group substituted with L-D and a moiety that is negatively charged at physiological pH and located 5 to 15 atoms from C-22 of the bile acid nucleus, or pharmaceutically acceptable salts thereof;

$R^8$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;

$R^9$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;

$R^{11}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$, $CON(R^{13})_2$ or L-D;

$R^{12}$ is alkyl, substituted alkyl, cycloalkyl, substituted cycloalkyl, aryl, substituted aryl, heteroaryl or substituted heteroaryl;

$R^{13}$ is alkyl, substituted alkyl, cycloalkyl, substituted cycloalkyl, aryl, substituted aryl, heteroaryl or substituted heteroaryl;

dashed lines represent possible sites of unsaturation;

L is a covalent bond or a linking group;

D is a drug;

or a pharmaceutically acceptable salt thereof;

provided that not more than one of the substituents $R^3$, $R^4$, $R^5$, $R^6$, and $R^7$ includes moiety L-D.

2. The compound according to claim 1, wherein the compound is selected from a group consisting of the following compounds:

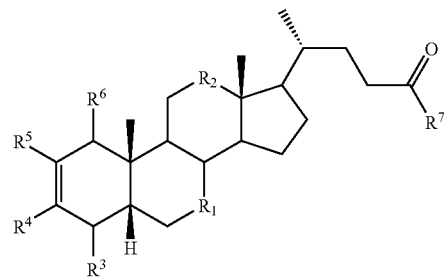

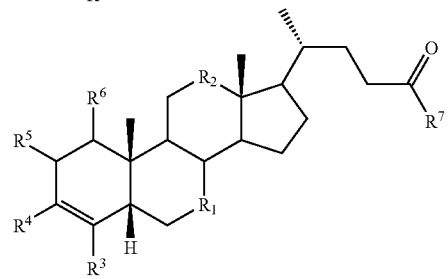

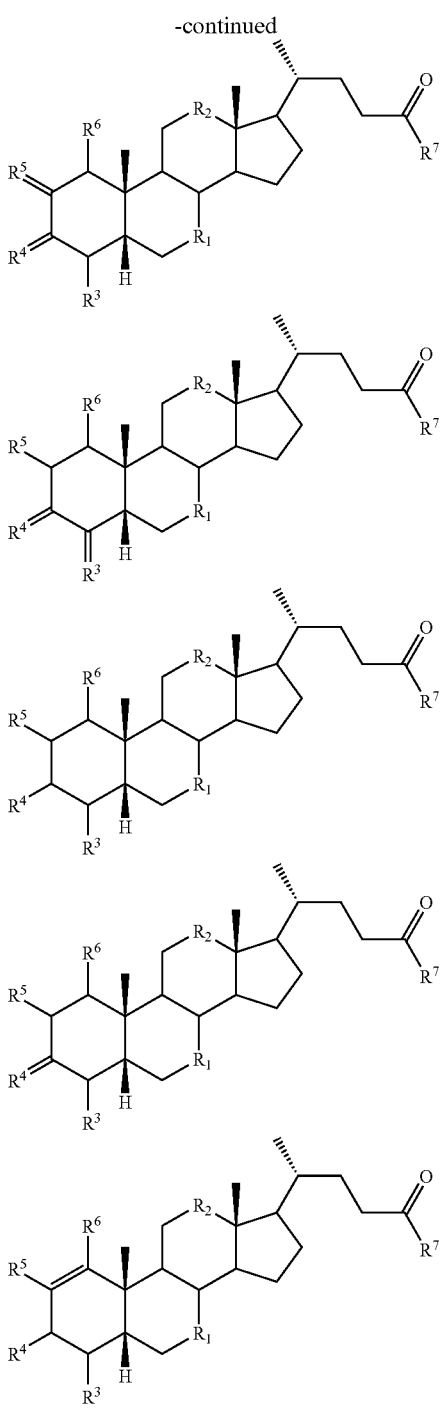

form a 7-membered ring, and wherein the ring is heterocycloalkyl-R⁹, substituted heterocycloalkyl-R⁹, heterocycloalkenyl-R⁹, substituted heterocycloalkenyl-R⁹, heteroaryl-R⁹ or substituted heteroaryl-R⁹.

6. The compound according to claim 1, wherein $R^4$ and $R^5$ together with the carbon atoms to which they are attached form an 8-membered ring, and wherein the ring is heterocycloalkyl-R⁹, substituted heterocycloalkyl-R⁹, heterocycloalkenyl-R⁹, substituted heterocycloalkenyl-R⁹, heteroaryl-R⁹ or substituted heteroaryl-R⁹.

7. The compound according to claim 1, wherein $R^7$ is an alkylamino group substituted with a moiety that is negatively charged at physiological pH and located 5 to 15 atoms from C-22 of the bile acid nucleus, and wherein the moiety is selected from the group consisting of —COOH, —SO₃H, —SO₂H, —PO₃H, —OPO₃H, —OSO₃H, —C(O)NHOH, -tetrazole, -catechol and pharmaceutically acceptable salts thereof.

8. The compound according to claim 1, wherein $R^7$ is a di-substituted alkylamino group substituted with L-D and a moiety that is negatively charged at physiological pH and located 5 to 15 atoms from C-22 of the bile acid nucleus, and wherein the moiety is selected from the group consisting of —COOH, —SO₃H, —SO₂H, —PO₃H, —OPO₃H, —OSO₃H, —C(O)NHOH, -tetrazole, -catechol and pharmaceutically acceptable salts thereof.

9. The compound according to claim 3, wherein $R^4$ and $R^5$ together with the carbon atoms to which they are attached form a 5-membered ring selected from the group consisting of the following 5-membered rings:

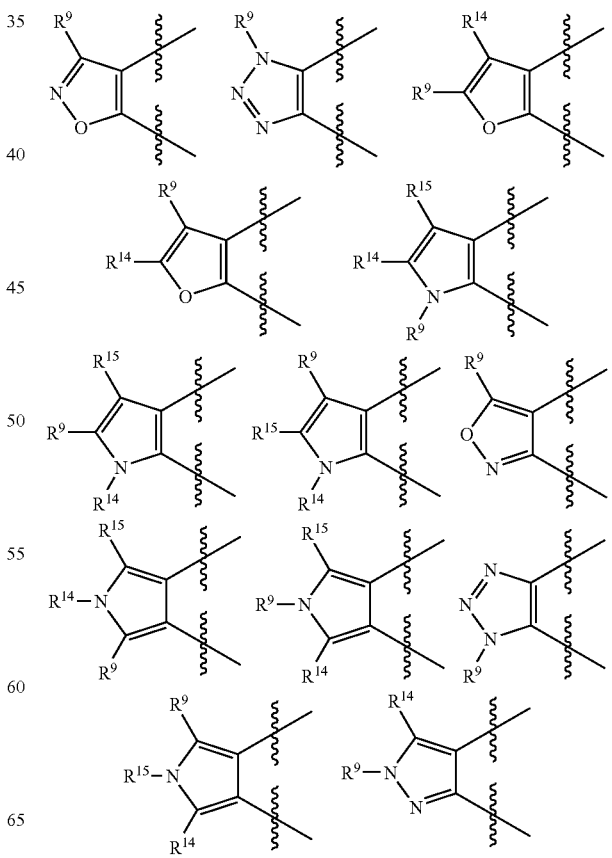

3. The compound according to claim 1, wherein $R^4$ and $R^5$ together with the carbon atoms to which they are attached form a 5-membered ring, and wherein the ring is heterocycloalkyl-R⁹, substituted heterocycloalkyl-R⁹, heteroaryl-R⁹ or substituted heteroaryl-R⁹.

4. The compound according to claim 1, wherein $R^4$ and $R^5$ together with the carbon atoms to which they are attached form a 6-membered ring, and wherein the ring is heterocycloalkyl-R⁹, substituted heterocycloalkyl-R⁹, heteroaryl-R⁹ or substituted heteroaryl-R⁹.

5. The compound according to claim 1, wherein $R^4$ and $R^5$ together with the carbon atoms to which they are attached -continued

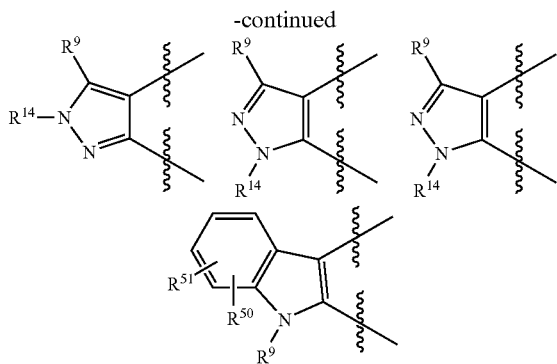

wherein
R⁹ is L-D;
R¹⁴ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂;
R¹⁵ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂; and
R⁵⁰ and R⁵¹ are independently H, halo, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂.

10. The compound according to claim 9, wherein L is a linking group, and wherein the linking group is of the formula —X—Y-Z;
wherein
X is selected from the group consisting of ester, amide, acyloxyalkyl ester, alkoxycarbonyloxyalkyl ester, glycolamide ester, amidomethyl ester, carbonate, carbamate, acyloxyalkyl ether, alkoxycarbonyloxyalkyl ether, acyloxyalkyl carbonate, acyloxyalkyl carbamate, alkoxycarbonyloxyalkyl carbamate, Mannich base, imide, N-acyloxyalkyl phosphoramidate, and N-alkoxycarbonyloxyalkyl phosphoramidate;
Y is of the formula —(R¹⁰⁰)m(R¹⁰¹)n(R¹⁰²)p-, wherein each of R¹⁰⁰, R¹⁰¹ and R¹⁰² are independently selected from the group consisting of alkylene, substituted alkylene, alkenylene, substituted alkenylene, alkynylene, substituted alkynylene, cycloalkylene, substituted cycloalkylene, cycloalkenylene, substituted cycloalkenylene, arylene, substituted arylene, heteroarylene, substituted heteroarylene, heterocyclene and substituted heterocyclene;
each of m, n and p are independently an integer from 0 to 3; and,
Z is selected from the group consisting of ether, thioether, ester, carbonate, carbamate, phosphate, phosphonate, phosphoramidate, amide, amine, urea, thiourea, sulfonamide, sulfoxide, sulfone, thioester, and disulfide.

11. The compound according to claim 10, wherein the linking group is a cleavable linking group.

12. The compound according to claim 11, wherein the linking group is selected from the group consisting of: —OC(O)(CH₂)qNHC(O)—, —OC(O)(alkylene-O)q-alkylene-, and —C(O)O(alkylene-O)q-alkylene, and wherein q is an integer of from 1 to 20.

13. The compound according to claim 4, wherein R⁴ and R⁵ together with the carbon atoms to which they are attached form a 6-membered ring selected from the group consisting of the following 6-membered rings:

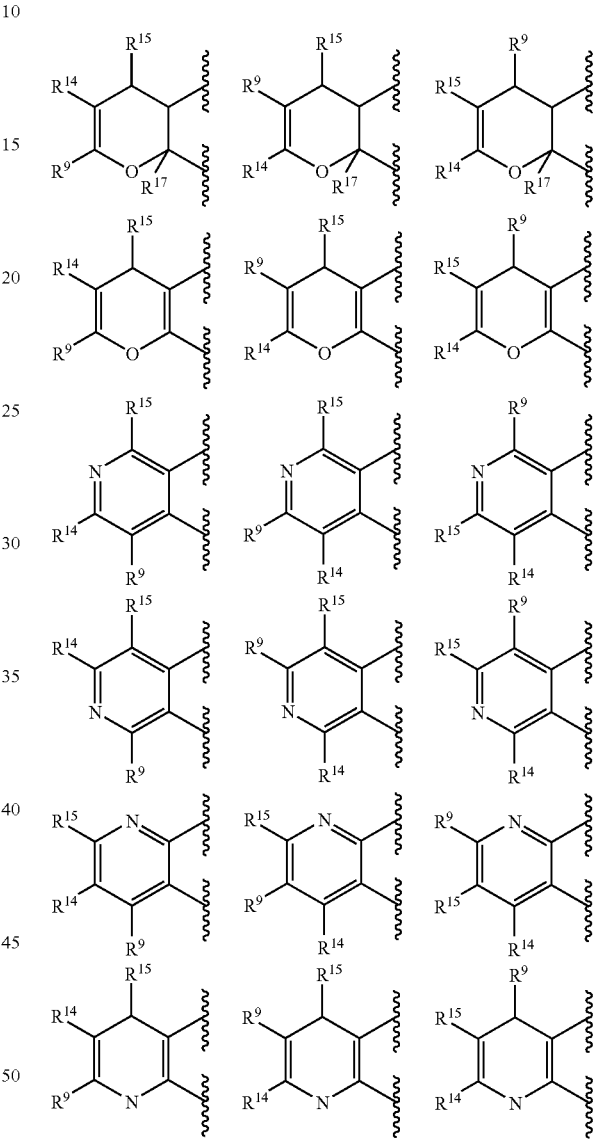

wherein
R⁹ is L-D;
R¹⁴ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂;
R¹⁵ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂; and, $R^{17}$ is OH, OP, NHP or $NR^{52}P$, wherein $R^{52}$ is alkyl or aryl and P is a protecting Group.

14. The compound according to claim 13, wherein L is a linking group, and wherein the linking group is of the formula —X—Y-Z;

wherein

X is selected from the group consisting of ester, amide, acyloxyalkyl ester, alkoxycarbonyloxyalkyl ester, glycolamide ester, amidomethyl ester, carbonate, carbamate, acyloxyalkyl ether, alkoxycarbonyloxyalkyl ether, acyloxyalkyl carbonate, acyloxyalkyl carbamate, alkoxycarbonyloxyalkyl carbamate, Mannich base, imide, N-acyloxyalkyl phosphoramidate, and N-alkoxycarbonyloxyalkyl phosphoramidate;

Y is of the formula —$(R^{100})m(R^{101})n(R^{102})p$-, wherein each of $R^{100}$, $R^{101}$ and $R^{102}$ are independently selected from the group consisting of alkylene, substituted alkylene, alkenylene, substituted alkenylene, alkynylene, substituted alkynylene, cycloalkylene, substituted cycloalkylene, cycloalkenylene, substituted cycloalkenylene, arylene, substituted arylene, heteroarylene, substituted heteroarylene, heterocyclene and substituted heterocyclene;

each of m, n and p are independently an integer from 0 to 3; and,

Z is selected from the group consisting of ether, thioether, ester, carbonate, carbamate, phosphate, phosphonate, phosphoramidate, amide, amine, urea, thiourea, sulfonamide, sulfoxide, sulfone, thioester, and disulfide.

15. The compound according to claim 14, wherein the linking group is a cleavable linking group.

16. The compound according to claim 15, wherein the linking group is selected from the group consisting of: —OC(O)$(CH_2)_q$NHC(O)—, —OC(O)(alkylene-O)$_q$-alkylene-, and —C(O)O(alkylene-O)$_q$-alkylene, and wherein q is an integer of from 1 to 20.

17. The compound according to claim 5, wherein $R^4$ and $R^5$ together with the carbon atoms to which they are attached form a 7-membered ring selected from the group consisting of the following 7-membered rings:

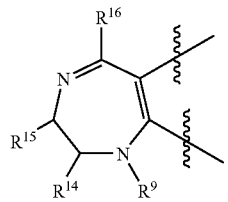
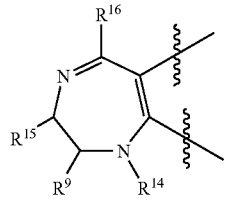
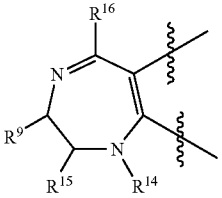
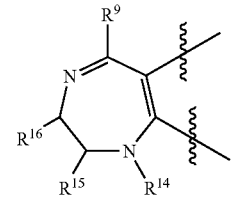
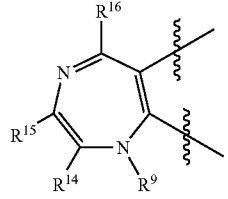
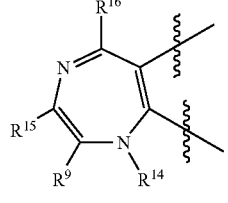

-continued

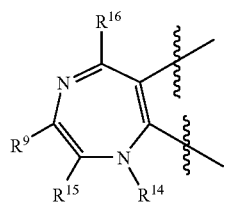
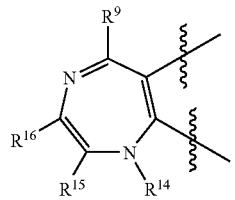
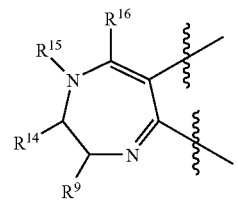
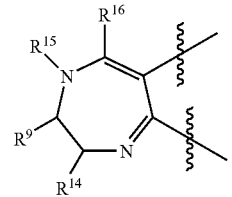
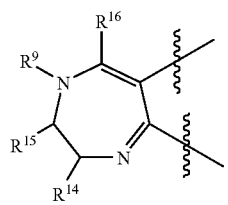
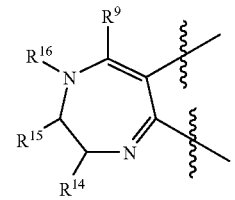
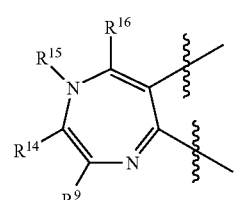
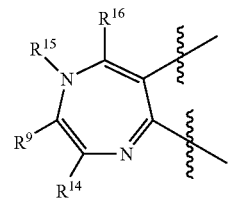
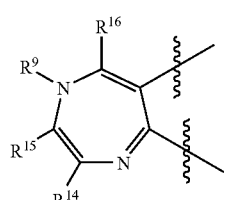
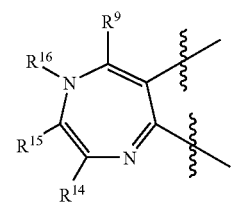
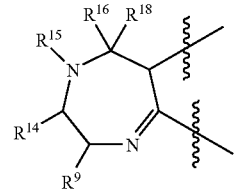
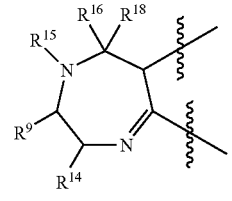
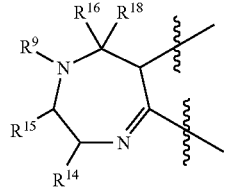
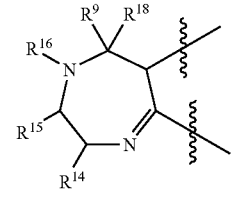
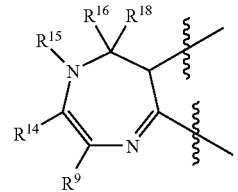
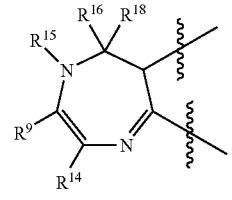

-continued

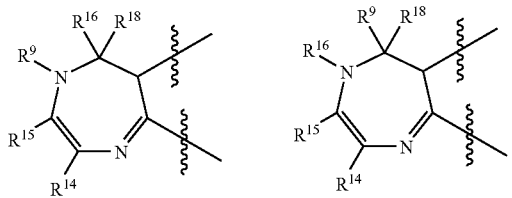

wherein

R⁹ is L-D;

R¹⁴ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂;

R¹⁵ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂;

R¹⁶ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂; and, R¹⁸ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, OR¹³, SH, SR¹³, NH₂, NHR¹³, N(R¹³)₂, CO₂H, CO₂R¹³, CONH₂, CONHR¹³ or CON(R¹³)₂.

18. The compound according to claim 6, wherein R⁴ and R⁵ together with the carbon atoms to which they are attached form a 8-membered ring selected from the group consisting of the following 8-membered rings:

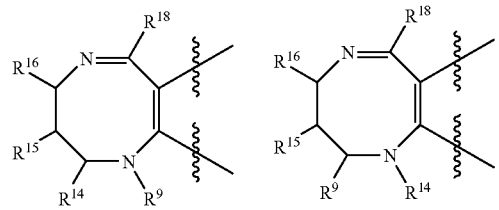

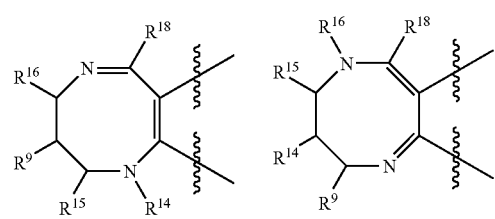

-continued

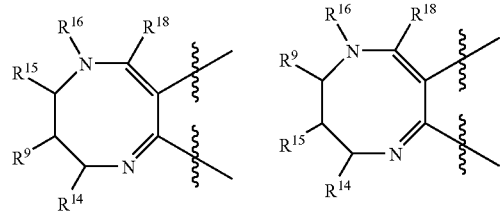

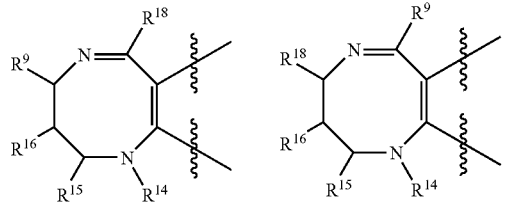

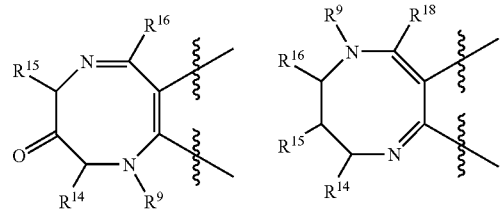

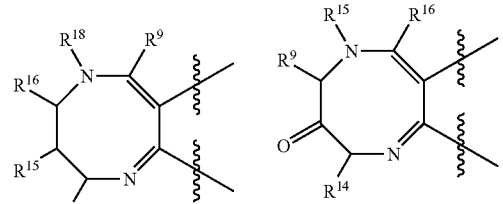

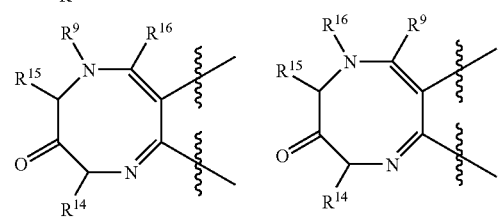

wherein

R⁹ is L-D;

R¹⁴ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$;

$R^{15}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$;

$R^{16}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$; and, $R^{18}$ is H, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl, substituted heteroaryl, OH, $OR^{13}$, SH, $SR^{13}$, $NH_2$, $NHR^{13}$, $N(R^{13})_2$, $CO_2H$, $CO_2R^{13}$, $CONH_2$, $CONHR^{13}$ or $CON(R^{13})_2$.

19. A pharmaceutical composition comprising a pharmaceutically acceptable excipient and a compound of claim 1.

20. The composition of claim 19, wherein the compound contains L-D.

21. The composition of claim 19 further comprising a pharmaceutically acceptable carrier.

* * * * *